(12) United States Patent
Johnson et al.

(10) Patent No.: US 10,954,301 B2
(45) Date of Patent: Mar. 23, 2021

(54) BISPECIFIC MOLECULES HAVING IMMUNOREACTIVITY WITH PD-1 AND CTLA-4, AND METHODS OF USE THEREOF

(71) Applicant: MacroGenics, Inc., Rockville, MD (US)

(72) Inventors: Leslie S. Johnson, Darnestown, MD (US); Gurunadh Reddy Chichili, Germantown, MD (US); Kalpana Shah, Boyds, MD (US); Ross La Motte-Mohs, Boyds, MD (US); Paul A. Moore, North Potomac, MD (US); Ezio Bonvini, Potomac, MD (US); Scott Koenig, Rockville, MD (US)

(73) Assignee: MACROGENICS, INC., Rockville, MD (US)

( * ) Notice: Subject to any disclaimer, the term of this patent is extended or adjusted under 35 U.S.C. 154(b) by 38 days.

(21) Appl. No.: 16/060,227

(22) PCT Filed: Dec. 12, 2016

(86) PCT No.: PCT/US2016/066060
§ 371 (c)(1),
(2) Date: Jun. 7, 2018

(87) PCT Pub. No.: WO2017/106061
PCT Pub. Date: Jun. 22, 2017

(65) Prior Publication Data
US 2019/0161548 A1    May 30, 2019

Related U.S. Application Data

(60) Provisional application No. 62/266,944, filed on Dec. 14, 2015.

(51) Int. Cl.
| | | |
|---|---|---|
| *C07K 16/28* | (2006.01) | |
| *C07K 16/30* | (2006.01) | |
| *C07K 16/46* | (2006.01) | |
| *C07K 16/44* | (2006.01) | |
| *A61K 39/395* | (2006.01) | |
| *A61P 31/00* | (2006.01) | |
| *A61P 35/00* | (2006.01) | |
| *A61K 38/00* | (2006.01) | |

(52) U.S. Cl.
CPC ........ *C07K 16/2827* (2013.01); *A61K 39/395* (2013.01); *A61P 31/00* (2018.01); *A61P 35/00* (2018.01); *C07K 16/28* (2013.01); *C07K 16/2803* (2013.01); *C07K 16/2818* (2013.01); *C07K 16/30* (2013.01); *C07K 16/44* (2013.01); *C07K 16/46* (2013.01); *C07K 16/468* (2013.01); *A61K 38/00* (2013.01); *C07K 2317/31* (2013.01); *C07K 2317/35* (2013.01); *C07K 2317/52* (2013.01); *C07K 2317/53* (2013.01); *C07K 2317/622* (2013.01); *C07K 2317/626* (2013.01); *C07K 2317/64* (2013.01); *C07K 2317/76* (2013.01); *C07K 2317/92* (2013.01); *C07K 2317/94* (2013.01); *C07K 2319/01* (2013.01)

(58) Field of Classification Search
None
See application file for complete search history.

(56) References Cited

U.S. PATENT DOCUMENTS

| | | |
|---|---|---|
| 3,842,067 A | 10/1974 | Sarantakis |
| 3,862,925 A | 1/1975 | Sarantakis et al. |
| 3,972,859 A | 8/1976 | Fujino et al. |
| 4,105,603 A | 8/1978 | Vale et al. |
| 4,526,938 A | 7/1985 | Churchill et al. |
| 4,816,567 A | 3/1989 | Cabilly et al. |
| 4,880,078 A | 11/1989 | Inoue et al. |
| 4,980,286 A | 12/1990 | Morgan et al. |
| 5,128,326 A | 7/1992 | Balazs et al. |

(Continued)

FOREIGN PATENT DOCUMENTS

| | | |
|---|---|---|
| CA | 2738352 A1 | 10/2011 |
| CA | 2932966 A1 | 6/2015 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
International Search Report PCT/US2016/066060 (WO 2017/106061) (dated 2017) (4 pages).
Ott P.A., et al.(2013) "CTLA-4 and PD-1/PD-L1 Blockade: New Immunotherapeutic Modalities with Durable Clinical Benefit in Melanoma Patients," Clin. Cancer Res. 19(19):5300-5309.

(Continued)

*Primary Examiner* — Nelson B Moseley, II
(74) *Attorney, Agent, or Firm* — Grant IP, Inc.

(57) ABSTRACT

The present invention is directed to bispecific molecules (e.g., diabodies, bispecific antibodies, trivalent binding molecules, etc.) that possess at least one epitope-binding site that is immunospecific for an epitope of PD-1 and at least one epitope-binding site that is immunospecific for an epitope of CTLA-4 (i.e., a "PD-1×CTLA-4 bispecific molecule"). The PD-1×CTLA-4 bispecific molecules of the present invention are capable of simultaneously binding to PD-1 and to CTLA-4, particularly as such molecules are arrayed on the surfaces of human cells. The invention is directed to pharmaceutical compositions that contain such PD-1×CTLA-4 bispecific molecules, and to methods involving the use of such bispecific molecules in the treatment of cancer and other diseases and conditions. The present invention also pertains to methods of using such PD-1×CTLA-4 bispecific molecules to stimulate an immune response.

8 Claims, 35 Drawing Sheets

Specification includes a Sequence Listing.

(56) References Cited

U.S. PATENT DOCUMENTS

| | | |
|---|---|---|
| 5,158,878 A | 10/1992 | Prinz et al. |
| 5,290,540 A | 3/1994 | Prince et al. |
| 5,324,821 A | 6/1994 | Favre et al. |
| 5,565,332 A | 10/1996 | Hoogenboom et al. |
| 5,580,717 A | 12/1996 | Dower et al. |
| 5,624,821 A | 4/1997 | Winter et al. |
| 5,679,377 A | 10/1997 | Bernstein et al. |
| 5,733,743 A | 3/1998 | Johnson et al. |
| 5,773,578 A | 6/1998 | Hercend et al. |
| 5,807,715 A | 9/1998 | Morrison et al. |
| 5,811,097 A | 9/1998 | Allison et al. |
| 5,821,337 A | 10/1998 | Carter et al. |
| 5,843,749 A | 12/1998 | Maisonpierre et al. |
| 5,855,913 A | 1/1999 | Hanes et al. |
| 5,866,692 A | 2/1999 | Shitara et al. |
| 5,874,064 A | 2/1999 | Edwards et al. |
| 5,885,573 A | 3/1999 | Bluestone et al. |
| 5,888,533 A | 3/1999 | Dunn |
| 5,912,015 A | 6/1999 | Bernstein et al. |
| 5,916,597 A | 6/1999 | Lee et al. |
| 5,934,272 A | 8/1999 | Lloyd et al. |
| 5,945,155 A | 8/1999 | Grill et al. |
| 5,952,136 A | 9/1999 | Daems et al. |
| 5,955,300 A | 9/1999 | Faure et al. |
| 5,985,309 A | 11/1999 | Edwards et al. |
| 5,985,320 A | 11/1999 | Edwards et al. |
| 5,989,463 A | 11/1999 | Tracy et al. |
| 5,997,867 A | 12/1999 | Waldmann et al. |
| 6,019,968 A | 2/2000 | Platz et al. |
| 6,054,297 A | 4/2000 | Carter et al. |
| 6,180,377 B1 | 1/2001 | Morgan et al. |
| 6,194,551 B1 | 2/2001 | Idusogie et al. |
| 6,218,149 B1 | 4/2001 | Morrison et al. |
| 6,265,150 B1 | 7/2001 | Terstappen et al. |
| 6,277,375 B1 | 8/2001 | Ward |
| 6,331,415 B1 | 12/2001 | Cabilly et al. |
| 6,472,511 B1 | 10/2002 | Leung et al. |
| 6,482,925 B1 | 11/2002 | El Tayar et al. |
| 6,682,736 B1 | 1/2004 | Hanson et al. |
| 6,803,192 B1 | 10/2004 | Chen |
| 6,808,710 B1 | 10/2004 | Wood et al. |
| 6,984,720 B1 * | 1/2006 | Korman ............ A01K 67/0276 530/388.22 |
| 7,034,121 B2 | 4/2006 | Carreno et al. |
| 7,083,784 B2 | 8/2006 | Dall'Acqua et al. |
| 7,101,550 B2 | 9/2006 | Wood et al. |
| 7,109,003 B2 | 9/2006 | Hanson et al. |
| 7,112,324 B1 | 9/2006 | Dorken et al. |
| 7,122,646 B2 | 10/2006 | Holliger et al. |
| 7,129,330 B1 | 10/2006 | Little et al. |
| 7,132,281 B2 | 11/2006 | Hanson et al. |
| 7,148,038 B2 | 12/2006 | Mather |
| 7,217,797 B2 | 5/2007 | Hinton et al. |
| 7,235,641 B2 | 6/2007 | Kufer et al. |
| 7,276,586 B2 | 10/2007 | Goddard et al. |
| 7,317,091 B2 | 1/2008 | Lazar et al. |
| 7,405,061 B2 | 7/2008 | Mather et al. |
| 7,411,057 B2 | 8/2008 | Hanson et al. |
| 7,488,802 B2 | 2/2009 | Collins et al. |
| 7,507,796 B2 | 3/2009 | Little et al. |
| 7,521,051 B2 | 4/2009 | Collins et al. |
| 7,527,969 B2 | 5/2009 | Mather et al. |
| 7,563,869 B2 | 7/2009 | Honjo et al. |
| 7,565,048 B1 | 7/2009 | Peckham |
| 7,569,672 B2 | 8/2009 | Mather et al. |
| 7,572,895 B2 | 8/2009 | Mather et al. |
| 7,572,896 B2 | 8/2009 | Mather et al. |
| 7,575,895 B2 | 8/2009 | Anderson et al. |
| 7,595,048 B2 | 9/2009 | Honjo et al. |
| 7,605,238 B2 | 10/2009 | Korman et al. |
| 7,635,757 B2 | 12/2009 | Freeman et al. |
| 7,638,492 B2 | 12/2009 | Wood et al. |
| 7,666,424 B2 | 2/2010 | Cheung et al. |
| 7,695,936 B2 | 4/2010 | Carter et al. |
| 7,722,868 B2 | 5/2010 | Freeman et al. |
| 7,737,258 B2 | 6/2010 | Cheung |
| 7,740,845 B2 | 6/2010 | Cheung |
| 7,794,710 B2 | 9/2010 | Chen et al. |
| 7,807,797 B2 | 10/2010 | Hanson et al. |
| 7,824,679 B2 | 11/2010 | Hanson et al. |
| 7,858,746 B2 | 12/2010 | Honjo et al. |
| 7,892,554 B2 | 2/2011 | Marks et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,017,114 B2 | 9/2011 | Korman et al. |
| 8,087,074 B2 | 12/2011 | Popp et al. |
| 8,088,376 B2 | 1/2012 | Chamberlain et al. |
| 8,088,905 B2 | 1/2012 | Collins et al. |
| 8,143,379 B2 | 3/2012 | Hanson et al. |
| 8,148,154 B2 | 4/2012 | Cheung et al. |
| 8,148,496 B2 | 4/2012 | Little et al. |
| 8,173,424 B2 | 5/2012 | Marks et al. |
| 8,318,916 B2 | 11/2012 | Korman et al. |
| 8,350,011 B2 | 1/2013 | Cartlidge et al. |
| 8,354,509 B2 | 1/2013 | Carven et al. |
| 8,414,892 B2 | 4/2013 | Cheung |
| 8,460,886 B2 | 6/2013 | Shibayama et al. |
| 8,460,927 B2 | 6/2013 | Chen |
| 8,491,895 B2 | 7/2013 | Hanson et al. |
| 8,501,471 B2 | 8/2013 | Cheung |
| 8,552,154 B2 | 10/2013 | Freeman et al. |
| 8,609,089 B2 | 12/2013 | Langermann et al. |
| 8,709,416 B2 | 4/2014 | Langermann et al. |
| 8,728,474 B2 | 5/2014 | Honjo et al. |
| 8,735,553 B1 | 5/2014 | Li et al. |
| 8,779,098 B2 | 7/2014 | Mather et al. |
| 8,779,105 B2 | 7/2014 | Korman et al. |
| 8,779,108 B2 | 7/2014 | Queva et al. |
| 8,784,815 B2 | 7/2014 | Korman et al. |
| 8,802,091 B2 | 8/2014 | Johnson et al. |
| 8,858,942 B2 | 10/2014 | Cartlidge et al. |
| 8,883,984 B2 | 11/2014 | Hanson et al. |
| 8,900,587 B2 | 12/2014 | Carven et al. |
| 8,952,136 B2 | 2/2015 | Carven et al. |
| 8,974,792 B2 | 3/2015 | Marks et al. |
| 8,981,063 B2 | 3/2015 | Chen |
| 9,005,629 B2 | 4/2015 | Pardoll et al. |
| 9,062,110 B2 | 6/2015 | Cheung |
| 9,062,112 B2 | 6/2015 | Chen |
| 9,067,999 B1 | 6/2015 | Honjo et al. |
| 9,073,994 B2 | 7/2015 | Honjo et al. |
| 9,084,776 B2 | 7/2015 | Korman et al. |
| 9,163,087 B2 | 10/2015 | Kuchroo et al. |
| 9,205,148 B2 | 12/2015 | Langermann et al. |
| 9,217,034 B2 | 12/2015 | Li et al. |
| 9,220,776 B2 | 12/2015 | Sharma et al. |
| 9,273,135 B2 | 3/2016 | Korman et al. |
| 9,284,375 B2 | 3/2016 | Johnson et al. |
| 9,296,816 B2 | 3/2016 | Johnson et al. |
| 9,358,289 B2 | 6/2016 | Korman et al. |
| 9,376,495 B2 | 6/2016 | Bonvini et al. |
| 9,387,247 B2 | 7/2016 | Korman et al. |
| 9,487,587 B2 | 11/2016 | Koenig |
| 9,492,539 B2 | 11/2016 | Korman et al. |
| 9,492,540 B2 | 11/2016 | Korman et al. |
| 9,587,021 B2 | 3/2017 | Huang et al. |
| 9,714,290 B2 | 7/2017 | Jones et al. |
| 9,822,181 B2 | 11/2017 | Bonvini et al. |
| 9,889,197 B2 | 2/2018 | Johnson et al. |
| 9,963,510 B2 | 5/2018 | Johnson et al. |
| 10,160,806 B2 | 12/2018 | Bonvini et al. |
| 10,577,422 B2 | 3/2020 | Shah et al. |
| 2002/0028486 A1 | 3/2002 | Morrison et al. |
| 2002/0086014 A1 | 7/2002 | Korman et al. |
| 2002/0147311 A1 | 10/2002 | Gillies et al. |
| 2003/0115614 A1 | 6/2003 | Kanda et al. |
| 2004/0058400 A1 | 3/2004 | Holliger et al. |
| 2004/0220388 A1 | 11/2004 | Mertens et al. |
| 2004/0241745 A1 | 12/2004 | Honjo et al. |
| 2005/0059051 A1 | 3/2005 | Chen |
| 2005/0079170 A1 | 4/2005 | Le gall et al. |
| 2006/0166291 A1 | 7/2006 | Mather et al. |
| 2006/0172349 A1 | 8/2006 | Mather et al. |

(56) References Cited

U.S. PATENT DOCUMENTS

| | | |
|---|---|---|
| 2006/0172350 A1 | 8/2006 | Mather et al. |
| 2007/0004909 A1 | 1/2007 | Johnson et al. |
| 2007/0031436 A1 | 2/2007 | Little et al. |
| 2007/0036783 A1 | 2/2007 | Humeau et al. |
| 2007/0087006 A1 | 4/2007 | Frantz et al. |
| 2007/0148164 A1 | 6/2007 | Farrington et al. |
| 2007/0166281 A1 | 7/2007 | Kosak |
| 2007/0199281 A1 | 8/2007 | Schoennagel et al. |
| 2007/0202100 A1 | 8/2007 | Wood et al. |
| 2008/0311117 A1 | 12/2008 | Collins et al. |
| 2009/0055944 A1 | 2/2009 | Korman et al. |
| 2009/0060910 A1 | 3/2009 | Johnson et al. |
| 2009/0110667 A1 | 4/2009 | Mozaffarian et al. |
| 2009/0123477 A1 | 5/2009 | Hanke et al. |
| 2009/0217401 A1 | 8/2009 | Korman et al. |
| 2009/0252741 A1 | 10/2009 | Liu et al. |
| 2009/0274666 A1 | 11/2009 | Chen |
| 2009/0313687 A1 | 12/2009 | Popp et al. |
| 2010/0028330 A1 | 2/2010 | Collins et al. |
| 2010/0040614 A1 | 2/2010 | Ahmed et al. |
| 2010/0099853 A1 | 4/2010 | Little et al. |
| 2010/0143245 A1 | 6/2010 | Cheung |
| 2010/0174053 A1 | 7/2010 | Johnson et al. |
| 2010/0266617 A1 | 10/2010 | Carven et al. |
| 2010/0266634 A1 | 10/2010 | Macdonald et al. |
| 2011/0020667 A1 | 1/2011 | Deeman et al. |
| 2011/0123550 A1 | 5/2011 | Shibayama et al. |
| 2011/0206672 A1 | 8/2011 | Little et al. |
| 2012/0114648 A1 | 5/2012 | Langermann et al. |
| 2012/0114649 A1 | 5/2012 | Langermann et al. |
| 2012/0294796 A1 | 11/2012 | Johnson et al. |
| 2013/0017114 A1 | 1/2013 | Nakamura et al. |
| 2013/0017199 A1 | 1/2013 | Langermann |
| 2013/0078234 A1 | 3/2013 | Takahashi et al. |
| 2013/0109843 A1 | 5/2013 | Carven et al. |
| 2013/0149236 A1 | 6/2013 | Johnson et al. |
| 2013/0189263 A1 | 7/2013 | Little et al. |
| 2013/0230514 A1 | 9/2013 | Langermann et al. |
| 2013/0295121 A1 | 11/2013 | Johnson et al. |
| 2013/0309250 A1 | 11/2013 | Cogswell et al. |
| 2014/0044738 A1 | 2/2014 | Langermann et al. |
| 2014/0093511 A1 | 4/2014 | Lonberg et al. |
| 2014/0099318 A1 | 4/2014 | Huang et al. |
| 2014/0105914 A1 | 4/2014 | Jones et al. |
| 2014/0170149 A1 | 6/2014 | Neijssen et al. |
| 2014/0212422 A1 | 7/2014 | Korman et al. |
| 2014/0220021 A1 | 8/2014 | Shibayama et al. |
| 2014/0234296 A1 | 8/2014 | Sharma et al. |
| 2014/0255407 A1 | 9/2014 | Koenig |
| 2014/0294852 A1 | 10/2014 | Korman et al. |
| 2014/0328750 A1 | 11/2014 | Johnson et al. |
| 2014/0348743 A1 | 11/2014 | Korman et al. |
| 2014/0356363 A1 | 12/2014 | Zhou et al. |
| 2015/0079109 A1 | 3/2015 | Li et al. |
| 2015/0166661 A1 | 6/2015 | Chen et al. |
| 2015/0175697 A1 | 6/2015 | Bonvini et al. |
| 2015/0203579 A1 | 7/2015 | Papadopoulos et al. |
| 2015/0299322 A1 | 10/2015 | Freeman et al. |
| 2015/0307620 A1 | 10/2015 | Vella et al. |
| 2016/0036937 A1 | 2/2016 | Ito et al. |
| 2016/0200827 A1 | 7/2016 | Bonvini et al. |
| 2017/0081424 A1 | 3/2017 | Bernett et al. |
| 2017/0198037 A1 | 7/2017 | Bonvini et al. |
| 2017/0210806 A1 | 7/2017 | Liu |
| 2017/0306025 A1 | 10/2017 | Du et al. |
| 2018/0094072 A1 | 4/2018 | Bonvini et al. |
| 2019/0127467 A1* | 5/2019 | Shah .................. A61P 1/18 |
| 2019/0169292 A1 | 6/2019 | Bonvini et al. |
| 2020/0255524 A1 | 8/2020 | Bonvini et al. |

FOREIGN PATENT DOCUMENTS

| | | | |
|---|---|---|---|
| CL | 2018002998 A1 | 12/2018 | |
| CL | 2019001517 A1 | 9/2019 | |
| CN | 104974253 | 10/2015 | |
| CN | 104974253 A | * 10/2015 | ........... A61K 39/395 |
| EP | 0 403 156 A1 | 12/1990 | |
| EP | 0 519 596 A1 | 12/1992 | |
| EP | 0 359 096 B1 | 11/1997 | |
| EP | 1 293 514 B1 | 11/2006 | |
| EP | 1 078 004 B1 | 10/2007 | |
| EP | 2 158 221 A2 | 3/2010 | |
| EP | 1 868 650 A4 | 12/2010 | |
| EP | 2 361 936 A1 | 8/2011 | |
| EP | 2 371 866 A2 | 10/2011 | |
| EP | 2 376 109 A1 | 10/2011 | |
| EP | 2 585 476 A2 | 5/2013 | |
| EP | 2 601 216 A1 | 6/2013 | |
| EP | 2 714 079 A2 | 4/2014 | |
| EP | 2 839 842 A1 | 2/2015 | |
| EP | 3 328 419 A1 | 6/2018 | |
| EP | 3 456 346 A1 | 3/2019 | |
| RU | 2406760 C2 | 12/2010 | |
| WO | WO 91/03493 A1 | 3/1991 | |
| WO | WO 91/05548 A1 | 5/1991 | |
| WO | WO 91/10682 A1 | 7/1991 | |
| WO | WO 92/19244 A2 | 11/1992 | |
| WO | WO 92/22583 A2 | 12/1992 | |
| WO | WO 93/11161 A1 | 6/1993 | |
| WO | WO 95/15171 A1 | 6/1995 | |
| WO | WO 95/20605 A1 | 8/1995 | |
| WO | WO 95/30750 A2 | 11/1995 | |
| WO | WO 96/20698 A2 | 7/1996 | |
| WO | WO 97/32572 A2 | 9/1997 | |
| WO | WO 97/44013 A1 | 11/1997 | |
| WO | WO 98/02463 A1 | 1/1998 | |
| WO | WO 98/23289 A1 | 6/1998 | |
| WO | WO 98/23741 A1 | 6/1998 | |
| WO | WO 98/31346 A1 | 7/1998 | |
| WO | WO 98/58059 A1 | 12/1998 | |
| WO | WO 99/15154 A1 | 4/1999 | |
| WO | WO 99/20253 A1 | 4/1999 | |
| WO | WO 99/55367 A1 | 11/1999 | |
| WO | WO 99/57150 A2 | 11/1999 | |
| WO | WO 99/58572 A1 | 11/1999 | |
| WO | WO 99/66903 A2 | 12/1999 | |
| WO | WO 00/37504 A2 | 6/2000 | |
| WO | WO 00/42072 A2 | 7/2000 | |
| WO | WO 01/00245 A2 | 1/2001 | |
| WO | WO 01/14424 A2 | 3/2001 | |
| WO | WO 01/14557 A1 | 3/2001 | |
| WO | WO 01/39722 A2 | 6/2001 | |
| WO | WO 01/54732 A1 | 8/2001 | |
| WO | WO 02/02781 A1 | 1/2002 | |
| WO | WO 02/086083 A2 | 10/2002 | |
| WO | WO 03/011911 A1 | 2/2003 | |
| WO | WO 03/012069 A2 | 2/2003 | |
| WO | WO 03/024191 A2 | 3/2003 | |
| WO | WO 03/025018 A2 | 3/2003 | |
| WO | WO 03/032814 A2 | 4/2003 | |
| WO | WO 03/035835 A2 | 5/2003 | |
| WO | WO 03/042402 A2 | 5/2003 | |
| WO | WO 03/087340 A2 | 10/2003 | |
| WO | WO 03/093443 A2 | 11/2003 | |
| WO | WO 03/099196 A2 | 12/2003 | |
| WO | WO 03/101485 A1 | 12/2003 | |
| WO | WO 2004/001381 A2 | 12/2003 | |
| WO | WO 2004/004771 A1 | 1/2004 | |
| WO | WO 2004/043239 A2 | 5/2004 | |
| WO | WO 2004/056875 A1 | 7/2004 | |
| WO | WO 2004/063351 A2 | 7/2004 | |
| WO | WO 2004/072286 A1 | 8/2004 | |
| WO | WO 2004/078928 A2 | 9/2004 | |
| WO | WO 2004/106381 A1 | 12/2004 | |
| WO | WO 2005/019258 A2 | 3/2005 | |
| WO | WO 2005/028498 A2 | 3/2005 | |
| WO | WO 2005/070966 A2 | 8/2005 | |
| WO | WO 2005/077415 A1 | 8/2005 | |
| WO | WO 2005/118635 A2 | 12/2005 | |
| WO | WO 2005/121179 A2 | 12/2005 | |
| WO | WO 2006/021955 A2 | 3/2006 | |
| WO | WO 2006/029219 A2 | 3/2006 | |
| WO | WO 2006/066568 A2 | 6/2006 | |
| WO | WO 2006/076584 A2 | 7/2006 | |

(56) References Cited

FOREIGN PATENT DOCUMENTS

| | | |
|---|---|---|
| WO | WO 2006/083852 A2 | 8/2006 |
| WO | WO 2006/084075 A2 | 8/2006 |
| WO | WO 2006/084078 A2 | 8/2006 |
| WO | WO 2006/084092 A2 | 8/2006 |
| WO | WO 2006/084226 A2 | 8/2006 |
| WO | WO 2006/088494 A2 | 8/2006 |
| WO | WO 2006/107617 A2 | 10/2006 |
| WO | WO 2006/107786 A2 | 10/2006 |
| WO | WO 2006/113665 A2 | 10/2006 |
| WO | WO 2006/121168 A1 | 11/2006 |
| WO | WO 2006/125668 A2 | 11/2006 |
| WO | WO 2006/133396 A2 | 12/2006 |
| WO | WO 2007/005874 A2 | 1/2007 |
| WO | WO 2007/021841 A2 | 2/2007 |
| WO | WO 2007/024249 A2 | 3/2007 |
| WO | WO 2007/024715 A2 | 3/2007 |
| WO | WO 2007/046893 A2 | 4/2007 |
| WO | WO 2007/075270 A2 | 7/2007 |
| WO | WO 2007/106707 A2 | 9/2007 |
| WO | WO 2007/110205 A2 | 10/2007 |
| WO | WO 2007/146968 A2 | 12/2007 |
| WO | WO 2008/003103 A2 | 1/2008 |
| WO | WO 2008/003116 A2 | 1/2008 |
| WO | WO 2008/019290 A2 | 2/2008 |
| WO | WO 2008/024188 A2 | 2/2008 |
| WO | WO 2008/027236 A2 | 3/2008 |
| WO | WO 2008/071447 A2 | 6/2008 |
| WO | WO 2008/083174 A2 | 7/2008 |
| WO | WO 2008/116219 A2 | 9/2008 |
| WO | WO 2008/119566 A2 | 10/2008 |
| WO | WO 2008/132601 A1 | 11/2008 |
| WO | WO 2008/140603 A2 | 11/2008 |
| WO | WO 2008/145142 A1 | 12/2008 |
| WO | WO 2008/146911 A1 | 12/2008 |
| WO | WO 2008/156712 A1 | 12/2008 |
| WO | WO 2008/157379 A2 | 12/2008 |
| WO | WO 2009/014708 A2 | 1/2009 |
| WO | WO 2009/018386 A1 | 2/2009 |
| WO | WO 2009/058492 A2 | 5/2009 |
| WO | WO 2009/073533 A2 | 6/2009 |
| WO | WO 2009/080251 A1 | 7/2009 |
| WO | WO 2009/080254 A1 | 7/2009 |
| WO | WO 2009/089004 A1 | 7/2009 |
| WO | WO 2009/101611 A1 | 8/2009 |
| WO | WO 2009/132876 A1 | 11/2009 |
| WO | WO 2010/019570 A2 | 2/2010 |
| WO | WO 2010/027797 A1 | 3/2010 |
| WO | WO 2010/028795 A1 | 3/2010 |
| WO | WO 2010/028796 A1 | 3/2010 |
| WO | WO 2010/028797 A1 | 3/2010 |
| WO | WO 2010/033279 A2 | 3/2010 |
| WO | WO 2010/036959 A2 | 4/2010 |
| WO | WO 2010/080538 A1 | 7/2010 |
| WO | WO 2010/089411 A2 | 8/2010 |
| WO | WO 2010/108127 A1 | 9/2010 |
| WO | WO 2010/136172 A1 | 12/2010 |
| WO | WO 2011/034660 A1 | 3/2011 |
| WO | WO 2011/044368 A1 | 4/2011 |
| WO | WO 2011/066342 A2 | 6/2011 |
| WO | WO 2011/069104 A2 | 6/2011 |
| WO | WO 2011/086091 A1 | 7/2011 |
| WO | WO 2011/109400 A2 | 9/2011 |
| WO | WO 2011/110604 A1 | 9/2011 |
| WO | WO 2011/117329 A1 | 9/2011 |
| WO | WO 2011/131746 A2 | 10/2011 |
| WO | WO 2011/133886 A2 | 10/2011 |
| WO | WO 2011/143545 A1 | 11/2011 |
| WO | WO 2011/147986 A1 | 12/2011 |
| WO | WO 2011/159877 A2 | 12/2011 |
| WO | WO 2012/009544 A2 | 1/2012 |
| WO | WO 2012/018687 A1 | 2/2012 |
| WO | WO 2012/023053 A2 | 2/2012 |
| WO | WO 2012/058768 A1 | 5/2012 |
| WO | WO 2012/120125 A1 | 9/2012 |
| WO | WO 2012/135408 A1 | 10/2012 |
| WO | WO 2012/143524 A2 | 10/2012 |
| WO | WO 2012/145493 A1 | 10/2012 |
| WO | WO 2012/145549 A1 | 10/2012 |
| WO | WO 2012/147713 A1 | 11/2012 |
| WO | WO 2012/156430 A1 | 11/2012 |
| WO | WO 2012/162067 A2 | 11/2012 |
| WO | WO 2012/162068 A2 | 11/2012 |
| WO | WO 2012/162583 A1 | 11/2012 |
| WO | WO 2013/003652 A1 | 1/2013 |
| WO | WO 2013/003761 A1 | 1/2013 |
| WO | WO 2013/006544 A1 | 1/2013 |
| WO | WO 2013/006867 A1 | 1/2013 |
| WO | WO 2013/012414 A1 | 1/2013 |
| WO | WO 2013/013700 A1 | 1/2013 |
| WO | WO 2013014668 A1 | 1/2013 |
| WO | WO 2013/041687 A1 | 3/2013 |
| WO | WO 2013/060867 A2 | 5/2013 |
| WO | WO 2013/070565 A1 | 5/2013 |
| WO | WO 2013/119903 A1 | 8/2013 |
| WO | WO 2013/163427 A1 | 10/2013 |
| WO | WO 2013/173223 | 11/2013 |
| WO | WO 2013/174873 A1 | 11/2013 |
| WO | WO 2014/008218 A1 | 1/2014 |
| WO | WO 2014/022540 A1 | 2/2014 |
| WO | WO 2014/022758 A1 | 2/2014 |
| WO | WO 2014/043708 A1 | 3/2014 |
| WO | WO 2014/055648 A1 | 4/2014 |
| WO | WO 2014/059251 A1 | 4/2014 |
| WO | WO 2014/066532 A1 | 5/2014 |
| WO | WO 2014/066834 A1 | 5/2014 |
| WO | WO 2014/072888 A1 | 5/2014 |
| WO | WO 2014/140180 A1 | 9/2014 |
| WO | WO 2014/159562 A1 | 10/2014 |
| WO | WO 2014/159940 A1 | 10/2014 |
| WO | WO 2014/164427 | 10/2014 |
| WO | WO 2014/179664 A2 | 11/2014 |
| WO | WO 2014/194302 A2 | 12/2014 |
| WO | WO 2014/209804 * 12/2014 ............ C07K 16/28 |
| WO | WO 2015/018420 A1 | 2/2015 |
| WO | WO 2015/026634 A1 | 2/2015 |
| WO | WO 2015/026684 A1 | 2/2015 |
| WO | WO 2015/026892 A1 | 2/2015 |
| WO | WO 2015/026894 A2 | 2/2015 |
| WO | WO 2015/036394 A1 | 3/2015 |
| WO | WO 2015/042246 A1 | 3/2015 |
| WO | WO 2015/048312 A1 | 4/2015 |
| WO | WO 2015/088930 A1 | 6/2015 |
| WO | WO 2015/094992 A1 | 6/2015 |
| WO | WO 2015/095418 A1 | 6/2015 |
| WO | WO 2015/103072 A1 | 7/2015 |
| WO | WO 2015/112534 A2 | 7/2015 |
| WO | WO 2015/112800 A1 | 7/2015 |
| WO | WO 2015/116539 A1 | 8/2015 |
| WO | WO 2015/119930 A1 | 8/2015 |
| WO | WO 2015/138920 A1 | 9/2015 |
| WO | WO 2015/176033 A1 | 11/2015 |
| WO | WO 2015/184203 A1 | 12/2015 |
| WO | WO 2015/184207 A1 | 12/2015 |
| WO | WO 2015/195163 A1 | 12/2015 |
| WO | WO 2015/200119 A1 | 12/2015 |
| WO | WO 2015/200828 A1 | 12/2015 |
| WO | WO 2016/014688 A2 | 1/2016 |
| WO | WO 2016/015685 A1 | 2/2016 |
| WO | WO 2016/020856 A2 | 2/2016 |
| WO | WO 2016/022630 A1 | 2/2016 |
| WO | WO 2016/023960 A1 | 2/2016 |
| WO | WO 2016/028672 A1 | 2/2016 |
| WO | WO 2016/036937 A1 | 3/2016 |
| WO | WO 2016/048938 A1 | 3/2016 |
| WO | WO 2016/054101 A1 | 4/2016 |
| WO | WO 2016/054555 A2 | 4/2016 |
| WO | WO 2016/068801 A1 | 5/2016 |
| WO | WO 2016/069727 A1 | 5/2016 |
| WO | WO 2016/077397 A2 | 5/2016 |
| WO | WO 2016/079050 A1 | 5/2016 |
| WO | WO 2016/092419 A1 | 6/2016 |
| WO | WO 2016/106159 A1 | 6/2016 |
| WO | WO 2016/115274 A1 | 7/2016 |
| WO | WO 2016/127179 A2 | 8/2016 |

(56) References Cited

FOREIGN PATENT DOCUMENTS

| WO | WO 2016/168716 A1 | 10/2016 |
|---|---|---|
| WO | WO 2016/200782 A1 | 12/2016 |
| WO | WO 2016/201051 A1 | 12/2016 |
| WO | WO 2017/011413 A1 | 1/2017 |
| WO | WO 2017/011414 A1 | 1/2017 |
| WO | WO 2017/019846 A1 | 2/2017 |
| WO | WO 2017/030926 A1 | 2/2017 |
| WO | WO 2017/062619 A1 | 4/2017 |
| WO | WO 2017/079112 A1 | 5/2017 |
| WO | WO 2017/106061 A1 | 6/2017 |
| WO | WO 2017/189433 A1 | 11/2017 |
| WO | WO 2017/193032 A2 | 11/2017 |
| WO | WO 2017/214092 A1 | 12/2017 |
| WO | WO 2018/106864 A1 | 6/2018 |

OTHER PUBLICATIONS

Written Opinion of the International Searching Authority PCT/US2016/066060 (WO 2017/106061) (dated 2017) (4 pages).
Extended European Search Report dated Nov. 27, 2018 in European Patent Application No. 16831339.3, filed on Jul. 28, 2016, 8 pages.
International Search Report and Written Opinion dated Oct. 24, 2016 in International Patent Application No. PCT/US2016/044430, filed on Jul. 28, 2016, 14 pages.
Partial Supplementary European Search Report dated Jan. 13, 2020 in Europe Patent Application No. 17810823.9, filed on Jun. 6, 2017, 19 pages.
Armour et al., "Recombinant Human IgG Molecules Lacking Fcgamma Receptor I Binding and Monocyte Triggering Activities", European Journal of Immunology, 1999, 29:2613-2624.
Jing et al., "Combined Immune Checkpoint Protein Blockade and Low Dose Whole Body Irradiation as Immunotherapy for Myeloma", Journal for ImmunoTherapy of Cancer, 2015, 3(2):1-15.
Matsuzaki et al., "Tumor-Infiltrating NY-ESO-1-Specific CD8+ T Cells Are Negatively Regulated by LAG-3 and PD-1 in Human Ovarian Cancer", Proceedings of the National Academy of Sciences, Apr. 27, 2010, 107(17):7875-7880.
Oganesyan et al., "Structural Characterization of a Human Fc Fragment Engineered for Extended Serum Half-Life", Molecular Immunology, 2009, 46:1750-1755.
Picarda et al., "Molecular Pathways: Targeting B7-H3 (CD276) for Human Cancer Immunotherapy", Clinical Cancer Research, Jul. 15, 2016, 22(14)3245-3431.
"Extended European Search Report dated Oct. 14, 2019 in Europe Patent Application No. 16876434.8, filed on Dec. 12, 2016", 10 pages.
"International Preliminary Report on Patentability dated Dec. 20, 2018 in International Patent Application No. PCT/US2017/036075, filed on Jun. 6, 2017", 10 pages.
"International Preliminary Report on Patentability dated Jun. 28, 2018 in International Patent Application No. PCT/US2016/066060, filed on Dec. 12, 2016", 6 pages.
"International Search Report and Written Opinion dated Sep. 1, 2017 in International Patent Application No. PCT/US2017/036075, filed on Jun. 6, 2017", 14 pages.
"Search Report and Written Opinion dated Oct. 4, 2019 in Singapore Patent Application No. 11201810883T, filed on Jun. 6, 2017", 9 pages.
"Search Report and Written Opinion dated Sep. 19, 2019 in Singapore Patent Application No. 11201804839W, filed on Dec. 12, 2016", 7 Pages.
"The Human IgG Subclasses: Molecular Analysis of Structure, Function and Regulation", Pergamon, Oxford, 1990, pp. 43-78.
"WHO Drug Information", 2017—Recommended International Nonproprietary Names, List 77, 2017, 31(1):150 pages.
"WHO Drug Information", World Health Organization, List 62, 2009, 23(3):240-241.
"WHO Drug Information", World Health Organization, Proposed INN: List 116, 2016, 30(4):627-629.
"WHO Drug Information", 2014—Recommended International Nonproprietary Names: List 71, 2014, 28(1):123 pages.
"WHO Drug Information", Recommended International Nonproprietary Names: List 74, 2015, 29(3):387.
"WHO Drug Information", Recommended International Nonproprietary Names: List 74, 2015, 29(3):393-394.
"WHO Drug Information", Recommended International Nonproprietary Names: List 74, 2016, 30(1):100-101.
Abdulghani, et al., "TRAIL Receptor Signaling and Therapeutics", Expert Opinion on Therapeutic Targets, Oct. 2010, 14(10):1091-1108.
Adenis, "Inhibitors of Epidermal Growth Factor Receptor and Colorectal Cancer", Bull Cancer, 2003, 90:S228-232. (Abstract of article provided).
Agarwal, et al., "The Role of Positive Costimulatory Molecules in Transplantation and Tolerance", Curr. Opin. Organ Transplant., 2008, 13:366-372.
Agata, T, et al., "Expression of the PD-1 Antigen on the Surface of Stimulated Mouse T and B Lymphocytes", International Immunology, 1996, 8(5):765-772.
Akcakanat, et al., "Heterogeneous Expression of GAGE, NY-ESO-1, MAGE-A and SSX Proteins in Esophageal Cancer: Implications for Immunotherapy", International Journal of Cancer, 2006, 118(1):123-128.
Al Hussaini, M, et al., "Targeting CD123 in AML Using a T-Cell Directed Dual-Affinity Re-Targeting (DART®) Platform", Blood, Nov. 2015, 127(1):122-131.
Alegre, et al., "A Non-Activating "Humanized" Anti-CD3 Monoclonal Antibody Retains Immunosuppressive Properties In Vivo", Transplantation, 1994, 57:1537-1543.
Alegre, M.L., et al., "Regulation of Surface and Intracellular Expression of CTLA4 on Mouse T Cells", Journal of Immunology, 1996, 157:4762-4770.
Allison, J.P., et al., "Manipulation of Costimulatory Signals to Enhance Antitumor T-Cell Responses", Current Opinion in Immunology, 1995, 7:682-686.
Almqvist, et al., "In Vitro and in Vivo Characterization of 177Lu-Hua33: A Radioimmunoconjugate against Colorectal Cancer", Nuclear Medicine and Biology, 2006, 33(8):991-998.
Alt, et al., "Novel Tetravalent and Bispecific IgG-Like Antibody Molecules Combining Single-Chain Diabodies with the Immunoglobin Gamma 1 Fc or CH3 Region", FEBS Letters, 1999, 454(1-2):90-94.
Andera, L., "Signaling Activated by the Death Receptors of the TNFR Family", Biomed Pap Med Fac Univ Palacky Olomouc Czech Repub, 2009, 153(3):173-180.
Antonia, et al., "Safety and Antitumour Activity of Durvalumab Plus Tremelimumab in Non-Small Cell Lung Cancer: A Multicentre, Phase 1b Study", The Lancet Oncology, Mar. 2016, 17(3):299-308.
Apostolovic, et al., "pH-Sensitivity of the E3/K3 Heterodimeric Coiled Coil", Biomacromolecules, Nov. 2008, 9(11):3173-3180.
Armstrong, et al., "Conformational Changes and Flexibility in T-Cell Receptor Recognition of Peptide-MHC Complexes", Biochemical Journal, Oct. 15, 2008, 415(Pt 2):183-196.
Arndt, et al., "Helix-stabilized Fv (hsFv) Antibody Fragments: Substituting the Constant Domains of a Fab Fragment for a Heterodimeric Coiled-coil Domain", Journal of Molecular Biology, Oct. 2002, 312(1):221-228.
Aruffo, et al., "Molecular Cloning of a CD28 cDNA by a High-Efficiency COS Cell Expression System", Proc. Natl. Acad. Sci. (U.S.A.), 1987, 84:8573-8577.
Asano, et al., "A Diabody for Cancer Immunotherapy and its Functional Enhancement by Fusion of Human Fc Domain", Abstract 3P-683, Journal of Biochemistry, 2004, 76(8):992.
Atwell, et al., "Stable Heterodimers from Remodeling the Domain Interface of a Homodimer Using a Phage Display Library", Journal of Molecular Biology, 1997, 270:26-35.
Bachanova, et al., "NK Cells in Therapy of Cancer", Critical Reviews in Oncogenesis, 2014, 19(1-2):133-141.
Baeuerle, et al., "Bispecific T Cell Engager for Cancer Therapy", Bispecific Antibodies, Jul. 2011, pp. 273-287.
Baeuerle, P.A., et al., "Bispecific T-Cell Engaging Antibodies for Cancer Therapy", Cancer Research, 2009, 69(12):4941-4944.

(56) References Cited

OTHER PUBLICATIONS

Banyer, et al., "Cytokines in innate and adaptive immunity", Reviews in Immunogenetics, 2000, 2:359-373.
Barber, et al., "Restoring Function in Exhausted CD8 T Cells During Chronic Viral Infection", Nature, 2006, 439:682-687.
Barderas, et al., "High Expression of IL-13 Receptor α2 in Colorectal Cancer Is Associated with Invasion, Liver Metastasis, and Poor Prognosis", Cancer Research, Jun. 2012, 72(11):2780-2790.
Bast, et al., "New Tumor Markers: CA125 and Beyond", International Journal of Gynecological Cancer, 2005, 15(3):274-281.
Bataille, et al., "The Phenotype of Normal, Reactive and Malignant Plasma Cells. Identification of "Many and Multiple Myelomas" and of New Targets for Myeloma Therapy", Haematologica, 2006, 91(9):1234-1240.
Bauer, et al., "Activation of NK cells and T cells by NKG2D, A Receptor for stress-inducible MICA", Science, Jul. 1999, 285(5428):727-729.
Beier, et al., "Master switches of T-cell activation and differentiation", European Respiratory Journal, Apr. 2007, 29(4):804-812.
Belizario, J. E., "Immunodeficient Mouse Models: An Overview", Bentham Open, The Open Immunology Journal, 2009, 2:79-85.
Bennett, et al., "Program Death-1 Engagement Upon TCR Activation has Distinct Effects on Costimulation and Cytokine-Driven Proliferation: Attenuation of ICOS, IL-4, and IL-21, but not CD28, IL-7, IL-15 Responses", The Journal of Immunology, 2003, 170:711-718.
Berger, R., et al., "Phase I Safety and Pharmacokinetic Study of CT-011, A Humanized Antibody Interacting with PD-1, In Patients with Advanced Hematologic Malignancies", Clinical Cancer Research, 2008, 14(10):3044-3051.
Bhattacharya-Chatterjee, et al., "Idiotype vaccines against human T cell leukemia. II. Generation and characterization of a monoclonal idiotype cascade (Ab1, Ab2, and Ab3)", The Journal of Immunology, Aug. 15, 1988, 141(4):1398-1403.
Bird, et al., "Single-Chain Antigen-Binding Proteins", Science, 1988, 242:423-426.
Blank, C, et al., "Contribution of the PD-L1-PD-1 Pathway to T-Cell Exhaustion: An Update on Implications for Chronic Infections and Tumor Evasion Cancer", Cancer Immunol Immunother, Dec. 2006, 56(5):739-745.
Blumenthal, et al., "Expression patterns of CEACAM5 and CEACAM6 in primary and metastatic cancers", BMC Cancer, 2007, 7(2):15 pages.
Bodey, B., "Cancer-Testis Antigens: Promising Targets for Antigen Directed Antineoplastic Immunotherapy", Expert Opinion on Biological Therapy, 2002, 2(6):577-584.
Boghaert, et al., "The oncofetal protein, 5T4, is a suitable target for antibody-guided anti-cancer chemotherapy with calicheamicin", International Journal of Oncology, Jan. 2008, 32(1):221-234.
Boks, M.A., et al., "An optimized CFSE based T-cell suppression assay to evaluate the suppressive capacity of regulatory T-cells induced by human tolerogenic dendritic cells", Scandinavian Journal of Immunology, 2010, 72:158-168.
Bou-Assaly, et al., "Cetuximab (Erbitux)", American Journal of Neuroradiology, Apr. 2010, 31(4):626-627.
Boucher, et al., "Protein Detection by Western Blot via Coiled-Coil Interactions", Analytical Biochemistry, Apr. 2010, 399(1):138-140.
Boyerinas, et al., "Antibody-Dependent Cellular Cytotoxicity Activity of a Novel Anti-PD-L1 Antibody Avelumab (MSB0010718C) on Human Tumor Cells", Cancer Immunology Research, Oct. 2015, 3(10):1148-1157.
Bozinov, et al., "Decreasing Expression of the Interleukin-13 Receptor IL-13Rα2 in Treated Recurrent Malignant Gliomas", Neurol Med Chir (Tokyo), 2010, 50(8):617-621.
Brahmer, J.R., et al., "Phase I Study of Single-Agent Anti-Programmed Death-1 (MDX-1106) in Refractory Solid Tumors: Safety, Clinical Activity, Pharmacodynamics, and Immunologic Correlates", Journal of Clinical Oncology, Jul. 1, 2010, 28(19):3167-3175.
Brandsma, "Fc receptor inside-out signaling and possible impact on antibody therapy", Immunological Reviews, Nov. 2015, 268(1):74-87.
Brown, J.A., et al., "Blockade of Programmed Death-1 Ligands on Dendritic Cells Enhances T-Cell Activation and Cytokine Production", The Journal of Immunology, 2003, 170:1257-1266.
Brown, et al., "Glioma IL_13Rα2 Is Associated with Mesenchymal Signature Gene Expression and Poor Patient Prognosis", PLoS One, Oct. 18, 2013, 8(10):e77769.
Brown, et al., "Tumor-Specific Genetically Engineered Murine-Human Chimeric Monoclonal Antibody", Cancer Research, 1987, 47(13):3577-3583.
Bruggemann, et al., "Comparison of the Effector Functions of Human Immunoglobulins using a Matched Set of Chimeric Antibodies", Journal of Experimental Medicine, Nov. 1987, 166(5):1351-1361.
Bruhns, et al., "Specificity and affinity of human Fcgamma receptors and their polymorphic variants for human IgG subclasses", Blood, Apr. 16, 2009, 113(16):3716-3725.
Buchacher, et al., "Generation of Human Monoclonal Antibodies against HIV-1 Proteins; Electrofusion and Epstein-Barr Virus Transformation for Peripheral Blood Lymphocyte Immortalization", AIDS Research and Human Retroviruses, 1994, 10(4):359-369.
Buchwald, et al., "Long-Term, Continuous Intravenous Heparin Administration by an Implantable Infusion Pump in Ambulatory Patients with Recurrent Venous Thrombosis", Surgery, 1980, 88(4):507-516.
Cachia, et al., "Synthetic Peptide Vaccine Development: Measurement of Polyclonal Antibody Affinity and Cross-Reactivity Using a New Peptide Capture and Release System for Surface Plasmon Resonance Spectroscopy", Journal of Molecular Recognition, 2004, 17(6):540-557.
Calin, et al., "Genomics of Chronic Lymphocytic Leukemia MicroRNAs as New Players with Clinical Significance", Seminars in Oncology, May 2006, 33(2):167-173.
Callahan, et al., "At the Bedside: CTLA-4- and PD-1-blocking antibodies in cancer immunotherapy", Journal of Leukocyte Biology, Jul. 2013, 94(1):41-53.
Cameron, et al., "Focal overexpression of CEACAM6 contributes to enhanced tumourigenesis in head and neck cancer via suppression of apoptosis", Molecular Cancer, Sep. 2012, 11(74):11 pages.
Canafax, et al., "Monoclonal antilymphocyte antibody (OKT3) treatment of acute renal allograft rejection", Pharmacotherapy, Aug. 1987, 7(4):121-124.
Carlo-Stella, et al., "Targeting Trail Agonistic Receptors for Cancer Therapy", Clinical Cancer Research, Apr. 2007, 13(8):2313-2317.
Caron, et al., "Engineered Humanized Dimeric Forms of IgG Are More Effective Antibodies", Journal of Experimental Medicine, 1992, 176:1191-1195.
Carreno, et al., "CTLA-4 (CD152) Can Inhibit T Cell Activation by Two Different Mechanisms Depending on Its Level of Cell Surface Expression", The Journal of Immunology, 2000, 165:1352-1356.
Carter, et al., "Humanization of an Anti-p185her2 Antibody for Human Cancer Therapy", Proc. Natl. Acad. Sci. (U.S.A.), 1992, 89:4285-4289.
Carter, et al., "PD-1:PD-L Inhibitory Pathway Affects both CD4(+) and CD8(+) T-cells and is Overcome by IL-2", European Journal of Immunology, 2002, 32(3):634-643.
Castelli, et al., "T-Cell Recognition of Melanoma-Associated Antigens", Journal of Cellular Physiology, 2000, 182(3):323-331.
Chan, et al., "The Use of Antibodies in the Treatment of Infectious Diseases", Singapore Medical Journal, 2009, 50(7):663-666.
Chang, et al., "Molecular Cloning of Mesothelin, a Differentiation Antigen Present on Mesothelium, Mesotheliomas, and Ovarian Cancers", Proc Natl Acad Sci U S A., Feb. 1996, 93(1):136-140.
Chapin, et al., "Distribution and surfactant association of carcinoembryonic cell adhesion molecule 6 in human lung", American Journal of Physiology—Lung Cellular and Molecular Physiology, 2012, 302(2):L216-L225.
Chapoval, et al., "B7-H3: A Costimulatory Molecule for T Cell Activation and IFN-γ Production", Nature Immunology, 2001, 2:269-274.

(56) References Cited

OTHER PUBLICATIONS

Chappel, et al., "Identification of a Secondary FcrRI Binding Site within a Genetically Engineered Human IgG Antibody", Journal of Biological Chemistry, 1993, 268(33):25124-25131.
Chappel, et al., "Identification of the Fc Gamma Receptor Class I Binding Site in Human IgG Through the use of Recombinant IgG1/IgG2 Hybrid and Point-Mutated Antibodies", Proc. Natl. Acad. Sci U.S.A., 1991, 88:9036-9040.
Chaudhari, et al., "Following the Trail to Apoptosis", Immunologic Research, 2006, 35(3):249-262.
Chen, et al., "EphA2 enhances the proliferation and invasion ability of LNCaP prostate cancer cells", Oncology Letters, 2014, 8(1):41-46.
Chen, et al., "Expression of B7-H1 in Inflammatory Renal Tubular Epithelial Cells", Nephron Experimental Nephrology, Feb. 2005, 102:e81-e92.
Chen, et al., "Molecular Mechanisms of T-Cell Co-Stimulation and Co-Inhibition", Nature Reviews Immunology, Apr. 2013, 13(4):227-242.
Chetty, et al., "CD3: Structure, Function, and Role of Immunostaining in Clinical Practice", The Journal of Pathology, 1994, 173(4):303-307.
Chichili, et al., "A CD3xCD123 Bispecific DART for Redirecting Host T Cells to Myelogenous Leukemia: Preclinical Activity and Safety in Nonhuman Primates", Science Translational Medicine, 2015, 7(289):289ra82.
Chothia, et al., "Canonical structures for the hypervariable regions of immunoglobulins", Journal of Molecular Biology, 1987, 196:901-917.
Chu, et al., "CD79: A Review", Applied Immunohistochemistry & Molecular Morphology, 2001, 9(2):97-106.
Chuang, et al., "Regulation of Cytotoxic T Lymphocyte-Associated Molecule-4 by Src Kinases", The Journal of Immunology, 1999, 162:1270-1277.
Co, et al., "Chimeric and Humanized Antibodies with Specificity for the CD33 Antigen", The Journal of Immunology, 1992, 148(4):1149-1154.
Co, et al., "Humanized Antibodies for Antiviral Therapy", Proc. Natl. Acad. Sci. (U.S.A.), 1991, 88:2869-2873.
Collins, et al., "The B7 Family of Immune-Regulatory Ligands", Genome Biology, 2005, 6(6):223.1-223.7.
Comerci, et al., "CD2 Promotes Human Natural Killer Cell Membrane Nanotube Formation", PLoS One, Oct. 2012, 7(10):e47664:1-12.
Coudert, et al., "Altered NKG2D function in NK cells induced by chronic exposure to NKG2D ligand-expressing tumor cells", Blood, Oct. 2005, 106:1711-1717.
Coyle, et al., "The Expanding B7 Superfamily: Increasing Complexity in Costimulatory Signals Regulating T Cell Function", Nature Immunol., 2001, 2(3):203-209.
Cracco, et al., "Immune Response in Prostate Cancer", Minerva Urologica e Nefrologica, Dec. 2005, 57(4):301-311.
Daugherty, et al., "Polymerase Chain Reaction Facilitates the Cloning, CDR-Grafting, and Rapid Expression of a Murine Monoclonal Antibody Directed Against the CD18 Component of Leukocyte Integrins", Nucleic Acids Research, 1991, 19(9):2471-2476.
Davies, et al., "Induction of alloantigen-specific anergy in human peripheral blood mononuclear cells by alloantigen stimulation with co-stimulatory signal blockade", Journal of Visualized Experiments, Mar. 2011, 49:e2673, 5 pages.
Davis, et al., "Therapy of B-Cell Lymphoma with Anti-CD20 Antibodies Can Result in the Loss of CD20 Antigen Expression", Clinical Cancer Research, Mar. 1999, 5(3):611-615.
De Crescenzo, et al., "Real-Time Monitoring of the Interactions of Two-Stranded de novo Designed Coiled-Coils: Effect of Chain Length on the Kinetic and Thermodynamic Constants of Binding", Biochemistry, 2003, 42:1754-1763.
De Haij, et al., "Renal tubular epithelial cells modulate T-cell responses via ICOS-L and B7-H1", Kidney International, Jun. 2005, 68:2091-2102.

Del Rio, et al., "Antibody-mediated signaling through PD-1 costimulates T cells and enhances CD28-dependent proliferation", European Journal of Immunology, 2005, 35:3545-3560.
Deng, et al., "Expression profiling of CEACAM6 associated with the tumorigenesis and progression in gastric adenocarcinoma", Genetics and Molecular Research, Sep. 26, 2014, 13(3):7686-7697.
Dennis, et al., "Glycoprotein Glycosylation and Cancer Progression", Biochimica et Biophysica Acta, 1999, 1473(1):21-34.
Di Bartolomeo, et al., "Bevacizumab treatment in the elderly patient with metastatic colorectal cancer", Clinical Interventions in Aging, 2015, 10:127-133.
Di Giacomo, "The Emerging Toxicity Profiles of Anti-CTLA-4 Antibodies Across Clinical Indications", Seminars in Oncology, Oct. 2010, 37(5):499-507.
Dimaio, et al., "Human Papillomaviruses and Cervical Cancer", Advances in Virus Research, 2006, 66:125-159.
Disis, et al., "Generation of T-cell immunity to the HER-2/neu protein after active immunization with HER-2/neu peptide-based vaccines", Journal of Clinical Oncology, 2002, 20:2624-2632.
Dong, et al., "B7-H1 pathway and its role in the evasion of tumor immunity", Journal of Molecular Medicine, Apr. 2003, 81:281-287.
Dong, et al., "B7-H1, a third member of the B7 family, co-stimulates T-cell proliferation and interleukin-10 secretion", Nature Medicine, Dec. 1999, 5(12):1365-1369.
Dong, et al., "Immune Regulation by Novel Costimulatory Molecules", Immunologic Research, 2003, 28(1):39-48.
Dong, et al., "Tumor-associated B7-H1 promotes T-cell apoptosis: a potential mechanism of immune evasion", Nature Medicine, Sep. 2002, 8(8):793-800.
Dorfman, et al., "Programmed Death-1 (PD-1) is a Marker of Germinal Center-associated T Cells and Angioimmunoblastic T-Cell Lymphoma", The American Journal of Surgical Pathology, 2006, 30:802-810.
Dougall, et al., "The neu-oncogene: signal transduction pathways, transformation mechanisms and evolving therapies", Oncogene, Aug. 1994, 9(8):2109-2123. (Abstract only).
Duncan, et al., "Localization of the Binding Site for the Human High-Affinity Fc Receptor on IgG", Nature, 1988, 332:563-564.
During, et al., "Controlled Release of Dopamine from a Polymeric Brain Implant: In Vivo Characterization", Annals of Neurology, 1989, 25(4):351-356.
Edelson, "Cutaneous T-cell lymphoma: a model for selective immunotherapy", The cancer journal from Scientific American, 1998, 4(2):62-71.
Egloff, et al., "Cyclin B1 and other Cyclins as Tumor Antigens in Immunosurveillance and Immunotherapy of Cancer", Cancer Research, Jan. 1, 2006, 66(1):6-9.
Eisen, et al., "Naptunnonnab Estafenatox: Targeted Immunotherapy with a Novel Immunotoxin", Current Oncology Reports, Feb. 2014, 16(2):370. 6 pages.
Eketorp, et al., "Alemtuzumab (anti-CD52 monoclonal antibody) as single-agent therapy in patients with relapsed/refractory chronic lymphocytic leukaemia (CLL)—a single region experience on consecutive patients", Annals of Hematology, Oct. 2014, 93(10):1725-1733.
Eppihimer, et al., "Expression and Regulation of the PD-L1 Immunoinhibitory Molecule on Microvascular Endothelial Cells", Microcirculation, Apr. 2002, 9(2):133-145.
Estin, et al., "Transfected Mouse Melanoma Lines That Express Various Levels of Human Melanoma-Associated Antigen p97", Journal of the National Cancer Institute, Apr. 1989, 81(6):445-458.
Fedorov, et al., "PD-1-and CTLA-4-based inhibitory chimeric antigen receptors (iCARs) divert off-targeting immunotherapy responses", Science Translational Medicine, Dec. 2013, 5(215):215ra172, 25 pages.
Feizi, T., "Demonstration by Monoclonal Antibodies that Carbohydrate Structures of Glycoproteins and Glycolipids are Onco-Developmental Antigens", Nature, 1985, 314(6006):53-57.
Fernandez-Rodriquez, et al., "Induced Heterodimerization and Purification of Two Target Proteins by a Synthetic Coiled-Coil Tag", Protein Science, 2012, 21:511-519.

(56) References Cited

OTHER PUBLICATIONS

Feuchtinger, T, et al., "Leukemia Related Co-Stimulation / Co-Inhibition Predict T-Cell Attack of Acute Lymphoblastic Leukemia Mediated by Blinatumomab", Blood, Dec. 2015, 126(23):3764-3764.
Field, et al., "Bevacizumab and Glioblastoma: Scientific Review, Newly Reported Updates, and Ongoing Controversies", Cancer, Apr. 2015, 121(7):997-1007.
Fitzgerald, et al., "Improved Tumour Targeting by Disulphide Stabilized Diabodies Expressed in Pichia pastoris", Protein Engineering, 1997, 10(10):1221-1225.
Flajnik, et al., "Evolution of the B7 Family: Co-Evolution of B7H6 and Nkp30, Identification of a New B7 Family Member, B7H7, and of B7's Historical Relationship with the MHC", Immunogenetics, Aug. 2012, 64(8):571-590.
Flesch, et al., "Functions of the Fc Receptors for Immunoglobulin G", Journal of Clinical Laboratory Analysis, 2000, 14:141-156.
Flies, et al., "The New B7s: Playing a Pivotal Role in Tumor Immunity", Journal of Immunother, 2007, 30(3):251-260.
Foon, et al., "Immune Response to the Carcinoembryonic Antigen in Patients Treated with an Anti-Idiotype Antibody Vaccine", Journal of Clinical Investigation, 1995, 96(1):334-342.
Foon, et al., "Preclinical and clinical evaluations of ABX-EGF, a fully human anti-epidermal growth factor receptor antibody", International Journal of Radiation Oncology*Biology*Physics, Mar. 2004, 58(3):984-990.
Freeman, et al., "Engagement of the PD-1 Immunoinhibitory Receptor by a Novel B7 Family Member Leads to Negative Regulation of Lymphocyte Activation", Journal of Experimental Medicine, Oct. 2, 2000, 192:1027-1034.
Fujisawa, et al., "A Novel Role of Interleukin-13 Receptor α2 in Pancreatic Cancer Invasion and Metastasis", Cancer Research, Nov. 2009, 69(22):8678-8685.
Fukushima, et al., "B7-H3 Regulates the Development of Experimental Allergic Conjunctivitis in Mice", Immunology Letters, 2007, 113:52-573.
Ganesan, A, "Solid-Phase Synthesis in the Twenty-First Century", Mini-Reviews in Medicinal Chemistry, 2006, 6(1):3-10.
Gao, et al., "Molecular interactions of coreceptor CD8 and MHC class I: the molecular basis for functional coordination with the T-cell receptor", Immunology Today, Dec. 2000, 21(12):630-636.
Gardnerova, et al., "The Use of TNF Family Ligands and Receptors and Agents which Modify their Interaction as Therapeutic Agents", Current Drug Targets, Dec. 2000, 1(4):327-364.
Ge, et al., "CD36: A Multiligand Molecule", Laboratory Hematology, 2005, 11(1):31-37. (Abstract of article provided).
Ghetie, et al., "Anti-CD19 inhibits the growth of human B-cell tumor lines in vitro and of Daudi cells in SCID mice by inducing cell cycle arrest", Blood, Mar. 1994, 83(5):1329-1336.
Ghosh, et al., "End-To-End and End-To-Middle Interhelical Interactions: New Classes of Interacting Helix Pairs in Protein Structures", Acta Crystallogr D Biol Crystallogr., 2009, 65(Pt 10):1032-1041.
Gil, et al., "Regulation of the INK4b-ARF-INK4a Tumour Suppressor Locus: All for one or one for all", Nature Reviews Molecular Cell Biology, 2006, 7:667-677.
Gill, et al., "Efficacy Against Human Acute Myeloid Leukemia and Myeloablation of Normal Hematopoiesis in a Mouse Model Using Chimeric Antigen Receptor-Modified T Cells", Blood, Mar. 2014, 123(15): 2343-2354.
Gorman, et al., "Reshaping A Therapeutic CD4 Antibody", Proc. Natl. Acad. Sci. (U.S.A.), 1991, 88:4181-4185.
Govindan, "Cetuximab in Advanced Non-Small Cell Lung Cancer", Clinical Cancer Research, Jun. 2004, 10(12):4241s-4244s.
Grabowski, et al., "Current management of ovarian cancer", Minerva Medica, Jun. 2015, 106(3):151-156. (Abstract of article provided).
Greenwald, R.J., et al., "The B7 Family Revisited", Annual Review of Immunology, 2005, 23:515-548.

Grigoryan, et al., "Structural Specificity in Coiled-Coil Interactions", Current Opinion in Structural Biology, Aug. 2008, 18(4):477-483.
Groh, et al., "Costimulation of CD8αβ T cells by NKG2D via engagement by MIC induced on virus-infected cells", Nature Immunology, Mar. 2001, 2(3):255-260.
Gross, J., et al., "Identification and Distribution of the Costimulatory Receptor CD28 in the Mouse", Journal of Immunology, Jul. 1992, 149(2):380-388.
Gruber, et al., "Efficient Tumor Cell Lysis Mediated by a Bispecific Single Chain Antibody Expressed in *Escherichia coli*", Journal of Immunology, 1994, 152(11):5368-5374.
Guy, et al., "Organization of Proximal Signal Initiation at the TCR:CD3 Complex", Immunological Reviews, Nov. 2009, 232(1):7-21.
Hall, et al., "Angiogenesis inhibition as a therapeutic strategy in non-small cell lung cancer (NSCLC)", Translational Lung Cancer Research, Oct. 2015, 4(5):515-523.
Hamid, et al., "Safety and Tumor Responses with Lambrolizumab (anti-PD-1) in Melanoma", The New England Journal of Medicine, 2013, 369:134-44.
Han, et al., "Evaluation of 3 Clinical Dendritic Cell Maturation Protocols containing Lipopolysaccharide and Interferon-Gamma", Journal of Immunotherapy, 2009, 32(4):399-407.
Hardy, et al., "A lymphocyte-activating monoclonal antibody induces regression of human tumors in severe combined immunodeficient mice", PNAS, 1997, 94:5756-5760.
Hardy, et al., "A Monoclonal Antibody against a Human B Lymphoblastoid Cell Line Induces Tumor Regression in Mice", Cancer Research, 1994, 54:5793-5796.
Harper, et al., "CTLA-4 and CD28 Activated Lymphocyte Molecules are Closely Related in Mouse and Human as to Sequence, Message Expression, Gene Structure, and Chromosomal Location", Journal of Immunology, 1991, 147:1037-1044.
Harris, et al., "Trimeric HIV-1 Glycoprotein Gp140 Immunogens and Native HIV-1 Envelope Glycoproteins Display the Same Closed and Open Quaternary Molecular Architectures", Proceedings of the National Academy of Sciences, Jul. 12, 2011, 108(28):11440-11445.
Heath, et al., "The human A33 antigen is a transmembrane glycoprotein and a novel member of the immunoglobulin superfamily", Proc Natl Acad Sci U S A., Jan. 21, 1997, 94(2):469-474.
Hellstrom, et al., "Monoclonal Antibodies to Cell Surface Antigens Shared by Chemically Induced Mouse Bladder Carcinomas", Cancer Research, May 1985, 45:2210-2218.
Hellstrom, et al., "Monoclonal Mouse Antibodies Raised against Human Lung Carcinoma", Cancer Research, Aug. 1986, 46(8):3917-3923.
Henttu, et al., "cDNA coding for the entire human prostate specific antigen shows high homologies to the human tissue kallikrein genes", Biochemical and Biophysical Research Communications, Apr. 1989, 160(2):903-910.
Herlyn, et al., "Monoclonal Antibody Detection of a Circulating Tumor-Associated Antigen. I. Presence of Antigen in Sera of Patients with Colorectal, Gastric, and Pancreatic Carcinoma", Journal of Clinical Immunology, 1982, 2(2):135-140.
Hilkens, et al., "Cell membrane-associated mucins and their adhesion-modulating property", Trends in Biochemical Sciences, Sep. 1992, 17(9):359-363.
Hodi, et al., "Biologic Activity of Cytotoxic T Lymphocyte-Associated Antigen 4 Antibody Blockade in Previously Vaccinated Metastatic Melanoma and Ovarian Carcinoma Patients", Proceedings of the National Academy of Sciences, Apr. 15, 2003, 100(8):4712-4717.
Hoelzer, D., "Targeted Therapy with Monoclonal Antibodies in Acute Lymphoblastic Leukemia", Current Opinion in Oncology, 2013, 25(6):701-706.
Hofmeyer, et al., "The Contrasting Role of B7-H3", Proc. Natl. Acad. Sci. (U.S.A.), 2008, 105(30):10277-10278.
Holliger, et al., "'Diabodies' Small Bivalent and Bispecific Antibody Fragments", Proceedings of the National Academy of Sciences, 1993, 90:6444-6448.

(56) References Cited

OTHER PUBLICATIONS

Holliger, et al., "Specific Killing of Lymphoma Cells by Cytotoxic T-Cells Mediated by a Bispecific Diabody", Protein Engineering, 1996, 9(3):299-305.
Holmberg, et al., "Theratope Vaccine (STn-KLH).", Expert Opinion on Biological Therapy, 2001, 1(5):881-891.
Hoon, et al., "Molecular Cloning of a Human Monoclonal Antibody Reactive to Ganglioside GM3 Antigen on Human Cancers", Cancer Research, Nov. 1993, 53(21):5244-5250.
Horssen, et al., "TNF-α in Cancer Treatment: Molecular Insights, Antitumor Effects, and Clinical Utility", Oncologist, Apr. 2006, 11(4):397-408.
Houghten, Richard A., et al., "General Method for the Rapid Solid-Phase Synthesis of Large Numbers of Peptides: Specificity of Antigen-Antibody Interaction at the Level of Individual Amino Acids", Proceedings of the National Academy of Sciences, 1985, 82(15):5131-5135.
Howard, et al., "Intracerebral Drug Delivery in Rats with Lesion-Induced Memory Deficits", Journal of Neurosurgery, 1989, 71(1):105-112.
Hutchins, et al., "Improved Biodistribution, Tumor Targeting, and Reduced Immunogenicity in Mice with A Gamma 4 Variant of Campath-1H", Proc. Natl. Acad. Sci. (U.S.A.), 1995, 92:11980-11984.
Hutloff, et al., "ICOS is an Inducible T-Cell Co-Stimulator Structurally and Functionally Related to CD28", Nature, 1999, 397:263-266.
Hynes, et al., "The biology of erbB-2/nue/HER-2 and its role in cancer", Biochimica et Biophysica Acta (BBA)—Reviews on Cancer, Dec. 30, 1994, 1198(2-3):165-184.
Idusogie, et al., "Engineered Antibodies with Increased Activity to Recruit Complement", Journal of Immunology, 2001, 166:2571-2575.
Idusogie, et al., "Mapping of the C1q Binding Site on Rituxan, A Chimeric Antibody with A Human IgG1 Fc", Journal of Immunology, 2000, 164:4178-4184.
Intlekofer, et al., "At the Bench: Preclinical rationale for CTLA-4 and PD-1 blockade as cancer immunotherapy", Journal of Leukocyte Biology, Apr. 2013, 94(1):25-39.
Ishida, et al., "Induced Expression of PD-1, a Novel Member of the Immunoglobulin Gene Superfamily, Upon Programmed Cell Death", The EMBO Journal, 1992, 11(11):3887-3895.
Israeli, et al., "Molecular cloning of a complementary DNA encoding a prostate-specific membrane antigen", Cancer Research, Jan. 1993, 53(2):227-230.
Ito, et al., "Effective Priming of Cytotoxic T Lymphocyte Precursors by Subcutaneous Administration of Peptide Antigens in Liposomes Accompanied by Anti-CD40 and Anti-CTLA-4 Antibodies", Immunobiology, 2000, 201:527-540.
Iwai, et al., "Involvement of PD-L1 on tumor cells in the escape from host immune system and tumor immunotherapy by PD-L1 blockade", Proc Natl Acad Sci U S A., Sep. 2002, 99(19):12293-12297.
Jamieson, et al., "The Role of the NKG2D Immunoreceptor in Immune Cell Activation and Natural Killing", Immunity, Jul. 2002, 17(1):19-29.
Jefferis, et al., "Interaction Sites on Human IgG-Fc for FcgammaR: Current Models", Immunology Letters, 2002, 82:57-65.
Jefferis, et al., "Modulation of Fc(Gamma)R and Human Complement Activation by IgG3-Core Oligosaccharide Interactions", Immunology Letters, 1996, 54:101-104.
Jefferis, et al., "Recognition Sites on Human IgG for Fc Gamma Receptors: The Role of Glycosylation", Immunology Letters, 1995, 44:111-117.
Jennings, Veronica M., "Review of Selected Adjuvants Used in Antibody Production", ILAR Journal, 1995, 37(3):119-125.
Johansson, et al., "Structure, Specificity, and Mode of Interaction for Bacterial Albumin-binding Modules", Journal of Biological Chemistry, 2002, 277(10):8114-8120.

Johnson, et al., "Effector Cell Recruitment with Novel Fv-Based Dual-Affinity Re-Targeting Protein Leads to Potent Tumor Cytolysis and in vivo B-Cell Depletion", Journal of Molecular Biology, 2010, 399(3):436-449.
Joliot, et al., "Antennapedia Homeobox Peptide Regulates Neural Morphogenesis", Proceedings of the National Academy of Sciences, 1991, 88:1864-1868.
Jones, et al., "Replacing the Complementarity-Determining Regions in a Human Antibody with Those From a Mouse", Nature, 1986, 321:522-525.
Junttila, T.T., et al., "Antitumor efficacy of a bispecific antibody that targets HER2 and activates T cells", Cancer Research, Oct. 2014, 74(19):5561-5571.
Jurcic, Joseph G., "Immunotherapy for Acute Myeloid Leukemia", Current Oncology Reports, 2005, 7:339-346.
Kanai, et al., "Blockade of B7-H1 suppresses the development of chronic intestinal inflammation", The Journal of Immunology, Oct. 15, 2003, 171(8):4156-4163.
Kasaian, et al., "IL-13 antibodies influence IL-13 clearance in humans by modulating scavenger activity of IL-13Rα2", The Journal of Immunology, Jul. 1, 2011, 187(1):561-569.
Kawai, et al., "Interferonα enhances CD317 expression and the antitumor activity of anti-CD317 monoclonal antibody in renal cell carcinoma xenograft models", Cancer Science, Dec. 2008, 99(12):2461-2466.
Kearney, et al., "Antigen-Dependent Clonal Expansion of a Trace Population of Antigen-Specific CD4+ T Cells in vivo is Dependent on CD28 Costimulation and Inhibited by CTLA-4", Journal of Immunology, 1995, 155:1032-1036.
Kettleborough, et al., "Humanization of a Mouse Monoclonal Antibody by CDR-Grafting: The Importance of Framework Residues on Loop Conformation", Protein Engineering, 1991, 4(7):773-783.
Khawli, et al., "Cytokine, Chemokine, and Co-Stimulatory Fusion Proteins for the Immunotherapy of Solid Tumors", Handbook of Experimental Pharmacology, 2008, 181:291-328.
Kohler, et al., "Continuous Cultures of Fused Cells Secreting Antibody of Predefined Specificity", Nature, 1975, 256:495-497.
Korman, et al., "Checkpoint Blockade in Cancer Immunotherapy", Advances in Immunology, 2007, 90:297-339.
Kounalakis, et al., "Tumor Cell and Circulating Markers in Melanoma: Diagnosis, Prognosis, and Management", Current Oncology Reports, 2005, 7(5):377-382.
Kreitman, "Immunotoxins for Targeted Cancer Therapy", The AAPS Journal, 2006, 8(3):E532-E551.
Kruisbeek, et al., "Proliferative Assays for T cell Function", Current Protocols in Immunology, 2004, 60:3.12.1-3.12.20.
Krupka, C, et al., "PD-1/PD-L1 Blocking Enhances CD33/CD3-Bispecific BiTE® Antibody (AMG 330) Mediated Lysis of Primary AML Cells", Blood, Dec. 4, 2014, 124(21):3738.
Ku, et al., "Single-Institution Experience with Ipilimumab in Advanced Melanoma Patients in the Compassionate Use Setting: Lymphocyte Count After 2 Doses Correlates With Survival", Cancer, Apr. 2010, 116(7):1767-1775.
Kuhns, et al., "Deconstructing the Form and Function of the TCR/CD3 Complex", Immunity, Feb. 2006, 24(2):133-139.
Kumar, et al., "Human Papilloma Virus in Oral Cavity Cancer and Relation to Change in Quality of Life Following Treatment—a Pilot Study from Northern India", Indian Journal of Surgical Oncology, 2006, 7(4):386-391.
Kuo, et al., "Engineering a CD123xCD3 bispecific scFv immunofusion for the treatment of leukemia and elimination of leukemia stem cells", Protein Engineering, Design and Selection, Oct. 2012, 25(10):561-569.
Kurrle, et al., "BMA 031—A TCR-Specific Monoclonal Antibody for Clinical Application", Transplantation Proceedings, 1989, 21(1 Pt 1):1017-1019.
Kwong, et al., "Generation, Affinity Maturation, and Characterization of a Human Anti-Human NKG2D Monoclonal Antibody with Dual Antagonistic and Agonistic Activity", Journal of Molecular Biology, Dec. 2008, 384(5):1143-1156.
La Motte-Mohs, et al., "MGD013, a Bispecific PD-1 x LAG-3 Dual-Affinity Re-Targeting (DART®) Protein with T-cell

(56) References Cited

OTHER PUBLICATIONS

Immunomodulatory Activity for Cancer Treatment", American Association for Cancer Research Annual Meeting (AACR), Apr. 16-20, 2016.
Langer, Robert, "New Methods of Drug Delivery", Science, 1990, 249:1527-1533.
Latchman, et al., "PD-L2 is a Second Ligand for PD-1 and Inhibits T-Cell Activation", Nature Immunology, 2001, 2:261-268.
Leach, et al., "Enhancement of Antitumor Immunity by CTLA-4 Blockade", Science, 1996, 271(5256):1734-1736.
Leahy, D. J., "A Structural View of CD4 and CD8", The FASEB Journal, Jan. 1995, 9(1):17-25.
Lee, et al., "Requirement for neuregulin receptor erbB2 in neural and cardiac development", Nature, Nov. 1995, 378:394-398.
Lee, et al., "Targeting Cyclins and Cyclin-Dependent Kinases in Cancer: Lessons from Mice, Hopes for Therapeutic Applications in Humans", Cell Cycle, 2006, 5(18):2110-2114.
Lefranc, et al., "Gm, Am and Km immunoglobulin allotypes of two populations in Tunisia", Human Genetics, 1979, 50:199-211.
Lefranc, et al., "The Human IgG Subclasses: Molecular Analysis of Structure, Function and Regulation", Pergamon, Oxford, 1990, 43-78.
Lenschow, et al., "CD28/B7 System of T Cell Costimulation", Ann. Rev. Immunol., 1996, 14:233-258.
Lepenies, et al., "The Role of Negative Costimulators During Parasitic Infections", Endocrine, Metabolic & Immune Disorders—Drug Targets, 2008, 8:279-288.
Levitsky, et al., "The Human 'Treg MLR': Immune Monitoring for Foxp3+ T Regulatory Cell Generation", Transplantation, Dec. 15, 2009, 88(11):1303-1311.
Levy, et al., "Inhibition of Calcification of Bioprosthetic Heart Valves by Local Controlled-Release Diphosphonate", Science, 1985, 228(4696):190-192.
Lewis-Wambi, et al., "Overexpression of CEACAM6 promotes migration and invasion of oestrogen-deprived breast cancer cells", European Journal of Cancer, Aug. 2008, 44(12):1770-1779.
Lindley, et al., "The Clinical Utility of Inhibiting CD28-Mediated Costimulation", Immunological Reviews, 2009, 229:307-321.
Linsley, et al., "Intracellular Trafficking of CTLA4 and Focal Localization Towards Sites of TCR Engagement", Immunity, Jun. 1996, 4:535-543.
Litowski, et al., "Designing Heterodimeric Two-Stranded Alpha-Helical Coiled-Coils. Effects of Hydrophobicity and Alpha-Helical Propensity on Protein Folding, Stability, and Specificity", Journal of Biological Chemistry, Oct. 4, 2002, 277(40):37272-37279.
Liu, et al., "B7DC/PDL2 Promotes Tumor Immunity by a PD-1-independent Mechanism", Journal of Experimental Medicine, Jun. 16, 2003, 197(12):1721-1730.
Liu, et al., "Bevacizumab in combination with anticancer drugs for previously treated advanced non-small cell lung cancer", Tumor Biology, Mar. 2015, 36(3):1323-1327.
Livingston, et al., "Improved survival in stage III melanoma patients with GM2 antibodies: a randomized trial of adjuvant vaccination with GM2 ganglioside", Journal of Clinical Oncology, May 1994, 12(5):1036-1044.
Livingston, et al., "Selection of GM2, Fucosyl GM1, Globo H and Polysialic Acid as Targets on Small Cell Lung Cancers for Antibody Mediated Immunotherapy", Cancer Immunology Immunotherapy, 2005, 54(10):1018-1025.
Lobuglio, et al., "Mouse-Human Chimeric Monoclonal Antibody in Man: Kinetics and Immune Response", Proc. Natl. Acad. Sci. (U.S.A.), Jun. 1989, 86:4220-4224.
Loke, et al., "Emerging Mechanisms of Immune Regulation: The Extended B7 Family and Regulatory T Cells", Arthritis Res. Ther., 2004, 6:208-214.
Loke, et al., "PD-L1 and PD-L2 are differentially regulated by Th1 and Th2 cells", Proc Natl Acad Sci U S A. 2003, Apr. 29, 2003, 100(9):5336-5341.
Lonberg, et al., "Human Antibodies from Transgenic Mice", International Reviews of Immunology, 1995, 13:65-93.
Loo, et al., "Development of an Fc-Enhanced Anti-B7-H3 Monoclonal Antibody with Potent Antitumor Activity", Clinical Cancer Research, 2012, 18(14):3834-3845.
Lotem, et al., "Presentation of Tumor Antigens by Dendritic Cells Genetically Modified with Viral and Nonviral Vectors", Journal of Immunotherapy, 2006, 29(6):616-627.
Lu, et al., "A Fully Human Recombinant IgG-Like Bispecific Antibody to Both the Epidermal Growth Factor Receptor and the Insulin-Like Growth Factor Receptor for Enhanced Antitumor Activity", Journal of Biological Chemistry, 2005, 280(20):19665-19672.
Lu, et al., "Structural mechanism of high affinity FcγRI recognition of immunoglobulin G", Immunological Review, Nov. 2015, 268(1):192-200.
Lu, et al., "The Effect of a Point Mutation on the Stability of IgG4 as Monitored by Analytical Ultracentrifugation", Journal of Pharmaceutical Sciences, Feb. 2008, 97(2):960-969.
Luheshi, N.M., et al., "Transformation of the tumour microenvironment by a CD40 agonist antibody correlates with improved responses to PD-L1 blockade in a mouse orthotopic pancreatic tumour model", Oncotarget, Feb. 23, 2016, 7(14):18508-18520.
Lund, et al., "Human Fc Gamma RI and Fc Gamma RII Interact with Distinct but Overlapping Sites on Human IgG", Journal of Immunology, 1991, 147:2657-2662.
Lund, et al., "Multiple Binding Sites on the CH2 Domain of IgG for Mouse Fc Gamma R11", Molecular Immunology, 1992, 29:53-59.
Lund, et al., "Multiple Interactions of IgG with Its Core Oligosaccharide Can Modulate Recognition by Complement and Human Fc Gamma Receptor I and Influence the Synthesis of Its Oligosaccharide Chains", Journal of Immunology, 1996, 157:4963-4969.
Lund, et al., "Oligosaccharide-Protein Interactions in IgG Can Modulate Recognition by Fc Gamma Receptors", The FASEB Journal, 1995, 9:115-119.
Mace, et al., "Cell Biological Steps and Checkpoints in Accessing NK Cell Cytotoxicity", Immunology & Cell Biology, Mar. 2014, 92(3):245-255.
MACROGENICS, "MacroGenics Highlights Progress at 2015 R&D Day", Document available at http://ir.macrogenics.com/static-files/80b32764-457e-4595-9294-a2a426316203, Oct. 13, 2015, 3 Pages.
Maeda, et al., "Construction of Reshaped Human Antibodies With HIV-Neutralizing Activity", Human Antibodies Hybridoma, 1991, 2:124-134.
Magistrelli, G., et al., "A Soluble form of CTLA-4 Generated by Alternative Splicing is Expressed by Nonstimulated Human T Cells", European Journal of Immunology, 1999, 29:3596-3602.
Mallone, et al., "Targeting T lymphocytes for immune monitoring and intervention in autoimmune diabetes", American Journal of Therapeutics, 2005, 12(6):534-550.
Mardiros, et al., "T cells expressing CD123-specific chimeric antigen receptors exhibit specific cytolytic effector functions and antitumor effects against human acute myeloid leukemia", Blood, Oct. 2013, 122(18):3138-3148.
Martin-Orozco, et al., "Inhibitory Costimulation and Anti-Tumor Immunity", Seminars in Cancer Biology, 2007, 17(4):288-298.
Marvin, et al., "Recombinant Approaches to IgG-Like Bispecific Antibodies", Acta Pharmacologica Sinica, 2005, 26:649-658.
Mathelin, et al., "Circulating Proteinic Biomarkers and Breast Cancer", Gynecol Obstet Fertil, 2006, 34(7-8):638-646.
Mazanet, et al., "B7-H1 Is Expressed by Human Endothelial Cells and Suppresses T-Cell Cytokine Synthesis", Journal of Immunology, 2002, 169:3581-3588.
McDermott, et al., "Atezolizumab, an Anti-Programmed Death-Ligand 1 Antibody, in Metastatic Renal Cell Carcinoma: Long-Term Safety, Clinical Activity, and Immune Correlates from a Phase Ia Study", Journal of Clinical Oncology, Mar. 10, 2016, 34(8):833-842.
Melero, et al., "Evolving synergistic combinations of targeted immunotherapies to combat cancer", Nature Reviews Cancer, Aug. 2015, 15:457-472.
Melero, et al., "Monoclonal Antibodies Against the 4-1BB T-Cell Activation Molecule Eradicate Established Tumors", Nature Medicine, 1997, 3(6):682-685.
Mellman, et al., "Cancer Immunotherapy Comes of Age", Nature, 2011, 480(7378):480-489.

(56) References Cited

OTHER PUBLICATIONS

Merrifield, et al., "Solid Phase Synthesis", Science, 1986, 232(4748):341-347.
Messmer, et al., "CD154 Gene Therapy for Human B-Cell Malignancies", Annals of the New York Academy of Sciences, 2005, 1062:51-60.
Miao, et al., "EphA2 is a Mediator of Vemurafenib Resistance and a Novel Therapeutic Target in Melanoma", Cancer Discovery, Mar. 2015, 5(3):274-287.
Midgley, et al., "Bevacizumab-current status and future directions", Annals of Oncology, Jul. 2005, 16(7):999-1004.
Miller, Jeffrey S., "Therapeutic applications: Natural killer cells in the clinic", Hematology, Dec. 2013, 2013(1):247-253.
Mittelman, et al., "Active Specific Immunotherapy in Patients with Melanoma. A Clinical Trial with Mouse Antiidiotypic Monoclonal Antibodies Elicited with Syngeneic Anti-High-Molecular-Weight-Melanoma-Associated Antigen Monoclonal Antibodies", Journal of Clinical Investigation, 1990, 86(6):2136-2144.
Mokyr, et al., "Realization of the Therapeutic Potential of CTLA-4 Blockade in Low-Dose Chemotherapy-treated Tumor-bearing Mice", Cancer Research, Dec. 1998, 58:5301-5304.
Moller, et al., "Bispecific-Monoclonal-Antibody-Directed Lysis of Ovarian Carcinoma Cells by Activated Human T Lymphocytes", Cancer Immunology, Immunotherapy, 1991, 33(4):210-216.
Moore, et al., "Application of Dual Affinity Retargeting Molecules to Achieve Optimal Redirected T-Cell Killing of B-Cell Lymphoma", Blood, 2011, 117(17):4542-4551.
Moore, P., "DART Molecules for Immunomodulatory Therapeutic Strategies", 8th GTC Immunotherapeutics and Immunomonitoring Conference, Jan. 25, 2016, 38 pages.
Moran, et al., "The TNFRs OX40, 4-1BB, and CD40 As Targets for Cancer Immunotherapy", Current Opinion in Immunology, Apr. 2013, 25(2):12 Pages.
Munoz, et al., "Interleukin-3 receptor alpha chain (CD123) is widely expressed in hematologic malignancies", Haematologica, Dec. 2001, 86(12):1261-1269.
Narita, Yoshitaka, "Bevacizumab for glioblastoma", Therapeutics and Clinical Risk Management, 2015, 11:1759-1765.
Nashan, et al., "Fine Specificity of a Panel of Antibodies Against the TCR/CD3 Complex", Transplantation Proceedings, Oct. 1987, 19(5):4270-4272.
Natali, et al., "Immunohistochemical Detection of Antigen in Human Primary and Metastatic Melanomas by the Monoclonal Antibody 140.240 and its possible Prognostic Significance", Cancer, 1987, 59(1):55-63.
Ning, et al., "Intratumoral Radioimmunotherapy of a Human Colon Cancer Xenograft Using a Sustained Release Gel", Radiotherapy & Oncology, May 1996, 39(2):179-189.
Nishimura, et al., "Facilitation of Beta Selection and Modification of Positive Selection in the Thymus of PD-1-Deficient Mice", Journal of Experimental Medicine, Mar. 6, 2000, 191:891-898.
Norman, Douglas J., "Mechanisms of Action and Overview of OKT3", Therapeutic Drug Monitoring, Dec. 1995, 17(6):615-620.
Oaks, M.K., et al., "A Native Soluble Form of CTLA-4", Cellular Immunology, 2000, 201:144-153.
O'Dwyer, P., "The Present and Future of Angiogenesis-Directed Treatments of Colorectal Cancer", Oncologist, 2006, 11(9):992-998.
Ohigashi, et al., "Clinical Significance of Programmed Death-1 Ligand-1 and Programmed Death-1 Ligand-2 Expression in Human Esophageal Cancer", Clinical Cancer Research, Apr. 2005, 11(8):2947-2953.
Olafsen, et al., "Covalent Disulfide-Linked Anti-CEA Diabody Allows Site-Specific Conjugation and Radiolabeling for Tumor Targeting Applications", Protein Engineering, Design and Selection, 2004, 17(1):21-27.
Osada, T, et al., "CEA/CD3-bispecific T cell-engaging (BiTE) antibody-mediated T lymphocyte cytotoxicity maximized by inhibition of both PD1 and PD-L1", Cancer Immunology, Immunotherapy, Mar. 6, 2015, 64(6):677-688.
Pal, et al., "Targeting HER2 Epitopes", Seminars in Oncology, Aug. 2006, 33(4):386-391.
Palena, et al., "Cancer Vaccines: Preclinical Studies and Novel Strategies", Advances in Cancer Research, 2006, 95:115-145.
Peeters, et al., "Production of Antibodies and Antibody Fragments in Plants", Vaccine, 2001, 19:2756-2761.
Peggs, et al., "Principles and Use of Anti-CTLA4 Antibody in Human Cancer Immunotherapy", Current Opinion in Immunology, 2006, 18(2):206-213.
Peipp, et al., "Bispecific Antibodies Targeting Cancer Cells", Biochemical Society Transactions, 2002, 30(4):507-511.
Peltz, et al., "Human FcγRIII: Cloning, expression, and identification of the chromosomal locus of two Fc receptors for IgG", Proc. Natl. Acad. Sci. (U.S.A.), Feb. 1989, 86(3):1013-1017.
Perez, et al., "Isolation and Characterization of a Cdna Encoding the KS1/4 Epithelial Carcinoma Marker", Journal of Immunology, 1989, 142(10):3662-3667.
Peters, et al., "Engineering an Improved IgG4 Molecule with Reduced Disulfide Bond Heterogeneity and Increased Fab Domain Thermal Stability", Journal of Biological Chemistry, Jul. 13, 2012, 287(29):24525-24533.
Petroff, et al., "B7 Family Molecules: Novel Immunomodulators At the Maternal-Fetal Interface", Placenta, 2002, 23:S95-S101.
Pietrantonio, et al., "Bevacizumab-based neoadjuvant chemotherapy for colorectal cancer liver metastases: Pitfalls and helpful tricks in a review for clinicians", Critical Reviews in Oncology/Hematology, Sep. 2015, 95(3):272-281.
Pizzitola, et al., "Chimeric Antigen Receptors Against CD33/CD123 Antigens Efficiently Target Primary Acute Myeloid Leukemia Cells in vivo", Leukemia, Aug. 2014, 28(8):1596-605.
Pollock, et al., "Transgenic Milk as a Method for the Production of Recombinant Antibodies", Journal of Immunological Methods, 1999, 231:147-157.
Portoles, et al., "The TCR/CD3 Complex: Opening the Gate to Successful Vaccination", Current Pharmaceutical Design, 2009, 15(28):3290-3300.
Prange, et al., "Beta-Catenin Accumulation in the Progression of Human Hepatocarcinogenesis Correlates with loss of E-Cadherin and Accumulation of P53, but not with Expression of Conventional WNT-1 Target Genes", The Journal of Pathology, 2003, 201(2):250-259.
Prasad, et al., "Murine B7-H3 Is a Negative Regulator of T Cells", The Journal of Immunology, 2004, 173:2500-2506.
Presta, et al., "Engineering Therapeutic Antibodies for Improved Function", Biochemical Society Transactions, 2002, 30(4):487-490.
Radhakrishnan, et al., "Immunotherapeutic potential of B7-DC (PD-L2) cross-linking antibody in conferring antitumor immunity", Cancer Research, Jul. 15, 2004, 64(14):4965-4972.
Ragnhammar, et al., "Effect of monoclonal antibody 17-1A and gm-CSF in patients with advanced colorectal carcinoma-long-lasting, complete remissions can be induced", International Journal of Cancer, Mar. 1993, 53(5):751-758.
Ragupathi, et al., "Antibody Inducing Polyvalent Cancer Vaccines", Cancer Treatment and Research, Feb. 2005, 123:157-180.
Raulet, David H., "Roles of the NKG2D Immunoreceptor and Its Ligands", Nature Reviews Immunology, Oct. 2003, 3:781-790.
Reddy, et al., "Elimination of Fc Receptor-Dependent Effector Functions of a Modified IgG4 Monoclonal Antibody to Human CD4", Journal of Immunology, 2000, 164:1925-1933.
Reff, et al., "Depletion of B Cells in vivo by a Chimeric Mouse Human Monoclonal Antibody to CD20", Blood, 1994, 83:435-445.
Renders, et al., "Engineered CD3 Antibodies for Immunosuppression", Clinical & Experimental Immunology, 2003, 133(3):307-309.
Ribas, et al., "Antitumor Activity in Melanoma and Anti-Self Responses in a Phase I Trial with the Anti-Cytotoxic T Lymphocyte-Associated Antigen 4 Monoclonal Antibody CP-675,206", Journal of Clinical Oncology, 2005, 23(35):8968-8977.
Ridgway, et al., "'Knobs-Into-Holes' Engineering of Antibody CH3 Domains for Heavy Chain Heterodimerization", Protein engineering, 1996, 9(7):617-621.
Riechmann, et al., "Reshaping Human Antibodies for Therapy", Nature, 1988, 332:323-327.

(56) References Cited

OTHER PUBLICATIONS

Riley, et al., "Design and Activity of a Murine and Humanized anti-CEACAM6 scFv in the Treatment of Pancreatic Cancer", Cancer research, Mar. 2009, 69(5):1933-1940.

Rimon, et al., "Gonadotropin-Induced Gene Regulation in Human Granulosa Cells Obtained from IVF Patients: Modulation of Genes Coding for Growth Factors and their Receptors and Genes Involved in Cancer and other Diseases", International Journal of Oncology, 2004, 24(5):1325-1338.

Ritprajak, et al., "Antibodies against B7-DC with differential binding properties exert opposite effects", Hybridoma (Larchmt), Feb. 2012, 31(1):40-47.

Ritter, et al., "Characterization of Posttranslational Modifications of Human A33 Antigen, a Novel Palmitoylated Surface Glycoprotein of Human Gastrointestinal Epithelium", Biochemical and Biophysical Research Communications, Jul. 30, 1997, 236(3):682-686.

Rosati, et al., "Chronic Lymphocytic Leukaemia: A Review of the Immuno-Architecture", Current Topics in Microbiology and Immunology, 2005, 294:91-107.

Rouard, et al., "Fc Receptors as Targets for Immunotherapy", International Reviews of Immunology, 1997, 16(1-2):147-185.

Rudd, et al., "Unifying Concepts in CD28, ICOS and CTLA4 Co-Receptor Signalling", Nature Reviews Immunology, Jul. 2003, 3:544-556.

Saleh, et al., "Generation of a human anti-idiotypic antibody that mimics the GD2 antigen", The Journal of Immunology, Sep. 15, 1993, 151(6):3390-3398.

Sato, et al., "Reshaping a Human Antibody to Inhibit the Interleukin 6-dependent Tumor Cell Growth", Cancer Research, 1993, 53:851-856.

Saudek, et al., "A Preliminary Trial of the Programmable Implantable Medication System for Insulin Delivery", The New England Journal of Medicine, 1989, 321:574-579.

Sayeed, et al., "Aberrant Regulation of the BST2 (Tetherin) Promoter Enhances Cell Proliferation and Apoptosis Evasion in High Grade Breast Cancer Cells", PLoS ONE, Jun. 2013, 8(6):e67191, 10 pages.

Schwartz, J.C., et al., "Structural Basis for Co-Stimulation by the Human CTLA-4-B7-2 Complex", Nature, Mar. 2001, 410:604-608.

Sefton, et al., "Implantable Pumps", Critical Reviews in Biomedical Engineering, 1980, 14:201-240. (Abstract of article provided).

Selvaraj, et al., "Functional Regulation of Human Neutrophil Fc Gamma Receptors", Immunologic Research, 2004, 29(1-3):219-230.

Sgouros, et al., "Modeling and dosimetry of monoclonal antibody M195 (anti-CD33) in acute myelogenous leukemia", Journal of Nuclear Medicine, Mar. 1993, 34(3):422-430.

Sharpe, A.H., et al., "The B7-CD28 Superfamily", Nature Reviews Immunology, 2002, 2:116-126.

Shaw, et al., "Characterization of a Mouse-Human Chimeric Monoclonal Antibody (17-1A) to a Colon Cancer Tumor-Associated Antigen", Journal of Immunology, 1987, 138(12):4534-4538.

Shearman, et al., "Construction, expression and characterization of humanized antibodies directed against the human α/β T cell receptor", The Journal of Immunology, Dec. 1991, 147(12):4366-4373.

Shearman, et al., "Construction, expression, and biologic activity of murine/human chimeric antibodies with specificity for the human α/β T cell receptor", The Journal of Immunology, Feb. 1991, 146(3):928-935.

Shen, et al., "GP41-specific Antibody Blocks Cell-free HIV-1 Transcytosis through Human Rectal Mucosa and Model Colonic Epithelium", Journal of Immunology, Apr. 2010, 184(7):3648-3655.

Shields, et al., "High Resolution Mapping of the Binding Site on Human Igg1 for Fc Gamma RI, Fc Gamma RII, Fc Gamma RIII, and Fcrn and Design of Igg1 Variants with Improved Binding to the Fc Gamma R", Journal of Biological Chemistry, 2001, 276:6591-6604.

Shipkova, et al., "Surface Markers of Lymphocyte Activation and Markers of Cell Proliferation", Clinica Chimica Acta, 2012, 413:1338-1349.

Shitara, et al., "A mouse/human chimeric anti-(ganglioside GD3) antibody with enhanced antitumor activities", Cancer Immunology, Immunotherapy, Nov. 1993, 36:373-380.

Shopes, Bob, "A Genetically Engineered Human IgG Mutant with Enhanced Cytolytic Activity", J. Immunol., 1992, 148:2918-2922.

Shultz, et al., "Humanized Mice for Immune System Investigation: Progress, Promise and Challenges", Nature Reviews Immunology, 2012, 12(11):786-798.

Sloan, et al., "Targeting HIV Reservoir in Infected CD4 T Cells by Dual-Affinity Retargeting Molecules (DARTs) that Bind HIV Envelope and Recruit Cytotoxic T Cells", PLOS Pathogens, 2015, 11(11):e1005233.

Smith-Garvin, et al., "T Cell Activation", Annual Review of Immunology, 2009, 27:591-619.

Song, et al., "Antibody Mediated Lung Targeting of Long-Circulating Emulsions", PDA Journal of Pharmaceutical Science & Technology, 1996, 50(6):372-377.

St. Clair, E William., "Novel Targeted Therapies for Autoimmunity", Current Opinion in Immunology, Dec. 2009, 21(6):648-657.

Staerz, et al., "Hybrid Antibodies Can Target Sites for Attack by T Cells", Nature, 1985, 314:628-631.

Stavenhagen, et al., "Fc Optimization of Therapeutic Antibodies Enhances Their Ability to Kill Tumor Cells in Vitro and Controls Tumor Expansion in Vivo Via Low-Affinity Activating Fcgamma Receptors", Cancer Research, 2007, 67(18):8882-8890.

Steinkruger, et al., "The d'—d—d' Vertical Triad is Less Discriminating Than the a'—a—a' Vertical Triad in the Antiparallel Coiled-coil Dimer Motif", Journal of the American Chemical Society, Feb. 2012, 134(5):2626-2633.

Stephan, et al., "Selective Cloning of Cell Surface Proteins Involved in Organ Development: Epithelial Glycoprotein Is Involved in Normal Epithelial Differentiation", Endocrinolgy, 1999, 140:5841-5854.

Stevenson, et al., "A Chimeric Antibody with Dual Fc Regions (bisFabFc) Prepared by Manipulations at the IgG Hinge", Anti-Cancer Drug Design, 1989, 3(4):219-230. (Abstract of article provided).

Stomski, et al., "Human interleukin-3 (IL-3) induces disulfide-linked IL-3 receptor alpha-and beta-chain heterodimerization, which is required for receptor activation but not high-affinity binding", Molecular and Cellular Biology, Jun. 1996, 16(6):3035-3046.

Stopforth, et al., "Regulation of Monoclonal Antibody Immunotherapy by FcγRIIB", Journal of Clinical Immunology, Feb. 27, 2016, 36(Suppl 1):S88-S94.

Straussman, et al., "Kinking the Coiled Coil—Negatively Charged Residues at the Coiled-coil Interface", Journal of Molecular Biology, 2007, 366(4):1232-1242.

Subudhi, et al., "The Balance of Immune Responses: Costimulation Verse Coinhibition", Journal of Molecular Medicine, 2005, 83:193-202.

Suh, et al., "Major clinical research advances in gynecologic cancer in 2014", Journal of Gynecological Oncology, Apr. 2015, 26(2):156-167.

Sun, et al., "Characterization of Mouse and Human B7-H3 Genes", Journal of Immunology, 2002, 168:6294-6297.

Sun, et al., "Mechanisms Contributing to T Cell Receptor Signaling and Assembly Revealed by the Solution Structure of an Ectodomain Fragment of the CD3ε:γ Heterodimer", Cell, Jun. 29, 2001, 105(7):913-923.

Suresh, et al., "New antibody approaches to lymphoma therapy", Journal of Hematology & Oncology, Sep. 9, 2014, 7:58.

Swinnen, et al., "OKT3 monoclonal antibodies induce interleukin-6 and interleukin-10: a possible cause of lymphoproliferative disorders associated with transplantation", Current Opinion in Nephrology and Hypertension, Jul. 1993, 2(4):670-678.

Swisher, et al., "The Many Faces of FcγRI: Implications for Therapeutic Antibody Function", Immunological Review, Nov. 2015, 268(1):160-174.

Tai, et al., "Potent in vitro and in vivo Activity of an Fc-Engineered Humanized Anti-HM1.24 Antibody Against Multiple Myeloma via Augmented Effector Function", Blood, 2012, 119(9):2074-2082.

(56) References Cited

OTHER PUBLICATIONS

Tailor, et al., "Nucleotide Sequence of Human Prostatic Acid Phosphatase Determined from a Full-Length CDNA Clone", Nucleic Acids Research, 1990, 18(16):4928.
Takemura, et al., "Construction of a Diabody (Small Recombinant Bispecific Antibody) Using a Refolding System", Protein Engineering, 2000, 13(8):583-588.
Tedder, "CD19: a promising B cell target for rheumatoid arthritis", Nature Reviews Rheumatology, Oct. 2009, 5(10):572-577.
Tellez-Avila, et al., "The carcinoembryonic antigen: apropos of an old friend", Rev Invest Clin., Nov. 2005, 57(6):814-819. (Abstract of article provided).
Tempest, et al., "Reshaping a Human Monoclonal Antibody to Inhibit Human Respiratory Syncytial Virus Infection in Vivo", Bio-Technology, 1991, 9:266-271.
Tettamanti, et al., "Targeting of acute myeloid leukaemia by cytokine-induced killer cells redirected with a novel CD123-specific chimeric antigen receptor", British Journal of Haematology, May 2013, 161(3):389-401.
Thepen, et al., "Fcγ Receptor 1 (CD64), a Target Beyond Cancer", Current Pharmaceutical Design, Aug. 2009, 15(23):2712-2718.
Thomas, et al., "Molecular Immunology Lessons from Therapeutic T-Cell Receptor Gene Transfer", Immunology, 2010, 129(2):170-177.
Thomas, et al., "Monoclonal Antibody Therapy for Hairy Cell Leukemia", Hematology/Oncology Clinics of North America, Oct. 2006, 20(5):1125-1136.
Thompson, et al., "Carcinoembryonic antigen gene family: Molecular biology and clinical perspectives", Journal of Clinical Laboratory Analysis, 1991, 5(5):344-366.
Topalian, S.L., et al., "Immune Checkpoint Blockade: A Common Denominator Approach to Cancer Therapy", Cancer Cell, Apr. 13, 2015, 27:450-461.
Topalian, et al., "Safety, Activity, and Immune Correlates of Anti-PD-1 Antibody in Cancer", The New England Journal of Medicine, 2012, 366(26):2443-2454.
Trauth, et al., "Monoclonal antibody-mediated tumor regression by induction of apoptosis", Science, Jul. 21, 1989, 245(4915):301-305.
Tripet, et al., "Kinetic Analysis of the Interactions between Troponin C and the C-terminal Troponin I Regulatory Region and Validation of a New Peptide Delivery/Capture System used for Surface Plasmon Resonance", Journal of Molecular Biology, 2002, 323(2):345-362.
Troussard, et al., "Hairy Cell Leukemia. What is New Forty Years after the First Description?", Hematology and Cell Therapy, 1998, 40(4):139-148. (Abstract of article provided).
Tsai, et al., "PD-I and PD-LI Antibodies for Melanoma", Human Vaccines & Immunotherapeutics, Nov. 2014, 10(11):3111-3116.
Tseng, et al., "B7-DC, a new dendritic cell molecule with potent costimulatory properties for T cells", Journal of Experimental Medicine, Apr. 2001, 193(7):839-846.
Tsushima, et al., "Preferential contribution of B7-H1 to programmed death-1-mediated regulation of hapten-specific allergic inflammatory responses", European Journal of Immunology, Oct. 2013, 33(10):2773-2782.
Turnis, "Combinatorial Immunotherapy PD-1 may not be LAG-ing behind any more", OncoImmunology, 2012, 1(7):1172-1174.
Van Der Merwe, et al., "Mechanisms for T cell receptor triggering", Nature Reviews Immunology, Dec. 2011, 11:47-55.
Van Sorge, et al., "FcγR polymorphisms: Implications for function, disease susceptibility and immunotherapy", Tissue Antigens, Mar. 2003, 61(3):189-202.
Verhoeyen, et al., "Reshaping Human Antibodies: Grafting an Antilysozyme Activity", Science, 1988, 239:1534-1536.
Veri, et al., "Therapeutic Control of B Cell Activation Via Recruitment of Fcgamma Receptor IIb (CD32B) Inhibitory Function with a Novel Bispecific Antibody Scaffold", Arthritis & Rheumatology, 2010, 62(7):1933-1943.
Vermeij, et al., "Potentiation of a p53-SLP Vaccine by Cyclophosphamide in Ovarian Cancer: A Single-Arm Phase II Study", International Journal of Cancer, 2012, 131(5):E670-680.

Viglietta, et al., "Modulating Co-Stimulation", Neurotherapeutics, 2007, 4:666-675.
Vijayasardahl, et al., "The Melanoma Antigen Gp75 is the Human Homologue of the Mouse B (Brown) Locus Gene Product", Journal of Experimental Medicine, 1990, 171(4):1375-1380.
Voena, et al., "Advances in cancer immunology and cancer immunotherapy", Discovery Medicine, Feb. 2016, 21(114):125-133.
Wallgren, et al., "The Direct Pathway of Human T-Cell Allorecognition is not Tolerized by Stimulation with Allogeneic Peripheral Blood Mononuclear Cells Irradiates with High-Dose Ultraviolet", Scandinavian Journal of Immunology, 2006, 63:90-96.
Walunas, et al., "CTLA-4 Can Function as a Negative Regulator of T Cell Activation", Immunity, 1994, 1:405-413.
Wang, et al., "Chimeric and humanized anti-HM1.24 antibodies mediate antibody-dependent cellular cytotoxicity against lung cancer cells", Lung Cancer, Jan. 2009, 63(1):23-31.
Wang, et al., "Co-Signaling Molecules of the B7-CD28 Family in Positive and Negative Regulation of T Lymphocyte Responses", Microbes and Infection, 2004, 6:759-766.
Wang, et al., "Expression of CTLA-4 by Human Monocytes", Scandinavian Journal of Immunology, 2002, 55:53-60.
Wang, et al., "HM1.24 (CD317) is a novel target against lung cancer for immunotherapy using anti-HM1.24 antibody", Cancer Immunology Immunotherapy, Jun. 2009, 58(6):967-976.
Wang, et al., "VISTA, a Novel Mouse Ig Superfamily Ligand that Negatively Regulates T Cell Responses", Journal of Experimental Medicine, 2011, 208(3):577-592.
Weinberg, et al., "Engagement of the OX-40 Receptor in Vivo Enhances Antitumor Immunity", Journal of Immunology, 2000, 164(4):2160-2169.
White, et al., "FcγRIIB as a key determinant of agonistic antibody efficacy", Current Topics in Microbiology and Immunology, 2014, 382:355-372. (Abstract of article provided).
Willemsen, et al., "Selection of human antibody fragments directed against tumor T-cell epitopes for adoptive T-cell therapy", Cytometry A., Nov. 2008, 73(11):1093-1099.
Winter, et al., "Making Antibodies by Phage Display Technology", Annual Review of Immunology, 1994, 12.433-455.
Winter, et al., "Man-made Antibodies", Nature, 1991, 349:293-299.
Wolff, et al., "Monoclonal Antibody Homodimers: Enhanced Antitumor Activity in Nude Mice", Cancer Research, 1993, 53:2560-2565.
Wong, et al., "EpCAM and gpA33 are markers of Barrett's metaplasia", Journal of Clinical Pathology, Mar. 2006, 59(3):260-263.
Woo, et al., "Immune Inhibitory Molecules LAG-3 and PD-1 Synergistically Regulate T Cell Function to Promote Tumoral Immune Escape", Cancer Research, 2012, 72(4):917-927.
Woolfson, et al., "The Design of Coiled-Coil Structures and Assemblies", Advances in Protein Chemistry, 2005, 70:79-112.
Wu, et al., "Multimerization of a Chimeric Anti-CD20 Single Chain Fv-Fv Fusion Protein Is Mediated Through Variable Domain Exchange", Protein Engineering, 2001, 14(12):1025-1033.
Wu, et al., "Receptor-Mediated in Vitro Gene Transformation by a Soluble DNA Carrier System", Journal of Biological Chemistry, 1987, 262(10):4429-4432.
Wucherpfennig, et al., "Structural Biology of the T-cell Receptor: Insights into Receptor Assembly, Ligand Recognition, and Initiation of Signaling", Cold Spring Harbor Perspectives in Biology, Apr. 2010, 2(4):14 pages.
Xie, et al., "A New Format of Bispecific Antibody: Highly Efficient Heterodimerization, Expression and Tumor Cell Lysis", Journal of Immunological Methods, 2005, 296:95-101.
Xu, et al., "High EphA2 protein expression in renal cell carcinoma is associated with a poor disease outcome", Oncology Letters, Aug. 2014, 8(2):687-692.
Xu, et al., "In Vitro Characterization of Five Humanized OKT3 Effector Function Variant Antibodies", Cellular Immunology, 2000, 200:16-26.
Yamazaki, et al., "Expression of Programmed Death 1 Ligands by Murine T-Cells and APC", The Journal of Immunology, 2002, 169:5538-5545.

(56) References Cited

OTHER PUBLICATIONS

Yazdi, et al., "A Comprehensive Review of Clinical Trials on EGFR Inhibitors Such as Cetuximab and Panitumumab as Monotherapy and in Combination for Treatment of Metastatic Colorectal Cancer", Avicenna Journal of Medical Biotechnology, 2015, 7(4):134-44.

Yi, et al., "Fine Tuning the Immune Response Through B7-H3 and B7-H4", Immunological reviews, 2009, 229:145-151.

Yokota, et al., "Rapid Tumor Penetration of a Single-Chain Fv and Comparison with Other Immunoglobulin Forms", Cancer Research, Jul. 1992, 52(12):3402-3408.

Youinou, et al., "Pathogenic effects of anti-Fc gamma receptor IIIb (CD16) on polymorphonuclear neutrophils in non-organ-specific autoimmune diseases", Autoimmunity Reviews, Feb. 2002, 1(1-2):13-19.

Youngnak, et al., "Differential binding properties of B7-H1 and B7-DC to programmed death-1", Biochemical and Biophysical Research Communications, Aug. 2003, 307(3):672-677.

Yu, et al., "Coexpression of different antigenic markers on moieties that bear CA 125 determinants", Cancer Research, Jan. 15, 1991, 51(2):468-475.

Zang, et al., "The B7 Family and Cancer Therapy: Costimulation and Coinhibition", Clinical Cancer Research, 2007, 13:5271-5279.

Zeng, et al., "A Ligand-Pseudoreceptor System Based on De Novo Designed Peptides for the Generation of Adenoviral Vectors with Altered Tropism", Journal of Gene Medicine, 2008, 10(4):355-367.

Zhang, et al., "The anti-tumor immune response induced by a combination of MAGE-3/MAGE-n-derived peptides", Oncology Reports, 2008, 20, 245-252.

Zheng, et al., "A Novel Anti-CEACAM5 Monoclonal Antibody, CC4, Suppresses Colorectal Tumor Growth and Enhances NK Cells-Mediated Tumor Immunity", Plos One, Jun. 2011, 6(6):11 pages.

Zhou, et al., "Lung Tumorigenesis Associated with Erb-B-2 and Erb-B-3 Overexpression in Human Erb-B-3 Transgenic Mice is Enhanced by Methylnitrosourea", Oncogene, 2002, 21(57):8732-8740.

Berezhnoy et al., "MGD019, a PD-1 x CTLA-4 Tetravalent Bispecific DART® Protein Provides Optimal Dual Checkpoint Blockade", Macrogenics, Sep. 2019, 1 page.

Brown et al., "Assessing the Binding Properties of the antiPD-1 Antibody Landscape Using Label-Free Biosensors", Mar. 5, 2020, PLOS One 15(3):e0229206, doi.org/10.1371/journal.pone.0229206, 21 pages.

Klooster, "Generation of Immuno-Modulatory Receptor Binding Bispecific Antibodies to Modulate Tumor Immunity", Database accession No. EMB-620749924, Nov. 1, 2016, 1 page.

Martin Andrew C.R., "Protein Sequence and Structure Analysis of Antibody Variable Domains", Antibody Engineering, 2010, 2(3):33-51.

Selby et al., "Preclinical Development of Ipilimumab and Nivolumab Combination Immunotherapy: Mouse Tumor Models, In Vitro Functional Studies, and Cynomolgus Macaque Toxicology", Sep. 9, 2016, PLOS One, 11(9):e0161779, doi.org/10.1371/journal.pone.0161779, 19 pages.

Zhao et al., "CD30/CD16A Tandab AFM13-Induced Target Cell Lysis by NK-Cells Is Enhanced by CD137 Co-Stimulation and Blocking PD-1", Blood, Dec. 3, 2015, 126(23):2747.

Johnson et al., "Antibodies Reactive with B7-H3 and Uses Thereof", GenBank: AJM49609.1, https://www.ncbi.nlm.nih.gov/protein/756698310, Feb. 12, 2015, 1 page.

Johnson et al., "Antibodies Reactive with B7-H3 and Uses Thereof", GenBank: AJM49613.1, https://www.ncbi.nlm.nih.gov/protein/756698314, Feb. 12, 2015, 1 page.

\* cited by examiner

BISPECIFIC MOLECULES HAVING IMMUNOREACTIVITY WITH PD-1 AND CTLA-4, AND METHODS OF USE THEREOF

CROSS-REFERENCE TO RELATED APPLICATIONS

This patent application is a 35 U.S.C. 371 national stage patent application of Patent Cooperation Treaty Patent Application No. PCT/US2016/066060 filed on Dec. 12, 2016, which claims the benefit of U.S. Patent Application No. 62/266,944 filed on Dec. 14, 2015. Each of the foregoing patent applications is incorporated herein by reference in its entirety.

REFERENCE TO SEQUENCE LISTING

This application includes one or more Sequence Listings pursuant to 37 C.F.R. 1.821 et seq., which are disclosed in computer-readable media (file name: 1301_0134PCT_ST25.txt, created on Dec. 4, 2016, and having a size of 186,040 bytes), which file is herein incorporated by reference in its entirety.

FIELD OF THE INVENTION

The present invention is directed to bispecific molecules (e.g., diabodies, bispecific antibodies, trivalent binding molecules, etc.) that possess at least one epitope-binding site that is immunospecific for an epitope of PD-1 and at least one epitope-binding site that is immunospecific for an epitope of CTLA-4 (i.e., a "PD-1×CTLA-4 bispecific molecule"). The present invention concerns such PD-1× CTLA-4 bispecific molecules that possess two epitope-binding sites that are immunospecific for one (or two) epitope(s) of PD-1 and two epitope-binding sites that are immunospecific for one (or two) epitope(s) of CTLA-4. The present invention also is directed to such PD-1×CTLA-4 bispecific molecules that additionally comprise an immunoglobulin Fc Region. The PD-1×CTLA-4 bispecific molecules of the present invention are capable of simultaneously binding to PD-1 and to CTLA-4, particularly as such molecules are arrayed on the surfaces of human cells. The invention is directed to pharmaceutical compositions that contain such PD-1×CTLA-4 bispecific molecules, and to methods involving the use of such bispecific molecules in the treatment of cancer and other diseases and conditions. The present invention also pertains to methods of using such PD-1×CTLA-4 bispecific molecules to stimulate an immune response.

BACKGROUND OF THE INVENTION

I. The Immune System Response to Cancer

The mammalian immune system is naturally poised to recognize and eliminate cancerous cells (Topalian, S. L. et al. (2015) "*Immune Checkpoint Blockade: A Common Denominator Approach to Cancer Therapy*," Cancer Cell 27:450-461). In healthy individuals, the immune system is in a quiescent state, inhibited by a repertoire of diverse inhibitory receptors and ligands. Such immune "checkpoint" pathways are important in maintaining self-tolerance (i.e., in preventing a subject from mounting an immune system attack against his/her own cells (an "autoimmune" reaction) and in limiting collateral tissue damage during anti-microbial or anti-allergic immune responses. Upon recognition of a cancer antigen, detection of a microbial pathogen, or the presence of an allergen, an array of activating receptors and ligands induce the activation of the immune system. Such activation leads to the activation of macrophages, Natural Killer (NK) cells and antigen-specific, cytotoxic, T-cells, and promotes the release of various cytokines, all of which act to counter the perceived threat to the health of the subject (Dong, C. et al. (2003) "*Immune Regulation by Novel Costimulatory Molecules*," Immunolog. Res. 28(1):39-48; Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). The immune system is capable of returning to its normal quiescent state when the countervailing inhibitory immune signals outweigh the activating immune signals.

Thus, the disease state of cancer (and indeed the disease states of infectious diseases) may be considered to reflect a failure to adequately activate a subject's immune system. Such failure may reflect an inadequate presentation of activating immune signals, or it may reflect an inadequate ability to alleviate inhibitory immune signals in the subject. In some instances, researchers have determined that cancer cells can co-opt the immune system to evade being detected by the immune system (Topalian, S. L. et al. (2015) "*Immune Checkpoint Blockade: A Common Denominator Approach to Cancer Therapy*," Cancer Cell 27:450-461).

Of particular importance is binding between the B7.1 (CD80) and B7.2 (CD86) ligands of the Antigen-Presenting Cell and the CD28 and CTLA-4 receptors of the CD4$^+$ T lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28 Mediated Costimulation*," Immunol. Rev. 229:307-321). Binding of B7.1 or of B7.2 to CD28 stimulates T-cell activation; binding of B7.1 or B7.2 to CTLA-4 inhibits such activation (Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T-cells (Gross, J., et al. (1992) "*Identification And Distribution Of The Costimulatory Receptor CD28 In The Mouse*," J. Immunol. 149:380-388), whereas CTLA-4 expression is rapidly upregulated following T-cell activation (Linsley, P. et al. (1996) "*Intracellular Trafficking Of CTLA4 And Focal Localization Towards Sites Of TCR Engagement*," Immunity 4:535-543). Since CTLA-4 is the higher affinity receptor (Sharpe, A. H. et al. (2002) "*The B7-CD28 Superfamily*," Nature Rev. Immunol. 2:116-126; Topalian, S. L. et al. (2015) "*Immune Checkpoint Blockade: A Common Denominator Approach to Cancer Therapy*," Cancer Cell 27:450-461), binding first initiates T-cell proliferation (via CD28) and then inhibits it (via nascent expression of CTLA-4), thereby dampening the effect when proliferation is no longer needed.

II. CTLA-4

Cytotoxic T-lymphocyte associated protein-4 (CTLA-4; CD152) is a single pass type I membrane protein that forms a disulfide linked homo-dimer (Schwartz J. C., et al. (2001) "*Structural Basis For Co-Stimulation By The Human CTLA-4/B7-2 Complex*," Nature 410:604-608). Alternate splice variants, encoding different isoforms, have been characterized including a soluble isoform which functions as a monomer (Magistrelli G., et al. (1999) "*A Soluble Form Of CTLA-4 Generated By Alternative Splicing Is Expressed By Nonstimulated Human T Cells*," Eur. J. Immunol. 29:3596-3602; Oaks M. K. et al. (2000) "*A Native Soluble Form Of CTLA-4*," Cell Immunol 201:144-153).

CTLA-4 is primarily an intracellular antigen whose surface expression is tightly regulated by restricted trafficking to the cell surface and rapid internalization (Alegre M-L, et al., (1996) "*Regulation Of Surface And Intracellular Expression Of CTLA4 On Mouse T Cells*," J. Immunol. 157:4762-4770; Linsley, P. S. et al. (1996) "*Intracellular Trafficking Of CTLA-4 And Focal Localization Towards Sites Of TCR Engagement*," Immunity 4:535-543). CTLA-4 is expressed at low levels on the surface of naïve effector T-cells (Alegre, M. L., et al. (1996) "*Regulation Of Surface And Intracellular Expression Of CTLA4 On Mouse T Cells*," J Immunol 157:4762-70), and constitutively expressed on T regulatory cells (Wang, X. B., et al. (2002) "*Expression Of CTLA-4 By Human Monocytes*," Scand. J. Immunol. 55:53-60).

The extracellular region of CTLA-4 comprises a single extracellular Ig(V) domain, followed by a transmembrane (TM) region and a small intracellular cytoplasmic tail (37 amino acids). The intracellular tail contains two tyrosine-based motifs, which interact with several intracellular proteins, including the lipid kinase phosphatidylinositol 3-kinase (PI3K), the phosphatases SHP-2 and PP2A and clathrin adaptor proteins AP-1 and AP-2 (Rudd, C. E. et al. (2003) "*Unifying Concepts In CD28, ICOS And CTLA4 Co Receptor Signalling*," Nat Rev Immunol. 3:544-56). CTLA-4 is related to CD28, with the two proteins having approximately 29% identity at the amino acid level (Harper, K. (1991) "*CTLA-4 And CD28 Activated Lymphocyte Molecules Are Closely Related In Mouse And Human As To Sequence, Message Expression, Gene Structure, And Chromosomal Location*," J. Immunol. 147:1037-1044).

When a naïve T effector cell is activated through its T-cell receptors (TCRs), CTLA-4 is recruited to the cell surface (Linsley, P. S., et al. (1996) "*Intracellular Trafficking Of CTLA-4 And Focal Localization Towards Sites Of TCR Engagement*," Immunity 4:535-43). Once CTLA-4 is expressed on the T-cell surface, it competes with CD28 (constitutively expressed on T-cells) for CD80/CD86, thereby shutting off further signaling through the TCR and thus down-regulating any further T-cell response by TCR signaling (Carreno, B. M., et al. (2000) "*CTLA-4 (CD152) Can Inhibit T Cell Activation By Two Different Mechanisms Depending On Its Level Of Cell Surface Expression*," J Immunol 165:1352-6; Chuang, E., et al. (1999) "*Regulation Of Cytotoxic T Lymphocyte Associated Molecule-4 By Src Kinases*," J Immunol 162:1270-7). Thus, CTLA-4 acts as a negative regulator of T effector cell activation that diminishes effector function and dictates the efficacy and duration of a T-cell response (Linsley, P. S., et al. (1996) "*Intracellular Trafficking Of CTLA-4 And Focal Localization Towards Sites Of TCR Engagement*," Immunity 4:535-43).

In addition, CTLA-4 may play a role in enhancing the negative effect of regulatory T-cells on the immune response to cancer (Tai, Y. T., et al., (2012) "*Potent in vitro And in vivo Activity Of An Fc-Engineered Humanized Anti-HM1.24 Antibody Against Multiple Myeloma via Augmented Effector Function*," Blood 119:2074-82). CTLA-4 has a much higher affinity for members of the B7 family than for CD28, and therefore its expression on a T-cell dictates a dominant negative regulation of the T-cell (Allison, J. P., et al. (1995) "*Manipulation Of Costimulatory Signals To Enhance Anti-tumor T-Cell Responses*," Curr Opin Immunol 7:682-6). The mechanism by which CTLA-4 contributes to the suppressor function of T regulatory cells is incompletely understood, but the expression of CTLA-4 on T regulatory cells enhances the suppressive function of these cells (Tai, Y. T., et al., (2012) "*Potent in vitro And in vivo Activity Of An Fc-Engineered Humanized Anti-HM1.24 Antibody Against Multiple Myeloma via Augmented Effector Function*," Blood 119:2074-82).

Blockage of CTLA-4 is reported to enhance T-cell responses in vitro (Walunas, T. L., et al. (1994) "*CTLA-4 Can Function As A Negative Regulator Of T Cell Activation*," Immunity 1:405-413) and in vivo (Kearney, E. R., et al. (1995) "*Antigen-Dependent Clonal Expansion Of A Trace Population Of Antigen-Specific CD4+ T Cells in vivo Is Dependent On CD28 Costimulation And Inhibited By CTLA-4*," J. Immunol. 155:1032-1036) and also to increase antitumor immunity (Leach, D. R. et al. (1996) "*Enhancement Of Antitumor Immunity By CTLA-4 Blockade*," Science 271:1734-1736). Thus, blockage of CTLA-4 using anti-CTLA-4 antibodies has been proposed to provide new treatments for disease, especially human diseases where immune stimulation might be beneficial such as for treatment of cancers and infectious diseases (see, Leach, D. R., et al. (1996) "*Enhancement Of Antitumor Immunity By CTLA-4 Blockade*," Science. 271:1734-1736; and PCT Publications No. WO 01/14424; WO 00/37504). Development of blockers of CTLA-4 function has focused on the use of monoclonal antibodies such as ipilimumab (see, e.g., Hodi, F. S., et al., (2003) "*Biologic Activity Of Cytotoxic T Lymphocyte Associated Antigen 4 Antibody Blockade In Previously Vaccinated Metastatic Melanoma And Ovarian Carcinoma Patients*," Proc. Natl. Acad. Sci. (U.S.A.) 100: 4717-4717) and tremelimumab (Ribas, A. et al. (2005) "*Antitumor Activity In Melanoma And Anti-Self Responses In A Phase I Trial With The Anti-Cytotoxic T Lymphocyte-Associated Antigen 4 Monoclonal Antibody CP-675,206*," Oncologist 12: 873-883).

III. Programmed Death-1 ("PD-1")

Programmed Death-1 ("PD-1," also known as "CD279") is type I membrane protein member of the extended CD28/CTLA-4 family of T-cell regulators that broadly negatively regulates immune responses (Ishida, Y. et al. (1992) "*Induced Expression Of PD-1, A Novel Member Of The Immunoglobulin Gene Superfamily, Upon Programmed Cell Death*," EMBO J. 11:3887-3895; United States Patent Application Publications No. 2007/0202100; 2008/0311117; 2009/00110667; U.S. Pat. Nos. 6,808,710; 7,101,550; 7,488, 802; 7,635,757; 7,722,868; PCT Publication No. WO 01/14557).

The receptor-ligand interactions of the PD-1 system appear to be even more complex than those of the CD28/CTLA-4 system. PD-1 is expressed on the cell surface of activated T-cells, B-cells, and monocytes (Agata, Y. et al. (1996) "*Expression Of The PD-1 Antigen On The Surface Of Stimulated Mouse T And B Lymphocytes*," Int. Immunol. 8(5):765-772; Yamazaki, T. et al. (2002) "*Expression Of Programmed Death 1 Ligands By Murine T-Cells And APC*," J. Immunol. 169:5538-5545) and at low levels in natural killer (NK) T-cells (Nishimura, H. et al. (2000) "*Facilitation Of Beta Selection And Modification Of Positive Selection In The Thymus Of PD-1-Deficient Mice*," J. Exp. Med. 191:891-898; Martin-Orozco, N. et al. (2007) "*Inhibitory Costimulation And Anti-Tumor Immunity*," Semin. Cancer Biol. 17(4):288-298).

The extracellular region of PD-1 consists of a single immunoglobulin (Ig)V domain with 23% identity to the equivalent domain in CTLA-4 (Martin-Orozco, N. et al. (2007) "*Inhibitory Costimulation And Anti-Tumor Immunity,*" Semin. Cancer Biol. 17(4):288-298). The extracellular IgV domain is followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals (Ishida, Y. et al. (1992) "*Induced Expression Of PD-1, A Novel Member Of The Immunoglobulin Gene Superfamily, Upon Programmed Cell Death,*" EMBO J. 11:3887-3895; Blank, C. et al. (2006) "*Contribution Of The PD-L1/PD-1 Pathway To T-Cell Exhaustion: An Update On Implications For Chronic Infections And Tumor Evasion Cancer,*" Immunol. Immunother. 56(5):739-745).

PD-1 mediates its inhibition of the immune system by binding to B7-H1 and B7-DC (also known as PD-L1 and PD-L2, Flies, D. B. et al. (2007) "*The New B7s: Playing a Pivotal Role in Tumor Immunity,*" J. Immunother. 30(3): 251-260; U.S. Pat. Nos. 6,803,192; 7,794,710; United States Patent Application Publication Nos. 2005/0059051; 2009/0055944; 2009/0274666; 2009/0313687; PCT Publication Nos. WO 01/39722; WO 02/086083).

B7-H1 and B7-DC are broadly expressed on the surfaces of many types of human and murine tissues, such as heart, placenta, muscle, fetal liver, spleen, lymph nodes, and thymus as well as murine liver, lung, kidney, islets cells of the pancreas and small intestine (Martin-Orozco, N. et al. (2007) "*Inhibitory Costimulation And Anti-Tumor Immunity,*" Semin. Cancer Biol. 17(4):288-298). In humans, B7-H1 protein expression has been found in human endothelial cells (Chen, Y. et al. (2005) "*Expression of B7-H1 in Inflammatory Renal Tubular Epithelial Cells,*" Nephron. Exp. Nephrol. 102:e81-e92; de Haij, S. et al. (2005) "*Renal Tubular Epithelial Cells Modulate T-Cell Responses Via ICOS-L And B7-H1*" Kidney Int. 68:2091-2102; Mazanet, M. M. et al. (2002) "*B7-H1 Is Expressed By Human Endothelial Cells And Suppresses T-Cell Cytokine Synthesis,*" J. Immunol. 169:3581-3588), myocardium (Brown, J. A. et al. (2003) "*Blockade Of Programmed Death-1 Ligands On Dendritic Cells Enhances T-Cell Activation And Cytokine Production,*" J. Immunol. 170:1257-1266), syncyciotrophoblasts (Petroff, M. G. et al. (2002) "*B7 Family Molecules: Novel Immunomodulators At The Maternal-Fetal Interface,*" Placenta 23:S95-S101). The molecules are also expressed by resident macrophages of some tissues, by macrophages that have been activated with interferon (IFN)-γ or tumor necrosis factor (TNF)-α (Latchman, Y. et al. (2001) "*PD-L2 Is A Second Ligand For PD-1 And Inhibits T-Cell Activation,*" Nat. Immunol 2:261-268), and in tumors (Dong, H. (2003) "*B7-H1 Pathway And Its Role In The Evasion Of Tumor Immunity,*" J. Mol. Med. 81:281-287).

The interaction between B7-H1 and PD-1 has been found to provide a crucial negative costimulatory signal to T and B-cells (Martin-Orozco, N. et al. (2007) "*Inhibitory Costimulation And Anti-Tumor Immunity,*" Semin. Cancer Biol. 17(4):288-298) and functions as a cell death inducer (Ishida, Y. et al. (1992) "*Induced Expression Of PD-1, A Novel Member Of The Immunoglobulin Gene Superfamily, Upon Programmed Cell Death,*" EMBO J. 11:3887-3895; Subudhi, S. K. et al. (2005) "*The Balance Of Immune Responses: Costimulation Verse Coinhibition,*" J. Molec. Med. 83:193-202). More specifically, interaction between low concentrations of the PD-1 receptor and the B7-H1 ligand has been found to result in the transmission of an inhibitory signal that strongly inhibits the proliferation of antigen-specific $CD8^+$ T-cells; at higher concentrations the interactions with PD-1 do not inhibit T-cell proliferation but markedly reduce the production of multiple cytokines (Sharpe, A. H. et al. (2002) "*The B7-CD28 Superfamily,*" Nature Rev. Immunol. 2:116-126). T-cell proliferation and cytokine production by both resting and previously activated CD4 and CD8 T-cells, and even naive T-cells from umbilical-cord blood, have been found to be inhibited by soluble B7-H1-Fc fusion proteins (Freeman, G. J. et al. (2000) "*Engagement Of The PD-1 Immunoinhibitory Receptor By A Novel B7 Family Member Leads To Negative Regulation Of Lymphocyte Activation,*" J. Exp. Med. 192:1-9; Latchman, Y. et al. (2001) "*PD-L2 Is A Second Ligand For PD-1 And Inhibits T-Cell Activation,*" Nature Immunol. 2:261-268; Carter, L. et al. (2002) "*PD-1:PD-L Inhibitory Pathway Affects Both CD4(+) and CD8(+) T-cells And Is Overcome By IL-2,*" Eur. J. Immunol. 32(3):634-643; Sharpe, A. H. et al. (2002) "*The B7-CD28 Superfamily,*" Nature Rev. Immunol. 2:116-126).

The role of B7-H1 and PD-1 in inhibiting T-cell activation and proliferation has suggested that these biomolecules might serve as therapeutic targets for treatments of inflammation and cancer. Thus, the use of anti-PD-1 antibodies to treat infections and tumors and to up-modulate an adaptive immune response has been proposed (see, United States Patent Application Publication Nos. 2010/0040614; 2010/0028330; 2004/0241745; 2008/0311117; 2009/0217401; U.S. Pat. Nos. 7,521,051; 7,563,869; 7,595,048; PCT Publication Nos. WO 2004/056875; WO 2008/083174). Antibodies capable of specifically binding to PD-1 have been reported by Agata, T. et al. (1996) "*Expression Of The PD-1 Antigen On The Surface Of Stimulated Mouse T And B Lymphocytes,*" Int. Immunol. 8(5):765-772; and Berger, R. et al. (2008) "*Phase I Safety And Pharmacokinetic Study Of CT-011, A Humanized Antibody Interacting With PD-1, In Patients With Advanced Hematologic Malignancies,*" Clin. Cancer Res. 14(10):3044-3051 (see, also, U.S. Pat. Nos. 8,008,449 and 8,552,154; US Patent Publications No. 2007/0166281; 2012/0114648; 2012/0114649; 2013/0017199; 2013/0230514 and 2014/0044738; and PCT Patent Publication Nos. WO 2003/099196; WO 2004/004771; WO 2004/056875; WO 2004/072286; WO 2006/121168; WO 2007/005874; WO 2008/083174; WO 2009/014708; WO 2009/073533; WO 2012/135408, WO 2012/145549; and WO 2013/014668).

However, despite all such prior advances, a need remains for improved compositions capable of more vigorously directing the body's immune system to attack cancer cells or pathogen-infected cells, especially at lower therapeutic concentrations and/or with reduced side effects. Although the adaptive immune system can be a potent defense mechanism against cancer and disease, it is often hampered by immune suppressive/evasion mechanisms in the tumor microenvironment, such as the expression of PD-1 and CTLA-4. Furthermore, co-inhibitory molecules expressed by tumor cells, immune cells, and stromal cells in the tumor milieu can dominantly attenuate T-cell responses against cancer cells. In addition, the use of anti-CTLA-4 antibodies induces well-identified side effects referred to as "immune-related adverse events" (irAEs). IrAEs include colitis/diarrhea, dermatitis, hepatitis, endocrinopathies, and inflammatory myopathy. These unique side effects are reported to arise due to breaking immune tolerance upon CTLA-4 blockade (Di Giacomo, A. M., et al. (2010) "*The Emerging Toxicity Profiles Of Anti-CTLA-4 Antibodies Across Clinical Indica-* tions," Semin Oncol. 37:499-507). Accordingly, therapies which overcome these limitations would be of great benefit.

As described in detail below, the present invention addresses this need by providing PD-1×CTLA-4 bispecific molecules. Such bispecific molecules are capable of binding to PD-1 and CTLA-4 molecules that are present on the surfaces of exhausted and tolerant tumor-infiltrating lymphocytes and other cell types, and of thereby impairing the ability of such cell-surface molecules to respond to their respective ligands. As such, the PD-1×CTLA-4 bispecific molecules of the present invention act to block PD-1- and CTLA-4-mediated immune system inhibition, so as to promote the activation or continued activation of the immune system. These attributes permit such bispecific molecules to have utility in stimulating the immune system and particularly in the treatment of cancer and pathogen-associated diseases and conditions. The present invention is directed to these and other goals.

SUMMARY OF THE INVENTION

The present invention is directed to bispecific molecules (e.g., diabodies, bispecific antibodies, trivalent binding molecules, etc.) that possess at least one epitope-binding site that is immunospecific for an epitope of PD-1 and at least one epitope-binding site that is immunospecific for an epitope of CTLA-4 (i.e., a "PD-1×CTLA-4 bispecific molecule"). The present invention concerns such PD-1×CTLA-4 bispecific molecules that possess two epitope-binding sites that are immunospecific for one (or two) epitope(s) of PD-1 and two epitope-binding sites that are immunospecific for one (or two) epitope(s) of CTLA-4. The present invention also is directed to such PD-1×CTLA-4 bispecific molecules that additionally comprise an immunoglobulin Fc Region. The PD-1×CTLA-4 bispecific molecules of the present invention are capable of simultaneously binding to PD-1 and to CTLA-4, particularly as such molecules are arrayed on the surfaces of human cells. The invention is directed to pharmaceutical compositions that contain such PD-1×CTLA-4 bispecific molecules, and to methods involving the use of such bispecific molecules in the treatment of cancer and other diseases and conditions. The present invention also pertains to methods of using such PD-1×CTLA-4 bispecific molecules to stimulate an immune response.

In detail, the invention provides a bispecific molecule possessing both one or more epitope-binding sites capable of immunospecific binding to (an) epitope(s) of PD-1 and one or more epitope-binding sites capable of immunospecific binding to (an) epitope(s) of CTLA-4, wherein the molecule comprises:
(A) a Heavy Chain Variable Domain and a Light Chain Variable Domain of an antibody that binds PD-1; and
(B) a Heavy Chain Variable Domain and a Light Chain Variable Domain of an antibody that binds CTLA-4;
wherein the bispecific binding molecule is:
(i) a diabody, the diabody being a covalently bonded complex that comprises two, three, four or five polypeptide chains; or
(ii) a trivalent binding molecule, the trivalent binding molecule being a covalently bonded complex that comprises three, four, five, or more polypeptide chains.

The invention concerns the embodiment of such bispecific molecules, wherein the bispecific binding molecule exhibits an activity that is enhanced relative to such activity exhibited by two monospecific molecules one of which possesses the Heavy Chain Variable Domain and the Light Chain Variable Domain of the antibody that binds PD-1 and the other of which possesses the Heavy Chain Variable Domain and the Light Chain Variable Domain of the antibody that binds CTLA-4.

The invention concerns the embodiment of all such bispecific molecules, wherein the molecule elicits fewer immune-related adverse events (irAEs) when administered to a subject in need thereof relative to such iREs elicited by the administration of a monospecific antibody that binds CTLA-4 such as ipilimumab.

The invention additionally concerns the embodiment of such bispecific molecules in which the molecule comprises an Fc Region. The invention additionally concerns the embodiment of such bispecific molecules wherein the Fc Region is a variant Fc Region that comprises:
(A) one or more amino acid modifications that reduces the affinity of the variant Fc Region for an FcγR; and/or
(B) one or more amino acid modifications that enhances the serum half-life of the variant Fc Region.

The invention additionally concerns the embodiment of such bispecific molecules wherein the modifications that reduces the affinity of the variant Fc Region for an FcγR comprise the substitution of L234A; L235A; or L234A and L235A, wherein the numbering is that of the EU index as in Kabat.

The invention additionally concerns the embodiment of such bispecific molecules wherein the modifications that that enhances the serum half-life of the variant Fc Region comprise the substitution of M252Y; M252Y and S254T; M252Y and T256E; M252Y, S254T and T256E; or K288D and H435K, wherein the numbering is that of the EU index as in Kabat.

The invention additionally concerns the embodiment of all such bispecific molecules wherein the molecule is the diabody and comprises two epitope-binding sites capable of immunospecific binding to an epitope of PD-1 and two epitope-binding sites capable of immunospecific binding to an epitope of CTLA-4.

The invention additionally concerns the embodiment of all such bispecific molecules wherein the molecule is the trivalent binding molecule and comprises two epitope-binding sites capable of immunospecific binding to an epitope of PD-1 and one epitope-binding site capable of immunospecific binding to an epitope of CTLA-4.

The invention additionally concerns the embodiment of all such bispecific molecules wherein the molecule is capable of binding to PD-1 and CTLA-4 molecules present on the cell surface.

The invention additionally concerns the embodiment of all such bispecific molecules wherein the molecule is capable of simultaneously binding to PD-1 and CTLA-4.

The invention additionally concerns the embodiment of all such bispecific molecules wherein the molecule promotes the stimulation of immune cells, and particularly wherein the stimulation of immune cells results in:
(A) immune cell proliferation; and/or
(B) immune cell production and/or release of at least one cytokine; and/or
(C) immune cell production and/or release of at least one lytic molecule; and/or
(D) immune cell expression of at least one activation marker.

The invention additionally concerns the embodiment of all such bispecific molecules wherein the immune cell is a T-lymphocyte or an NK-cell.

The invention additionally concerns the embodiment of all such bispecific molecules wherein the epitope-binding sites capable of immunospecific binding to an epitope of PD-1 comprise:
(A) the VH Domain of PD-1 mAb 1 (SEQ ID NO:47) and the VL Domain of PD-1 mAb 1 (SEQ ID NO:48); or
(B) the VH Domain of PD-1 mAb 2 (SEQ ID NO:49) and the VL Domain of PD-1 mAb 2 (SEQ ID NO:50); or
(C) the VH Domain of PD-1 mAb 3 (SEQ ID NO:51) and the VL Domain of PD-1 mAb 3 (SEQ ID NO:52); or
(D) the VH Domain of PD-1 mAb 4 (SEQ ID NO:53) and the VL Domain of PD-1 mAb 4 (SEQ ID NO:54); or
(E) the VH Domain of PD-1 mAb 5 (SEQ ID NO:55) and the VL Domain of PD-1 mAb 5 (SEQ ID NO:56); or
(F) the VH Domain of PD-1 mAb 6 (SEQ ID NO:57) and the VL Domain of PD-1 mAb 6 (SEQ ID NO:58); or
(G) the VH Domain of PD-1 mAb 6-I VH (SEQ ID NO:86) and the VL Domain of PD-1 mAb 6-SQ VL (SEQ ID NO:87); or
(H) the VH Domain of PD-1 mAb 7 (SEQ ID NO:59) and the VL Domain of PD-1 mAb 7 (SEQ ID NO:60); or
(I) the VH Domain of PD-1 mAb 8 (SEQ ID NO:61) and the VL Domain of PD-1 mAb 8 (SEQ ID NO:62).

The invention additionally concerns the embodiment of all such bispecific molecules wherein the epitope-binding site(s) capable of immunospecific binding to an epitope of CTLA-4 comprise:
(A) the VH Domain of CTLA-4 mAb 1 (SEQ ID NO:76) and the VL Domain of CTLA-4 mAb 1 (SEQ ID NO:77); or
(B) the VH Domain of CTLA-4 mAb 2 (SEQ ID NO:78) and the VL Domain of CTLA-4 mAb 2 (SEQ ID NO:79); or
(C) the VH Domain of CTLA-4 mAb 3 (SEQ ID NO:90) and the VL Domain of CTLA-4 mAb 3 (SEQ ID NO:91).

The invention additionally concerns the embodiment of such bispecific molecules wherein:
(A) the epitope-binding sites capable of immunospecific binding to an epitope of PD-1 comprise the VH Domain of PD-1 mAb 6-I VH (SEQ ID NO:86) and the VL Domain of PD-1 mAb 6-SQ (SEQ ID NO:87); and
(B) the epitope-binding site(s) capable of immunospecific binding to an epitope of CTLA-4 comprise(s) the VH Domain of CTLA-4 mAb 3 (SEQ ID NO:90) and the VL Domain of CTLA-4 mAb 3 (SEQ ID NO:91).

The invention additionally concerns the embodiment of all such bispecific molecules wherein the molecule comprises:
(A) two polypeptide chains having SEQ ID NO:95, and two polypeptide chain having SEQ ID NO:96; or
(B) two polypeptide chains having SEQ ID NO:97, and two polypeptide chain having SEQ ID NO:98; or
(C) two polypeptide chains having SEQ ID NO:99, and two polypeptide chain having SEQ ID NO:100; or
(D) two polypeptide chains having SEQ ID NO:102, and two polypeptide chain having SEQ ID NO:103; or
(E) two polypeptide chains having SEQ ID NO:101, and two polypeptide chain having SEQ ID NO:100; or
(F) one polypeptide chains having SEQ ID NO:104, one polypeptide chain having SEQ ID NO:105, one polypeptide chain having SEQ ID NO:106, and one polypeptide chain having SEQ ID NO:107; or
(G) one polypeptide chains having SEQ ID NO:108, one polypeptide chain having SEQ ID NO:105, one polypeptide chain having SEQ ID NO:109, and one polypeptide chain having SEQ ID NO:107.

The invention additionally concerns the embodiment of such bispecific molecules in which the molecule comprises an Albumin-Binding Domain, and especially a deimmunized Albumin-Binding Domain.

The invention additionally concerns a pharmaceutical composition that comprises an effective amount of any of such bispecific molecules and a pharmaceutically acceptable carrier.

The invention additionally concerns the use of such pharmaceutical composition or the use of any of the above-described bispecific molecules to promote stimulation of an immune-mediated response of a subject in need thereof, and in particular, wherein such molecule promotes the stimulation of immune cells, and in particular, stimulation of NK-cells and/or T-lymphocytes. The invention particularly concerns the embodiments wherein such stimulation results in immune cell proliferation, immune cell production and/or release of cytokines (e.g., IFNγ, IL-2, TNFα, etc.), immune cell production and/or release of lytic molecules (e.g., granzyme, perforin, etc.), and/or immune cell expression of activation markers (e.g., CD69, CD25, CD107a, etc.). The invention further concerns methods of treating cancer or other diseases that involve the use or administration of any of the above-described PD-1×CTLA-4 bispecific molecules to stimulate an immune mediated response. The invention particularly concerns the embodiments in which the immune stimulatory activity of any of the above-described PD-1×CTLA-4 bispecific molecules is more potent than the joint or combined administration of a separate anti-PD-1 antibody and a separate anti-CTLA-4 antibody (especially, wherein such antibodies are monospecific for such molecules). The invention also concerns embodiments in which immune cells, particularly NK-cells and/or T-lymphocytes, stimulated by the above-described PD-1×CTLA-4 bispecific molecules exhibit enhanced proliferation, altered production and/or release of cytokines (e.g., IFNγ, IL-2, TNFα, etc.), altered production and/or release of lytic molecules, and/or altered expression of activation markers relative to that exhibited by such cells stimulated by the joint or combined administration of a separate anti-PD-1 antibody and a separate anti-CTLA-4 antibody. The invention also concerns embodiments in which the above-described PD-1×CTLA-4 bispecific molecules have a reduced incidence of irAEs. The invention additionally concerns the embodiments in which any of the above-described PD-1×CTLA-4 bispecific molecules are used in the treatment of a disease or condition associated with a suppressed immune system, especially cancer or an infection.

The invention additionally concerns such a use to treat a disease or condition associated with a suppressed immune system, or in the treatment of such a disease or condition. The invention particularly concerns such a use in the treatment of a disease or condition associated with a suppressed immune system, or wherein the disease or condition is cancer or an infection (particularly, an infection characterized by the presence of a bacterial, fungal, viral or protozoan pathogen).

The invention particularly concerns such a use wherein:
(A) the use is in the treatment of cancer, and the cancer is characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer; or (B) the use is in the treatment of infection, and the infection is a chronic viral, bacterial, fungal and parasitic infection, characterized the presence of Epstein Barr virus, Hepatitis A Virus (HAV); Hepatitis B Virus (HBV); Hepatitis C Virus (HCV); herpes viruses (e.g. HSV-1, HSV-2, HHV-6, CMV), Human Immunodeficiency Virus (HIV), Vesicular Stomatitis Virus (VSV), *Bacilli, Citrobacter, Cholera, Diphtheria, Enterobacter, Gonococci, Helicobacter pylori, Klebsiella, Legionella, Meningococci, mycobacteria, Pseudomonas, Pneumonococci, rickettsia* bacteria, *Salmonella, Serratia, Staphylococci, Streptococci, Tetanus, Aspergillus* (*A. fumigatus, A. niger*, etc.), *Blastomyces dermatitidis, Candida* (*C. albicans, C. krusei, C. glabrata, C. tropicalis*, etc.), *Cryptococcus neoformans*, Genus *Mucorales* (*mucor, absidia, rhizopus*), *Sporothrix schenkii, Paracoccidioides brasiliensis, Coccidioides immitis, Histoplasma capsulatum, Leptospirosis, Borrelia burgdorferi*, helminth parasite (hookworm, tapeworms, flukes, flatworms (e.g. *Schistosomia*), *Giardia lambia, trichinella, Dientamoeba Fragilis, Trypanosoma brucei, Trypanosoma cruzi*, or *Leishmania donovani*.

The invention particularly concerns such use in the treatment of cancer, wherein the cancer is colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer, a rectal cancer, acute myeloid leukemia (AML), chronic myelogenous leukemia (CIVIL), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

BRIEF DESCRIPTION OF THE DRAWINGS

FIG. 3A shows an Fc Region-containing diabody which contains a peptide Heterodimer-Promoting Domain comprising a cysteine residue. FIG. 3B shows an Fc Region-containing diabody, which contains E-coil and K-coil Heterodimer-Promoting Domains comprising a cysteine residue and a linker (with an optional cysteine residue). FIG. 3C, shows an Fc-Region-Containing diabody, which contains antibody CH1 and CL domains.

FIGS. 6A and 6B, respectively, illustrate schematically the domains of trivalent binding molecules comprising two diabody-type binding domains and a Fab-type binding domain having different domain orientations in which the diabody-type binding domains are N-terminal or C-terminal to an Fc Region. The molecules in FIGS. 6A and 6B comprise four chains. FIGS. 6C and 6D, respectively, illustrate schematically the domains of trivalent binding molecules comprising two diabody-type binding domains N-terminal to an Fc Region, and a linked Fab-type binding domain, or an scFv-type binding domain. The trivalent binding molecules in FIGS. 6E and 6F, respectively illustrate schematically the domains of trivalent binding molecules comprising two diabody-type binding domains C-terminal to an Fc Region, and a Fab-type binding domain in which the light chain and heavy chain are linked via a polypeptide spacer, or an scFv-type binding domain. The trivalent binding molecules in FIGS. 6C-6F comprise three chains. VL and VH Domains that recognize the same epitope are shown using the same shading or fill pattern.

FIGS. 8A-8B show the binding curves of CTLA-4 mAb 3 G4P, DART D, TRIDENT A or DART B to soluble hCTLA-4-Avi-His (1 μg/mL) (FIG. 8A) or hPD-1-His (1 μg/mL) (FIG. 8B) that had been coated onto support plates. Goat anti-human-Fc-HRP (1:10,000) was employed as the secondary detection molecule to detect binding. FIGS. 8C-8D show the results of a study on the effect of altering orientations and binding domains on binding. PD-1×CTLA-4 bispecific molecules comprising the CTLA-4 binding domains of CTLA-4 mAb 1 (e.g., DART B) and CTLA-4 mAb 3 (e.g., DART C and DART D) were incubated in the presence of soluble human PD-1 (FIG. 8C) or soluble human CTLA-4-Avi-His (FIG. 8D), that had been coated onto support plates. Goat anti-human-Fcγ-HRP was employed as the secondary detection molecule to detect binding using PICO chemiluminescent substrate.

FIG. 11A shows the results for DART C, DART D, DART E, CTLA-4 mAb 1, CTLA-4 mAb 3 G1AA, and PD-1 mAb 6 G4P. FIG. 11B shows the results for CTLA-4 mAb 1, CTLA-4 mAb 3 G1AA, PD-1 mAb 6 G4P and TRIDENT A.

FIG. 15A (PD-L1); FIG. 15B (PD-L2).

FIGS. 19A-19B show fluorescence-activated cell sorting (FACS) dot plots of the expression of PD-1 vs. CTLA-1 by such PBMCs in the absence (FIG. 19A) or presence (FIG. 19B) of SEB stimulation. FIG. 19C shows the effect of the SEB stimulation on IFN-γ secretion. PBMCs were stimulated with *Staphylococcus aureus* enterotoxin type B (SEB) at 0.5 ng/ml for 48 hours. Cells were then harvested, washed and re-plated in 96 well plates with antibodies at various concentrations with fresh SEB for an additional 48 hours. The supernatant was then harvested and analyzed by flow cytometry ELISA for IFN-γ production. Both the bispecific DART and the TRIDENT protein showed an increase in IFN-γ response that recapitulated the response observed with the combination of the individual parental mAbs. Similar results were seen in a SEB Stimulation assay in which the PBMCs were cultured with a high concentration (500 ng/mL) of SEB for 72 hours. Presented are six series, each relating to a different binding molecule. Each series is composed of seven columns, which relate to the result obtained with 25 nM, 6.25 nM, 1.56 nM, 0.39 nM, 0.09 nM, 0.02 nM or 0.006 nM binding molecule (respectively, from left to right). FIG. 19D shows the release of IL-2 for a representative donor. PBMCs were stimulated with 0.5 ng/ml SEB for 48 hours, harvested and re-plated in 96-well plates with fresh SEB and either DART D, TRIDENT A, CTLA-4 mAb 3 G1AA, PD-1 mAb 6 G4P or the combination of CTLA-4 mAb 3 G1AA/PD-1 mAb 6 G4P (Ab Combo 1) for an additional 48 hours, and the released IL-2 was measured. Presented are seven series, each relating to a different binding molecule or condition. Each series is composed of three columns, which relate to the result obtained with 0.5 nM, 5 nM or 50 nM binding molecule (respectively, from left to right). When antibodies were used in combination, each antibody was added at the indicated concentration so that the total concentration of antibody added is doubled.

FIG. 22A shows the ALC in thousands of cells/μl (th/μl). FIG. 22B shows the percent change in the ALC normalized to Day 1 (D1).

DETAILED DESCRIPTION OF THE INVENTION

Figure 1:
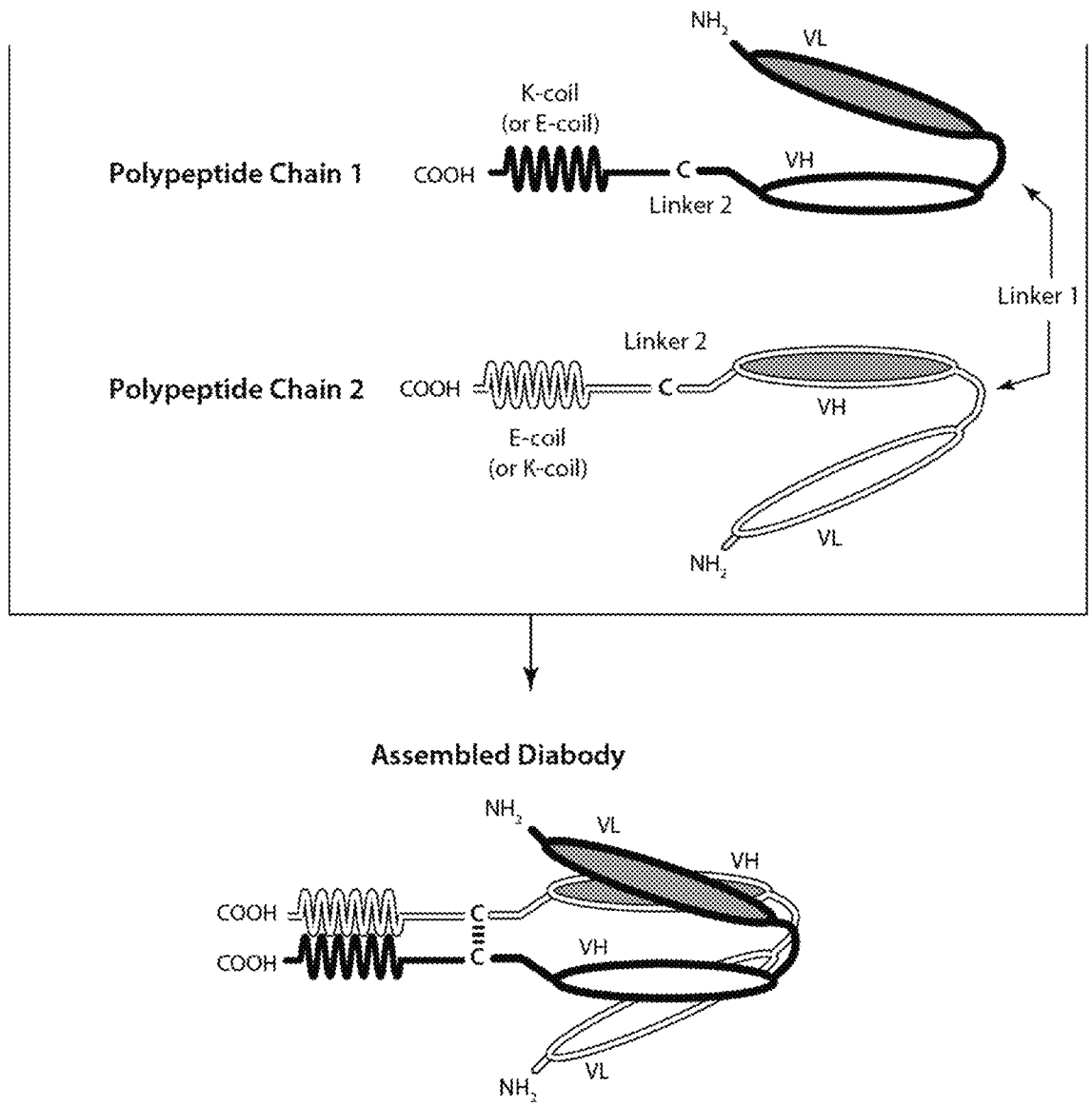
FIG. 1 provides a schematic of a representative covalently bonded diabody having two epitope-binding sites composed of two polypeptide chains, each having an E-coil or K-coil Heterodimer-Promoting Domain (alternative Heterodimer-Promoting Domains are provided below). A cysteine residue may be present in a linker and/or in the Heterodimer-Promoting Domain as shown in FIG. 3B. VL and VH Domains that recognize the same epitope are shown using the same shading or fill pattern.

The present invention is directed to bispecific molecules (e.g., diabodies, bispecific antibodies, trivalent binding molecules, etc.) that possess at least one epitope-binding site that is immunospecific for an epitope of PD-1 and at least one epitope-binding site that is immunospecific for an epitope of CTLA-4 (i.e., a "PD-1×CTLA-4 bispecific molecule"). The present invention concerns such PD-1× CTLA-4 bispecific molecules that possess two epitope-binding sites that are immunospecific for one (or two) epitope(s) of PD-1 and two epitope-binding sites that are immunospecific for one (or two) epitope(s) of CTLA-4. The present invention also is directed to such PD-1×CTLA-4 bispecific molecules that additionally comprise an immunoglobulin Fc Region. The PD-1×CTLA-4 bispecific molecules of the present invention are capable of simultaneously binding to PD-1 and to CTLA-4, particularly as such molecules are arrayed on the surfaces of human cells. The invention is directed to pharmaceutical compositions that contain such PD-1×CTLA-4 bispecific molecules, and to methods involving the use of such bispecific molecules in the treatment of cancer and other diseases and conditions. The present invention also pertains to methods of using such PD-1×CTLA-4 bispecific molecules to stimulate an immune response.

T-cell activation requires two distinct signals (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). The first signal is provided by a T-Cell Receptor (TCR) molecule, expressed on the surface of a T-cell, that has recognized a peptide antigen that has become associated with a human leukocyte antigen (HLA) expressed on the surface of an Antigen-Presenting Cell (APC). The second signal is provided by the interaction of cognate pairs of co-stimulatory ligands: B7-1 and B7-2 expressed on APCs and their corresponding receptors: CD28 and CTLA-4 expressed on T-cells.

The binding of B7-1 and B7-2 molecules to CD28 stimulates T-cell proliferation and additionally induces increased expression of CTLA-4. CTLA-4 is a negative-regulator that competes with B7-1 and B7-2 for binding to CD28. Thus, the process responds to disease in two phases: the initial phase involves stimulating T-cell proliferation; the subsequent phase "winds down" the immune response and returns the subject to a quiescent immune state. Antibodies that bind CD28 can mimic the binding of B7-1 or B7-2 and thus induce or enhance T-cell effector function and the generation of tumor eradicating immunity; such antibodies are co-stimulatory. Conversely, antibodies that block CTLA-4 from binding to B7-1 and B7-2 can prevent T-cells from returning to a quiescent state; such T-cells thus maintain a sustained proliferation that can lead to autoimmunity and the development of immune-related adverse events" (irAEs) (Wang, L. et al. (Mar. 7, 2011) "*VISTA, A Novel Mouse Ig Superfamily Ligand That Negatively Regulates T-Cell Responses*," J. Exp. Med. 10.1084/jem.20100619: 1-16; Lepenies, B. et al. (2008) "*The Role Of Negative Costimulators During Parasitic Infections*," Endocrine, Metabolic & Immune Disorders—Drug Targets 8:279-288). Of particular importance is binding between the B7.1 (CD80) and B7.2 (CD86) ligands of the Antigen-Presenting Cell and the CD28 and CTLA-4 receptors of the CD4+ T lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). Binding of B7.1 or of B7.2 to CD28 stimulates T-cell activation; binding of B7.1 or B7.2 to CTLA-4 inhibits such activation (Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T-cells (Gross, J., et al. (1992) "*Identification And Distribution Of The Costimulatory Receptor CD28 In The Mouse*," J. Immunol. 149:380-388), whereas CTLA-4 expression is rapidly upregulated following T-cell activation (Linsley, P. et al. (1996) "*Intracellular Trafficking Of CTLA4 And Focal Localization Towards Sites Of TCR Engagement*," Immunity 4:535-543). Since CTLA-4 is the higher affinity receptor (Sharpe, A. H. et al. (2002) "*The B7-CD28 Superfamily*," Nature Rev. Immunol. 2:116-126) binding first initiates T-cell proliferation (via CD28) and then inhibits it (via nascent expression of CTLA-4), thereby dampening the effect when proliferation is no longer needed.

In parallel with the above-described interactions, a second set of receptors and binding ligands function to inhibit the immune system, thereby serving as a brake to slow the CD28/B7-1/B7-2-mediated enhancement of the immune response. This auxiliary response involves the binding of the programmed cell death-1 protein (PD-1) receptor, expressed on the surface of T-cells, to corresponding ligands: PD-L1, expressed on Antigen-Presenting Cells (APCs) and PD-L2, expressed on epithelial cells (Chen L. et al. (2013) "*Molecular Mechanisms Of T-Cell Co-Stimulation And Co-Inhibition*," Nature Reviews Immunology 13(4):227-242). In contrast to agonist antibodies that bind to CD28 to directly stimulate T-cell responses, antibodies that bind to either PD-1 or PD-L1 antagonize or block PD-1/PD-L1 engagement and thus maintain T-cell activation by preventing the delivery of a negative signal to the T-cell. As such, antibodies that bind to either PD-1 or PD-L1 augment or maintain T-cell proliferation, cytotoxicity, and/or cytokine secretion. Taken together agonist antibodies, such as anti-CD28, target positive signal pathways and are therefore co-stimulators, while antagonistic antibodies, such as anti-CTLA-4 and anti-PD-1, target negative signal pathways and are called checkpoint inhibitors.

As provided above, CTLA-4 and PD-1 represent the canonical checkpoint inhibitors which exert distinct inhibitory effects on T-cell activation. The PD-1×CTLA-4 bispecific molecules of the present invention are capable of binding to PD-1 and CTLA-4 cell-surface molecules that are present on the surfaces of lymphocytes, and of thereby impairing the ability of such cell-surface molecules to respond to their respective receptors. Without being bound by any theory or mechanism, the inventors believe that PD-1 binding can release T-cell inhibition (e.g., at tumor sites and/or as a result of infection) and that CTLA-1 binding can stimulate polyclonal activation and stimulation. As such, the PD-1×CTLA-4 bispecific molecules of the present invention are able to attenuate PD-1 and CTLA-4-mediated immune system inhibition, and promote continued immune system activation. It has been demonstrated herein that bispecific molecules which target two immunomodulatory pathways are more potent than the combination of separate antibodies. The instant invention also provides PD-1×CTLA-4 bispecific molecules having PD-1:CTLA-4 binding ratios of 1:1, 1:2, 2:2 and 2:1 which allow for full blockade of both PD-1 and CTLA-4 as well as blockade that is biased toward CTLA-4 when co-expressed with PD-1. Accordingly, the PD-1×CTLA-4 bispecific molecules of the present invention provide unexpected superiority as compared to the combination of separate anti-PD-1 and anti-CTLA-4 antibodies. Additionally, the PD-1×CTLA-4 bispecific molecules of the present invention may provide immune stimulation with reduced risk of irAEs.

I. Antibodies and Their Binding Domains

The antibodies of the present invention are immunoglobulin molecules capable of specific binding to a target, such as a carbohydrate, polynucleotide, lipid, polypeptide, etc., through at least one antigen recognition site, located in the Variable Domain of the immunoglobulin molecule. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and epitope-binding fragments of any of the above. In particular, the term "antibody" includes immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. As used herein, an Fc Region is said to be of a particular IgG isotype, class or subclass if its amino acid sequence is most homologous to that isotype relative to other IgG isotypes. In addition to their known uses in diagnostics, antibodies have been shown to be useful as therapeutic agents. Antibodies are capable of immunospecifically binding to a polypeptide or protein or a non-protein molecule due to the presence on such molecule of a particular domain or moiety or conformation (an "epitope"). An epitope-containing molecule may have immunogenic activity, such that it elicits an antibody production response in an animal; such molecules are termed "antigens". The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Over 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', $F(ab')_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3): 119-125). In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences.

Natural antibodies (such as IgG antibodies) are composed of two Light Chains complexed with two Heavy Chains. Each Light Chain contains a Variable Domain (VL) and a Constant Domain (CL). Each Heavy Chain contains a Variable Domain (VH), three Constant Domains (CH1, CH2 and CH3), and a Hinge Region located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with light chains having a single Constant Domain and heavy chains usually having three Constant Domains and a Hinge Region. Thus, the structure of the light chains of an IgG molecule is n-VL-CL-c and the structure of the IgG heavy chains is n-VH-CH1-H-CH2-CH3-c (where H is the Hinge Region, and n and c represent, respectively, the N-terminus and the C-terminus of the polypeptide). The Variable Domains of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody heavy chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or a diabody or a single-chain binding molecule (e.g., an scFv, a BiTe, etc.), or is another type of protein. Accordingly, as used herein, the term "epitope-binding fragment" means a fragment of an antibody capable of immunospecifically binding to an epitope, and the term "epitope-binding site" refers to a portion of a molecule comprising an epitope-binding fragment. An epitope-binding fragment may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an Fab$_2$ fragment, etc.). Unless specifically noted, the order of domains of the protein molecules described herein is in the N-terminal to C-Terminal direction.

The invention particularly encompasses PD-1×CTLA-4 bispecific binding molecules comprising one, two, or more than two single-chain Variable Domain fragments ("scFv") of an anti-PD-1 antibody and one, two, or more than two single-chain Variable Domain fragments of an anti-CTLA-4 antibody. Single-chain Variable Domain fragments are made by linking Light and Heavy chain Variable Domains using a short linking peptide. Linkers can be modified to provide additional functions, such as to permit the attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The invention also particularly encompasses PD-1× CTLA-4 bispecific molecules comprising humanized anti-PD-1 and anti-CTLA-4 antibodies. The term "humanized" antibody refers to a chimeric molecule, generally prepared using recombinant techniques, having an antigen-binding site of an immunoglobulin from a non-human species and a remaining immunoglobulin structure of the molecule that is based upon the structure and/or sequence of a human immunoglobulin. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains; (2) designing the humanized antibody or caninized antibody, i.e., deciding which antibody framework region to use during the humanizing or canonizing process; (3) the actual humanizing or caninizing methodologies/techniques; and (4) the transfection and expression of the humanized antibody. See, for example, U.S. Pat. Nos. 4,816,567; 5,807, 715; 5,866,692; and 6,331,415.

The antigen-binding site may comprise either a complete Variable Domain fused onto Constant Domains or only the complementarity determining regions (CDRs) of such Variable Domain grafted to appropriate framework regions. Antigen-binding sites may be wild-type or modified by one or more amino acid substitutions. This eliminates the constant region as an immunogen in human individuals, but the possibility of an immune response to the foreign variable domain remains (LoBuglio, A. F. et al. (1989) "*Mouse/ Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable domains as well so as to reshape them as closely as possible to human form. It is known that the variable domains of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of "humanized" antibody molecules comprising an antigen-binding site derived from a non-human immunoglobulin have been described, including chimeric antibodies having rodent or modified rodent Variable Domain and their associated complementarity determining regions (CDRs) fused to human constant domains (see, for example, Winter et al. (1991) "*Man-made Antibodies*," Nature 349:293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986)

"Replacing The Complementarity-Determining Regions In A Human Antibody With Those From A Mouse," Nature 321: 522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

II. Fcγ Receptors (FcγRs)

The CH2 and CH3 Domains of the two heavy chains interact to form the Fc Region, which is a domain that is recognized by cellular Fc Receptors, including but not limited to Fc gamma Receptors (FcγRs). As used herein, the term "Fc Region" is used to define a C-terminal region of an IgG heavy chain. The amino acid sequence of the CH2-CH3 Domain of an exemplary human IgG1 is (SEQ ID NO:1):

```
       231        240        250        260        270        280
       APELLGGPSV FLFPPKPKDT LMISRTPEVT CVVVDVSHED PEVKFNWYVD 290        300        310        320        330
       GVEVHNAKTK PREEQYNSTY RVVSVLTVLH QDWLNGKEYK CKVSNKALPA 340        350        360        370        380
       PIEKTISKAK GQPREPQVYT LPPSREEMTK NQVSLTCLVK GFYPSDIAVE 390        400        410        420        430
       WESNGQPENN YKTTPPVLDS DGSFFLYSKL TVDKSRWQQG NVFSCSVMHE 440    447
       ALHNHYTQKS LSLSPGX
``` as numbered by the EU index as set forth in Kabat, wherein X is a lysine (K) or is absent.

The amino acid sequence of the CH2-CH3 Domain of an exemplary human IgG2 is (SEQ ID NO:2):

```
       231        240        250        260        270        280
       APPVA-GPSV FLFPPKPKDT LMISRTPEVT CVVVDVSHED PEVQFNWYVD 290        300        310        320        330
       GVEVHNAKTK PREEQFNSTF RVVSVLTVVH QDWLNGKEYK CKVSNKGLPA 340        350        360        370        380
       PIEKTISKTK GQPREPQVYT LPPSREEMTK NQVSLTCLVK GFYPSDISVE 390        400        410        420        430
       WESNGQPENN YKTTPPMLDS DGSFFLYSKL TVDKSRWQQG NVFSCSVMHE 440    447
       ALHNHYTQKS LSLSPGX
``` as numbered by the EU index as set forth in Kabat, wherein X is a lysine (K) or is absent.

The amino acid sequence of the CH2-CH3 Domain of an exemplary human IgG3 is (SEQ ID NO:3):

```
       231        240        250        260        270        280
       APELLGGPSV FLFPPKPKDT LMISRTPEVT CVVVDVSHED PEVQFKWYVD 290        300        310        320        330
       GVEVHNAKTK PREEQYNSTF RVVSVLTVLH QDWLNGKEYK CKVSNKALPA 340        350        360        370        380
       PIEKTISKTK GQPREPQVYT LPPSREEMTK NQVSLTCLVK GFYPSDIAVE 390        400        410        420        430
       WESSGQPENN YNTTPPMLDS DGSFFLYSKL TVDKSRWQQG NIFSCSVMHE 440    447
       ALHNRFTQKS LSLSPGX
``` as numbered by the EU index as set forth in Kabat, wherein X is a lysine (K) or is absent.

The amino acid sequence of the CH2-CH3 Domain of an exemplary human IgG4 is (SEQ ID NO:4):

```
        231       240       250       260       270       280
        APEFLGGPSV FLFPPKPKDT LMISRTPEVT CVVVDVSQED PEVQFNWYVD 290       300       310       320       330
        GVEVHNAKTK PREEQFNSTY RVVSVLTVLH QDWLNGKEYK CKVSNKGLPS 340       350       360       370       380
        SIEKTISKAK GQPREPQVYT LPPSQEEMTK NQVSLTCLVK GFYPSDIAVE 390       400       410       420       430
        WESNGQPENN YKTTPPVLDS DGSFFLYSRL TVDKSRWQEG NVFSCSVMHE 440       447
        ALHNHYTQKS LSLSLGX
``` as numbered by the EU index as set forth in Kabat, wherein X is a lysine (K) or is absent.

Throughout the present specification, the numbering of the residues in the constant region of an IgG heavy chain is that of the EU index as in Kabat et al., SEQUENCES OF PROTEINS OF IMMUNOLOGICAL INTEREST, 5$^{th}$ Ed. Public Health Service, NH1, MD (1991) ("Kabat"), expressly incorporated herein by references. The term "EU index as in Kabat" refers to the numbering of the human IgG1 EU antibody. Amino acids from the Variable Domains of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid, and the CDRs are identified as defined by Kabat (it will be understood that CDR$_H$1 as defined by Chothia, C. & Lesk, A. M. ((1987) "Canonical structures for the hypervariable regions of immunoglobulins," J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "The Human IgG Subclasses: Molecular Analysis Of Structure, Function And Regulation." Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the PD-1×CTLA-4 bispecific molecules of the invention. Specifically encompassed by the instant invention are PD-1×CTLA-4 bispecific molecules lacking the C-terminal residue of the CH3 Domain. Also specifically encompassed by the instant invention are such constructs comprising the C-terminal lysine residue of the CH3 Domain.

As stated above, the Fc Region of natural IgG antibodies is capable of binding to cellular Fc gamma Receptors (FcγRs). Such binding results in the transduction of activating or inhibitory signals to the immune system. The ability of such binding to result in diametrically opposing functions reflects structural differences among the different FcγRs, and in particular reflects whether the bound FcγR possesses an immunoreceptor tyrosine-based activation motif (ITAM) or an immunoreceptor tyrosine-based inhibitory motif (ITIM). The recruitment of different cytoplasmic enzymes to these structures dictates the outcome of the FcγR-mediated cellular responses. ITAM-containing FcγRs include FcγRI, FcγRIIA, FcγRIIIA, and activate the immune system when bound to an Fc Region. FcγRIIB is the only currently known natural ITIM-containing FcγR; it acts to dampen or inhibit the immune system when bound to an Fc Region. Human neutrophils express the FcγRIIA gene. FcγRIIA clustering via immune complexes or specific antibody cross-linking serves to aggregate ITAMs with receptor-associated kinases which facilitate ITAM phosphorylation. ITAM phosphorylation serves as a docking site for Syk kinase, the activation of which results in the activation of downstream substrates (e.g., PI$_3$K). Cellular activation leads to release of pro-inflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular Ca'. Thus cross-linking of FcγRIIB dampens the activating response to FcγR ligation and inhibits cellular responsiveness. B-cell activation, B-cell proliferation and antibody secretion is thus aborted.

III. Bispecific Antibodies, Multispecific Diabodies and DART® Diabodies

The ability of an antibody to bind an epitope of an antigen depends upon the presence and amino acid sequence of the antibody's VL and VH Domains. Interaction of an antibody's Light Chain and Heavy Chain and, in particular, interaction of its VL and VH Domains forms one of the two epitope-binding sites of a natural antibody, such as an IgG. Natural antibodies are capable of binding to only one epitope species (i.e., they are monospecific), although they can bind multiple copies of that species (i.e., exhibiting bivalency or multivalency).

The binding domains of an antibody, and of the PD-1×CTLA-4 bispecific molecules of the present invention, bind to epitopes in an "immunospecific" manner. As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "immunospecific binding" does not necessarily require (although it can include) exclusive binding. Generally, but not necessarily, reference to binding means "immunospecific" binding. Two molecules are said to be capable of binding to one another in a "physiospecific" manner, if such binding exhibits the specificity with which receptors bind to their respective ligands.

One aspect of the present invention reflects the recognition that the functionality of antibodies can be enhanced by generating multispecific antibody-based molecules that can simultaneously bind to one or more epitope(s) of PD-1 and also one or more epitope(s) of CTLA-4. For molecules having more than one epitope-binding site immunospecific for an epitope of PD-1, such epitopes may be identical to one another, overlapping, or distinct from one another; binding to one such epitope may compete with or not compete with binding to another of such epitopes. Likewise, for molecules having more than one epitope-binding site immunospecific for an epitope of CTLA-4, such epitopes may be identical to one another, overlapping, or distinct from one another; binding to one such epitope may compete with or not compete with binding to the second of such epitopes. It is expressly contemplated that such characteristics may be independently varied to yield PD-1×CTLA-4 bispecific molecules that, for example, possess:

(1) the ability to bind to two identical epitopes of PD-1 and to:
  (a) two identical epitopes of CTLA-4; or
  (b) two overlapping epitopes of CTLA-4; or
  (c) two distinct epitopes of CTLA-4;
  or
(2) the ability to bind to two overlapping epitopes of PD-1 and to:
  (a) two identical epitopes of CTLA-4; or
  (b) two overlapping epitopes of CTLA-4; or
  (c) two distinct epitopes of CTLA-4;
  or
(3) the ability to bind to two distinct epitopes of PD-1 and to:
  (a) two identical epitopes of CTLA-4; or
  (b) two overlapping epitopes of CTLA-4; or
  (c) two distinct epitopes of CTLA-4.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use linker peptides either to fuse a further epitope-binding fragment (e.g., an scFv, VL, VH, etc.) to, or within the antibody core (IgA, IgD, IgE, IgG or IgM), or to fuse multiple epitope-binding fragments (e.g., two Fab fragments or scFvs). Alternative formats use linker peptides to fuse an epitope-binding fragment (e.g., an scFv, VL, VH, etc.) to a dimerization domain such as the CH2-CH3 Domain or alternative polypeptides (WO 2005/070966, WO 2006/107786A WO 2006/107617A, WO 2007/046893). PCT Publications Nos. WO 2013/174873, WO 2011/133886 and WO 2010/136172 disclose a trispecific antibody in which the CL and CH1 Domains are switched from their respective natural positions and the VL and VH Domains have been diversified (WO 2008/027236; WO 2010/108127) to allow them to bind to more than one antigen. PCT Publications Nos. WO 2013/163427 and WO 2013/119903 disclose modifying the CH2 Domain to contain a fusion protein adduct comprising a binding domain. PCT Publications Nos. WO 2010/028797, WO2010028796 and WO 2010/028795 disclose recombinant antibodies whose Fc Regions have been replaced with additional VL and VH Domains, so as to form trivalent binding molecules. PCT Publications Nos. WO 2003/025018 and WO2003012069 disclose recombinant diabodies whose individual chains contain scFv Domains. PCT Publications No. WO 2013/006544 discloses multivalent Fab molecules that are synthesized as a single polypeptide chain and then subjected to proteolysis to yield heterodimeric structures. PCT Publications Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another).

The art has additionally noted the capability to produce diabodies that differ from such natural antibodies in being capable of binding two or more different epitope species (i.e., exhibiting bispecificity or multispecificity in addition to bivalency or multivalency) (see, e.g., Holliger et al. (1993) "'*Diabodies': Small Bivalent And Bispecific Antibody Fragments,*" Proc. Natl. Acad. Sci. (U.S.A.) 90:6444-6448; US 2004/0058400 (Hollinger et al.); US 2004/0220388/WO 02/02781 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity,*" J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications,*" Protein Eng. Des. Sel. 17(1):21-27; Wu, A. et al. (2001) "*Multimerization Of A Chimeric Anti-CD20 Single Chain Fv-Fv Fusion Protein Is Mediated Through Variable Domain Exchange,*" Protein Engineering 14(2):1025-1033; Asano et al. (2004) "*A Diabody For Cancer Immunotherapy And Its Functional Enhancement By Fusion*

Of Human Fc Domain," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

The design of a diabody is based on the antibody derivative known as a single-chain Variable Domain fragment (scFv). Such molecules are made by linking Light and/or Heavy Chain Variable Domains using a short linking peptide. Bird et al. (1988) ("*Single-Chain Antigen-Binding Proteins*," Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen Binding Proteins*," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The provision of bispecific binding molecules (e.g., non-monospecific diabodies) provides a significant advantage over antibodies, including but not limited to, a "trans" binding capability sufficient to co-ligate and/or co-localize different cells that express different epitopes and/or a "cis" binding capability sufficient to co-ligate and/or co-localize different molecules expressed by the same cell. Bispecific binding molecules (e.g., non-monospecific diabodies) thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221).

The ability to produce bispecific diabodies has led to their use (in "trans") to co-ligate two cells together, for example, by co-ligating receptors that are present on the surface of different cells (e.g., cross-linking cytotoxic T-cells to tumor cells) (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305; Marvin et al. (2005) "*Recombinant Approaches To IgG-Like Bispecific Antibodies*," Acta Pharmacol. Sin. 26:649-658). Alternatively, or additionally, bispecific diabodies can be used (in "cis") to co-ligate molecules, such as receptors, etc., that are present on the surface of the same cell. Co-ligation of different cells and/or receptors is useful to modulation effector functions and/or immune cell signaling. However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8):583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8):583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bispecific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies, termed DART® (Dual Affinity Re-Targeting Reagents) diabodies; see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; and Sloan, D. D. et al. (2015) "*Targeting HIV Reservoir in Infected CD4 T Cells by Dual-Affinity Retargeting Molecules (DARTs) that Bind HIV Envelope and Recruit Cytotoxic T Cells*," PLoS Pathog. 11(11):e1005233. doi: 10.1371/journal.ppat.1005233; Al Hussaini, M. et al. (2015) "*Targeting CD123 In AML Using A T-Cell Directed Dual-Affinity Re-Targeting (DART®) Platform*," Blood pii: blood-2014-05-575704; Chichili, G. R. et al. (2015) "*A CD3×CD123 Bispecific DART For Redirecting Host T Cells To Myelogenous Leukemia: Preclinical Activity And Safety In Nonhuman Primates*," Sci. Transl. Med. 7(289):289ra82; Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor Iib*

(CD32B) Inhibitory Function With A Novel Bispecific Antibody Scaffold," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond one or more pairs of such polypeptide chains to one another. For example, the addition of a cysteine residue to the C-terminus of such constructs has been shown to allow disulfide bonding between the involved polypeptide chains, stabilizing the resulting diabody without interfering with the diabody's binding characteristics.

Many variations of such molecules have been described (see, e.g., United States Patent Publications No. 2015/0175697; 2014/0255407; 2014/0099318; 2013/0295121; 2010/0174053; 2009/0060910; 2007-0004909; European Patent Publication No. EP 2714079; EP 2601216; EP 2376109; EP 2158221; EP 1868650; and PCT Publications No. WO 2012/162068; WO 2012/018687; WO 2010/080538; WO 2006/113665) and are provided herein.

Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700) which are formed by the homo-dimerization of two identical chains each possessing a VH1, VL2, VH2, and VL2 Domain.

IV. Preferred PD-1×CTLA-4 Bispecific Molecules

One embodiment of the present invention relates to PD-1×CTLA-4 bispecific molecules that are capable of binding to a "first epitope" and a "second epitope," such epitopes not being identical to one another. Such bispecific molecules comprise "VL1"/"VH1" domains that are capable of binding to the first epitope and "VL2"/"VH2" domains that are capable of binding to the second epitope. The notations "VL1" and "VH1" denote, respectively, the Light Chain Variable Domain and Heavy Chain Variable Domain that bind the "first" epitope of such bispecific molecules. Similarly, the notations "VL2" and "VH2" denote, respectively, the Light Chain Variable Domain and Heavy Chain Variable Domain that bind the "second" epitope of such bispecific molecules. It is irrelevant whether a particular epitope is designated as the first vs. the second epitope; such notations having relevance only with respect to the presence and orientation of domains of the polypeptide chains of the binding molecules of the present invention. In one embodiment, one of such epitopes is an epitope of human PD-1 and the other of such epitopes is an epitope of CTLA-4. In certain embodiments, a bispecific molecule comprises more than two epitope-binding sites. Such bispecific molecules will bind at least one epitope of PD-1 and at least one epitope of CTLA-4 and may further bind additional epitopes of PD-1 and/or additional epitopes of CTLA-4.

The present invention particularly relates to PD-1×CTLA-4 bispecific molecules (e.g., bispecific antibodies, bispecific diabodies, trivalent binding molecules, etc.) that possess epitope-binding fragments of antibodies that enable them to be able to coordinately bind to at least one epitope of PD-1 and at least on epitope of CTLA-4. Selection of the VL and VH Domains of the polypeptide domains of such molecules is coordinated such that the VL Domain and VH Domain of the same polypeptide chain are not capable of forming an epitope-binding site capable of binding either PD-1 or CTLA-4. Such selection is additionally coordinated so that polypeptides chains that make up such PD-1× CTLA-4 bispecific molecules assemble to form at least one functional antigen binding site that is specific for at least one epitope of PD-1 and at least one functional antigen binding site that is specific for at least one epitope of CTLA-4.

The present invention particularly relates to such PD-1× CTLA-4 bispecific molecules that exhibit an activity that is enhanced relative to such activity of two monospecific molecules one of which possesses the Heavy Chain Variable Domain and the Light Chain Variable Domain of the antibody that binds PD-1 and the other of which possesses the Heavy Chain Variable Domain and the Light Chain Variable Domain of the antibody that binds CTLA-4. Examples of such activity includes attenuating the activity of PD-1, attenuating the activity of CTLA-4, enhancing immune system activation, enhancing effector function, enhancing anti-tumor activity. As used herein, such attenuation of activity refers to a decrease of 10% or more, a decrease of 20% or more, a decrease of 50% or more, a decrease of 80% or more, or a decrease of 90% or more in a PD-1 and/or CTLA-4 inhibitory activity, or the complete elimination of such PD-1 and/or CTLA-4 inhibitory activity. As used herein, such enhancement of activity refers to an enhancement of 10% or more, an enhancement of 20% or more, an enhancement of 50% or more, an enhancement of 80% or more, or an enhancement of 90% or more in an immune system-activating activity mediated by or affected by the expression or presence of PD-1 and/or CTLA-4, relative to the activity exhibited by two monospecific molecules one of which possesses the Heavy Chain Variable Domain and the Light Chain Variable Domain of the antibody that binds PD-1 and the other of which possesses the Heavy Chain Variable Domain and the Light Chain Variable Domain of the antibody that binds CTLA-4. Examples of immune system-activating activity include, but are not limited to immune cell (e.g., T-lymphocyte, NK-cell) proliferation, immune cell production and/or release of cytokines, immune cell production and/or release of lytic molecules (e.g., granzyme, perforin, etc.), and/or immune cell expression of activation markers. Cytokines which are released upon activation of the immune system are known in the art and include, but are not limited to: IFNγ, IL-2, and TNFα, (see, e.g., Janeway, C. A. et al. 2011) IMMUNOBIOLOGY" 8th ed. Garland Science Publishing, NY; Banyer, J. L. (2000) "*Cytokines in innate and adaptive immunity*," Rev Immunogenet. 2:359-373). Activation markers expressed by immune cells are known in the art and include, but are not limited to, CD69, CD25, and CD107a (see, e.g., Janeway, C. A. et al. (2011) IMMUNOBIOLOGY" 8th ed. Garland Science Publishing, NY; Shipkova, M. and Wieland, E. (2012) "*Surface markers of lymphocyte activation and markers of cell proliferation*," Clin Chim Acta 413:1338-1349).

A. PD-1×CTLA-4 Bispecific Antibodies

The instant invention encompasses bispecific antibodies capable of simultaneously binding to PD-1 and CTLA-4. In some embodiments, the bispecific antibody capable of simultaneously binding to PD-1 and CTLA-4 is produced using any of the methods described in PCT Publications No. WO 1998/002463, WO 2005/070966, WO 2006/107786 WO 2007/024715, WO 2007/075270, WO 2006/107617, WO 2007/046893, WO 2007/146968, WO 2008/003103, WO 2008/003116, WO 2008/027236, WO 2008/024188, WO 2009/132876, WO 2009/018386, WO 2010/028797, WO2010028796, WO 2010/028795, WO 2010/108127, WO 2010/136172, WO 2011/086091, WO 2011/133886, WO 2012/009544, WO 2013/003652, WO 2013/070565, WO 2012/162583, WO 2012/156430, WO 2013/174873, and WO 2014/022540, each of which is hereby incorporated herein by reference in its entirety.

B. PD-1×CTLA-4 Bispecific Diabodies Lacking Fc Regions

One embodiment of the present invention relates to bispecific diabodies that comprise, and most preferably are composed of, a first polypeptide chain and a second polypeptide chain, whose sequences permit the polypeptide chains to covalently bind to each other to form a covalently associated diabody that is capable of simultaneously binding to PD-1 and to CTLA-4.

The first polypeptide chain of such an embodiment of bispecific diabodies comprises, in the N-terminal to C-terminal direction, an N-terminus, the VL Domain of a monoclonal antibody capable of binding to either PD-1 or CTLA-4 (i.e., either $VL_{PD-1}$ or $VL_{CTLA-4}$), a first intervening spacer peptide (Linker 1), a VH Domain of a monoclonal antibody capable of binding to either CTLA-4 (if such first polypeptide chain contains $VL_{PD-1}$) or PD-1 (if such first polypeptide chain contains $VL_{CTLA-4}$), a second intervening spacer peptide (Linker 2) optionally containing a cysteine residue, a Heterodimer-Promoting Domain and a C-terminus (FIG. 1).

The second polypeptide chain of this embodiment of bispecific diabodies comprises, in the N-terminal to C-terminal direction, an N-terminus, a VL Domain of a monoclonal antibody capable of binding to either PD-1 or CTLA-4 (i.e., either $VL_{PD-1}$ or $VL_{CTLA-4}$, and being the VL Domain not selected for inclusion in the first polypeptide chain of the diabody), an intervening spacer peptide (Linker 1), a VH Domain of a monoclonal antibody capable of binding to either CTLA-4 (if such second polypeptide chain contains $VL_{PD-1}$) or to PD-1 (if such second polypeptide chain contains $VL_{CTLA-4}$), a second intervening spacer peptide (Linker 2) optionally containing a cysteine residue, a Heterodimer-Promoting Domain, and a C-terminus (FIG. 1).

The VL Domain of the first polypeptide chain interacts with the VH Domain of the second polypeptide chain to form a first functional antigen-binding site that is specific for a first antigen (i.e., either PD-1 or CTLA-4). Likewise, the VL Domain of the second polypeptide chain interacts with the VH Domain of the first polypeptide chain in order to form a second functional antigen-binding site that is specific for a second antigen (i.e., either CTLA-4 or PD-1). Thus, the selection of the VL and VH Domains of the first and second polypeptide chains is coordinated, such that the two polypeptide chains of the diabody collectively comprise VL and VH Domains capable of binding to both an epitope of PD-1 and to an epitope of CTLA-4 (i.e., they collectively comprise $VL_{PD-1}/VH_{PD-1}$ and $VL_{CTLA-4}/VH_{CTLA-4}$).

Most preferably, the length of the intervening linker peptide (Linker 1, which separates such VL and VH Domains) is selected to substantially or completely prevent the VL and VH Domains of the polypeptide chain from binding to one another (for example consisting of from 0, 1, 2, 3, 4, 5, 6, 7, 8 or 9 intervening linker amino acid residues). Thus the VL and VH Domains of the first polypeptide chain are substantially or completely incapable of binding to one another. Likewise, the VL and VH Domains of the second polypeptide chain are substantially or completely incapable of binding to one another. A preferred intervening spacer peptide (Linker 1) has the sequence (SEQ ID NO:5): GGGSGGGG.

The length and composition of the second intervening spacer peptide (Linker 2) is selected based on the choice of one or more polypeptide domains that promote such dimerization (i.e., a "Heterodimer-Promoting Domain"). Typically, the second intervening spacer peptide (Linker 2) will comprise 3-20 amino acid residues. In particular, where the employed Heterodimer-Promoting Domain(s) do/does not comprise a cysteine residue a cysteine-containing second intervening spacer peptide (Linker 2) is utilized. A cysteine-containing second intervening spacer peptide (Linker 2) will contain 1, 2, 3 or more cysteines. A preferred cysteine-containing spacer peptide (Linker 2) has the sequence is SEQ ID NO:6: GGCGGG. Alternatively, Linker 2 does not comprise a cysteine (e.g., GGG, GGGS (SEQ ID NO:7), LGGGSG (SEQ ID NO:8), GGGSGGGSGGG (SEQ ID NO:9), ASTKG (SEQ ID NO:10), LEPKSS (SEQ ID NO:11), APSSS (SEQ ID NO:12), etc.) and a Cysteine-Containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:13) or VEPKSC (SEQ ID NO:14) or AEPKSC (SEQ ID NO:15) on one polypeptide chain and GFNRGEC (SEQ ID NO:16) or FNRGEC (SEQ ID NO:17) on the other polypeptide chain (US2007/0004909).

In a preferred embodiment, the Heterodimer-Promoting Domains will comprise tandemly repeated coil domains of opposing charge for example, "E-coil" helical domains (SEQ ID NO:18: EVAALEK-EVAALEK-EVAALEK-EVAALEK), whose glutamate residues will form a negative charge at pH 7, and "K-coil" domains (SEQ ID NO:19: KVAALKE-KVAALKE-KVAALKE-KVAALKE), whose lysine residues will form a positive charge at pH 7. The presence of such charged domains promotes association between the first and second polypeptides, and thus fosters heterodimer formation. Heterodimer-Promoting Domains that comprise modifications of the above-described E-coil and K-coil sequences so as to include one or more cysteine residues may be utilized. The presence of such cysteine residues permits the coil present on one polypeptide chain to become covalently bonded to a complementary coil present on another polypeptide chain, thereby covalently bonding the polypeptide chains to one another and increasing the stability of the diabody. Examples of such particularly preferred are Heterodimer-Promoting Domains include a Modified E-Coil having the amino acid sequence EVAACEK-EVAALEK-EVAALEK-EVAALEK (SEQ ID NO:20), and a modified K-coil having the amino acid sequence KVAACKE-KVAALKE-KVAALKE-KVAALKE (SEQ ID NO:21).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules*," J. Biol. Chem. 277(10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:22): LAEAKVLANR ELDKYGVSDY YKNLID-NAKS AEGVKALIDE ILAALP.

As disclosed in WO 2012/162068 (herein incorporated by reference), "deimmunized" variants of SEQ ID NO:22 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

```
                                        (SEQ ID NO: 23)
LAEAKVLANR ELDKYGVSDY YKNLID66NAKS70 A71EGVKALIDE

ILAALP,
``` or the amino acid sequence:

```
                                        (SEQ ID NO: 24)
LAEAKVLANR ELDKYGVSDY YKNA64A65NNAKT VEGVKALIA79E

ILAALP,
``` or the amino acid sequence:

```
                                        (SEQ ID NO: 25)
LAEAKVLANR ELDKYGVSDY YKNLIS66NAKS70 VEGVKALIA79E

ILAALP,
``` are particularly preferred as such deimmunized ABD exhibit substantially wild-type binding while providing attenuated MHC class II binding. Thus, the first polypeptide chain of such a diabody having an ABD contains a third linker (Linker 3) preferably positioned C-terminally to the E-coil (or K-coil) Domain of such polypeptide chain so as to intervene between the E-coil (or K-coil) Domain and the ABD (which is preferably a deimmunized ABD). A preferred sequence for such Linker 3 is SEQ ID NO:7: GGGS.

C. PD-1×CTLA-4 Bispecific Diabodies Containing Fc Regions

Figure 2:
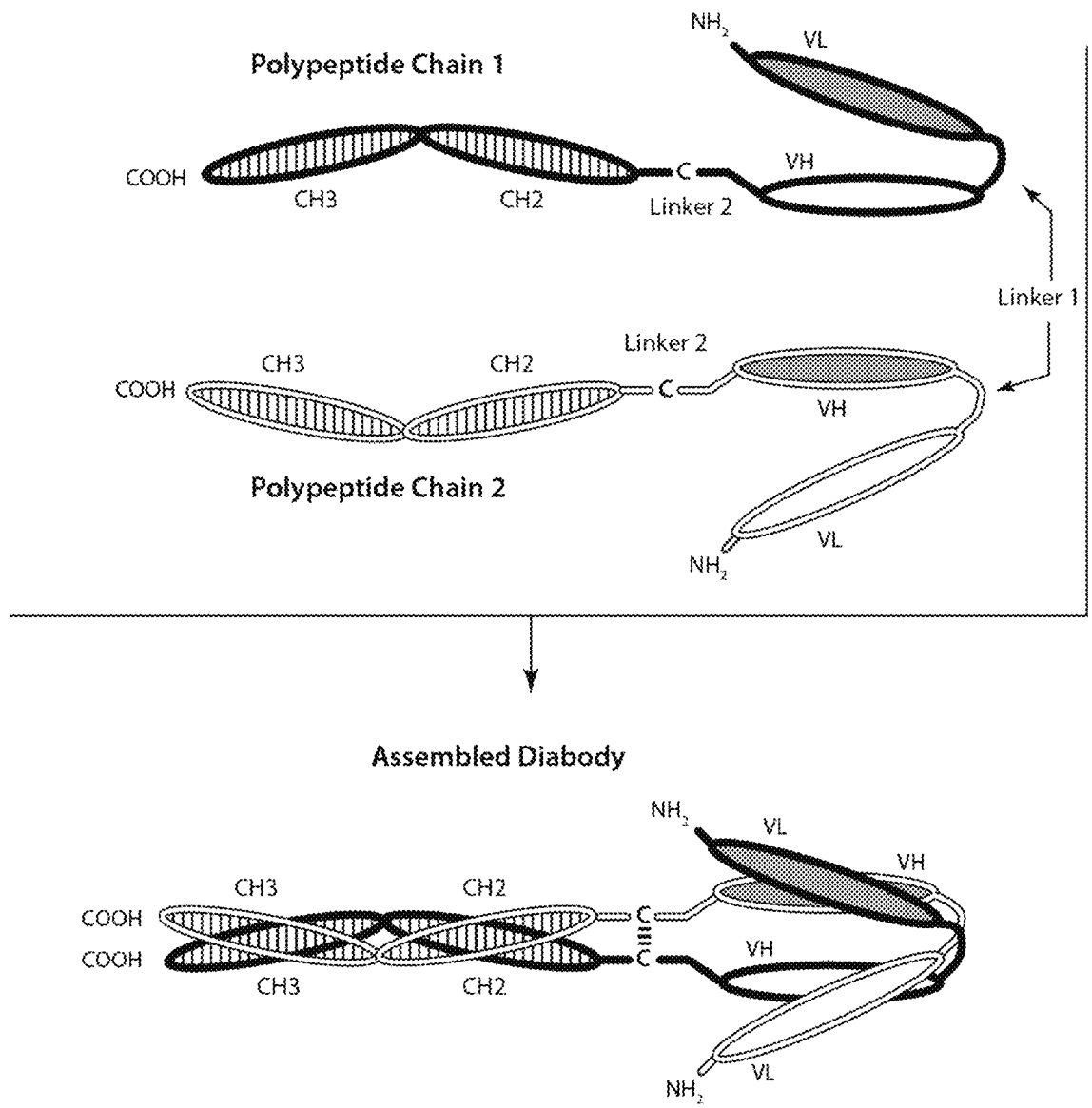
FIG. 2 provides a schematic of a representative covalently bonded diabody molecule having two epitope-binding sites composed of two polypeptide chains, each having a CH2 and CH3 Domain, such that the associated chains form all or part of an Fc Region. VL and VH Domains that recognize the same epitope are shown using the same shading or fill pattern.

One embodiment of the present invention relates to bispecific diabodies capable of simultaneously binding to PD-1 and CTLA-4 that comprise an Fc Region. The addition of an IgG CH2-CH3 Domain to one or both of the diabody polypeptide chains, such that the complexing of the diabody chains results in the formation of an Fc Region, increases the biological half-life and/or alters the valency of the diabody. Incorporating an IgG CH2-CH3 Domains onto both of the diabody polypeptides will permit a two-chain bispecific Fc-Region-containing diabody to form (FIG. 2).

Figure 3A:
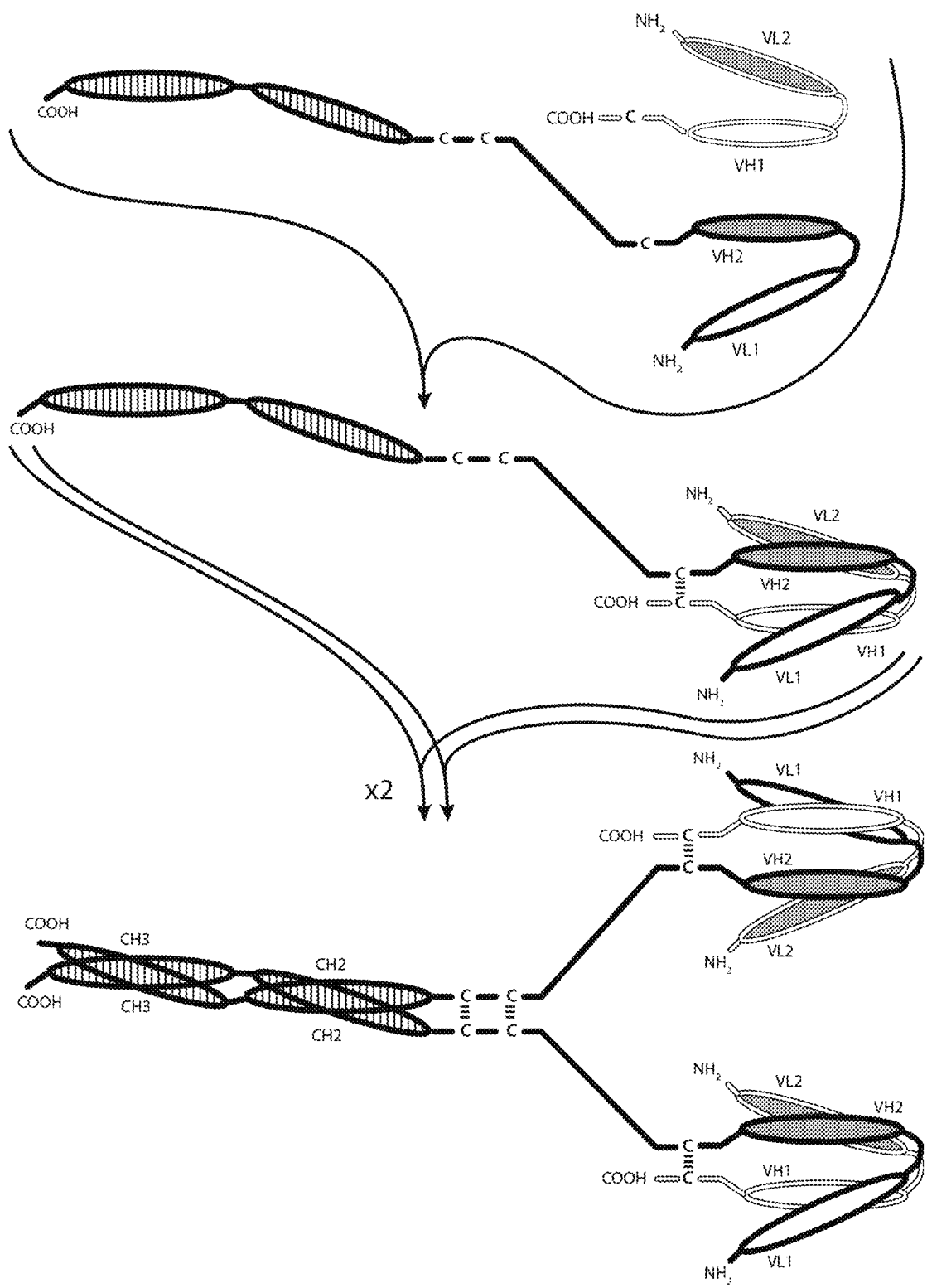
FIGS. 3A-3C provide schematics showing representative covalently bonded tetravalent diabodies having four epitope-binding sites composed of two pairs of polypeptide chains (i.e., four polypeptide chains in all). One polypeptide of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments wherein the two pairs of polypeptide chains are the same and the VL and VH Domains recognize different epitopes (as shown in FIGS. 3A-3B), the resulting molecule possesses four epitope-binding sites and is bispecific and bivalent with respect to each bound epitope. In such embodiments wherein the VL and VH Domains recognize the same epitope (e.g., the same VL Domain CDRs and the same VH Domain CDRs are used on both chains) the resulting molecule possesses four epitope-binding sites and is monospecific and tetravalent with respect to a single epitope. Alternatively, the two pairs of polypeptides may be different. In such embodiments wherein the two pairs of polypeptide chains are different and the VL and VH Domains of each pair of polypeptides recognize different epitopes (as shown by the different shading and patterns in FIG. 3C), the resulting molecule possesses four epitope-binding sites and is tetraspecific and monovalent with respect to each bound epitope.
Figure 3B:
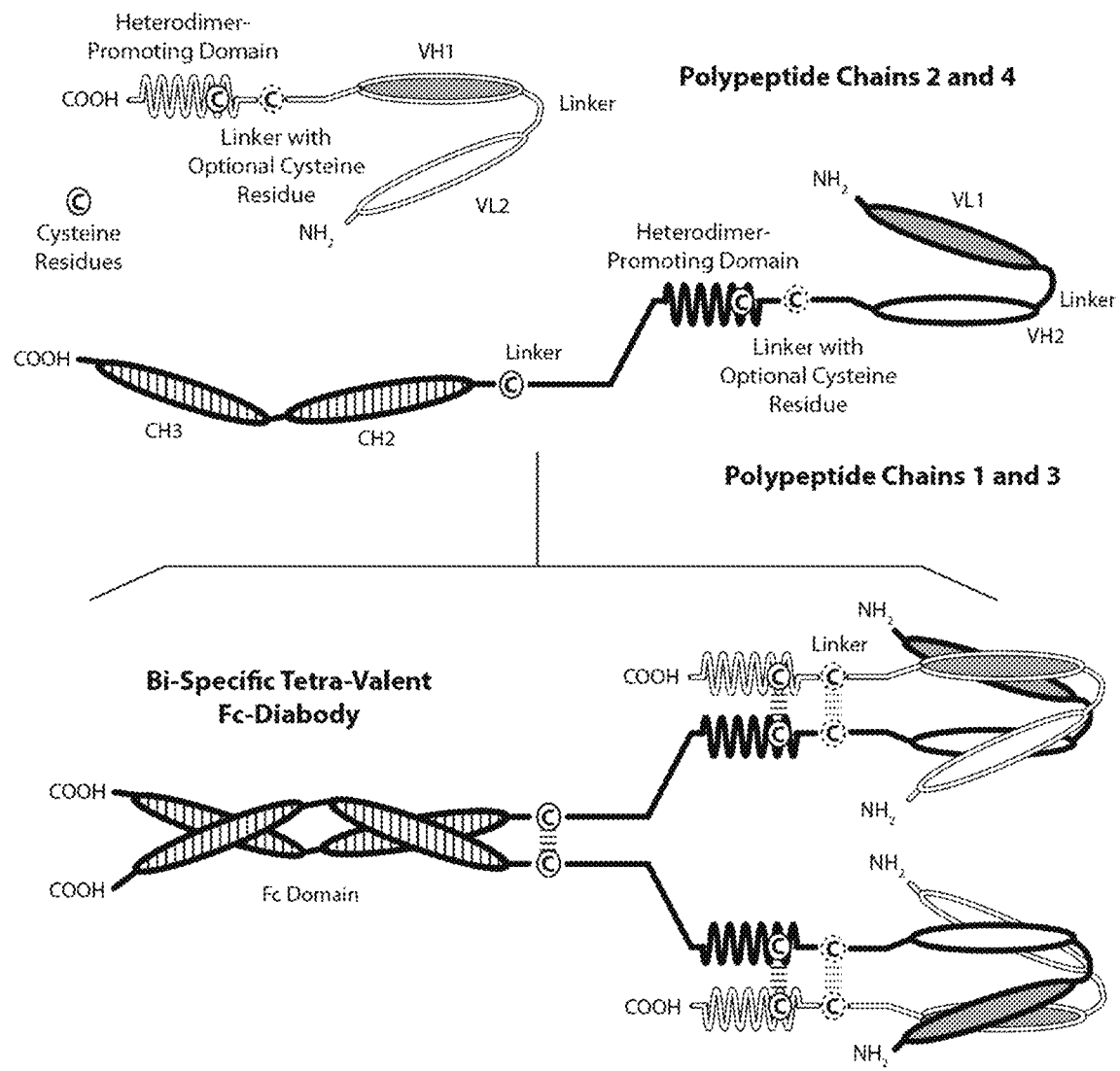
Figure 3C:
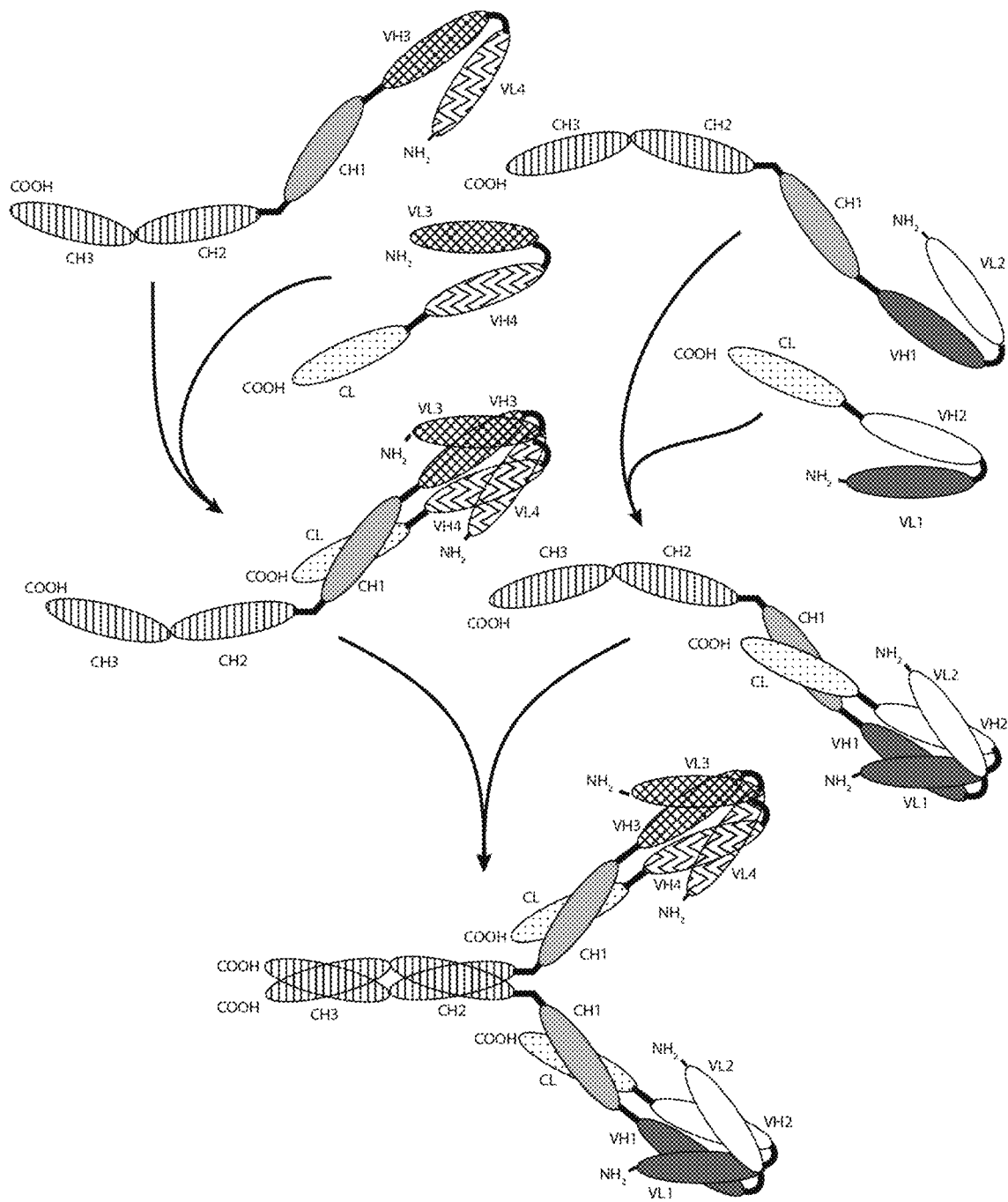

Alternatively, incorporating an IgG CH2-CH3 Domains onto only one of the diabody polypeptides will permit a more complex four-chain bispecific Fc Region-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B, United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). Thus, for example, in lieu of the CH1 Domain, one may employ a peptide having the amino acid sequence GVEPKSC (SEQ ID NO:13) VEPKSC (SEQ ID NO:14), or AEPKSC (SEQ ID NO:15), derived from the Hinge Region of a human IgG, and in lieu of the CL Domain, one may employ the C-terminal 6 amino acids of the human kappa light chain, GFNRGEC (SEQ ID NO:16) or FNRGEC (SEQ ID NO:17). A representative peptide containing four-chain diabody is shown in FIG. 3A. Alternatively, or in addition, one may employ a peptide comprising tandem coil domains of opposing charge such as the "E-coil" helical domains (SEQ ID NO:18: EVAALEK-EVAALEK-EVAALEK-EVAALEK or SEQ ID NO:19: EVAACEK-EVAALEK-EVAALEK-EVAALEK); and the "K-coil" domains (SEQ ID NO:20: KVAALKE-KVAAL KE-KVAALKE-KVAALKE or SEQ ID NO:21: KVAA CKE-KVAALKE-KVAALKE-KVAALKE). A representative coil domain-containing four-chain diabody is shown in FIG. 3B.

The bispecific Fc Region-containing molecules of the present invention may include additional intervening spacer peptides (Linkers), generally such Linkers will be incorporated between a peptide Heterodimer-Promoting Domain (e.g., an E-coil or K-coil) and CH2-CH3 Domains and/or between CH2-CH3 Domains and a Variable Domain (i.e., VH or VL). Typically, the additional Linkers will comprise 3-20 amino acid residues. Linkers that may be employed in the bispecific Fc Region-containing diabody molecules of the present invention include: GGGS (SEQ ID NO:7), LGGGSG (SEQ ID NO:8), GGGSGGGSGGG (SEQ ID NO:9), ASTKG (SEQ ID NO:10), DKTHTCPPCP (SEQ ID NO:26), EPKSCDKTHTCPPCP (SEQ ID NO:27), LEPKSS (SEQ ID NO:11), APSSS (SEQ ID NO:28), and APSSSPME (SEQ ID NO:29), LEPKSADKTHTCPPC SEQ ID NO:30), GGC, and GGG. SEQ ID NO:11 may be used in lieu of GGG or GGC for ease of cloning. Additionally, the amino acids GGG, or SEQ ID NO:11 may be immediately followed by SEQ ID NO:26 to form the alternate linkers: GGGDKTHTCPPCP (SEQ ID NO:31); and LEP-KSSDKTHTCPPCP (SEQ ID NO:32). Bispecific Fc Region-containing molecules of the present invention may incorporate an IgG Hinge Region in addition to or in place of a linker. Exemplary Hinge Regions include: EPKSCDKTHTCPPCP (SEQ ID NO:33) from IgG1, ERKCCVECPPCP (SEQ ID NO:34) from IgG2, ESKY-GPPCPSCP (SEQ ID NO:35) from IgG4, and ESKY-GPPCPPCP (SEQ ID NO:36) an IgG4 hinge variant comprising a stabilizing S228P substitution (as numbered by the EU index as set forth in Kabat) to reduce strand exchange.

As provided in FIG. 3A-3C, bispecific Fc Region-containing diabodies of the invention may comprise four different chains. The first and third polypeptide chains of such a diabody contain three domains: (i) a VL1-containing Domain, (ii) a VH2-containing Domain, (iii) Heterodimer-Promoting Domain and (iv) a Domain containing a CH2-CH3 sequence. The second and fourth polypeptide chains contain: (i) a VL2-containing Domain, (ii) a VH1-containing Domain and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The notations "VL3" and "VH3" denote, respectively, the Light Chain Variable Domain and Variable Heavy Chain Domain that bind a "third" epitope of such diabody. Similarly, the notations "VL4" and "VH4" denote, respectively, the Light Chain Variable Domain and Variable Heavy Chain Domain that bind a "fourth" epitope of such diabody. The general structure of the polypeptide chains of a representative four-chain bispecific Fc Region-containing diabodies of invention is provided in Table 1:

TABLE 1

| Bispecific | $2^{nd}$ Chain | $NH_2$-VL2-VH1-HPD-COOH |
|---|---|---|
| | $1^{st}$ Chain | $NH_2$-VL1-VH2-HPD-CH2—CH3—COOH |
| | $1^{st}$ Chain | $NH_2$-VL1-VH2-HPD-CH2—CH3—COOH |
| | $2^{nd}$ Chain | $NH_2$-VL2-VH1-HPD-COOH |
| Tetraspecific | $2^{nd}$ Chain | $NH_2$-VL2-VH1-HPD-COOH |
| | $1^{st}$ Chain | $NH_2$-VL1-VH2-HPD-CH2—CH3—COOH |
| | $3^{rd}$ Chain | $NH_2$-VL3-VH4-HPD-CH2—CH3—COOH |
| | $4^{th}$ Chain | $NH_2$-VL4-VH3-HPD-COOH |

HPD = Heterodimer-Promoting Domain

In a specific embodiment, diabodies of the present invention are bispecific, tetravalent (i.e., possess four epitope-binding sites), Fc-containing diabodies that are composed of four total polypeptide chains (FIGS. 3A-3C). The bispecific, tetravalent, Fc-containing diabodies of the invention comprise two epitope-binding sites immunospecific for PD-1 (which may be capable of binding to the same epitope of PD-1 or to different epitopes of PD-1), and two epitope-binding sites immunospecific for CTLA-4 (which may be capable of binding to the same epitope of CTLA-4 or to different epitopes of CTLA-4).

Figure 4A:
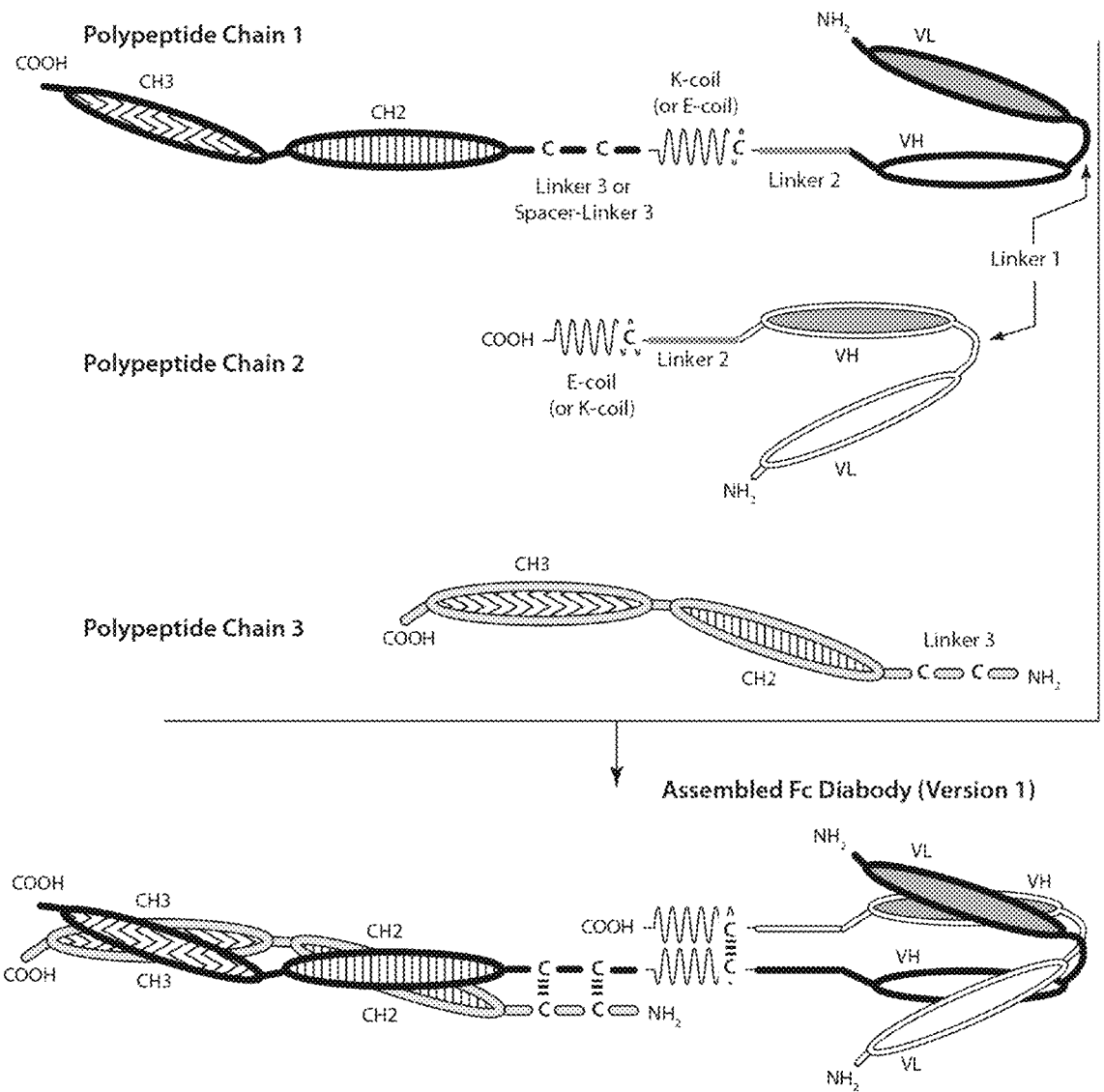
FIGS. 4A and 4B provide schematics of a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain. VL and VH Domains that recognize the same epitope are shown using the same shading or fill pattern.
Figure 4B:
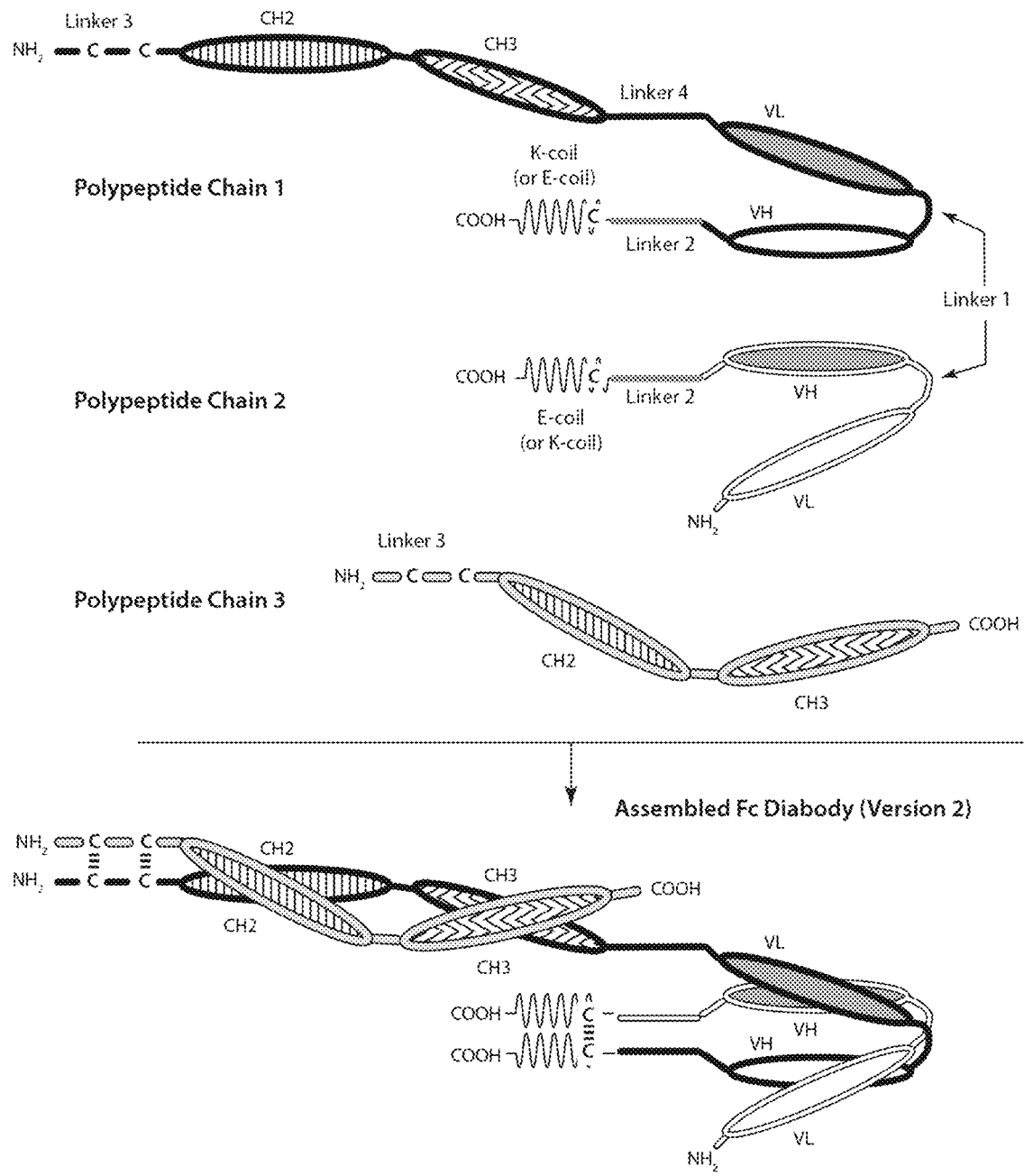

In a further embodiment, the bispecific Fc Region-containing diabodies may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such a diabody contains: (i) a VL2-containing Domain, (ii) a VH1-containing Domain and (iii) a Domain that promotes heterodimerization and covalent bonding with the diabody's first polypeptide chain. The third polypeptide of such a diabody comprises a CH2-CH3 sequence. Thus, the first and second polypeptide chains of such a diabody associate together to form a VL1/VH1 binding site that is capable of binding to the first epitope (i.e., either PD-1 or CTLA-4), as well as a VL2/VH2 binding site that is capable of binding to the second epitope (i.e., either CTLA-4 or PD-1). The first and second polypeptides are bonded to one another through a disulfide bond involving cysteine residues in their respective Third Domains. Notably, the first and third polypeptide chains complex with one another to form an Fc Region that is stabilized via a disulfide bond. Such bispecific diabodies have enhanced potency. FIGS. 4A and 4B illustrate the structures of such diabodies. Such Fc-Region-containing bispecific diabodies may have either of two orientations (Table 2):

TABLE 2

| First Orientation | $3^{rd}$ Chain | $NH_2$—CH2—CH3—COOH |
|---|---|---|
| | $1^{st}$ Chain | $NH_2$-VL1-VH2-HPD-CH2—CH3—COOH |
| | $2^{nd}$ Chain | $NH_2$-VL2-VH1-HPD-COOH |
| Second Orientation | $3^{rd}$ Chain | $NH_2$—CH2—CH3—COOH |
| | $1^{st}$ Chain | $NH_2$—CH2—CH3-VL1-VH2-HPD-COOH |
| | $2^{nd}$ Chain | $NH_2$-VL2-VH1-HPD-COOH |

HPD = Heterodimer-Promoting Domain

In a specific embodiment, diabodies of the present invention are bispecific, bivalent (i.e., possess two epitope-binding sites), Fc-containing diabodies that are composed of three total polypeptide chains (FIGS. 4A-4B). The bispecific, bivalent Fc-containing diabodies of the invention comprise one epitope-binding site immunospecific for PD-1, and one epitope-binding site specific for CTLA-4.

In a further embodiment, the bispecific Fc Region-containing diabodies may comprise a total of five polypeptide chains. In a particular embodiment, two of the five polypeptide chains have the same amino acid sequence. The first polypeptide chain of such a diabody contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such a diabody contain: (i) a VL1-containing domain, and (ii) a CL-containing domain. The second and/or fifth polypeptide chains of such a diabody may be light chains of an antibody that contains a VL1 complementary to the VH1 of the first/third polypeptide chain. The first, second and/or fifth polypeptide chains may be isolated from a naturally occurring antibody. Alternatively, they may be constructed recombinantly. The third polypeptide chain of such a diabody contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Figure 5:
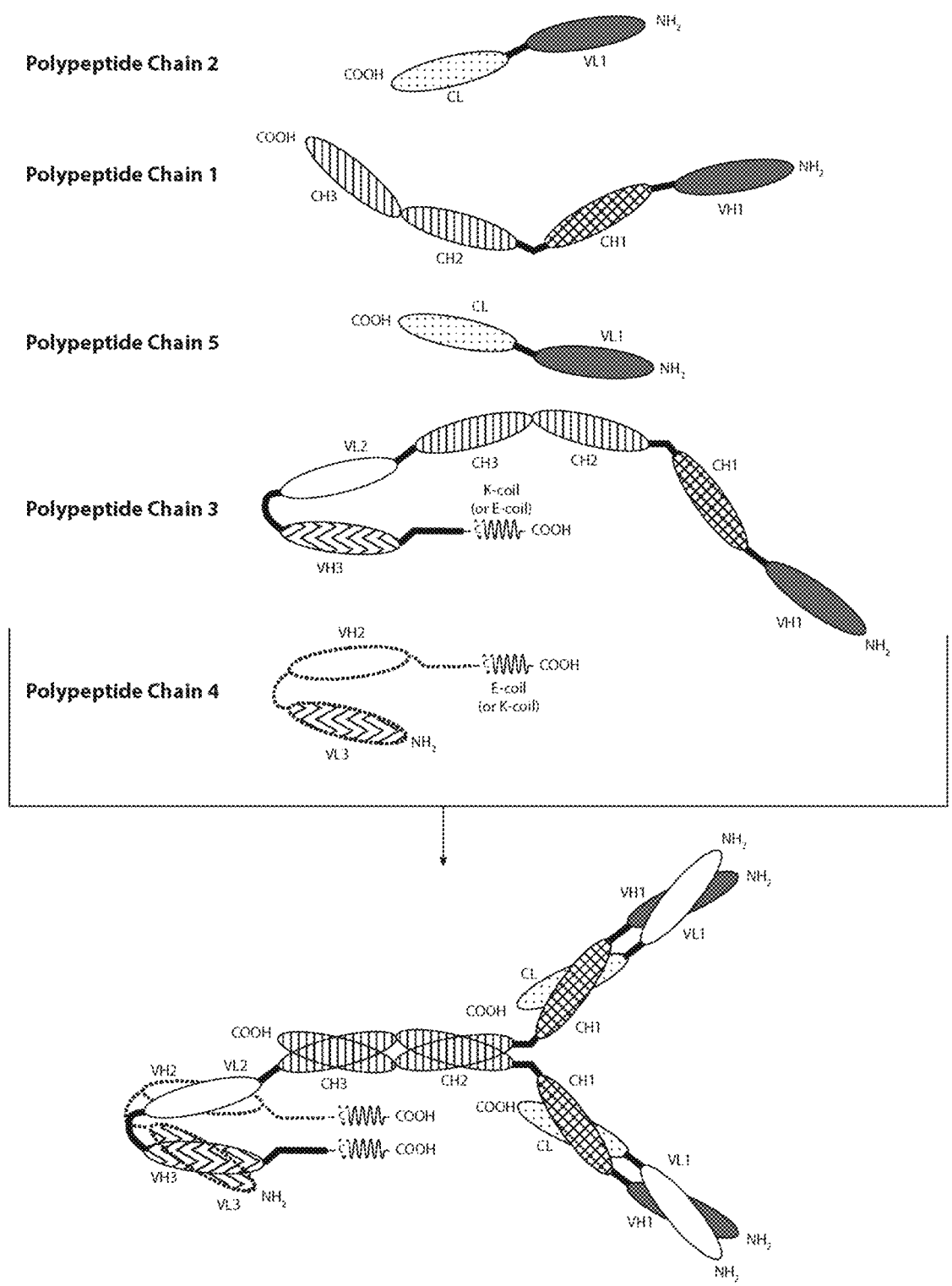
FIG. 5 provides the schematics of a representative covalently bonded diabody molecule having four epitope-binding sites composed of five polypeptide chains. Two of the polypeptide chains possess a CH2 and CH3 Domain, such that the associated chains form an Fc Region that comprises all or part of an Fc Region. The polypeptide chains comprising the linked VL and VH Domains further comprise a Heterodimer-Promoting Domain. VL and VH Domains that recognize the same epitope are shown using the same shading or fill pattern.

Thus, the first and second, and the third and fifth, polypeptide chains of such diabodies associate together to form two VL1/VH1 binding sites capable of binding a first epitope. The third and fourth polypeptide chains of such diabodies associate together to form a VL2/VH2 binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Region. Such bispecific diabodies have enhanced potency. FIG. 5 illustrates the structure of such diabodies. It will be understood that the VL1/VH1, VL2/VH2, and VL3/VH3 Domains may be the same or different so as to permit binding that is monospecific, bispecific or trispecific. However, as provided herein, these domains are preferably selected so as to bind PD-1 and CTLA-4.

The VL and VH Domains of the polypeptide chains are selected so as to form VL/VH binding sites specific for a desired epitope. The VL/VH binding sites formed by the association of the polypeptide chains may be the same or different so as to permit tetravalent binding that is monospecific, bispecific, trispecific or tetraspecific. In particular, the VL and VH Domains may be selected such that a bispecific diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 5). The general structure of the polypeptide chains of representative five-chain Fc Region-containing diabodies of invention is provided in Table 3:

TABLE 3

| | | |
|---|---|---|
| Bispecific (2 × 2) | 2$^{nd}$ Chain | NH$_2$-VL1-CL-COOH |
| | 1$^{st}$ Chain | NH$_2$-VH1-CH1—CH2—CH3—COOH |
| | 3$^{rd}$ Chain | NH$_2$-VH1-CH1—CH2—CH3-VL2-VH2-HPD-COOH |
| | 5$^{nd}$ Chain | NH$_2$-VL1-CL-COOH |
| | 4$^{th}$ Chain | NH$_2$-VL2-VH2-HPD-COOH |
| Bispecific (3 × 1) | 2$^{nd}$ Chain | NH$_2$-VL1-CL-COOH |
| | 1$^{st}$ Chain | NH$_2$-VH1-CH1—CH2—CH3—COOH |
| | 3$^{rd}$ Chain | NH$_2$-VH1-CH1—CH2—CH3-VL1-VH2-HPD-COOH |
| | 5$^{nd}$ Chain | NH$_2$-VL1-CL-COOH |
| | 4$^{th}$ Chain | NH$_2$-VL2-VH1-HPD-COOH |
| Trispecific (2 × 1 × 1) | 2$^{nd}$ Chain | NH$_2$-VL1-CL-COOH |
| | 1$^{st}$ Chain | NH$_2$-VH1-CH1—CH2—CH3—COOH |
| | 3$^{rd}$ Chain | NH$_2$-VH1-CH1—CH2—CH3-VL2-VH3-HPD-COOH |
| | 5$^{nd}$ Chain | NH$_2$-VL1-CL-COOH |
| | 4$^{th}$ Chain | NH$_2$-VL3-VH2-HPD-COOH |

HPD = Heterodimer-Promoting Domain

In a specific embodiment, diabodies of the present invention are bispecific, tetravalent (i.e., possess four epitope-binding sites), Fc-containing diabodies that are composed of five total polypeptide chains having two epitope-binding sites immunospecific for PD-1 (which may be capable of binding to the same epitope of PD-1 or to different epitopes of PD-1), and two epitope-binding sites specific for CTLA-4 (which may be capable of binding to the same epitope of CTLA-4 or to different epitopes of CTLA-4). In another embodiment, the bispecific, tetravalent, Fc-containing diabodies of the invention comprise three epitope-binding sites immunospecific for PD-1 (which may be capable of binding to the same epitope of PD-1 or to two or three different epitopes of PD-1), and one epitope-binding site specific for CTLA-4. In another embodiment, the bispecific, tetravalent, Fc-containing diabodies of the invention comprise one epitope-binding sites immunospecific for PD-1, and three epitope-binding sites specific for CTLA-4 (which may be capable of binding to the same epitope of CTLA-4 or to two or three different epitopes of CTLA-4).

D. PD-1×CTLA-4 Bispecific Trivalent Binding Molecules Containing Fc Regions

A further embodiment of the present invention relates to bispecific trivalent binding molecules comprising an Fc Region capable of simultaneously binding to an epitope of PD-1 and an epitope present on CTLA-4. Such bispecific trivalent binding molecules comprise three epitope-binding sites, two of which are Diabody-Type Binding Domains, which provide binding Site A and binding Site B, and one of which is a Fab-Type Binding Domain (or an scFv-Type Binding Domain), which provides binding Site C (see, e.g., FIGS. 6A-6F, and PCT Application No: PCT/US15/33081; and PCT/US15/33076). Such bispecific trivalent molecules thus comprise "VL1"/"VH1" domains that are capable of binding to the first epitope and "VL2"/"VH2" domains that are capable of binding to the second epitope and "VL3" and "VH3" domains that are capable of binding to the "third" epitope of such trivalent molecule. A "Diabody-Type Binding Domain" is the type of epitope-binding site present in a diabody, and especially, a DART® diabody, as described above. Each of a "Fab-Type Binding Domain" and an "scFv-Type Binding Domain" are epitope-binding sites that are formed by the interaction of the VL Domain of an immunoglobulin light chain and a complementing VH Domain of an immunoglobulin heavy chain. Fab-Type Binding Domains differ from Diabody-Type Binding Domains in that the two polypeptide chains that form a Fab-Type Binding Domain comprise only a single epitope-binding site, whereas the two polypeptide chains that form a Diabody-Type Binding Domain comprise at least two epitope-binding sites. Similarly, scFv-Type Binding Domains also differ from Diabody-Type Binding Domains in that they comprise only a single epitope-binding site. Thus, as used herein Fab-Type, and scFv-Type Binding Domains are distinct from Diabody-Type Binding Domains.

Typically, the trivalent binding molecules of the present invention will comprise four different polypeptide chains (see FIGS. 6A-6B), however, the molecules may comprise fewer or greater numbers of polypeptide chains, for example by fusing such polypeptide chains to one another (e.g., via a peptide bond) or by dividing such polypeptide chains to form additional polypeptide chains, or by associating fewer or additional polypeptide chains via disulfide bonds. FIGS. 6C-6F illustrate this aspect of the present invention by schematically depicting such molecules having three polypeptide chains. As provided in FIGS. 6A-6F, the trivalent binding molecules of the present invention may have alternative orientations in which the Diabody-Type Binding Domains are N-terminal (FIGS. 6A, 6C and 6D) or C-terminal (FIGS. 6B, 6E and 6F) to an Fc Region.

In certain embodiments, the first polypeptide chain of such trivalent binding molecules of the present invention contains: (i) a VL1-containing Domain, (ii) a VH2-containing Domain, (iii) a Heterodimer-Promoting Domain, and (iv) a Domain containing a CH2-CH3 sequence. The VL1 and VL2 Domains are located N-terminal or C-terminal to the CH2-CH3-containing domain as presented in Table 4 (also see, FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the heavy chain of an antibody that contains a VH3 and a heavy chain constant region, or a polypeptide that contains such domains. The fourth polypeptide of such embodiments contains: (i) a VL3-containing Domain and (ii) a CL-containing Domain. The fourth polypeptide chains may be a light chain of an antibody that contains a VL3 complementary to the VH3 of the third polypeptide chain, or a polypeptide that contains such domains. The third or fourth polypeptide chains may be isolated from naturally occurring antibodies. Alternatively, they may be constructed recombinantly, synthetically or by other means.

The Light Chain Variable Domain of the first and second polypeptide chains are separated from the Heavy Chain Variable Domains of such polypeptide chains by an intervening spacer peptide having a length that is too short to permit their VL1/VH2 (or their VL2/VH1) domains to associate together to form epitope-binding site capable of binding to either the first or second epitope. A preferred intervening spacer peptide (Linker 1) for this purpose has the sequence (SEQ ID NO:9): GGGSGGGG. Other Domains of the trivalent binding molecules may be separated by one or more intervening spacer peptides (Linkers), optionally comprising a cysteine residue. In particular, as provided above, such Linkers will typically be incorporated between Variable Domains (i.e., VH or VL) and peptide Heterodimer-Promoting Domains (e.g., an E-coil or K-coil) and between such peptide Heterodimer-Promoting Domains (e.g., an E-coil or K-coil) and CH2-CH3 Domains. Exemplary linkers useful for the generation of trivalent binding molecules are provided above and are also provided in PCT Application Nos: PCT/US15/33081; and PCT/US15/33076. Thus, the first and second polypeptide chains of such trivalent binding molecules associate together to form a VL1/VH1 binding site capable of binding a first epitope, as well as a VL2/VH2 binding site that is capable of binding to a second epitope. The third and fourth polypeptide chains of such trivalent binding molecules associate together to form a VL3/VH3 binding site that is capable of binding to a third epitope.

As described above, the trivalent binding molecules of the present invention may comprise three polypeptides. Trivalent binding molecules comprising three polypeptide chains may be obtained by linking the domains of the fourth polypeptide N-terminal to the VH3-containing Domain of the third polypeptide (e.g., using an intervening spacer peptide (Linker 4)). Alternatively, a third polypeptide chain of a trivalent binding molecule of the invention containing the following domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an epitope-binding site. One preferred intervening spacer peptide for this purpose has the sequence: GGGGSGGGGSGGGGS (SEQ ID NO:37).

It will be understood that the VL1/VH1, VL2/VH2, and VL3/VH3 Domains of such trivalent binding molecules may be different so as to permit binding that is bispecific or trispecific. However, as provided herein, these domains are selected so as to provide a trivalent binding molecule capable of binding PD-1 and CTLA-4.

In particular, the VL and VH Domains may be selected such that a trivalent binding molecule comprises two binding sites for PD-1 (which may be capable of binding to the same epitope of PD-1 or to different epitopes of PD-1) and one binding sites for a CTLA-4, or one binding site for PD-1 and two binding sites for CTLA-4 (which may be capable of binding to the same epitope of CTLA-4 or to different epitopes of CTLA-4), or one binding site for PD-1, one binding site for CTLA-4 and one binding site for a third antigen that is not PD-1 or CTLA-4. The general structure of the polypeptide chains of representative trivalent binding molecules of invention is provided in FIGS. 6A-6F and in Table 4:

TABLE 4

| Four Chain 1st Orientation | 2nd Chain<br>1st Chain<br>3rd Chain<br>2nd Chain | NH₂-VL2-VH1-HPD-COOH<br>NH₂-VL1-VH2-HPD-CH2—CH3—COOH<br>NH₂-VH3-CH1—CH2—CH3—COOH<br>NH₂-VL3-CL-COOH |
|---|---|---|
| Four Chain 2nd Orientation | 2nd Chain<br>1st Chain<br>3rd Chain<br>2nd Chain | NH₂-VL2-VH1-HPD-COOH<br>NH₂—CH2—CH3-VL1-VH2-HPD-COOH<br>NH₂-VH3-CH1—CH2—CH3—COOH<br>NH₂-VL3-CL-COOH |

TABLE 4-continued

| Three Chain 1st Orientation | 2nd Chain<br>1st Chain<br>3rd Chain | NH₂-VL2-VH1-HPD-COOH<br>NH₂-VL1-VH2-HPD-CH2—CH3—COOH<br>NH₂-VL3-VH3-HPD-CH2—CH3—COOH |
|---|---|---|
| Three Chain 2nd Orientation | 2nd Chain<br>1st Chain<br>3rd Chain | NH₂-VL2-VH1-HPD-COOH<br>NH₂—CH2—CH3-VL1-VH2-HPD-COOH<br>NH₂-VL3-VH3-HPD-CH2—CH3—COOH |

HPD = Heterodimer-Promoting Domain

One embodiment of the present invention relates to bispecific trivalent binding molecules that comprise two epitope-binding sites for PD-1 and one epitope-binding site for CTLA-4.

The two epitope-binding sites for PD-1 may bind the same epitope or different epitopes. Another embodiment of the present invention relates to bispecific trivalent binding molecules that comprise, one epitope-binding site for PD-1 and two epitope-binding sites for CTLA-4. The two epitope-binding sites for CTLA-4 may bind the same epitope or different epitopes of CTLA-4. As provided above, such bispecific trivalent binding molecules may comprise three, four, five, or more polypeptide chains.

V. Constant Domains and Fc Regions

Provided herein are antibody Constant Domains useful in the generation of the PD-1×CTLA-4 bispecific molecules (e.g., antibodies, diabodies, trivalent binding molecules, etc.) of the invention.

A preferred CL Domain is a human IgG CL Kappa Domain. The amino acid sequence of an exemplary human CL Kappa Domain is (SEQ ID NO:38):

RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC

Alternatively, an exemplary CL Domain is a human IgG CL Lambda Domain. The amino acid sequence of an exemplary human CL Lambda Domain is (SEQ ID NO:39):

QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS

As provided herein, the PD-1×CTLA-4 bispecific molecules of the invention may comprise an Fc Region. The Fc Region of such molecules of the invention may be of any isotype (e.g., IgG1, IgG2, IgG3, or IgG4). The PD-1× CTLA-4 bispecific molecules of the invention may further comprise a CH1 Domain and/or a Hinge Region. When present, the CH1 Domain and/or Hinge Region may be of any isotype (e.g., IgG1, IgG2, IgG3, or IgG4), and is preferably of the same isotype as the desired Fc Region.

An exemplary CH1 Domain is a human IgG1 CH Domain. The amino acid sequence of an exemplary human IgG1 CH1 Domain is (SEQ ID NO:40):

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV

An exemplary CH1 Domain is a human IgG2 CH Domain. The amino acid sequence of an exemplary human IgG2 CH1 Domain is (SEQ ID NO:41):

```
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV
```

An exemplary CH1 Domain is a human IgG4 CH1 Domain. The amino acid sequence of an exemplary human IgG4 CH1 Domain is (SEQ ID NO:42):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV
```

One exemplary Hinge Region is a human IgG1 Hinge Region. The amino acid sequence of an exemplary human IgG1 Hinge Region is (SEQ ID NO:33):

```
EPKSCDKTHTCPPCP.
```

Another exemplary Hinge Region is a human IgG2 Hinge Region. The amino acid sequence of an exemplary human IgG2 Hinge Region is (SEQ ID NO:34):

```
ERKCCVECPPCP.
```

Another exemplary Hinge Region is a human IgG4 Hinge Region. The amino acid sequence of an exemplary human IgG4 Hinge Region is (SEQ ID NO:35): ESKYGPPCPSCP. As described herein, an IgG4 Hinge Region may comprise a stabilizing mutation such as the S228P substitution. The amino acid sequence of an exemplary stabilized IgG4 Hinge Region is (SEQ ID NO:36):

```
ESKYGPPCPPCP.
```

The Fc Region of the Fc Region-containing molecules (e.g., antibodies, diabodies, trivalent molecules, etc.) of the present invention may be either a complete Fc Region (e.g., a complete IgG Fc Region) or only a fragment of an Fc Region. Optionally, the Fc Region of the Fc Region-containing molecules of the present invention lacks the C-terminal lysine amino acid residue.

In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Region of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatal Fc Receptor (FcRn) mediates the recycling of IgG molecules from the endosome to the cell surface and release into the blood. The amino acid sequence of exemplary wild-type IgG1 (SEQ ID NO:1), IgG2 (SEQ ID NO:2), IgG3 (SEQ ID NO:3), and IgG4 (SEQ ID NO:4) are presented above.

Modification of the Fc Region may lead to an altered phenotype, for example altered serum half-life, altered stability, altered susceptibility to cellular enzymes or altered effector function. It may therefore be desirable to modify an Fc Region-containing PD-1×CTLA-4 bispecific molecule of the present invention with respect to effector function, for example, so as to enhance the effectiveness of such molecule in treating cancer. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). Molecules of the invention possessing such conferred or altered effector function activity are useful for the treatment and/or prevention of a disease, disorder or infection in which an enhanced efficacy of effector function activity is desired.

Accordingly, in certain embodiments, the Fc Region of the Fc Region-containing molecules of the present invention may be an engineered variant Fc Region. Although the Fc Region of the bispecific Fc Region-containing molecules of the present invention may possess the ability to bind to one or more Fc receptors (e.g., FcγR(s)), more preferably such variant Fc Region have altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Region), e.g., will have enhanced binding to an activating receptor and/or will have substantially reduced or no ability to bind to inhibitory receptor(s). Thus, the Fc Region of the Fc Region-containing molecules of the present invention may include some or all of the CH2 Domain and/or some or all of the CH3 Domain of a complete Fc Region, or may comprise a variant CH2 and/or a variant CH3 sequence (that may include, for example, one or more insertions and/or one or more deletions with respect to the CH2 or CH3 domains of a complete Fc Region). Such Fc Regions may comprise non-Fc polypeptide portions, or may comprise portions of non-naturally complete Fc Regions, or may comprise non-naturally occurring orientations of CH2 and/or CH3 Domains (such as, for example, two CH2 domains or two CH3 domains, or in the N-terminal to C-terminal direction, a CH3 Domain linked to a CH2 Domain, etc.).

Fc Region modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890). Table 5 lists exemplary single, double, triple, quadruple and quintuple substitutions (relative to the amino acid sequence of SEQ ID NO:1) of exemplary modification that increase binding to activating receptors and/or reduce binding to inhibitory receptors.

TABLE 5

Variations of Preferred Activating Fc Regions

Single-Site Variations

| | | | |
|---|---|---|---|
| F243L | R292G | D270E | R292P |
| Y300L | P396L | | |

Double-Site Variations

| | | | |
|---|---|---|---|
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

Triple-Site Variations

| | |
|---|---|
| F243L, P247L and N421K | P247L, D270E and N421K |
| F243L, R292P and Y300L | R255L, D270E and P396L |
| F243L, R292P and V305I | D270E, G316D and R416G |
| F243L, R292P and P396L | D270E, K392T and P396L |
| F243L, Y300L and P396L | D270E, P396L and Q419H |
| V284M, R292L and K370N | R292P, Y300L and P396L |

Quadruple-Site Variations

| | |
|---|---|
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D and R416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |

Quintuple-Site Variations

| | |
|---|---|
| L235V, F243L, R292P, Y300L and P396L | F243L, R292P, V305I, Y300L and P396L |
| L235P, F243L, R292P, Y300L and P396L | |

Exemplary variants of human IgG1 Fc Regions with reduced binding to CD32B and/or increased binding to CD16A contain F243L, R292P, Y300L, V305I or P296L substitutions. These amino acid substitutions may be present in a human IgG1 Fc Region in any combination. In one embodiment, the human IgG1 Fc Region variant contains a F243L, R292P and Y300L substitution. In another embodiment, the human IgG1 Fc Region variant contains a F243L, R292P, Y300L, V305I and P296L substitution.

In certain embodiments, it is preferred for the Fc Regions of PD-1×CTLA-4 bispecific molecules of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1). In a specific embodiment, the PD-1×CTLA-4 bispecific molecules of the present invention comprise an IgG Fc Region that exhibits reduced ADCC effector function. In a preferred embodiment the CH2-CH3 Domains of such PD-1×CTLA-4 bispecific molecules include any 1, 2, 3, or 4 of the substitutions: L234A, L235A, D265A, N297Q, and N297G. In another embodiment, the CH2-CH3 Domains contain an N297Q substitution, an N297G substitution, L234A and L235A substitutions or a D265A substitution, as these mutations abolish FcR binding. Alternatively, a CH2-CH3 Domain of a naturally occurring Fc region that inherently exhibits decreased (or substantially no) binding to FcγRIIIA (CD16a) and/or reduced effector function (relative to the binding and effector function exhibited by the wild-type IgG1 Fc Region (SEQ ID NO:1)) is utilized. In a specific embodiment, the PD-1×CTLA-4 bispecific molecules of the present invention comprise an IgG2 Fc Region (SEQ ID NO:2) or an IgG4 Fc Region (SEQ ID:NO:4). When an IgG4 Fc Region is utilized, the instant invention also encompasses the introduction of a stabilizing mutation, such as the Hinge Region S228P substitution described above (see, e.g., SEQ ID NO:36). Since the N297G, N297Q, L234A, L235A and D265A substitutions abolish effector function, in circumstances in which effector function is desired, these substitutions would preferably not be employed.

A preferred IgG1 sequence for the CH2 and CH3 Domains of the Fc Region-containing molecules of the present invention having reduced or abolished effector function will comprise the substitutions L234A/L235A (SEQ ID NO:43):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

The serum half-life of proteins comprising Fc Regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from the subject's body (e.g., human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the PD-1×CTLA-4 bispecific molecules of the present invention comprise a variant Fc Region, wherein the variant Fc Region comprises at least one amino acid modification relative to a wild-type Fc Region, such that the molecule has an increased half-life (relative to a molecule comprising a wild-type Fc Region). In some embodiments, the PD-1×CTLA-4 bispecific molecules of the present invention comprise a variant IgG Fc Region, wherein the variant Fc Region comprises a half-live extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436. Numerous mutations capable of increasing the half-life of an Fc Region-containing molecule are known in the art and include, for example M252Y, S254T, T256E, and combinations thereof. For example, see the mutations described in U.S. Pat. Nos. 6,277,375; 7,083,784; 7,217,797; 8,088,376; U.S. Publication Nos. 2002/0147311; 2007/0148164; and International Publication Nos. WO 98/23289; WO 2009/058492; and WO 2010/033279, which are herein incorporated by reference in their entireties. PD-1×CTLA-4 bispecific molecules with enhanced half-life also include those possessing variant Fc Regions comprising substitutions at two or more of Fc Region residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I.

In a specific embodiment, a PD-1×CTLA-4 bispecific molecule possesses a variant IgG Fc Region comprising substitutions of:
(A) M252Y, S254T and T256E;
(B) M252Y and S254T;
(C) M252Y and T256E;
(D) T250Q and M428L;
(E) T307Q and N434A;
(F) A378V and N434A;
(G) N434A and Y436I;
(H) V308P and N434A; or
(I) K288D and H435K.

In a preferred embodiment PD-1×CTLA-4 bispecific molecules possess a variant IgG Fc Region comprising any 1, 2, or 3 of the substitutions: M252Y, S254T and T256E. The invention further encompasses PD-1×CTLA-4 bispecific molecules possessing variant Fc Regions comprising:
(A) one or more mutations which alter effector function and/or FcγR; and
(B) one or more mutations which extend serum half-life.

A preferred IgG1 sequence for the CH2 and CH3 Domains of the Fc Region-containing molecules of the present invention having increased serum half-life will comprise the substitutions M252Y, S254T and T256E (SEQ ID NO:80):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

As will be noted, the CH2-CH3 Domains of SEQ ID NO:80 includes substitutions at positions 234 and 235 with alanine, and thus form an Fc Region exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Region (SEQ ID NO:1). The invention also encompasses such IgG1 CH2-CH3 Domains, which comprise the wild-type alanine residues, alternative and/or additional substitutions which modify effector function and/or FγR binding activity of the Fc region.

A preferred IgG4 sequence for the CH2 and CH3 Domains of the Fc Region-containing molecules of the present invention having increased serum half-life will comprise the substitutions M252Y, S254T and T256E (SEQ ID NO:81):

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGX
``` wherein, X is a lysine (K) or is absent.

For certain antibodies, diabodies and trivalent binding molecules whose Fc Region-containing first and third polypeptide chains are not identical, it is desirable to reduce or prevent homodimerization from occurring between the CH2-CH3 Domains of two first polypeptide chains or between the CH2-CH3 Domains of two third polypeptide chains. The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Region to foster heterodimerization. Methods of protein engineering to favor heterodimerization over homodimerization are well known in the art, in particular with respect to the engineering of immunoglobulin-like molecules, and are encompassed herein (see e.g., Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101; each of which is hereby incorporated herein by reference in its entirety).

A preferred knob is created by modifying an IgG Fc Region to contain the modification T366W. A preferred hole is created by modifying an IgG Fc Region to contain the modification T366S, L368A and Y407V. To aid in purifying the hole-bearing third polypeptide chain homodimer from the final bispecific heterodimeric Fc Region-containing molecule, the protein A binding site of the hole-bearing CH2 and CH3 Domains of the third polypeptide chain is preferably mutated by amino acid substitution at position 435 (H435R). Thus, the hole-bearing third polypeptide chain homodimer will not bind to protein A, whereas the bispecific heterodimer will retain its ability to bind protein A via the protein A binding site on the first polypeptide chain. In an alternative embodiment, the hole-bearing third polypeptide chain may incorporate amino acid substitutions at positions 434 and 435 (N434A/N435K).

A preferred IgG1 amino acid sequence for the CH2 and CH3 Domains of the first polypeptide chain of an Fc Region-containing molecule of the present invention will have the "knob-bearing" sequence (SEQ ID NO:44):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein X is a lysine (K) or is absent.

A preferred IgG1 amino acid sequence for the CH2 and CH3 Domains of the second polypeptide chain of an Fc Region-containing molecule of the present invention having two polypeptide chains (or the third polypeptide chain of an Fc Region-containing molecule having three, four, or five polypeptide chains) will have the "hole-bearing" sequence (SEQ ID NO:45):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein X is a lysine (K) or is absent.

As will be noted, the CH2-CH3 Domains of SEQ ID NO:44, and SEQ ID NO:45 include substitutions at positions 234 and 235 with alanine, and thus form an Fc Region exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Region (SEQ ID NO:1). The invention also encompasses such IgG1 CH2-CH3 Domains, which comprise the wild-type alanine residues, alternative and/or additional substitutions which modify effector function and/or FγR binding activity of the Fc region. The invention also encompasses such CH2-CH3 Domains, which further comprise one or more half-live extending amino acid substitutions. In particular, as provided above, the invention encompasses such hole-bearing and such knob-bearing CH2-CH3 Domains which further comprise the M252Y/S254T/T256E.

A preferred IgG1 amino acid sequence, for the CH2 and CH3 Domains further comprising M252Y/S254T/T256E, of the first polypeptide chain of an Fc Region-containing molecule of the present invention will have the "knob-bearing" sequence (SEQ ID NO:82):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein X is a lysine (K) or is absent.

A preferred IgG1 amino acid sequence, for the CH2 and CH3 Domains further comprising M252Y/S254T/T256E, of the second polypeptide chain of an Fc Region-containing molecule of the present invention having two polypeptide chains (or the third polypeptide chain of an Fc Region-containing molecule having three, four, or five polypeptide chains) will have the "hole-bearing" sequence (SEQ ID NO:83):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein X is a lysine (K) or is absent.

A preferred IgG4 amino acid sequence for the CH2 and CH3 Domains, comprising M252Y/S254T/T256E, of the first polypeptide chain of an Fc Region-containing molecule of the present invention will have the "knob-bearing" sequence (SEQ ID NO:84):

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLWCLVK GFYPSDIAVE WESNGQPENN

YKTTPPVLDS DGSFFLYSRL TVDKSRWQEG NVFSCSVMHE

ALHNHYTQKS LSLSLGX
``` wherein X is a lysine (K) or is absent.

A preferred IgG4 amino acid sequence, for the CH2 and CH3 Domains comprising M252Y/S254T/T256E, of the second polypeptide chain of an Fc Region-containing molecule of the present invention having two polypeptide chains (or the third polypeptide chain of an Fc Region-containing molecule having three, four, or five polypeptide chains) will have the "hole-bearing" sequence (SEQ ID NO:85):

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLSCAVK GFYPSDIAVE WESNGQPENN

YKTTPPVLDS DGSFFLVSRL TVDKSRWQEG NVFSCSVMHE

ALHNRYTQKS LSLSLGX
``` wherein X is a lysine (K) or is absent.

As will be noted, the CH2-CH3 Domains of SEQ ID NO:84, and SEQ ID NO:85 include the M252Y/S254T/T256E substitutions, and thus form an IgG4 Fc Region exhibiting increased serum half-life. The invention also encompasses IgG4 CH2-CH3 Domains, which comprise the wild-type M252/S254/T256 residues.

It is preferred that the first polypeptide chain will have a "knob-bearing" CH2-CH3 sequence, such as that of SEQ ID NO:44. However, as will be recognized, a "hole-bearing" CH2-CH3 Domain (e.g., SEQ ID NO:45) could be employed in the first polypeptide chain, in which case, a "knob-bearing" CH2-CH3 Domain (e.g., SEQ ID NO:44) would be employed in the second polypeptide chain of an Fc Region-containing molecule of the present invention having two polypeptide chains (or in the third polypeptide chain of an Fc Region-containing molecule having three, four, or five polypeptide chains).

In other embodiments, the invention encompasses PD-1×CTLA-4 bispecific molecules comprising CH2 and/or CH3 Domains that have been engineered to favor heterodimerization over homodimerization using mutations known in the art, such as those disclosed in PCT Publication No. WO 2007/110205; WO 2011/143545; WO 2012/058768; WO 2013/06867, all of which are incorporated herein by reference in their entirety.

VI. Anti-PD-1 Binding Capabilities

Antibodies that are immunospecific for PD-1 are known (see, e.g., U.S. Patent Applications No. 62/198,867; 62/239,559; 62/255,140 U.S. Pat. Nos. 8,008,449; 8,552,154; PCT Patent Publications WO 2012/135408; WO 2012/145549; and WO 2013/014668). Preferred PD-1 binding capabilities useful in the generation of the PD-1×CTLA-4 bispecific molecules of the present invention are capable of binding to a continuous or discontinuous (e.g., conformational) portion (epitope) of human PD-1 (CD279) and will preferably also exhibit the ability to bind to PD-1 molecules of one or more non-human species, in particular, primate species (and especially a primate species, such as cynomolgus monkey). Additional desired antibodies may be made by isolating antibody-secreting hybridomas elicited using PD-1 or a peptide fragment thereof. A representative human PD-1 polypeptide (NCBI Sequence NP 005009.2; including a 20 amino acid residue signal sequence, shown underlined) and the 268 amino acid residue mature protein) has the amino acid sequence (SEQ ID NO:46):

```
MQIPQAPWPV VWAVLQLGWR PGWFLDSPDR PWNPPTFSPA

LLVVTEGDNA TFTCSFSNTS ESFVLNWYRM SPSNQTDKLA
```

-continued
```
AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL
```

Preferred anti-PD-1 binding molecules (e.g., antibodies) useful in the generation of the PD-1×CTLA-4 bispecific molecules of the instant invention possess the VL and/or VH Domains of the anti-human PD-1 monoclonal antibody "PD-1 mAb 1" (nivolumab, CAS Reg. No.:946414-94-4, also known as 5C4, BMS-936558, ONO-4538, MDX-1106, and marketed as OPDIVO® by Bristol-Myers Squibb); "PD-1 mAb 2" (pembrolizumab, (formerly known as lambrolizumab), CAS Reg. No.:1374853-91-4, also known as MK-3475, SCH-900475, and marketed as KEYTRUDA® by Merck); "PD-1 mAb 3" (EH12.2H7; Dana Farber), "PD-1 mAb 4" (pidilizumab, CAS Reg. No.: 1036730-42-3 also known as CT-011, CureTech), or any of the anti-PD-1 antibodies in Table 6; and more preferably possess 1, 2 or all 3 of the $CDR_L$s of the VL Region and/or 1, 2 or all 3 of the CDRHs of the VH Domain of such anti-PD-1 monoclonal antibodies. Additional anti-PD-1 antibodies possessing unique binding characteristics useful in the methods and compositions of the instant inventions have recently been identified (see, United States Patent Application Nos. 62/198,867; 62/239,559; 62/255,140). Particularly, preferred are PD-1-binding molecules which possess a humanized VH and/or VL Domain of the anti-PD-1 antibody "PD-1 mAb 5" (hPD-1 mAb 2, MacroGenics); "PD-1 mAb 6" (hPD-1 mAb 7, MacroGenics); "PD-1 mAb 7" (hPD-1 mAb 9, MacroGenics); or "PD-1 mAb 8" (hPD-1 mAb 15, MacroGenics); and more preferably possess 1, 2 or all 3 of the $CDR_L$s of the VL Region and/or 1, 2 or all 3 of the CDRHs of the VH Domain of such humanized anti-PD-1 monoclonal antibodies.

A. PD-1 mAb 1

The amino acid sequence of the VH Domain of PD-1 mAb 1 (SEQ ID NO:47) is shown below ($CDR_H$ residues are shown underlined).

```
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSS
```

The amino acid sequence of the VL Domain of PD-1 mAb 1 (SEQ ID NO:48) is shown below ($CDR_L$ residues are shown underlined).

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIK
```

B. PD-1 mAb 2

The amino acid sequence of the VH Domain of PD-1 mAb 2 (SEQ ID NO:49) is shown below ($CDR_H$ residues are shown underlined).

```
QVQLVQSGVE VKKPGASVKV SCKASGYTFT NYYMYWVRQA

PGQGLEWMGG INPSNGGTNF NEKFKNRVTL TTDSSTTTAY

MELKSLQFDD TAVYYCARRD YRFDMGFDYW GQGTTVTVSS
```

The amino acid sequence of the VL Domain of PD-1 mAb 2 (SEQ ID NO:50) is shown below (CDR$_L$ residues are shown underlined).

```
EIVLTQSPAT LSLSPGERAT LSCRASKGVS TSGYSYLHWY

QQKPGQAPRL LIYLASYLESGVPARFSGSG SGTDFTLTIS

SLEPEDFAVY YCQHSRDLPL TFGGGTKVEIK
```

C. PD-1 mAb 3

The amino acid sequence of the VH Domain of PD-1 mAb 3 (SEQ ID NO:51) is shown below (CDR$_H$ residues are shown underlined).

```
QVQLQQSGAE LAKPGASVQM SCKASGYSFT SSWIHWVKQR

PGQGLEWIGY IYPSTGFTEY NQKFKDKATL TADKSSSTAY

MQLSSLTSED SAVYYCARWR DSSGYHAMDY WGQGTSVTVSS
```

The amino acid sequence of the VL Domain of PD-1 mAb 3 (SEQ ID NO:52) is shown below (CDR$_L$ residues are shown underlined).

```
DIVLTQSPAS LTVSLGQRAT ISCRASQSVS TSGYSYMHWY

QQKPGQPPKL LIKFGSNLES GIPARFSGSG SGTDFTLNIH

PVEEEDTATY YCQHSWEIPY TFGGGTKLEI K
```

D. PD-1 mAb 4

The amino acid sequence of the VH Domain of PD-1 mAb 4 (SEQ ID NO:53) is shown below (CDR$_H$ residues are shown underlined).

```
QVQLVQSGSE LKKPGASVKI SCKASGYTFT NYGMNWVRQA

PGQGLQWMGW INTDSGESTY AEEFKGRFVF SLDTSVNTAY

LQITSLTAED TGMYFCVRVG YDALDYWGQG TLVTVSS
```

The amino acid sequence of the VL Domain of PD-1 mAb 4 (SEQ ID NO:54) is shown below (CDR$_L$ residues are shown underlined).

```
EIVLTQSPSS LSASVGDRVT ITCSARSSVS YMHWFQQKPG

KAPKLWIYRT SNLASGVPSR FSGSGSGTSY CLTINSLQPE

DFATYYCQQR SSFPLTFGGG TKLEIK
```

E. PD-1 mAb 5

The amino acid sequence of the VH Domain of PD-1 mAb 5 (SEQ ID NO:55) is shown below (CDR$_H$ residues are shown underlined).

```
EVQLVESGGG LVQPGGSLRL SCAASGFVFS SFGMHWVRQA

PGKGLEWVAY ISSGSMSISY ADTVKGRFTI SRDNAKNTLY

LQMNSLRTED TALYYCASLS DYFDYWGQGT TVTVSS
```

The amino acid sequence of the VL Domain of PD-1 mAb 5 (SEQ ID NO:56) is shown below (CDR$_L$ residues are shown underlined).

```
DVVMTQSPLS LPVTLGQPAS ISCRSSQSLV HSTGNTYLHW

YLQKPGQSPQ LLIYRVSNRF SGVPDRFSGS GSGTDFTLKI

SRVEAEDVGV YYCSQTTHVP WTFGQGTKLE IK
```

F. PD-1 mAb 6

The amino acid sequence of the VH Domain of PD-1 mAb 6 (SEQ ID NO:57) is shown below (CDR$_H$ residues are shown underlined).

```
QVQLVQSGAE VKKPGASVKV SCKASGYSFT SYWMNWVRQA

PGQGLEWX₁GV IHPSDSETWL DQKFKDRVTI TVDKSTSTAY

MELSSLRSED TAVYYCAREH YGTSPFAYWG QGTLVTVSS
``` wherein $X_1$ is I or A

The amino acid sequence of the VL Domain of PD-1 mAb 6 (SEQ ID NO:58) is shown below (CDR$_L$ residues are shown underlined).

```
EIVLTQSPAT LSLSPGERAT LSCRAX₁ESVD NYGMSFMNWF

QQKPGQPPKL LIHAASNX₂GS GVPSRFSGSG SGTDFTLTIS

SLEPEDFAVY FCQQSKEVPY TFGGGTKVEI K
``` wherein: $X_1$ is N or S and $X_2$ is Q or R; or
$X_1$ is N and $X_2$ is Q; or
$X_1$ is S and $X_2$ is Q; or
$X_1$ is S and $X_2$ is R In particular embodiments the amino acid sequence of PD-1 mAb 6 comprises:
(a) SEQ ID NO:57, wherein $X_1$ is I; and SEQ ID NO:58, wherein $X_1$ is N and $X_2$ is Q; or
(b) SEQ ID NO:57, wherein $X_1$ is I; and SEQ ID NO:58, wherein $X_1$ is S and $X_2$ is Q.

An exemplary anti-PD-1 VH Domain designated "PD-1 mAb 6-I VH" comprises SEQ ID NO:57 wherein $X_1$ is I and has the amino acid sequence (SEQ ID NO:86):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSS
```

An exemplary anti-PD-1 VL Domain designated "PD-1 mAb 6-SQ VL" comprises SEQ ID NO:58 wherein $X_1$ is S and $X_2$ is Q and has the amino acid sequence (SEQ ID NO:87):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI K
```

An exemplary anti-PD-1 antibody that possesses a PD-1 mAb 6-I VH domain and a PD-1 mAb 6-SQ VL domain is designated as "PD-1 mAb 6-ISQ."

G. PD-1 mAb 7

The amino acid sequence of the VH Domain of PD-1 mAb 7 (SEQ ID NO:59) is shown below (CDR$_H$ residues are shown underlined).

```
EVQLVESGGG LX₁RPGGSLKL SCAASGFTFS SYLVX₂WVRQA

PGKGLEWX₃AT ISGGGGNTYY SDSVKGRFTI SRDNAKNSLY

LQMNSX₄RAED TATYYCARYG FDGAWFAYWG QGTLVTVSS
``` wherein: $X_1$ is V or A; $X_2$ is S or G; $X_3$ is V or T; $X_4$ is L or A; or $X_1$ is V, $X_2$ is S, $X_3$ is V, and $X_4$ is L; or $X_1$ is A, $X_2$ is G, $X_3$ is T, and $X_4$ is A The amino acid sequence of the VL Domain of PD-1 mAb 7 (SEQ ID NO:60) is shown below (CDR$_L$ residues are shown underlined).

```
DIQMTQSPSS LSASVGDRVT ITCRASENIY X₁YLAWYQQKP

GKAPKLLIYX₂ AKTLAAGVPS RFSGSGSGTD FTLTISSLQP

EDFATYYCQH HYAVPWTFGQ GTKLEIK
``` wherein: $X_1$ is S or N and $X_2$ is N or D; or $X_1$ is S and $X_2$ is N; or $X_1$ is N and $X_2$ is D In particular embodiments PD-1 mAb 7 comprises:

(a) SEQ ID NO:59, wherein $X_1$ is V, $X_2$ is S, $X_3$ is V, and $X_4$ is L; and SEQ ID NO:60, wherein $X_1$ is S and $X_2$ is N; or (b) SEQ ID NO:59, wherein $X_1$ is A, $X_2$ is G, $X_3$ is T, and $X_4$ is A; and SEQ ID NO:60, wherein $X_1$ is N and $X_2$ is D.

H. PD-1 mAb 8

The amino acid sequence of the VH Domain of PD-1 mAb 8 (SEQ ID NO:61) is shown below (CDR$_H$ residues are shown underlined).

```
EVQLVESGGG LVRPGGSLRL SCAASGFTFS SYLISWVRQA

PGKGLEWVAA ISGGGADTYY ADSVKGRFTI SRDNAKNSLY

LQMNSLRAED TATYYCARRG TYAMDYWGQG TLVTVSS
```

The amino acid sequence of the VL Domain of PD-1 mAb 8 (SEQ ID NO:62) is shown below (CDR$_L$ residues are shown underlined).

```
DIQMTQSPSS LSASVGDRVT ITCRASENIY NYLAWYQQKP

GKAPKLLIYD AKTLAAGVPS RFSGSGSGTD FTLTISSLQP

EDFATYYCQH HYAVPWTFGQ GTKLEIK
```

I. Additional Anti-PD-1 Antibodies

Additional anti-PD-1 antibodies which may be utilized to generate the PD-1×CTLA-4 bispecific molecules of the instant invention are provided in Table 6.

TABLE 6

| Additional Anti-PD-1 Antibodies | |
|---|---|
| PD-1 Antibodies | Reference/Source |
| PD1-17; PD1-28; PD1-33; PD1-35; and PD1-F2 | U.S. Pat. Nos. 7,488,802; 7,521,051; and 8,088,905; PCT Patent Publication WO 2004/056875 |
| 17D8; 2D3; 4H1; 5C4; 4A11; 7D3; and 5F4 | U.S. Pat. Nos. 8,008,449; 8,779,105; and 9,084,776; PCT Patent Publication WO 2006/121168 |
| hPD-1.08A; hPD-1.09A; 109A; K09A; 409A; h409A11; h409A16; h409A17; Codon optimized 109A; and Codon optimized 409A | U.S. Pat. Nos. 8,354,509; 8,900,587; and 5,952,136; PCT Patent Publication WO 2008/156712 |
| 1E3; 1E8; and 1H3 | US Patent Publication 2014/0044738; PCT Patent Publication WO 2012/145493 |
| 9A2; 10B11; 6E9; APE1922; APE1923; APE1924; APE1950; APE1963; and APE2058 | PCT Patent Publication WO 2014/179664 |
| GA1; GA2; GB1; GB6; GH1; A2; C7; H7; SH-A4; SH-A9; RG1H10; RG1H11; RG2H7; RG2H10; RG3E12; RG4A6; RG5D9; RG1H10-H2A-22-1S; RG1H10-H2A-27-2S; RG1H10-3C; RG1H10-16C; RG1H10-17C; RG1H10-19C; RG1H10-21C; and RG1H10-23C2 | US Patent Publication 2014/0356363; PCT Patent Publication WO 2014/194302 |
| H1M7789N; H1M7799N; H1M7800N; H2M7780N; H2M7788N; H2M7790N; H2M7791N; H2M7794N; H2M7795N; H2M7796N; H2M7798N; H4H9019P; H4xH9034P2; H4xH9035P2; H4xH9037P2; H4xH9045P2; H4xH9048P2; H4H9057P2; H4H9068P2; H4xH9119P2; H4xH9120P2; H4Xh9128p2; H4Xh9135p2; H4Xh9145p2; H4Xh8992p; H4Xh8999p; and H4Xh9008p; | US Patent Publication 2015/0203579; PCT Patent Publication WO 2015/112800 |
| PD-1 mAb 1; PD-1 mAb 2; hPD-1 mAb 2; PD-1 mAb 3; PD-1 mAb 4; PD-1 mAb 5; PD-1 mAb 6; PD-1 mAb 7; hPD-1 mAb 7; PD-1 mAb 8; PD-1 mAb 9; hPD-1 mAb 9; PD-1 mAb 10; PD-1 mAb 11; PD-1 mAb 12; PD-1 mAb 13; PD-1 mAb 14; PD-1 mAb 15; and hPD-1 mAb 15 | US Patent Applications No. 62/198,867 and 62/239,559 |

J. Exemplary anti-PD-1 Antibody

An exemplary anti-PD-1 antibody designated "PD-1 mAb 6 G4P" comprises: a heavy chain having the VH Domain of PD-1 mAb 61 (SEQ ID NO:86), an IgG4 CH1 Domain (SEQ ID NO:42), a stabilized IgG 4 Hinge (SEQ ID NO:36), and IgG4 CH2-CH3 Domains lacking the C-terminal lysine (SEQ ID NO:4); and a light chain having the VL Domain of PD-1 mAb 6SQ (SEQ ID NO:87) and a kappa CL (SEQ ID NO:38).

The amino acid sequence of the complete heavy chain of PD-1 mAb 6 G4P (SEQ ID NO:88) is shown below.

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APCSRSTSES TAALGCLVKD YFPEPVTVSW

NSGALTSGVH TFPAVLQSSG LYSLSSVVTV PSSSLGTKTY

TCNVDHKPSN TKVDKRVESK YGPPCPPCPA PEFLGGPSVF

LFPPKPKDTL MISRTPEVTC VVVDVSQEDP EVQFNWYVDG

VEVHNAKTKP REEQFNSTYR VVSVLTVLHQ DWLNGKEYKC

KVSNKGLPSS IEKTISKAKG QPREPQVYTL PPSQEEMTKN

QVSLTCLVKG FYPSDIAVEW ESNGQPENNY KTTPPVLDSD

GSFFLYSRLT VDKSRWQEGN VFSCSVMHEA LHNHYTQKSL

SLSLG
```

The amino acid sequence of the complete light chain of PD-1 mAb 6 G4P (SEQ ID NO:89) is shown below.

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

VII. Anti-CTLA-4 Binding Capabilities

Antibodies that are immunospecific for CTLA-4 are known (see, e.g., U.S. Pat. Nos. 6,984,720; 6,682,736; 7,034,121; 7,109,003; 7,132,281; 7,411,057; 7,605,238; 7,807,797; 7,824,679; 8,017,114; 8,143,379; 8,318,916; 8,491,895; 8,784,815; and 8,883,984; US Patent Publications 2009/0123477; 2009/0252741; and 2014/0105914; PCT Patent Publications No. WO 00/37504; WO 01/14424; WO 01/54732; WO 2006/029219; WO 2006/066568; and WO 2012/120125; and Table 7). Preferred CTLA-4 binding capabilities useful in the generation of the PD-1×CTLA-4 bispecific molecules of the present invention are capable of binding to a continuous or discontinuous (e.g., conformational) portion (epitope) of human CTLA-4 and will preferably also exhibit the ability to bind to CTLA-4 molecules of one or more non-human species, in particular, primate species (and especially a primate species, such as cynomolgus monkey). Additional desired antibodies may be made by isolating antibody-secreting hybridomas elicited using CTLA-4 or a peptide fragment thereof. A representative human CTLA-4 polypeptide (NCBI Sequence NP 005205.2; including a 35 amino acid residue signal sequence (shown underlined) and the 188 amino acid residues of the mature protein) has the amino acid sequence (SEQ ID NO:75):

```
MACLGFQRHK AQLNLATRTW PCTLLFFLLF IPVFCKAMHV

AQPAVVLASS RGIASFVCEY ASPGKATEVR VTVLRQADSQ

VTEVCAATYM MGNELTFLDD SICTGTSSGN QVNLTIQGLR

AMDTGLYICK VELMYPPPYY LGIGNGTQIY VIDPEPCPDS

DFLLWILAAV SSGLFFYSFL LTAVSLSKML KKRSPLTTGV

YVKMPPTEPE CEKQFQPYFI PIN
```

Preferred anti-CTLA-4 binding molecules (e.g., antibodies) useful in the generation of the PD-1×CTLA-4 bispecific molecules of the instant invention possess the VL and/or VH Domains of the anti-human CTLA-4 monoclonal antibody "CTLA-4 mAb 1" (ipilimumab, CAS Reg. No.: 477202-00-9, also known as MDX010, and marketed as YERVOY® by Bristol-Myers Squibb); "CTLA-4 mAb 2" (tremelimumab, CAS Reg. No.: 745013-59-6, also known as CP-675206); "CTLA-4 mAb 3" (4B6 as provided in Table 7) or any of the other anti-CTLA-4 antibodies in Table 7; and more preferably possess 1, 2 or all 3 of the CDR$_L$s of the VL Region and/or 1, 2 or all 3 of the CDRHs of the VH Domain of such anti-CTLA-4 monoclonal antibodies.

A. CTLA-4 mAb 1

The amino acid sequence of the VH Domain of CTLA-4 mAb 1 (SEQ ID NO:76) is shown below (CDR$_H$ residues are shown underlined).

```
QVQLVESGGG VVQPGRSLRL SCAASGFTFS SYTMHWVRQA

PGKGLEWVTF ISYDGNNKYY ADSVKGRFTI SRDNSKNTLY

LQMNSLRAED TAIYYCARTG WLGPFDYWGQ GTLVTVSS
```

The amino acid sequence of the VL Domain of CTLA-4 mAb 1 (SEQ ID NO:77) is shown below (CDR$_L$ residues are shown underlined).

```
EIVLTQSPGT LSLSPGERAT LSCRASQSVG SSYLAWYQQK

PGQAPRLLIY GAFSRATGIP DRFSGSGSGT DFTLTISRLE

PEDFAVYYCQ QYGSSPWTFG QGTKVEIK
```

B. CTLA-4 mAb 2

The amino acid sequence of the VH Domain of CTLA-4 mAb 2 (SEQ ID NO:78) is shown below (CDR$_H$ residues are shown underlined).

```
QVQLVESGGG VVQPGRSLRL SCAASGFTFS SYGMHWVRQA

PGKGLEWVAV IWYDGSNKYY ADSVKGRFTI SRDNSKNTLY

LQMNSLRAED TAVYYCARDP RGATLYYYY GMDVWGQGTT

VTVSS
```

The amino acid sequence of the VL Domain of CTLA-4 mAb 2 (SEQ ID NO:79) is shown below (CDR$_L$ residues are shown underlined).

```
DIQMTQSPSS LSASVGDRVT ITCRASQSIN SYLDWYQQKP

GKAPKLLIYA ASSLQSGVPS RFSGSGSGTD FTLTISSLQP

EDFATYYCQQ YYSTPFTFGP GTKVEIK
```

C. CTLA-4 mAb 3

The amino acid sequence of the VH Domain of CTLA-4 mAb 3 (SEQ ID NO:90) is shown below (CDR$_H$ residues are shown underlined).

```
QVQLVESGGG VVQPGRSLRL SCAASGFTFS SYTMHWVRQA

PGKGLEWVTF ISYDGSNKHY ADSVKGRFTV SRDNSKNTLY

LQMNSLRAED TAIYYCARTG WLGPFDYWGQ GTLVTVSS
```

The amino acid sequence of the VL Domain of CTLA-4 mAb 3 (SEQ ID NO:91) is shown below (CDR$_L$ residues are shown underlined).

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIK
```

D. Additional Anti-CTLA-4 Antibodies

Additional anti-CTLA-4 antibodies which may be utilized to generate the PD-1×CTLA-4 bispecific molecules of the instant invention are provided in Table 7.

TABLE 7

Additional Anti-CTLA-4 Antibodies

| CTLA-4 Antibodies | Reference/Source |
|---|---|
| mAb 26 | U.S. Pat. No. 7,034,121; PCT Patent Publication WO 01/54732 |
| 10D1; 1E2; and 4B6 | U.S. Pat. Nos. 6,984,720; 7,605,238; 8,017,114; 8,318,916; and 8,784,815; PCT Patent Publication WO 01/14424 |
| 2.1.3; 3.1.1; 4.1.1; 4.8.1; 4.9.1; 4.10.2; 4.13.1; 4.14.3; 6.1.1; 11.2.1; 11.6.1; 11.7.1; 12.2.1; 12.3.1; 12.3.1.1; 12.9.1; and 12.9.1.1 | U.S. Pat. Nos. 6,682,736; 7,109,003; 7,132,281; 7,411,057; 7,807,797; 7,824,679; 8,143,379; 8,491,895; and 8,883,984; PCT Patent Publication WO 00/37504 |
| 3B10; 8H5; 8H5-1B1; 3B10-4F7; 7B9-1A3; 2C7-1G10; 3B10-6E3; and 8H5-1A1 | US Patent Publication 2014/0105914; PCT Patent Publication WO 2012/120125 |
| 3.7F10A2; 4.3F6B5; 4.4A7F4; 4.6C1E3; 4.7A8H8; 4.7E11F1; 4.8H10H5; TGN2122; and TGN2422 | US Patent Publication 2009/0123477; PCT Patent Publication WO 2006/066568 |
| L3D10; L1B11; K4G4; KM10; and YL2 | US Patent Publication 2009/0252741; PCT Patent Publication WO 2006/029219 |

E. Exemplary anti-CTLA-4 Antibodies

An exemplary anti-CTLA-4 antibody designated "CTLA-4 mAb 3 G1AA" comprises a heavy chain having the VH Domain of CTLA-4 mAb 3 (SEQ ID NO:90), an IgG1 CH1 Domain (SEQ ID NO:40), an IgG1 Hinge (SEQ ID NO:33), and IgG1 CH2-CH3 Domains the substitutions L234A/L235A (SEQ ID NO:43).

The amino acid sequence of the complete heavy chain of CTLA-4 mAb 3 G1AA (SEQ ID NO:92) is shown below.

```
QVQLVESGGG VVQPGRSLRL SCAASGFTFS SYTMHWVRQA

PGKGLEWVTF ISYDGSNKHY ADSVKGRFTV SRDNSKNTLY

LQMNSLRAED TAIYYCARTG WLGPFDYWGQ GTLVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLTCLV KGFYPSDIAV EWESNGQPEN NYKTTPPVLD

SDGSFFLYSK LTVDKSRWQQ GNVFSCSVMH EALHNHYTQK

SLSLSPGK
```

An alternative exemplary anti-CTLA-4 antibody designated "CTLA-4 mAb 3 G4P" comprises a heavy chain having the VH Domain of CTLA-4 mAb 3 (SEQ ID NO:90), an IgG4 CH1 Domain (SEQ ID NO:42), a stabilized IgG4 Hinge (SEQ ID NO:36), and IgG4 CH2-CH3 Domains lacking the C-terminal lysine (SEQ ID NO:4). The amino acid sequence of the complete heavy chain of CTLA-4 mAb 3 G4P is shown below (SEQ ID NO:93).

```
QVQLVESGGG VVQPGRSLRL SCAASGFTFS SYTMHWVRQA

PGKGLEWVTF ISYDGSNKHY ADSVKGRFTV SRDNSKNTLY

LQMNSLRAED TAIYYCARTG WLGPFDYWGQ GTLVTVSSAS

TKGPSVFPLA PCSRSTSEST AALGCLVKDY FPEPVTVSWN

SGALTSGVHT FPAVLQSSGL YSLSSVVTVP SSSLGTKTYT

CNVDHKPSNT KVDKRVESKY GPPCPPCPAP EFLGGPSVFL

FPPKPKDTLM ISRTPEVTCV VVDVSQEDPE VQFNWYVDGV

EVHNAKTKPR EEQFNSTYRV VSVLTVLHQD WLNGKEYKCK

VSNKGLPSSI EKTISKAKGQ PREPQVYTLP PSQEEMTKNQ

VSLTCLVKGF YPSDIAVEWE SNGQPENNYK TTPPVLDSDG
```

```
SFFLYSRLTV DKSRWQEGNV FSCSVMHEAL HNHYTQKSLS

LSLG
```

The amino acid sequence of the complete light chain of CTLA-4 mAb 3 G1AA and CTLA-4 mAb 3 G4P (SEQ ID NO:94) is shown below.

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIKRT VAAPSVFIFP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC
```

The exemplary anti-CTLA-4 antibodies, CTLA-4 mAb 3 G1AA and CTLA-4 mAb 3 G4P, both comprise a light chain having the VL Domain of CTLA-4 mAb 3 (SEQ ID NO:91) and a kappa CL (SEQ ID NO:38).

VIII. Exemplary PD-1×CTLA-4 Bispecific Molecules

A. Exemplary Four Chain Fc Region-Containing Diabodies Having E/K-Coils

Three exemplary PD-1×CTLA-4 bispecific, four-chain, Fc Region-containing diabodies, comprising E/K-coil Heterodimer-Promoting Domains were generated (designated "DART B," "DART C," and "DART D"). The structure of these Fc Region-containing diabodies is detailed below. These exemplary PD-1×CTLA-4 diabodies are intended to illustrate, but in no way limit, the scope of the invention.

1. DART B

DART B is a bispecific, four-chain, Fc Region-containing diabody having two binding sites specific for PD-1, two binding sites specific for CTLA-4, a variant IgG4 Fc Region engineered for extended half-life, and E/K-coil Heterodimer-Promoting Domains. The first and third polypeptide chains of DART B comprise, in the N-terminal to C-terminal direction: an N-terminus, a VL Domain of a monoclonal antibody capable of binding to CTLA-4 (VL$_{CTLA-4}$ CTLA-4 mAb 1 VL) (SEQ ID NO:77); an intervening linker peptide (Linker 1: GGGSGGGG (SEQ ID NO:5)); a VH Domain of a monoclonal antibody capable of binding to PD-1 (VH$_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (E-coil) Domain (EVAACEK-EVAALEK-EVAALEK-EVAALEK (SEQ ID NO:20)); a stabilized IgG4 hinge region (SEQ ID NO:36); a variant of an IgG4 CH2-CH3 Domain comprising substitutions M252Y/S254T/T256E and lacking the C-terminal residue (SEQ ID NO:81); and a C-terminus.

The amino acid sequence of the first and third polypeptide chains of DART B is (SEQ ID NO:95):

```
EIVLTQSPGT LSLSPGERAT LSCRASQSVG SSYLAWYQQK

PGQAPRLLIY GAFSRATGIP DRFSGSGSGT DFTLTISRLE

PEDFAVYYCQ QYGSSPWTFG QGTKVEIKGG GSGGGGQVQL

VQSGAEVKKP GASVKVSCKA SGYSFTSYWM NWVRQAPGQG

LEWIGVIHPS DSETWLDQKF KDRVTITVDK STSTAYMELS

SLRSEDTAVY YCAREHYGTS PFAYWGQGTL VTVSSGGCGG

GEVAACEKEV AALEKEVAAL EKEVAALEKE SKYGPPCPPC

PAPEFLGGPS VFLFPPKPKD TLYITREPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLG
```

The second and fourth polypeptide chains of DART B comprise, in the N-terminal to C-terminal direction: an N-terminus, a VL Domain of a monoclonal antibody capable of binding to PD-1 (VL$_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding CTLA-4 (VH$_{CTLA-4}$ CTLA-4 mAb 1 VH) (SEQ ID NO:76); a cysteine-containing intervening linker peptide (Linker 2: GGCGGG (SEQ ID NO:6)); a cysteine-containing Heterodimer-Promoting (K-coil) Domain (KVAACKE-KVAALKE-KVAALKE-KVAALKE (SEQ ID NO:21); and a C-terminus.

The amino acid sequence of the second and fourth polypeptide chains of DART B is (SEQ ID NO:96):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVESGGGV VQPGRSLRLS CAASGFTFSS YTMHWVRQAP

GKGLEWVTFI SYDGNNKYYA DSVKGRFTIS RDNSKNTLYL

QMNSLRAEDT AIYYCARTGW LGPFDYWGQG TLVTVSSGGC

GGGKVAACKE KVAALKEKVA ALKEKVAALK E
```

2. DART C

DART C is a bispecific, four-chain, Fc Region-containing diabody having two binding sites specific for PD-1, two binding sites specific for CTLA-4, a variant IgG4 Fc Region engineered for extended half-life, and E/K-coil Heterodimer-Promoting Domains. The first and third polypeptide chains of DART C comprise, in the N-terminal to C-terminal direction: an N-terminus, a VL Domain of a monoclonal antibody capable of binding to CTLA-4 (VL$_{CTLA-4}$ CTLA-4 mAb 3 VL) (SEQ ID NO:91); an intervening linker peptide (Linker 1: GGGSGGGG (SEQ ID NO:5)); a VH Domain of a monoclonal antibody capable of binding to PD-1 (VH$_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (E-coil) Domain (EVAACEK-EVAALEK-EVAALEK-EVAALEK (SEQ ID NO:20)); a stabilized IgG4 hinge region (SEQ ID NO:36); a variant of an IgG4 CH2-CH3 Domain comprising substitutions M252Y/S254T/T256E and lacking the C-terminal residue (SEQ ID NO:81); and a C-terminus.

The amino acid sequence of the first and third polypeptide chains of DART C is (SEQ ID NO:97):

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIKGG GSGGGGQVQL

VQSGAEVKKP GASVKVSCKA SGYSFTSYWM NWVRQAPGQG

LEWIGVIHPS DSETWLDQKF KDRVTITVDK STSTAYMELS

SLRSEDTAVY YCAREHYGTS PFAYWGQGTL VTVSSGGCGG

GEVAACEKEV AALEKEVAAL EKEVAALEKE SKYGPPCPPC

PAPEFLGGPS VFLFPPKPKD TLYITREPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLG
```

The second and fourth polypeptide chains of DART C comprise, in the N-terminal to C-terminal direction: an N-terminus, a VL Domain of a monoclonal antibody capable of binding to PD-1 ($VL_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding CTLA-4 ($VH_{CTLA-4}$ CTLA-4 mAb 3 VH) (SEQ ID NO:90); a cysteine-containing intervening linker peptide (Linker 2: GGCGGG (SEQ ID NO:6)); a cysteine-containing Heterodimer-Promoting (K-coil) Domain (KVAACKE-KVAALKE-KVAALKE-KVAALKE (SEQ ID NO:21); and a C-terminus.

The amino acid sequence of the second and fourth polypeptide chains of DART C is (SEQ ID NO:98):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVESGGGV VQPGRSLRLS CAASGFTFSS YTMHWVRQAP

GKGLEWVTFI SYDGSNKHYA DSVKGRFTVS RDNSKNTLYL

QMNSLRAEDT AIYYCARTGW LGPFDYWGQG TLVTVSSGGC

GGGKVAACKE KVAALKEKVA ALKEKVAALK E
```

3. DART D

DART D is a bispecific, four-chain, Fc Region-containing diabody having two binding sites specific for PD-1, two binding sites specific for CTLA-4, a variant IgG4 Fc Region engineered for extended half-life, and E/K-coil Heterodimer-Promoting Domains. The first and third polypeptide chains of DART D comprise, in the N-terminal to C-terminal direction: an N-terminus, a VL Domain of a monoclonal antibody capable of binding to PD-1 ($VL_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding CTLA-4 ($VH_{CTLA-4}$ CTLA-4 mAb 3 VH) (SEQ ID NO:90); a cysteine-containing intervening linker peptide (Linker 2: GGCGGG (SEQ ID NO:6)); a cysteine-containing Heterodimer-Promoting (E-coil) Domain (EVAACEK-EVAALEK-EVAALEK-EVAALEK (SEQ ID NO:20)); a stabilized IgG4 hinge region (SEQ ID NO:36); a variant of an IgG4 CH2-CH3 Domain comprising substitutions M252Y/S254T/T256E and lacking the C-terminal residue (SEQ ID NO:81); and a C-terminus.

The amino acid sequence of the first and third polypeptide chains of DART D is (SEQ ID NO:99):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVESGGGV VQPGRSLRLS CAASGFTFSS YTMHWVRQAP

GKGLEWVTFI SYDGSNKHYA DSVKGRFTVS RDNSKNTLYL

QMNSLRAEDT AIYYCARTGW LGPFDYWGQG TLVTVSSGGC

GGGEVAACEK EVAALEKEVA ALEKEVAALE KESKYGPPCP

PCPAPEFLGG PSVFLFPPKP KDTLYITREP EVTCVVVDVS

QEDPEVQFNW YVDGVEVHNA KTKPREEQFN STYRVVSVLT

VLHQDWLNGK EYKCKVSNKG LPSSIEKTIS KAKGQPREPQ

VYTLPPSQEE MTKNQVSLTC LVKGFYPSDI AVEWESNGQP

ENNYKTTPPV LDSDGSFFLY SRLTVDKSRW QEGNVFSCSV

MHEALHNHYT QKSLSLSLG
```

The second and fourth polypeptide chains of DART D comprise, in the N-terminal to C-terminal direction: an N-terminus, a VL Domain of a monoclonal antibody capable of binding to CTLA-4 ($VL_{CTLA-4}$ CTLA-4 mAb 3 VL) (SEQ ID NO:91); an intervening linker peptide (Linker 1: GGGSGGGG (SEQ ID NO:5)); a VH Domain of a monoclonal antibody capable of binding to PD-1 ($VH_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (K-coil) Domain (KVAACKE-KVAALKE-KVAALKE-KVAALKE (SEQ ID NO:21); and a C-terminus.

The amino acid sequence of the second and fourth polypeptide chains of DART D is (SEQ ID NO:100):

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIKGG GSGGGGQVQL

VQSGAEVKKP GASVKVSCKA SGYSFTSYWM NWVRQAPGQG

LEWIGVIHPS DSETWLDQKF KDRVTITVDK STSTAYMELS

SLRSEDTAVY YCAREHYGTS PFAYWGQGTL VTVSSGGCGG

GKVAACKEKV AALKEKVAAL KEKVAALKE
```

4. DART F

DART F is a bispecific, four-chain, Fc Region-containing diabody having two binding sites specific for PD-1, two binding sites specific for CTLA-4, a variant IgG1 Fc Region engineered to reduce/eliminate effector function and to extend half-life, and E/K-coil Heterodimer-Promoting Domains. The first and third polypeptide chains of DART F comprise, in the N-terminal to C-terminal direction: an N-terminus, a VL Domain of a monoclonal antibody capable of binding to PD-1 (VL$_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding CTLA-4 (VH$_{CTLA-4}$ CTLA-4 mAb 3 VH) (SEQ ID NO:90); a cysteine-containing intervening linker peptide (Linker 2: GGCGGG (SEQ ID NO:6)); a cysteine-containing Heterodimer-Promoting (E-coil) Domain (EVAACEK-EVAALEK-EVAALEK-EVAALEK (SEQ ID NO:20)); an IgG1 hinge region (SEQ ID NO:33); a variant of an IgG1 CH2-CH3 Domain comprising substitutions L235A/L235A/M252Y/S254T/T256E and lacking the C-terminal residue (SEQ ID NO:80); and a C-terminus.

The amino acid sequence of the first and third polypeptide chains of DART F (SEQ ID NO:101) is:

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVESGGGV VQPGRSLRLS CAASGFTFSS YTMHWVRQAP

GKGLEWVTFI SYDGSNKHYA DSVKGRFTVS RDNSKNTLYL

QMNSLRAEDT AIYYCARTGW LGPFDYWGQG TLVTVSSGGC

GGGEVAACEK EVAALEKEVA ALEKEVAALE KLEPKSADKT

HTCPPCPAPE AAGGPSVFLF PPKPKDTLYI TREPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLTCLVKGFY PSDIAVEWES

NGQPENNYKT TPPVLDSDGS FFLYSKLTVD KSRWQQGNVF

SCSVMHEALH NHYTQKSLSL SPG
```

The second and fourth polypeptide chains of DART F comprise, in the N-terminal to C-terminal direction: an N-terminus, a VL Domain of a monoclonal antibody capable of binding to CTLA-4 (VL$_{CTLA-4}$ CTLA-4 mAb 3 VL) (SEQ ID NO:91); an intervening linker peptide (Linker 1: GGGSGGGG (SEQ ID NO:5)); a VH Domain of a monoclonal antibody capable of binding to PD-1 (VH$_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (K-coil) Domain (KVAACKE-KVAALKE-KVAALKE-KVAALKE (SEQ ID NO:21); and a C-terminus.

The amino acid sequence of the second and fourth polypeptide chains of DART F is the same as that of the second and fourth polypeptide chains of DART D (SEQ ID NO:100).

B. Exemplary Four-Chain Fc Region-Containing Diabodies Having CL/CH1 Domains: DART E An exemplary PD-1×CTLA-4 bispecific, four-chain, Fc Region-containing diabody comprising CL/CH1 Domains designated "DART E" was generated. The structure of this Fc Region-containing diabodies is detailed below. This exemplary PD-1×CTLA-4 diabody is intended to illustrate, but in no way limit, the scope of the invention.

DART E is a bispecific, four-chain, Fc Region-containing diabody having two binding sites specific for PD-1, two binding sites specific for CTLA-4, CL/CH1 Domains, and a variant IgG4 Fc Region engineered for extended half-life. The first and third polypeptide chains of DART E comprise, in the N-terminal to C-terminal direction: an N-terminus; a VL Domain of a monoclonal antibody capable of binding to CTLA-4 (VL$_{CTLA-4}$ CTLA-4 mAb 3 VL) (SEQ ID NO:91); an intervening linker peptide (Linker 1: GGGSGGGG (SEQ ID NO:5)); a VH Domain of a monoclonal antibody capable of binding to PD-1 (VH$_{PD-1}$ PD-1 mAb 6-I VH) (SEQ ID NO:86); an intervening linker peptide (Linker 2: LGGGSG (SEQ ID NO:8)); an IgG4 CH1 Domain (SEQ ID NO:42); a stabilized IgG4 hinge region (SEQ ID NO: 36); a variant of an IgG4 CH2-CH3 Domain comprising substitutions M252Y/S254T/T256E and lacking the C-terminal residue (SEQ ID NO:81); and a C-terminus.

The amino acid sequence of the first and third polypeptide chains of DART E is (SEQ ID NO:102):

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIKGG GSGGGGQVQL

VQSGAEVKKP GASVKVSCKA SGYSFTSYWM NWVRQAPGQG

LEWIGVIHPS DSETWLDQKF KDRVTITVDK STSTAYMELS

SLRSEDTAVY YCAREHYGTS PFAYWGQGTL VTVSSLGGGS

GASTKGPSVF PLAPCSRSTS ESTAALGCLV KDYFPEPVTV

SWNSGALTSG VHTFPAVLQS SGLYSLSSVV TVPSSSLGTK

TYTCNVDHKP SNTKVDKRVE SKYGPPCPPC PAPEFLGGPS

VFLFPPKPKD TLYITREPEV TCVVVDVSQE DPEVQFNWYV

DGVEVHNAKT KPREEQFNST YRVVSVLTVL HQDWLNGKEY

KCKVSNKGLP SSIEKTISKA KGQPREPQVY TLPPSQEEMT

KNQVSLTCLV KGFYPSDIAV EWESNGQPEN NYKTTPPVLD

SDGSFFLYSR LTVDKSRWQE GNVFSCSVMH EALHNHYTQK

SLSLSLG
```

The second and fourth polypeptide chains of DART E comprise, in the N-terminal to C-terminal direction: an N-terminus; a VL Domain of a monoclonal antibody capable of binding to PD-1 (VL$_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding CTLA-4 (VH$_{CTLA-4}$ CTLA-4 mAb 3 VH) (SEQ ID NO:90); an intervening linker peptide (Linker 2: LGGGSG (SEQ ID NO:8)); a Kappa CL Domain (SEQ ID NO:38); and a C-terminus.

The amino acid sequence of the second and fourth polypeptide chains of DART E is (SEQ ID NO:103):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVESGGGV VQPGRSLRLS CAASGFTFSS YTMHWVRQAP

GKGLEWVTFI SYDGSNKHYA DSVKGRFTVS RDNSKNTLYL

QMNSLRAEDT AIYYCARTGW LGPFDYWGQG TLVTVSSLGG

GSGRTVAAPS VFIFPPSDEQ LKSGTASVVC LLNNFYPREA
```

-continued

```
KVQWKVDNAL QSGNSQESVT EQDSKDSTYS LSSTLTLSKA

DYEKHKVYAC EVTHQGLSSP VTKSFNRGEC
```

C. Exemplary Trivalent Binding Molecules Containing Fc Regions

Two exemplary PD-1×CTLA-4 bispecific, four-chain, Fc Region-containing trivalent binding molecules were generated (designated "TRIDENT A" and "TRIDENT B"). The structure of these Fc Region-containing trivalent binding molecules is detailed below. Also presented below is a three chain variant designated "TRIDENT C," which may be generated. These exemplary PD-1×CTLA-4 trivalent binding molecules are intended to illustrate, but in no way limit, the scope of the invention.

1. TRIDENT A

TRIDENT A is a bispecific, four chain, Fc Region-containing trivalent binding molecule having two binding sites specific for PD-1, one binding sites specific for CTLA-4, a variant knob/hole-bearing IgG4 Fc Region engineered for extended half-life, E/K-coil Heterodimer-Promoting Domains and CL/CH1 Domains. The first polypeptide chain of TRIDENT A comprises, in the N-terminal to C-terminal direction: a VL Domain of a monoclonal antibody capable of binding to PD-1 ($VL_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding to PD-1 ($VH_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (E-coil) Domain (EVAACEK-EVAALEK-EVAALEK-EVAALEK (SEQ ID NO:20)); a stabilized IgG4 hinge region (SEQ ID NO: 36); a knob-bearing IgG4 CH2-CH3 Domain comprising substitutions M252Y/S254T/T256E and lacking the C-terminal residue (SEQ ID NO:84); and a C-terminus.

The amino acid sequence of the first polypeptide chain of TRIDENT A is (SEQ ID NO:104):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYSFTS YWMNWVRQAP

GQGLEWIGVI HPSDSETWLD QKFKDRVTIT VDKSTSTAYM

ELSSLRSEDT AVYYCAREHY GTSPFAYWGQ GTLVTVSSGG

CGGGEVAACE KEVAALEKEV AALEKEVAAL EKESKYGPPC

PPCPAPEFLG GPSVFLFPPK PKDTLYITRE PEVTCVVVDV

SQEDPEVQFN WYVDGVEVHN AKTKPREEQF NSTYRVVSVL

TVLHQDWLNG KEYKCKVSNK GLPSSIEKTI SKAKGQPREP

QVYTLPPSQE EMTKNQVSLW CLVKGFYPSD IAVEWESNGQ

PENNYKTTPP VLDSDGSFFL YSRLTVDKSR WQEGNVFSCS

VMHEALHNHY TQKSLSLSLG
```

The second polypeptide chain of TRIDENT A comprises, in the N-terminal to C-terminal direction: an N-terminus, a VL Domain of a monoclonal antibody capable of binding to PD-1 ($VL_{PD-1}$PD-1 mAb 6-SQ VL) (SEQ ID NO:87); an intervening linker peptide (Linker 1: GGGSGGGG (SEQ ID NO:5)); a VH Domain of a monoclonal antibody capable of binding to PD-1 ($VH_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (K-coil) Domain (KVAACKE-KVAALKE-KVAALKE-KVAALKE (SEQ ID NO:21)); and a C-terminus.

The amino acid sequence of the second polypeptide chain of TRIDENT A is (SEQ ID NO:105):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYSFTS YWMNWVRQAP

GQGLEWIGVI HPSDSETWLD QKFKDRVTIT VDKSTSTAYM

ELSSLRSEDT AVYYCAREHY GTSPFAYWGQ GTLVTVSSGG

CGGGKVAACK EKVAALKEKV AALKEKVAAL KE
```

The third polypeptide chains of TRIDENT A comprises, in the N-terminal to C-terminal direction: an N-terminus; a VH Domain of a monoclonal antibody capable of binding CTLA-4 ($VH_{CTLA-4}$ CTLA-4 mAb 3 VH) (SEQ ID NO:90); an IgG4 CH1 Domain (SEQ ID NO:42); a stabilized IgG4 hinge region (SEQ ID NO: 36); a hole-bearing IgG4 CH2-CH3 Domain comprising substitutions M252Y/S254T/T256E and lacking the C-terminal residue (SEQ ID NO:81); and a C-terminus.

The amino acid sequence of the third polypeptide chain of TRIDENT A (SEQ ID NO:106):

```
QVQLVESGGG VVQPGRSLRL SCAASGFTFS SYTMHWVRQA

PGKGLEWVTF ISYDGSNKHY ADSVKGRFTV SRDNSKNTLY

LQMNSLRAED TAIYYCARTG WLGPFDYWGQ GTLVTVSSAS

TKGPSVFPLA PCSRSTSEST AALGCLVKDY FPEPVTVSWN

SGALTSGVHT FPAVLQSSGL YSLSSVVTVP SSSLGTKTYT

CNVDHKPSNT KVDKRVESKY GPPCPPCPAP EFLGGPSVFL

FPPKPKDTLY ITREPEVTCV VVDVSQEDPE VQFNWYVDGV

EVHNAKTKPR EEQFNSTYRV VSVLTVLHQD WLNGKEYKCK

VSNKGLPSSI EKTISKAKGQ PREPQVYTLP PSQEEMTKNQ

VSLSCAVKGF YPSDIAVEWE SNGQPENNYK TTPPVLDSDG

SFFLVSRLTV DKSRWQEGNV FSCSVMHEAL HNRYTQKSLS

LSLG
```

The fourth polypeptide chain of TRIDENT A comprises, in the N-terminal to C-terminal direction: an N-terminus; a VL Domain of a monoclonal antibody capable of binding to CTLA-4 ($VL_{CTLA-4}$ CTLA-4 mAb 3 VL) (SEQ ID NO:91); a Kappa CL Domain (SEQ ID NO:38); and a C-terminus.

The amino acid sequence of the fourth polypeptide chain of TRIDENT A is (SEQ ID NO:107):

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIKRT VAAPSVFIFP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC
```

2. TRIDENT B

TRIDENT B is a bispecific, four-chain, Fc Region-containing trivalent binding molecule having two binding sites specific for PD-1, one binding sites specific for CTLA-4, a variant knob/hole-bearing IgG1 Fc Region engineered to reduce/eliminate effector function and to extend half-life, E/K-coil Heterodimer-Promoting Domains and CL/CH1 Domains. The first polypeptide chain of TRIDENT B comprises, in the N-terminal to C-terminal direction: a VL Domain of a monoclonal antibody capable of binding to PD-1 (VL$_{PD-1}$ PD-1 mAb 6-SQ VL) (SEQ ID NO:87); an intervening linker peptide (Linker 1: GGGSGGGG (SEQ ID NO:5)); a VH Domain of a monoclonal antibody capable of binding to PD-1 (VH$_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (E-coil) Domain (EVAACEK-EVAALEK-EVAALEK (SEQ ID NO:20)); a linker (SEQ ID NO: 31); a knob-bearing IgG1 CH2-CH3 Domain comprising substitutions L234A/L235A/M252Y/S254T/T256E and lacking the C-terminal residue (SEQ ID NO:82); and a C-terminus.

The amino acid sequence of the first polypeptide chain of TRIDENT B is (SEQ ID NO:108):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYSFTS YWMNWVRQAP

GQGLEWIGVI HPSDSETWLD QKFKDRVTIT VDKSTSTAYM

ELSSLRSEDT AVYYCAREHY GTSPFAYWGQ GTLVTVSSGG

CGGGEVAACE KEVAALEKEV AALEKEVAAL EKGGGDKTHT

CPPCPAPEAA GGPSVFLFPP KPKDTLYITR EPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL WCLVKGFYPS DIAVEWESNG

QPENNYKTTP PVLDSDGSFF LYSKLTVDKS RWQQGNVFSC

SVMHEALHNH YTQKSLSLSP GK
```

The second polypeptide chain of TRIDENT B comprises, in the N-terminal to C-terminal direction: an N-terminus, a VL Domain of a monoclonal antibody capable of binding to PD-1 (VL$_{PD-1}$PD-1 mAb 6-SQ VL) (SEQ ID NO:87); an intervening linker peptide (Linker 1: GGGSGGGG (SEQ ID NO:5)); a VH Domain of a monoclonal antibody capable of binding to PD-1 (VH$_{PD-1}$ PD-1 mAb 6-I VH) (SEQ ID NO:86); a cysteine-containing intervening linker peptide (Linker 2: GGCGGG (SEQ ID NO:6)); a cysteine-containing Heterodimer-Promoting (K-coil) Domain (KVAACKE-KVAALKE-KVAALKE-KVAALKE (SEQ ID NO:21)); and a C-terminus.

The amino acid sequence of the second polypeptide chain of TRIDENT B is the same as that of the second polypeptide chain of TRIDENT A (SEQ ID NO:105):

The third polypeptide chains of TRIDENT B comprises, in the N-terminal to C-terminal direction: an N-terminus; a VH Domain of a monoclonal antibody capable of binding CTLA-4 (VH$_{CTLA-4}$ CTLA-4 mAb 3 VH) (SEQ ID NO:90); an IgG1 CH1 Domain (SEQ ID NO:40); an IgG1 hinge region (SEQ ID NO:33); a hole-bearing IgG1 CH2-CH3 Domain comprising substitutions L234A/L235A/M252Y/S254T/T256E and lacking the C-terminal residue (SEQ ID NO:83); and a C-terminus.

The amino acid sequence of the third polypeptide chain of TRIDENT B is (SEQ ID NO:109):

```
QVQLVESGGG VVQPGRSLRL SCAASGFTFS SYTMHWVRQA

PGKGLEWVTF ISYDGSNKHY ADSVKGRFTV SRDNSKNTLY

LQMNSLRAED TAIYYCARTG WLGPFDYWGQ GTLVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLYITREPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The fourth polypeptide chain of TRIDENT B comprises, in the N-terminal to C-terminal direction: an N-terminus; a VL Domain of a monoclonal antibody capable of binding to CTLA-4 (VL$_{CTLA-4}$ CTLA-4 mAb 3 VL) (SEQ ID NO:91); a Kappa CL Domain (SEQ ID NO:38); and a C-terminus.

The amino acid sequence of the fourth polypeptide chain of TRIDENT B is the same as that of the second polypeptide chain of TRIDENT A (SEQ ID NO:107).

3. TRIDENT C

As provided herein, trivalent binding molecules comprising three polypeptide chain may be generated by combining (e.g., fusing encoding polynucleotides, etc.) the binding domains of two separate polypeptide chains into one chain. One bispecific, three-chain, Fc Region-containing trivalent binding molecule that may be generated has two binding sites specific for PD-1, one binding sites specific for CTLA-4, a variant knob/hole-bearing IgG4 Fc Region engineered for extended half-life, and E/K-coil Heterodimer-Promoting Domains ("TRIDENT C"). The first and second polypeptide chains of TRIDENT C may be identical to those of TRIDENT A provided above.

Where the first and second chains are identical to those of TRIDENT A, the third polypeptide chain of TRIDENT C may comprise, in the N-terminal to C-terminal direction: an N-terminus; a VL Domain of a monoclonal antibody capable of binding to CTLA-4 (VL$_{CTLA-4}$ CTLA-4 mAb 3 VL) (SEQ ID NO:91); an intervening spacer peptide (GGGGSGGGGSGGGGS (SEQ ID NO:37)); a VH Domain of a monoclonal antibody capable of binding CTLA-4 (VH$_{CTLA-4}$ CTLA-4 mAb 3 VH) (SEQ ID NO:90); a stabilized IgG4 hinge region (SEQ ID NO: 36); a hole-bearing IgG4 CH2-CH3 Domain comprising substitutions M252Y/S254T/T256E and lacking the C-terminal residue (SEQ ID NO:85); and a C-terminus.

Thus, the amino acid sequence of the third polypeptide chain of TRIDENT C is (SEQ ID NO:110):

```
EIVLTQSPGT LSLSPGERAT LSCRASQSVS SSFLAWYQQK

PGQAPRLLIY GASSRATGIP DRFSGSGSGT DFTLTISRLE

PEDFAVYYCQ QYGSSPWTFG QGTKVEIKGG GGSGGGGSGG

GGSQVQLVES GGGVVQPGRS LRLSCAASGF TFSSYTMHWV

RQAPGKGLEW VTFISYDGSN KHYADSVKGR FTVSRDNSKN

TLYLQMNSLR AEDTAIYYCA RTGWLGPFDY WGQGTLVTVS

SESKYGPPCP PCPAPEFLGG PSVFLFPPKP KDTLYITREP

EVTCVVVDVS QEDPEVQFNW YVDGVEVHNA KTKPREEQFN

STYRVVSVLT VLHQDWLNGK EYKCKVSNKG LPSSIEKTIS

KAKGQPREPQ VYTLPPSQEE MTKNQVSLSC AVKGFYPSDI

AVEWESNGQP ENNYKTTPPV LDSDGSFFLV SRLTVDKSRW

QEGNVFSCSV MHEALHNRYT QKSLSLSLG
```

IX. Methods of Production

The PD-1×CTLA-4 bispecific molecules of the present invention are most preferably produced through the recombinant expression of nucleic acid molecules that encode such polypeptides, as is well-known in the art.

Polypeptides of the invention may be conveniently prepared using solid phase peptide synthesis (Merrifield, B. (1986) "*Solid Phase Synthesis*," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135; Ganesan, A. (2006) "*Solid-Phase Synthesis In The Twenty First Century*," Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized, single-chain, etc. are known in the art, and have been described above. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

Vectors containing polynucleotides of interest (e.g., polynucleotides encoding the polypeptide chains of the PD-1×CTLA-4 bispecific molecules of the present invention) can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of expressing a polypeptide or protein of interest. Non-limiting examples of suitable mammalian host cells include but are not limited to COS, HeLa, and CHO cells.

The invention includes polypeptides comprising an amino acid sequence of the PD-1×CTLA-4 bispecific molecule of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available.

The invention includes variants of PD-1×CTLA-4 bispecific molecules, including functionally equivalent polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the polypeptides or antibodies of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma. For purposes of this invention, an antibody fusion protein contains one or more polypeptide domains that specifically bind to PD-1 and/or CTLA-4 and another amino acid sequence to which it is not attached in the native molecule, for example, a heterologous sequence or a homologous sequence from another region.

X. Uses of the PD-1×CTLA-4 Bispecific Molecules of the Present Invention

The present invention encompasses compositions, including pharmaceutical compositions, comprising the PD-1×CTLA-4 bispecific molecules of the present invention (e.g., bispecific antibodies, bispecific diabodies, trivalent binding molecules, etc.), polypeptides derived from such molecules, polynucleotides comprising sequences encoding such molecules or polypeptides, and other agents as described herein.

As discussed above, both PD-1 and CTLA-4 play important roles in negatively regulating immune responses (e.g., immune cell proliferation, function and homeostasis). The PD-1×CTLA-4 bispecific molecules of the present invention have the ability to inhibit PD-1 function, and thus reverse the PD-1-mediated immune system inhibition. In addition, the PD-1×CTLA-4 bispecific molecules of the present invention have the ability to inhibit CTLA-4 function and thus augment the immune system by blocking immune system inhibition mediated by PD-1 and CTLA-4. The PD-1×CTLA-4 bispecific molecules of the present invention also allow for full blockade of both PD-1 and CTLA-4, as well as blockade that is biased toward CTLA-4 when co-expressed with PD-1. Thus, the PD-1×CTLA-4 bispecific molecules of the invention are useful for relieving T-cell exhaustion and/or augmenting an immune response (e.g., a T-cell and/or NK-cell mediated immune response) of a subject. In particular, the PD-1×CTLA-4 bispecific molecules of the invention and may be used to treat any disease or condition associated with an undesirably suppressed immune system, including cancer and diseases that are associated with the presence of a pathogen (e.g., a bacterial, fungal, viral or protozoan infection).

The cancers that may be treated by the PD-1×CTLA-4 bispecific molecules of the present invention include cancers characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

In particular, PD-1×CTLA-4 bispecific molecules of the present invention may be used in the treatment of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer.

Infections that may be treated by the PD-1×CTLA-4 bispecific molecules of the present invention include chronic viral, bacterial, fungal and parasitic infections. Chronic infections that may be treated by the PD-1×CTLA-4 bispecific molecules of the present invention include Epstein Barr virus, Hepatitis A Virus (HAV); Hepatitis B Virus (HBV); Hepatitis C Virus (HCV); herpes viruses (e.g. HSV-1, HSV-2, CMV), Human Immunodeficiency Virus (HIV), Vesicular Stomatitis Virus (VSV), *Bacilli, Citrobacter, Cholera, Diphtheria, Enterobacter, Gonococci, Helicobacter pylori, Klebsiella, Legionella, Meningococci*, mycobacteria, *Pseudomonas, Pneumonococci, rickettsia* bacteria, *Salmonella, Serratia, Staphylococci, Streptococci, Tetanus, Aspergillus* (*A. fumigatus, A. niger*, etc.), *Blastomyces dermatitidis, Candida* (*C. albicans, C. krusei, C. glabrata, C. tropicalis*, etc.), *Cryptococcus neoformans*, Genus *Mucorales* (*mucor, absidia, rhizopus*), *Sporothrix schenkii, Paracoccidioides brasiliensis, Coccidioides immitis, Histoplasma capsulatum, Leptospirosis, Borrelia burgdorferi*, helminth parasite (hookworm, tapeworms, flukes, flatworms (e.g. *Schistosomia*), *Giardia lambia, trichinella, Dientamoeba Fragilis, Trypanosoma brucei, Trypanosoma cruzi*, and *Leishmania donovani*.

XI. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of the PD-1×CTLA-4 bispecific molecules of the present invention, or a combination of such agents and a pharmaceutically acceptable carrier. Preferably, compositions of the invention comprise a prophylactically or therapeutically effective amount of the PD-1×CTLA-4 bispecific molecules of the present invention and a pharmaceutically acceptable carrier. The invention also encompasses such pharmaceutical compositions that additionally include a second therapeutic antibody (e.g., tumor-specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with a PD-1×CTLA-4 bispecific molecule of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the PD-1×CTLA-4 bispecific molecules of the present invention. The kit can further comprise one or more other prophylactic and/or therapeutic agents useful for the treatment of cancer, in one or more containers.

XII. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "Receptor Mediated In Vitro Gene Transformation By A Soluble DNA Carrier System," J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the PD-1×CTLA-4 bispecific molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that preparations of the PD-1×CTLA-4 bispecific molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the PD-1×CTLA-4 bispecific molecules of the present invention are supplied as a dry sterile lyophilized powder in a hermetically sealed container.

The lyophilized preparations of the PD-1×CTLA-4 bispecific molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such PD-1×CTLA-4 bispecific molecules when provided in liquid form are supplied in a hermetically sealed container.

The amount of such preparations of the invention that will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition, in one embodiment, is an amount sufficient to effect beneficial or desired results including, without limitation, clinical results such as decreasing symptoms resulting from the disease, attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

An effective amount can be administered in one or more administrations. For purposes of this invention, an effective amount of drug, compound, or pharmaceutical composition is an amount sufficient: to kill and/or reduce the proliferation of cancer cells, and/or to eliminate, reduce and/or delay the development of metastasis from a primary site of cancer; or to reduce the proliferation of (or the effect of) an infectious pathogen and to reduce and/or delay the development of the pathogen-mediated disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the PD-1×CTLA-4 bispecific molecules encompassed by the invention, the dosage administered to a patient is preferably determined based upon the body weight (kg) of the recipient subject. For the PD-1×CTLA-4 bispecific molecules encompassed by the invention, the dosage administered to a patient is typically from about 0.01 µg/kg to about 150 mg/kg or more of the subject's body weight.

The dosage and frequency of administration of a PD-1× CTLA-4 bispecific molecule of the present invention may be reduced or altered by enhancing uptake and tissue penetration of the molecule by modifications such as, for example, lipidation.

The dosage of a PD-1×CTLA-4 bispecific molecule of the invention administered to a patient may be calculated for use as a single agent therapy. Alternatively, the molecule may be used in combination with other therapeutic compositions and the dosage administered to a patient are lower than when the molecules are used as a single agent therapy.

The pharmaceutical compositions of the invention may be administered locally to the area in need of treatment; this may be achieved by, for example, and not by way of limitation, local infusion, by injection, or by means of an implant, the implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

Where the composition of the invention is a nucleic acid encoding a PD-1×CTLA-4 bispecific molecule of the present invention, the nucleic acid can be administered in vivo to promote expression of its encoded PD-1×CTLA-4 bispecific molecule by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of a PD-1×CTLA-4 bispecific molecule of the present invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

XIII. Exemplary Embodiments

The invention is particularly directed to the embodiments E1-E26:

E1. A bispecific molecule possessing both one or more epitope-binding sites capable of immunospecific binding to (an) epitope(s) of PD-1 and one or more epitope-binding sites capable of immunospecific binding to (an) epitope(s) of CTLA-4, wherein such molecule comprises:
(A) a Heavy Chain Variable Domain and a Light Chain Variable Domain of an antibody that binds PD-1; and
(B) a Heavy Chain Variable Domain and a Light Chain Variable Domain of an antibody that binds CTLA-4;
wherein such molecule is:
(i) a diabody, such diabody being a covalently bonded complex that comprises two, three, four or five polypeptide chains; or
(ii) a trivalent binding molecule, such trivalent binding molecule being a covalently bonded complex that comprises three, four, five, or more polypeptide chains.

E2. The bispecific molecule of Embodiment E1, wherein such molecule exhibits an activity that is enhanced relative to such activity exhibited by two monospecific molecules one of which possesses such Heavy Chain Variable Domain and such Light Chain Variable Domain of such antibody that binds PD-1 and the other of which possesses such Heavy Chain Variable Domain and such Light Chain Variable Domain of such antibody that binds CTLA-4.

E3. The bispecific molecule of Embodiment E1 or E2, wherein such molecule elicits fewer immune-related adverse events (irAEs) when administered to a subject in need thereof relative to such iREs elicited by the administration of a monospecific antibody that binds CTLA-4.

E4. The bispecific molecule of Embodiment E3, wherein said monospecific antibody that binds CTLA-4 is ipilimumab.

E5. The bispecific molecule of any one of Embodiments E1-E4, wherein such molecule comprises an Fc Region.

E6. The bispecific molecule of Embodiment E5, wherein such Fc Region is a variant Fc Region that comprises:
(A) one or more amino acid modifications that reduces the affinity of the variant Fc Region for an FcγR; and/or
(B) one or more amino acid modifications that enhances the serum half-life of the variant Fc Region.

E7. The bispecific molecule of Embodiment E6, wherein such modifications that reduces the affinity of the variant Fc Region for an FcγR comprise the substitution of L234A; L235A; or L234A and L235A, wherein such numbering is that of the EU index as in Kabat.

E8. The bispecific molecule of Embodiment E6 or E7, wherein such modifications that that enhances the serum half-life of the variant Fc Region comprise the substitution of M252Y; M252Y and S254T; M252Y and T256E; M252Y, S254T and T256E; or K288D and H435K, wherein such numbering is that of the EU index as in Kabat.

E9. The bispecific molecule of any one of Embodiments E1-E8, wherein such molecule is such diabody and comprises two epitope-binding sites capable of immunospecific binding to an epitope of PD-1 and two epitope-binding sites capable of immunospecific binding to an epitope of CTLA-4.

E10. The bispecific molecule of any one of Embodiments E1-E8, wherein such molecule is such trivalent binding molecule and comprises two epitope-binding sites capable of immunospecific binding to an epitope of PD-1 and one epitope-binding site capable of immunospecific binding to an epitope of CTLA-4.

E11. The bispecific molecule of any one of Embodiments E1-E10, wherein such molecule is capable of binding to PD-1 and CTLA-4 molecules present on the cell surface.

E12. The bispecific molecule of any one of Embodiments E1-E11, wherein such molecule is capable of simultaneously binding to PD-1 and CTLA-4.

E13. The bispecific molecule of any one of Embodiments E1-E12, wherein such molecule promotes the stimulation of immune cells.

E14. The bispecific molecule of Embodiment E13, wherein such stimulation of immune cells results in:
(A) immune cell proliferation; and/or
(B) immune cell production and/or release of at least one cytokine; and/or
(C) immune cell production and/or release of at least one lytic molecule; and/or
(D) immune cell expression of at least one activation marker.

E15. The bispecific molecule of Embodiment E13 or E14, wherein such immune cell is a T-lymphocyte or an NK-cell.

E16. The bispecific molecule of any one of Embodiments E1-E15, wherein such epitope-binding sites capable of immunospecific binding to an epitope of PD-1 comprise:
(A) the VH Domain of PD-1 mAb 1 (SEQ ID NO:47) and the VL Domain of PD-1 mAb 1 (SEQ ID NO:48); or
(B) the VH Domain of PD-1 mAb 2 (SEQ ID NO:49) and the VL Domain of PD-1 mAb 2 (SEQ ID NO:50); or
(C) the VH Domain of PD-1 mAb 3 (SEQ ID NO:51) and the VL Domain of PD-1 mAb 3 (SEQ ID NO:52); or
(D) the VH Domain of PD-1 mAb 4 (SEQ ID NO:53) and the VL Domain of PD-1 mAb 4 (SEQ ID NO:54); or
(E) the VH Domain of PD-1 mAb 5 (SEQ ID NO:55) and the VL Domain of PD-1 mAb 5 (SEQ ID NO:56); or
(F) the VH Domain of PD-1 mAb 6 (SEQ ID NO:57) and the VL Domain of PD-1 mAb 6 (SEQ ID NO:58); or
(G) the VH Domain of PD-1 mAb 6-I VH (SEQ ID NO:86) and the VL Domain of PD-1 mAb 6-SQ VL (SEQ ID NO:87); or
(H) the VH Domain of PD-1 mAb 7 (SEQ ID NO:59) and the VL Domain of PD-1 mAb 7 (SEQ ID NO:60); or
(I) the VH Domain of PD-1 mAb 8 (SEQ ID NO:61) and the VL Domain of PD-1 mAb 8 (SEQ ID NO:62).

E17. The bispecific molecule of any one of Embodiments E1-E16, wherein such epitope-binding site(s) capable of immunospecific binding to an epitope of CTLA-4 comprise:
(A) the VH Domain of CTLA-4 mAb 1 (SEQ ID NO:76) and the VL Domain of CTLA-4 mAb 1 (SEQ ID NO:77); or
(B) the VH Domain of CTLA-4 mAb 2 (SEQ ID NO:78) and the VL Domain of CTLA-4 mAb 2 (SEQ ID NO:79); or
(C) the VH Domain of CTLA-4 mAb 3 (SEQ ID NO:90) and the VL Domain of CTLA-4 mAb 3 (SEQ ID NO:91).

E18. The bispecific molecule of Embodiment 17, wherein:
(A) such epitope-binding sites capable of immunospecific binding to an epitope of PD-1 comprise the VH Domain of PD-1 mAb 6-I VH (SEQ ID NO:86) and the VL Domain of PD-1 mAb 6-SQ (SEQ ID NO:87); and
(B) such epitope-binding site(s) capable of immunospecific binding to an epitope of CTLA-4 comprise(s) the VH Domain of CTLA-4 mAb 3 (SEQ ID NO:90) and the VL Domain of CTLA-4 mAb 3 (SEQ ID NO:91).

E19. The bispecific molecule of any one of Embodiments E1-E18, wherein such molecule comprises:
(A) two polypeptide chains having SEQ ID NO:95, and two polypeptide chain having SEQ ID NO:96; or
(B) two polypeptide chains having SEQ ID NO:97, and two polypeptide chain having SEQ ID NO:98; or
(C) two polypeptide chains having SEQ ID NO:99, and two polypeptide chain having SEQ ID NO:100; or
(D) two polypeptide chains having SEQ ID NO:102, and two polypeptide chain having SEQ ID NO:103; or
(E) two polypeptide chains having SEQ ID NO:101, and two polypeptide chain having SEQ ID NO:100; or
(F) one polypeptide chains having SEQ ID NO:104, one polypeptide chain having SEQ ID NO:105, one polypeptide chain having SEQ ID NO:106, and one polypeptide chain having SEQ ID NO:107; or
(G) one polypeptide chains having SEQ ID NO:108, one polypeptide chain having SEQ ID NO:105, one polypeptide chain having SEQ ID NO:109, and one polypeptide chain having SEQ ID NO:107.

E20. A pharmaceutical composition that comprises an effective amount of the bispecific molecule of any of Embodiments E1-E19 and a pharmaceutically acceptable carrier.

E21. The bispecific molecule of any one of Embodiments E1-E19, wherein such molecule is used to promote stimulation of an immune-mediated response of a subject in need thereof.

E22. The bispecific molecule of any one of Embodiments E1-E19, wherein such molecule is used in the treatment of a disease or condition associated with a suppressed immune system.

E23. The bispecific molecule of Embodiment E22, wherein the disease or condition is cancer or an infection.

E24. The bispecific molecule of Embodiment E23, wherein such cancer is characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

E25. The bispecific molecule of Embodiment E24, wherein such infection is characterized by the presence of a bacterial, fungal, viral or protozoan pathogen.

E26. The bispecific molecule of Embodiment E25, wherein such infection is characterized by the presence of Epstein Barr virus, Hepatitis A Virus (HAV); Hepatitis B Virus (HBV); Hepatitis C Virus (HCV); herpes viruses (e.g. HSV-1, HSV-2, CMV), Human Immunodeficiency Virus (HIV), Vesicular Stomatitis Virus (VSV), *Bacilli, Citrobacter, Cholera, Diphtheria, Enterobacter, Gonococci, Helicobacter pylori, Klebsiella, Legionella, Meningococci, mycobacteria, Pseudomonas, Pneumonococci, rickettsia* bacteria, *Salmonella, Serratia, Staphylococci, Streptococci, Tetanus, Aspergillus* (*A. fumigatus, A. niger*, etc.), *Blastomyces dermatitidis, Candida* (*C. albicans, C. krusei, C. glabrata, C. tropicalis*, etc.), *Cryptococcus neoformans*, Genus *Mucorales* (*mucor, absidia, rhizopus*), *Sporothrix schenkii, Paracoccidioides brasiliensis, Coccidioides immitis, Histoplasma capsulatum, Leptospirosis, Borrelia burgdorferi*, helminth parasite (hookworm, tapeworms, flukes, flatworms (e.g. *Schistosomia*), *Giardia lambia, trichinella, Dientamoeba Fragilis, Trypanosoma brucei, Trypanosoma cruzi*, and *Leishmania donovani*.

EXAMPLES

Having now generally described the invention, the same will be more readily understood through reference to the following Examples. The following examples illustrate various methods for compositions in the diagnostic or treatment methods of the invention. The examples are intended to illustrate, but in no way limit, the scope of the invention.

Example 1

Bispecific Molecules Provide Enhanced Stimulation of Immune Responses

A bispecific molecule having specificity for distinct cell surface proteins that modulate two immunomodulatory pathways, PD-1 and LAG-3, was generated and designated "DART A."

DART A is a bispecific, four chain, Fc Region-containing diabody having two binding sites specific for PD-1, two binding sites specific for LAG-3, a variant IgG4 Fc Region engineered for extended half-life, and cysteine-containing E/K-coil Heterodimer-Promoting Domains. As provided in more detail below, DART A comprises the binding specificities (i.e., the VH and VL Domains) of a humanized anti-PD-1 antibody (hPD-1 mAb 6) and a humanized anti-LAG-3 antibody (hLAG-3 mAb 1). The amino acid sequence of the first and third polypeptide chains of DART A is (SEQ ID NO:63):

```
DIQMTQSPSS LSASVGDRVT ITCRASQDVS SVVAWYQQKP

GKAPKLLIYS ASYRYTGVPS RFSGSGSGTD FTLTISSLQP

EDFATYYCQQ HYSTPWTFGG GTKLEIKGGG SGGGGQVQLV

QSGAEVKKPG ASVKVSCKAS GYSFTSYWMN WVRQAPGQGL

EWIGVIHPSD SETWLDQKFK DRVTITVDKS TSTAYMELSS

LRSEDTAVYY CAREHYGTSP FAYWGQGTLV TVSSGGCGGG

EVAACEKEVA ALEKEVAALE KEVAALEKES KYGPPCPPCP

APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLG
```

In SEQ ID NO:63, amino acid residues 1-107 correspond to the amino acid sequence of a VL Domain of a humanized monoclonal antibody capable of binding to LAG-3 (hLAG-3 mAb 1); residues 108-115 correspond to the intervening spacer peptide (Linker 1: GGGSGGGG (SEQ ID NO:5)); residues 116-234 correspond to the VH Domain of a monoclonal antibody capable of binding to PD-1 (hPD-1 mAb 6, SEQ ID NO:57, wherein $X_1$ is I); residues 235-240 correspond to an intervening spacer peptide (Linker 2: GGCGGG (SEQ ID NO:6)); residues 241-268 correspond to a cysteine-containing Heterodimer-Promoting (E-coil) Domain (EVAACEK-EVAALEK-EVAALEK-EVAALEK (SEQ ID NO:20)); residues 269-280 correspond to a stabilized IgG4 Hinge Region (SEQ ID NO:36); residues to 281-496 correspond to a variant of IgG4 CH2-CH3 Domain comprising substitutions M252Y/S254T/T256E and lacking the C-terminal residue.

The amino acid sequence of the second and fourth polypeptide chains of DART A is (SEQ ID NO:64):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYTFTD YNMDWVRQAP

GQGLEWMGDI NPDNGVTIYN QKFEGRVTMT TDTSTSTAYM

ELRSLRSDDT AVYYCAREAD YFYFDYWGQG TTLTVSSGGC

GGGKVAACKE KVAALKEKVA ALKEKVAALK E
```

In SEQ ID NO:64, amino acid residues 1-111 correspond to the amino acid sequence of a VL Domain of a monoclonal antibody capable of binding to PD-1 (hPD-1 mAb 6, SEQ ID NO:58 wherein $X_1$ is S and $X_2$ is Q); residues 112-119 correspond to an intervening spacer peptide (Linker 1: GGGSGGGG (SEQ ID NO:5)); residues 120-237 correspond to a VH Domain of a humanized monoclonal antibody capable of binding LAG-3 (hLAG-3 mAb 1); residues 238-243 correspond to a cysteine-containing spacer linker peptide (Linker 2: GGCGGG (SEQ ID NO:6)); residues 244-271 correspond to a cysteine-containing Heterodimer-Promoting (K-coil) Domain (KVAACKE-KVAALKE-KVAALKE-KVAALKE (SEQ ID NO:21)).

The ability of DART A to stimulate T-cells was examined in a *Staphylococcus aureus* enterotoxin type B ("SEB") assay. SEB is a microbial superantigen capable of activating a large proportion of T-cells (5-30%) in SEB-responsive donors. SEB binds to MHC II outside the peptide binding grove and thus is MHC II dependent, but unrestricted and TCR mediated. SEB-stimulation of T-cells results in oligoclonal T-cell proliferation and cytokine production (although donor variability may be observed). Within 48 hours of SEB-stimulation PMBCs upregulate PD-1 and LAG-3 with a further enhancement at day 5, post-secondary culture in 96-well plate with SEB-stimulation. Upregulation of the immune check point proteins PD-1 and LAG-3 following SEB-stimulation of PBMCs limits cytokine release upon SEB restimulation. The ability of DART A to enhance cytokine release through checkpoint inhibition was examined and compared to the activity of the parental anti-PD-1 and anti-LAG-3 antibodies alone and in combination.

Briefly, PBMCs were purified using the Ficoll-Paque Plus (GE Healthcare) density gradient centrifugation method according to manufacturer's instructions from whole blood obtained under informed consent from healthy donors (Biological Specialty Corporation) and T-cells were then purified using the Dynabeads® Untouched Human T-Cells Kit (Life Technologies) according to manufacturer's instructions. Purified PBMCs were cultured in RPMI-media+10% heat inactivated FBS+1% Penicillin/Streptomycin in T-25 bulk flasks for 2-3 days alone or with SEB (Sigma-Aldrich) at 0.5 ng/mL (primary stimulation). At the end of the first round of SEB-stimulation, PBMCs were washed twice with PBS and immediately plated in 96-well tissue culture plates at a concentration of 1-5×$10^5$ cells/well in media alone, media with a control antibody, media with SEB at 0.5 ng/mL (secondary stimulation) and no antibody, or media with SEB and DART A, a control IgG or an anti-PD-1 antibody+/−an anti-LAG-3 mAb, and cultured for an additional 2-3 days. At the end of the second stimulation, supernatants were harvested to measure cytokine secretion using human DuoSet ELISA Kits for IFNγ, TNFα, IL-10, and IL-4 (R&D Systems) according to the manufacturer's instructions.

Figure 7:
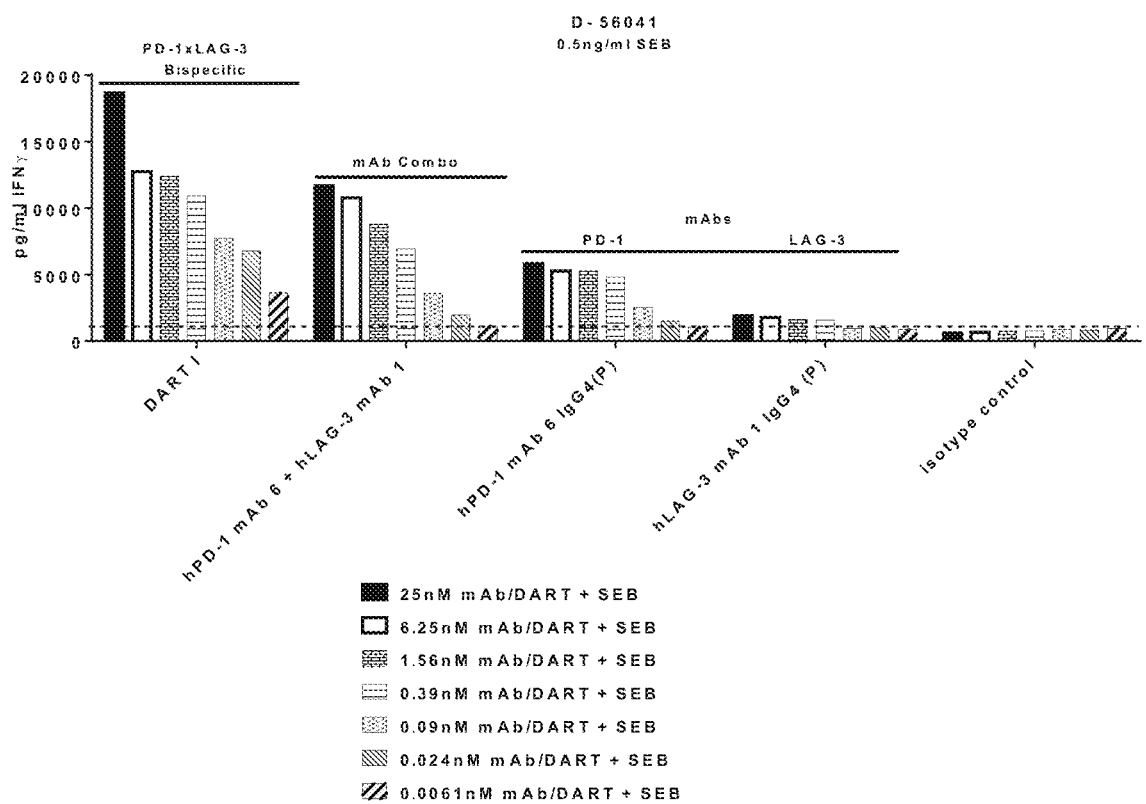
FIG. 7 illustrates the principles of the present invention by showing that an exemplary bispecific molecule (a PD-1× LAG-3 bispecific molecule, designated as DART A) is able to stimulate cytokine production to levels higher than those observed upon the joint or combined administration of the parental anti-PD-1 and anti-LAG-3 antibodies. Shown are IFNγ secretion profiles of PBMCs from a representative donor, stimulated with SEB (0.5 ng/mL) and treated with the exemplary bispecific molecule (PD-1×LAG-3 bispecific molecule DART A) or with the anti-PD-1 and anti-LAG-3 antibodies alone or in combination.

In these assays DART A (a PD-1×LAG-3 bispecific molecule) and the anti-PD-1 and anti-LAG-3 antibodies were used at a concentration of 0.0061, 0.024, 0.09, 0.39, 1.56, 6.25 or 25 nM. For these studies, where a combination of antibodies is used each antibody is provided at the indicated concentration and thus the total antibody concentration is twice the concentration used for each antibody (i.e., 0.0122, 0.048, 0.18, 0.78, 3.12, 12.5 or 50 nM). FIG. 7 shows the IFNγ secretion profiles from SEB-stimulated PBMCs from a representative donor (D: 56041). Similar results were seen for PD-1×LAG-3 bispecific molecules comprising VH/VL domains from alternative PD-1 and LAG-3 antibodies, and for PD-1×LAG-3 bispecific molecules have alternative structures (see, e.g., FIG. 3C, and for numerous donors).

The results of these studies demonstrate that PD-1× LAG-3 bispecific molecules dramatically enhanced IFNγ production from SEB-stimulated PBMCs upon restimulation. These results show that bispecific molecules that target two immunomodulatory pathways were more potent than the combination of separate antibodies targeting the same pathways.

Example 2

PD-1×CTLA-4 Bispecific Molecules

Bispecific molecules having specificity for PD-1 and CTLA-4 may be generated using methods provided herein and known in the art. The general structure of the polypeptide chains of several PD-1×CTLA-4 bispecific molecules is provided in Table 8. In particular, bispecific bivalent diabody molecules, comprising two polypeptide chains, having one binding site for PD-1 and one binding site for CTLA-4 may be generated wherein the polypeptide chains have the general structure of Variation I (also see, e.g., FIG. 1). Bispecific bivalent diabody molecules, comprising three polypeptide chains, having one binding site for PD-1, one binding site for CTLA-4 and an Fc Region may be generated wherein the polypeptide chains have the general structure of Variation II (also see, e.g., FIG. 4A). Bispecific tetravalent diabody molecules, comprising four polypeptide chains, having two identical binding sites for PD-1, two identical binding sites for CTLA-4 and an Fc Region may be generated wherein the polypeptide chains have the general structure of Variations III or IV (also see, e.g., FIGS. 3A-3C). In addition, bispecific trivalent molecules, comprising four polypeptide chains, having two binding sites for PD-1 and one binding site for CTLA-4 (or two binding sites for CTLA-4 and one binding site for PD-1), and an Fc Region may be generated wherein the polypeptide chains have the general structure of Variation V (also see, e.g., FIG. 6A). In addition, bispecific bivalent antibody molecules comprising four polypeptide chains having one binding site for PD-1, one binding site for CTLA-4 and an Fc Region may be generated wherein the polypeptide chains have the general structure of Variation VI (also see, e.g., U.S. Pat. No. 7,695,936 and PCT Patent Publication WO 2011/143545).

TABLE 8

| Variation | Polypeptide Chain | Domains |
| --- | --- | --- |
| I | First | (VL1)-(Linker 1)-(VH2)-(Linker 2)-(HPD) |
|  | Second | (VL2)-(Linker 1)-(VH1)-(Linker 2)-(HPD) |
| II | First | (VL1)-(Linker 1)-(VH2)-(Linker 2)-(HPD)-(Linker 3)-(modified CH2—CH3 Domain) |
|  | Second | (VL2)-(Linker 1)-(VH1)-(Linker 2)-(HPD) |
|  | Third | (Linker3)-(modified CH2—CH3 Domain) |
| III | First and Third | (VL1)-(Linker 1)-(VH2)-(Linker 2)-(HPD)-(Linker 3)-(CH2—CH3 Domain) |
|  | Second and Fourth | (VL2)-(Linker 1)-(VH1)-(Linker 2)-(HPD) |
| IV | First and Third | (VL1)-(Linker 1)-(VH2)-(Linker 2)-(CH1)-(Hinge)-(CH2—CH3 Domain) |
|  | Second and Fourth | (VL2)-(Linker 1)-(VH1)-(Linker 2)-(CL) |
| V | First | (VL1)-(Linker 1)-(VH2)-(Linker 2)-(HPD)-(Linker 3)-(modified CH2—CH3 Domain) |
|  | Second | (VL2)-(Linker 1)-(VH1)-(Linker 2)-(HPD) |
|  | Third | (VH3)-(CH1)-(Hinge)-(modified CH2—CH3 Domain) |
|  | Fourth | (VL3)-(CL) |
| VI | First | (VL1)-(Linker 1)-(VH2)-(Linker 2)-(HPD)-(Linker 3)-(modified CH2—CH3 Domain) |
|  | Second | (VL2)-(Linker 1)-(VH1)-(Linker 2)-(HPD) |
|  | Third | (VL3)-(Linker 4)-(VH3)-(CH1)-(Hinge)-(modified CH2—CH3 Domain) |

TABLE 8-continued

| Variation | Polypeptide Chain | Domains |
|---|---|---|
| VII | First | (VH1)-(CH1)-(Hinge)-(modified CH2—CH3 Domain) |
| | Second | (VL1)-(CL) |
| | Third | (VH2)-(CH1)-(Hinge)-(modified CH2—CH3 Domain) |
| | Fourth | (VL2)-(CL) |

HPD = Heterodimer-Promoting Domain

For each Variation of the bispecific molecules provided in Table 8:
(a) VL1 and VH1 are the variable domains of an anti-PD-1 antibody and VL2 and VH2 are the variable domains of an anti-CTLA-4 antibody; or
(b) VL1 and VH1 are the variable domains of an anti-CTLA-4 antibody and VL2 and VH2 are the variable domains of an anti-PD-1 antibody.

For Variations V and VI: VL3 and VH3 are the variable domains of an anti-PD-1 antibody or are the variable domains of an anti-CTLA-4 antibody.

Linkers, Heterodimer-Promoting Domains and constant regions (e.g., CH1, Hinge, CH2-CH3 Domains) useful in the generation of such bispecific molecules are provided above. In particular, as detailed herein, for molecules whose first and third polypeptide chains are not identical the CH2-CH3 Domains are modified to promote heterodimerization and reduce or prevent homodimerization, for example by modifying the CH2-CH3 Domain one chain to comprise a "hole" and modifying the CH2-CH3 Domains on the other chain to comprise a "knob." As detailed above, the Hinge and/or CH2-CH3 Domains may comprise amino acid substitutions, which stabilize the bispecific molecules and/or alter effector function and/or enhance serum half-life.

Example 3

Universal Bispecific Adaptor ("UBA") Molecules

Alternatively, a bispecific molecule (e.g., a bispecific antibody, a bispecific diabody, trivalent binding molecule, etc.) may be constructed that comprises one epitope-binding site that specifically binds to PD-1 (or CTLA-4) and a second epitope-binding site that specifically binds a hapten, e.g. fluorescein isothiocyanate (also known as fluoroisothiocyanate or FITC). Such a bispecific molecule serves as a universal bispecific adaptor ("UBA") molecule able to co-ligate a binding domain specific for PD-1 (or CTLA-4) with a fluorescein-conjugated binding molecule (e.g., an antibody, scFv, etc.) specific for CTLA-4 (or PD-1). For example, the FITC-reactive arm of such a universal bispecific adaptor molecule may be used to bind to a FITC labeled antibody that binds CTLA-4 (or PD-1) thereby generating a universal bispecific adaptor molecule that is adapted to bind PD-1 and CTLA-4. Such universal bispecific adaptor molecules are useful for the rapid assessment of bispecific molecules.

The anti-fluorescein antibody, 4-4-20 ("mAb 4-4-20") may be employed as a source of FITC-specific binding domains (Gruber, M. et al. (1994) "*Efficient Tumor Cell Lysis Mediated By A Bispecific Single Chain Antibody Expressed In Escherichia coli*," J. Immunol. 152(11): 5368-5374).

Amino Acid Sequence Of The Heavy Chain Variable Domain Of mAb 4-4-20 (SEQ ID NO:65) (CDR$_H$ residues are underlined):

EVKLDETGGG LVQPGRPMKL SCVASGFTFS DYWMNWVRQS

PEKGLEWVAQ IRNKPYNYET YYSDSVKGRF TISRDDSKSS

VYLQMNNLRV EDMGIYYCTG SYYGMDYWGQ GTSVTVSS

Amino Acid Sequence Of The Light Chain Variable Domain Of mAb 4-4-20 (SEQ ID NO:66) (CDR$_L$ residues are underlined):

DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IK

Any of the bispecific formats provided herein may be utilized (see, e.g., Tables 1, 2, 3, and 4). Preferred bispecific molecules comprise only one hapten (e.g., fluorescein) binding site and will bind a single hapten-labeled antibody, thereby exhibiting a 1:1 ratio of universal adaptor bispecific molecule to hapten-labeled antibody in the resulting complexes. Such universal bispecific adaptor molecules may be constructed using, for example, the VL and VH Domains of an anti-PD-1 antibody and an anti-fluorescein antibody. Preferably, such a universal bispecific adaptor molecule is covalently bonded diabody or a trivalent binding molecule comprising two, three, four, five, or more polypeptide chains. Representative universal bispecific adaptor molecules which may be constructed are provided below.

A. UBA 1

One universal bispecific adaptor molecule that may be generated is a covalently bonded diabody composed of two polypeptide chains comprising one PD-1 epitope-binding site and one fluorescein binding site ("UBA 1").

The first polypeptide chain of UBA 1 comprises, in the N-terminal to C-terminal direction, an N-terminus, the VL Domain of mAb 4-4-20 (SEQ ID NO:66), an intervening spacer peptide (Linker 1, GGGSGGGG (SEQ ID NO:5)), the VH Domain of PD-1 mAb 6 (SEQ ID NO:57, wherein X$_1$ is I)), an intervening spacer peptide (Linker 2, GGCGGG (SEQ ID NO:6)), the E-coil Heterodimer-Promoting Domain: EVAALEK-EVAALEK-EVAALEK-EVAALEK (SEQ ID NO:18)), and a C-terminus.

Thus, the amino acid sequence of the first polypeptide chain of UBA 1 is (SEQ ID NO:67):

DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSG

GCGGGEVAAL EKEVAALEKE VAALEKEVAA LEK

The second polypeptide chain of UBA 1 comprises, in the N-terminal to C-terminal direction, an N-terminus, a VL Domain of PD-1 mAb 6 (SEQ ID NO:58, wherein X$_1$ is S and X$_2$ is Q)), an intervening spacer peptide (Linker 1, GGGSGGGG (SEQ ID NO:5)), the VH Domain of mAb 4-4-20 (SEQ ID NO:65)), an intervening spacer peptide (Linker 2, GGCGGG (SEQ ID NO:6)), the K-coil Heterodimer-Promoting Domain: KVAALKE-KVAALKE-KVAALKE-KVAALKE (SEQ ID NO:19)) and a C-terminus.

Thus, the amino acid sequence of the second polypeptide chain of UBA 1 is (SEQ ID NO:68):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGGSGGGG

EVKLDETGGG LVQPGRPMKL SCVASGFTFS DYWMNWVRQS

PEKGLEWVAQ IRNKPYNYET YYSDSVKGRF TISRDDSKSS

VYLQMNNLRV EDMGIYYCTG SYYGMDYWGQ GTSVTVSSGG

CGGGKVAALK EKVAALKEKV AALKEKVAAL KE
```

B. UBA 2

As provided above, incorporating an IgG CH2-CH3 Domains onto one polypeptide chain of a diabody such as UBA 1 will permit a more complex four-chain bispecific Fc Region-containing diabody to form. Thus a second universal bispecific adaptor molecule that may be generated is a covalently bonded diabody composed of four polypeptide chains comprising two PD-1 epitope-binding sites, two fluorescein binding sites, and an Fc Region ("UBA 2"). It will be noted that UBA 2 may bind two fluorescein labeled molecules via the two fluorescein binding sites.

The first and third polypeptide chains of UBA 2 comprises, in the N-terminal to C-terminal direction, an N-terminus, a VL Domain of a mAb 4-4-20 (SEQ ID NO:66), an intervening spacer peptide (Linker 1, GGGSGGGG (SEQ ID NO:5)), the VH Domain of PD-1 mAb 6 (SEQ ID NO:57, wherein $X_1$ is I)), an intervening spacer peptide (Linker 2, GGCGGG (SEQ ID NO:7)), the E-coil Heterodimer-Promoting Domain: EVAALEK-EVAALEK-EVAALEK-EVAALEK (SEQ ID NO:18)), an intervening spacer peptide (Linker 3, GGGDKTHTCPPCP (SEQ ID NO:31)), an IgG1 Fc Region comprising substitutions L234A/L235A (SEQ ID NO:43), wherein X is K)), and a C-terminus.

Thus, the amino acid sequence of the first and third polypeptide chains of UBA 2 is (SEQ ID NO:69):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LTCLVKGFYP SDIAVEWESN

GQPENNYKTT PPVLDSDGSF LYSKLTVDK SRWQQGNVFS

CSVMHEALHN HYTQKSLSLS PGK
```

The second and fourth polypeptide chains of UBA 2 are identical to the second polypeptide chain of UBA 1. Thus, the second and fourth polypeptide chains of UBA 2 each have the amino acid sequence of SEQ ID NO:68.

C. UBA 3

A third universal bispecific adaptor molecule that may be generated is a covalently bonded diabody composed of three polypeptide chains comprising one PD-1 epitope-binding site, one fluorescein binding site, and an Fc Region ("UBA 3").

The first polypeptide chain of UBA 3 comprises, in the N-terminal to C-terminal direction, an N-terminus, the VL Domain of mAb 4-4-20 (SEQ ID NO:66), an intervening spacer peptide (Linker 1, GGGSGGGG (SEQ ID NO:5)), the VH Domain of PD-1 mAb 6 (SEQ ID NO:57, wherein $X_1$ is I)), an intervening spacer peptide (Linker 2, GGCGGG (SEQ ID NO:6)), the E-coil Heterodimer-Promoting Domain: EVAALEK-EVAALEK-EVAALEK-EVAALEK (SEQ ID NO:18)), an intervening spacer peptide (Linker 3, GGGDKTHTCPPCP (SEQ ID NO:31)), a "knob-bearing" IgG1 Fc Region comprising substitutions L234A/L235A (SEQ ID NO:44, wherein X is K)), and a C-terminus.

Thus, the amino acid sequence of the first polypeptide chain of UBA 3 is (SEQ ID NO:70):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF LYSKLTVDK SRWQQGNVFS

CSVMHEALHN HYTQKSLSLS PGK
```

The second polypeptide chain of UBA 3 may be identical to the second polypeptide chain of UBA 1. Thus, the second polypeptide chain of UBA 3 has the amino acid sequence of SEQ ID NO:68.

The third polypeptide chains of UBA 3 comprises, in the N-terminal to C-terminal direction, an N-terminus, a spacer peptide (Linker 3, DKTHTCPPCP (SEQ ID NO:26)), a "hole-bearing" IgG1 Fc Region comprising substitutions L234A/L235A (SEQ ID NO:45, wherein X is K)), and a C-terminus.

Thus, the amino acid sequence of the third polypeptide chain of UBA 3 is (SEQ ID NO:71):

```
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK
```

```
GQPREPQVYT LPPSREEMTK NQVSLSCAVK GFYPSDIAVE

WESNGQPENN YKTTPPVLDS DGSFFLVSKL TVDKSRWQQG

NVFSCSVMHE ALHNRYTQKS LSLSPGK
```

D. UBA 4

A fourth universal bispecific adaptor molecule that may be generated is a covalently bonded trivalent binding molecule composed of four polypeptide chains comprising two PD-1 epitope-binding sites, one fluorescein binding site, and an Fc Region ("UBA 4").

The first polypeptide chain of UBA 4 is identical to the first polypeptide chain of UBA 3. Thus, the first polypeptide chains of UBA 4 has the amino acid sequence of SEQ ID NO:70.

The second polypeptide chain of UBA 4 is identical to the second polypeptide chain of UBA 1. Thus, the second polypeptide chain of UBA 4 has the amino acid sequence of SEQ ID NO:68.

The third polypeptide chain of UBA 4 comprises, in the N-terminal to C-terminal direction, the VH Domain of PD-1 mAb 6 (SEQ ID NO:57, wherein $X_1$ is I)), an IgG1 CH1 Domain (SEQ ID NO:40), an IgG1 Hinge Region (SEQ ID NO:33), a "hole-bearing" IgG1 Fc Region comprising substitutions L234A/L235A (SEQ ID NO:45, wherein X is K)), and a C-terminus.

Thus, the amino acid sequence of the third polypeptide chain of UBA 4 is (SEQ ID NO:72):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK
```

The fourth polypeptide chain of UBA 4 comprises, in the N-terminal to C-terminal direction, the VL Domain of PD-1 mAb 6 (SEQ ID NO:58, wherein $X_1$ is S and $X_2$ is Q)), a CL Domain (e.g., an IgG Kappa Domain (SEQ ID NO:38), and a C-terminus.

Thus, the amino acid sequence of the fourth polypeptide chain of UBA 4 is (SEQ ID NO:73):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

E. UBA 5

Figure 6A:
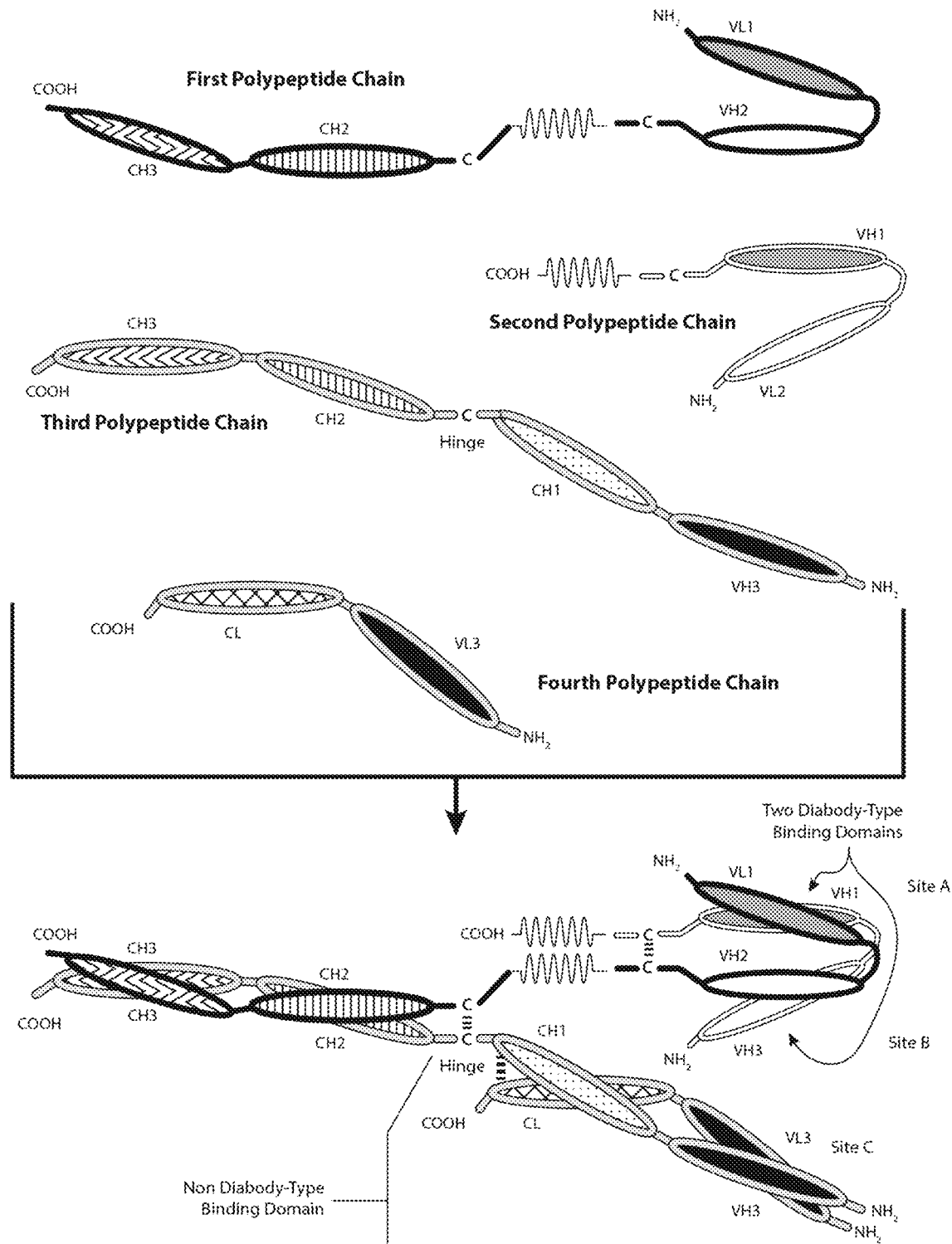
FIGS. 6A-6F provide schematics of representative Fc Region-containing trivalent binding molecules having three epitope-binding sites.
Figure 6B:
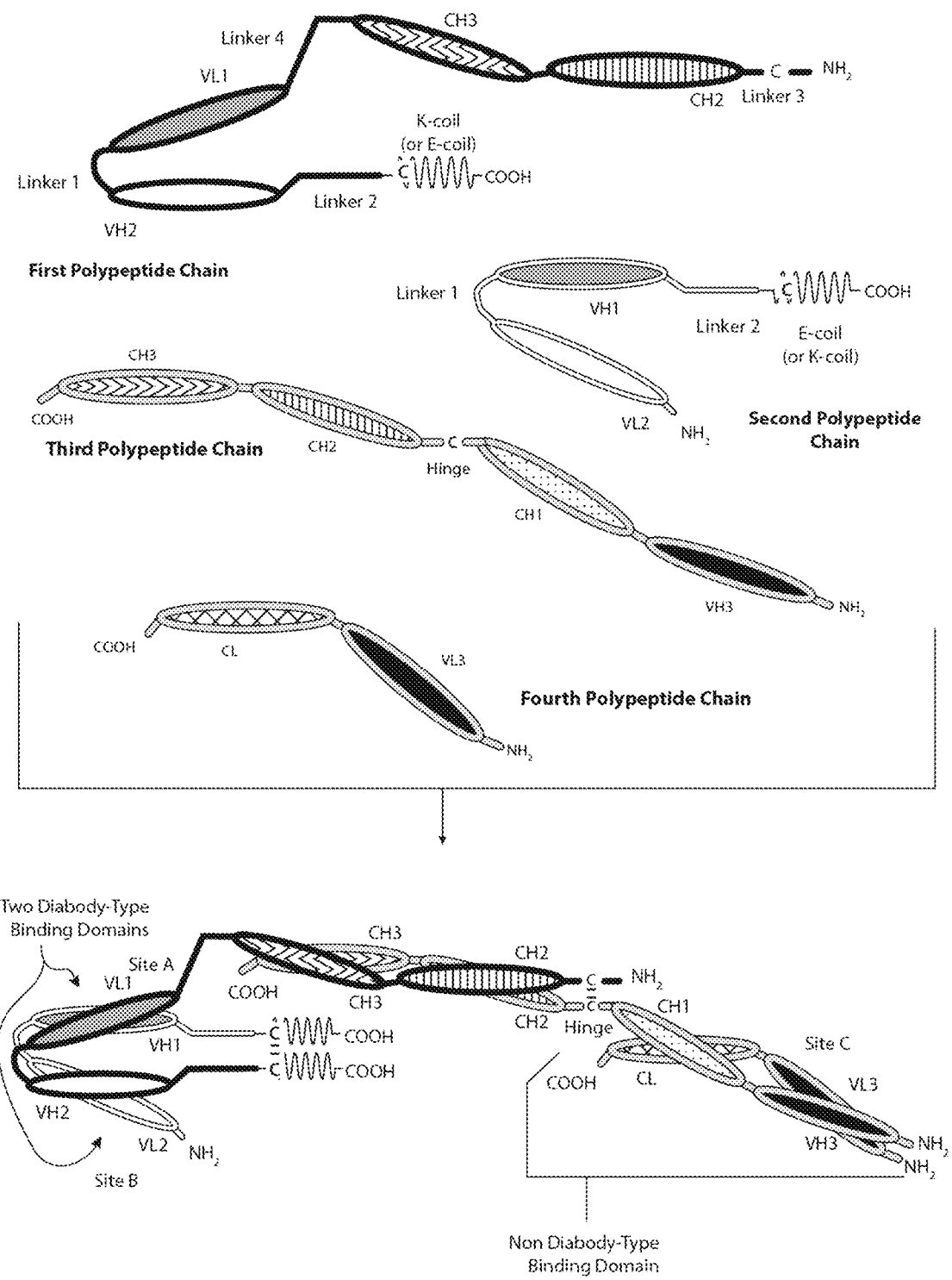
Figure 6C:
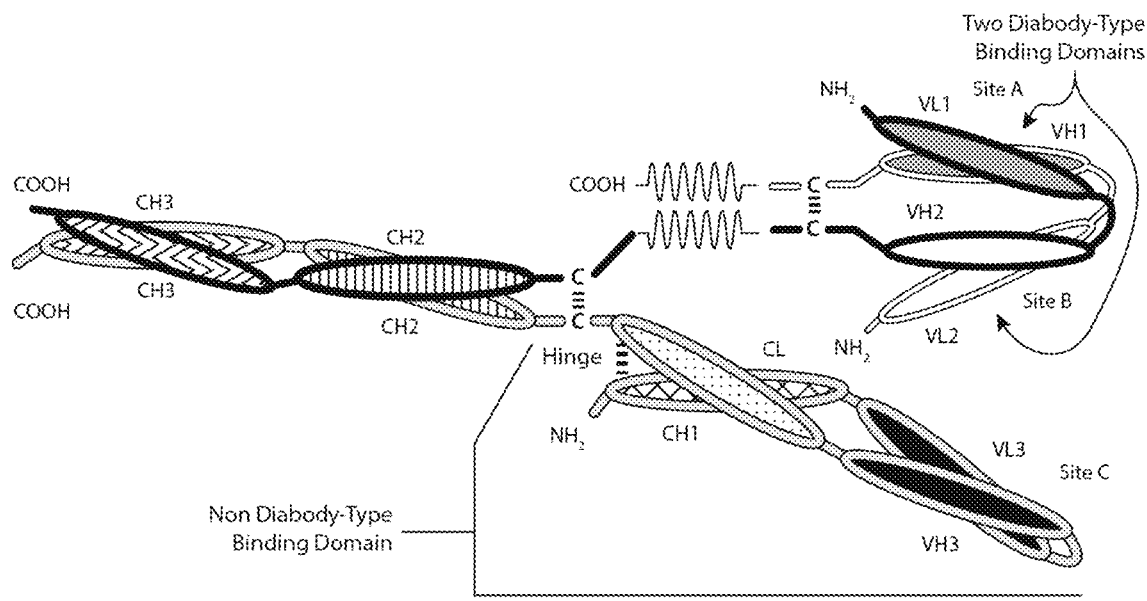
Figure 6D:
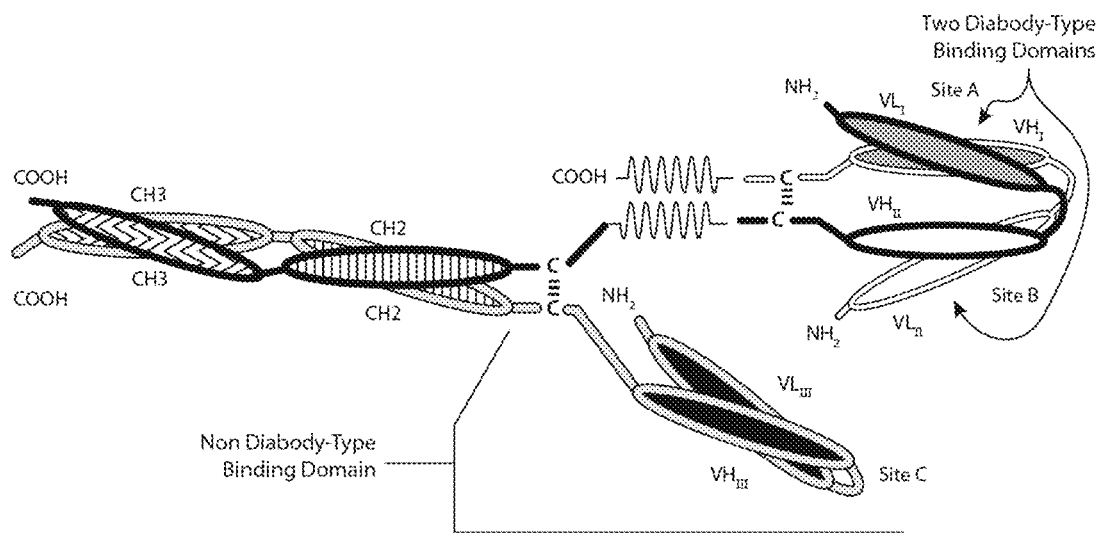
Figure 6E:
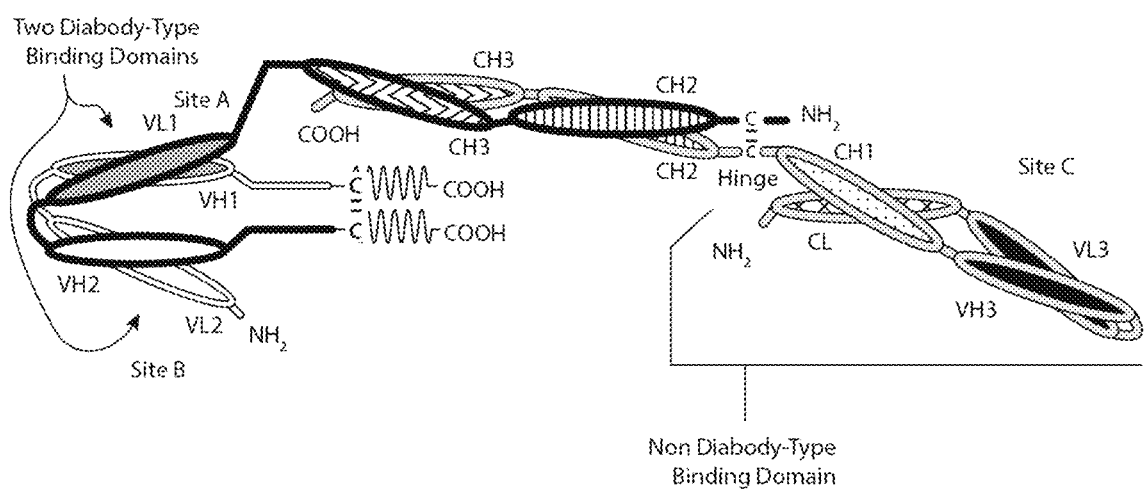
Figure 6F:
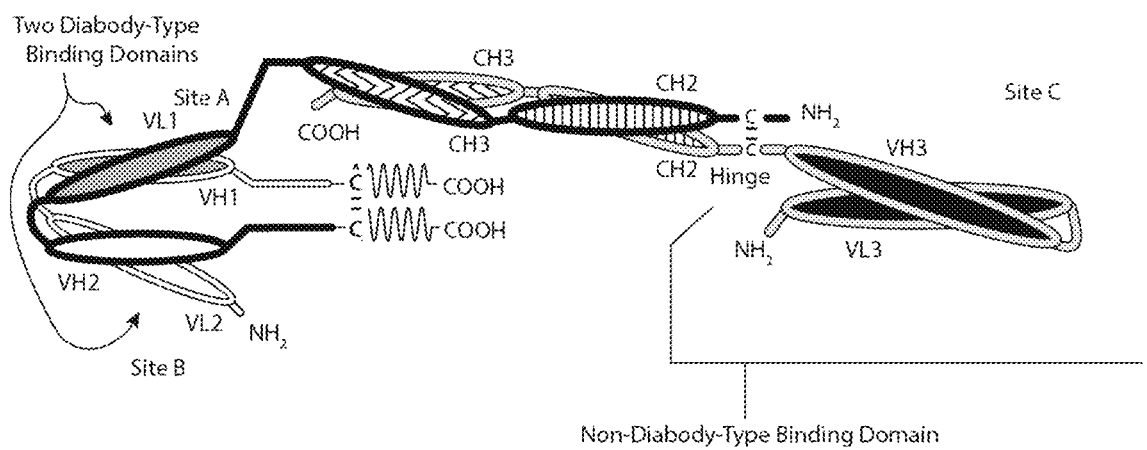

A fifth universal bispecific adaptor molecule that may be generated is a covalently bonded trivalent binding molecule composed of three polypeptide chains comprising two PD-1 epitope-binding sites, one fluorescein binding site, and an Fc Region ("UBA 4") (see, e.g., FIG. 6C-6D).

The first polypeptide chain of UBA 5 is identical to the first polypeptide chain of UBA 3. Thus, the first polypeptide chains of UBA 5 has the amino acid sequence of SEQ ID NO:70.

The second polypeptide chain of UBA 5 is identical to the second polypeptide chain of UBA 1. Thus, the second polypeptide chain of UBA 5 has the amino acid sequence of SEQ ID NO:68.

The third polypeptide chain of UBA 5 comprises, in the N-terminal to C-terminal direction, the VL Domain of PD-1 mAb 6 (SEQ ID NO:58, wherein $X_1$ is S and $X_2$ is Q)), an intervening spacer peptide (Linker 4, GGGGSGGGGSGGGGS (SEQ ID NO:37)), the VH Domain of PD-1 mAb 6 (SEQ ID NO:57, wherein $X_1$ is I)), an IgG1 CH1 Domain (SEQ ID NO:40), an IgG1 Hinge Region (SEQ ID NO:33), a "hole-bearing" IgG1 Fc Region comprising substitutions L234A/L235A (SEQ ID NO:45, wherein X is K)), and a C-terminus.

Thus, the amino acid sequence of the third polypeptide chain of UBA 5 is (SEQ ID NO:74):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGGSGGGG

SGGGGSQVQL VQSGAEVKKP GASVKVSCKA SGYSFTSYWM

NWVRQAPGQG LEWIGVIHPS DSETWLDQKF KDRVTITVDK

STSTAYMELS SLRSEDTAVY YCAREHYGTS PFAYWGQGTL

VTVSSASTKG PSVFPLAPSS KSTSGGTAAL GCLVKDYFPE

PVTVSWNSGA LTSGVHTFPA VLQSSGLYSL SSVVTVPSSS

LGTQTYICNV NHKPSNTKVD KRVEPKSCDK THTCPPCPAP

EAAGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLSCAVKGF YPSDIAVEWE SNGQPENNYK

TTPPVLDSDG SFFLVSKLTV DKSRWQQGNV FSCSVMHEAL

HNRYTQKSLS LSPGK
```

Using conventional methods, anti-CTLA-4 antibodies may be labeled with fluorescein. When such labeled molecules are incubated in the presence of a universal bispecific adaptor molecule provided above having an epitope-binding site that binds to PD-1 and an epitope-binding site that binds to fluorescein, they form a PD-1×CTLA-4 bispecific molecule, which may be assayed as described below.

It will be appreciated in view of the teachings provided herein that different VH Domains, VL Domains, linkers, heterodimer promoting domains, and/or IgG Constant Domains could be utilized to generate alternative universal bispecific adaptor molecules. For example, the VH and VL Domains of an anti-CTLA-4 antibody and/or a different anti-PD-1 antibody could be used in place of the VH and VL Domains of the employed anti-PD-1 antibody to generate alternative or equivalent universal bispecific adaptor molecules. Alternatively, the VH and VL Domains of an anti-CTLA-4 antibody may be used in place of the VH and VL Domains of the anti-fluorescein antibody to generate PD-1× CTLA-4 bispecific molecules having the general structure of Variations I, II, III, V and VI provided above. Such PD-1× CTLA-4 bispecific molecules may be used directly in the assays described below.

Example 4

Assays

The PD-1×CTLA-4 bispecific molecules of the present invention may be characterized in any of a variety of ways. In particular, PD-1×CTLA-4 bispecific molecules of the invention may be assayed for their ability to immunospecifically bind to the PD-1 and CTLA-4 molecules (e.g., as present on a cell surface, etc.), and/or the binding kinetics of the interactions with antigen may be determined. Where the bispecific molecules comprise an Fc region (or portion thereof), their ability to exhibit Fc-FcγR interactions, e.g., specific binding of an Fc region (or portion thereof) to an FcγR, mediation of effector function, signal transduction, etc., may be assayed. The immunomodulatory activity and/or in vivo anti-tumor efficacy of the PD-1×CTLA-4 bispecific molecules of the invention may be assayed using in vitro and in vivo assays known in the art.

A. Preparation of Immune Cells and Cell Expressing PD-1 and/or CTLA-4

1. Isolation of PBMCs and Immune Cell Subpopulations from Human Whole Blood

PBMCs from healthy human donors are isolated from whole blood, for example, using Ficoll gradient centrifugation. Briefly, whole blood is diluted 1:1 with sterile phosphate buffered saline (PBS). The diluted blood (35 mL) is layered onto 15 mL of Ficoll-Paque™ Plus in a 50 mL tube and the tubes are centrifuged at 400×g (1320 rpm) for 30 minutes with the brake off. The buffy-coat layer between the two phases is collected into 50 mL tubes and centrifuged at 600×g (1620 rpm) for 5 minutes. The supernatant is discarded and the cell pellet is washed 3 times with PBS (e.g., by centrifuging the tubes at 600×g (1620 rpm) for 5 minutes). Viable cell count is determined using Trypan Blue dye. The PBMCs are resuspended in complete culture medium (e.g., RPMI 1640, 10% FBS, 1% pen/strep) and incubated at 37° C. with 5% $CO_2$ overnight or are further processed to isolate a desired immune cell subpopulation such as T cells, (e.g., T regs, CD8, CD4), NK cells, dendritic cells and monocytes as described below.

Particular immune cell subpopulations are readily isolated from PBMCs using a commercial preparation kit (e.g., the Untouched™ human T cell isolation kits for isolation of T-cells, CD4 T-cells, CD8 T-cells, Monocytes, Dendritic Cells (Life Technologies/ThermoFisher Scientific); the DYNABEADS® Regulatory CD4+/CD35+ T Cell Kit for isolation of T regulatory cells (CD4+/CD25+) (ThermoFisher), etc.), according to the manufacturer's instructions. After isolation, the immune cell subpopulation (e.g., T cells) are resuspended in the appropriate complete culture medium (e.g., RPMI 1640, 10% FBS, 1% penicillin/streptomycin, which may be supplemented with cytokines (e.g., IL-2, GM-CF, IL-4, TNF-α, etc.) and incubated at 37° C. with 5% $CO_2$ overnight. As provided herein such purified subpopulations are useful to evaluate cell surface expression of PD-1 and/or CTLA-4 and for evaluation of the immune stimulatory activity of the PD-1×CTLA-4 bispecific molecules of the invention.

2. Isolation Of PBMCs From Cynomolgus Monkey Or Rhesus Monkey Whole Blood

PMBCs from Cynomolgus monkey or Rhesus monkey are isolated from whole blood, for example using Ficoll gradient centrifugation. Briefly, whole blood is diluted 1:3 with sterile PBS. Diluted blood (35 mL) is layered onto 15 mL of 90% Ficoll-Paque™ Plus (90 mL Ficoll+10 mL PBS) in a 50 mL polypropylene centrifuge tube and centrifuged at 931×g (2000 rpm) for 30 minutes at room temperature with the brake off. The buffy-coat layer between the two phases is collected and transferred to a clean 50 mL tube and washed with 45 mL PBS by centrifuging the tubes at 600×g (1620 rpm) for 5 minutes. The supernatant is discarded and the pellet is rinsed 3× with PBS. Cynomolgus or Rhesus monkey PBMCs are then resuspended in 30 mL of complete culture medium and viable cell count is determined by Trypan Blue dye exclusion.

Particular immune cell subpopulations are readily isolated from non-human primate PBMCs using a commercial preparation kit (e.g., Pan T-cell, CD4+ T-Cell, and CD4+/CD25+ Treg isolation kits (Miltenyl Biotech)), according to the manufacturer's instructions. Alternatively, flow cytometric sorting using non-human primate specific or cross-reactive mAbs can be used for sorting.

3. Generation Of Human Immature Or Mature Myeloid-Derived Dendritic Cells (mDC) Cells From Isolated Human Monocytes Human monocytes are isolated from donor derived purified PBMCs using a commercial preparation kit (e.g., the Untouched™ human monocyte kit (Life Technologies/ThermoFisher Scientific) according to manufacturer's instructions. Isolated human monocytes are induced to differentiate into human immature mDCs by culturing monocytes (e.g., in alpha Minimum Essential Media with nucleosides (aMEM) media+2% human AB-negative serum+1% penicillin/streptomycin) for 5-7 days in the presence of recombinant human granulocyte macrophage-colony stimulating factor (e.g., hGM-CSF; Peprotech, 100 ng/ml) and recombinant human interleukin-4 (hIL-4; Peprotech, 40 ng/ml). Immature mDCs are harvested and washed with PBS by centrifuging the tubes at 600×g (1620 rpm) for 5 minutes for use as stimulator cells in allogeneic mixed lymphocyte reaction (allo-MLR) assays, such as those detailed below.

In certain allo-MLR experiments immature mDCs are induced to differentiate by adding TNFα or a cocktail of additional cytokines (IFNγ, IL-1(3) and mitogens (LPS) for two additional days of culture (see, e.g., Han, T. (2009) "*Evaluation of* 3 *Clinical Dendritic Cell Maturation Protocols Containing LPS and IFN-gamma*," J Immunother 32:399). The purity, maturation and activation of mDCs may be evaluated by flow cytometry using one or more of the following antibodies: anti-CD14, anti-CD80, anti-CD83, anti-CD86, anti-HLA-DR; and the appropriate isotype controls. The flow cytometric data from such evaluations may be acquired on a FACSCalibur/Fortessa (Becton Dickinson/ BD Biosciences) and analyzed using FlowJo software (TreeStar).

4. Expression of PD-1 and CTLA-4

Cells expressing PD-1 and/or CTLA-4 may be generated using methods known in the art. For example, cells (e.g., NSO, Jurkat, CHO, etc.) may be engineered to express PD-1 and/or CTLA-4 using retroviral vectors containing the appropriate gene (e.g., human PD-1 gene). Alternatively, immune cells may be stimulated to induce or increase the expression of PD-1 and/or CTLA-4. Briefly, purified immune cells (e.g., PBMCs, T-cells, dendritic cells, etc.) isolated as described above are cultured for 2-6 days in the presence or absence of a mitogen and the expression of PD-1 and/or CTLA-4 is examined on the untreated (Naïve) and stimulated cells, for example using flow cytometry. Commercial anti-PD-1 and anti-CTLA-4 antibodies can be used for preliminary evaluation of the expression patterns on Naïve cells and in response to mitogen stimulation. Additionally, or optionally the PD-1×CTLA-4 bispecific molecules of the invention may be used.

Mitogens which may be utilized for such studies are well known in the art and include, but are not limited to: CD3/CD28 beads, lipopolysaccharides (LPS), *Staphylococcus aureus* enterotoxin types A-E (e.g., SEB), phorbol myristate acetate (PMA), phytohemagglutinin (PHA), concanavalin A (conA), pokeweed mitogen (PWM), etc. Mitogen(s) identified as inducing/enhancing the expression of PD-1 and/or CTLA-4 may be used in functional assays to evaluate the stimulatory activity of the PD-1×CTLA-4 bispecific molecules of the present invention. See for example the "SEB", and "MLR" assays described herein.

B. Binding Assays

Immunoassays that can be used to analyze immunospecific binding to PD-1 or CTLA-4 molecules, binding cross-reactivity, or Fc-FcγR interactions include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunochromatographic assays, immunodiffusion assays, agglutination assays, complement-fixation assays, immunoradiometric assays, fluorescent immunoassays, and protein A immunoassays, etc. (see, e.g., Ausubel et al., 2008, Current Protocols in Molecular Biology). Binding affinity for a target antigen is typically measured or determined by standard antibody-antigen assays, such as Biacore competitive assays, saturation assays, or immunoassays such as ELISA or RIA. Fluorescence activated cell sorting (FACS), using any of the techniques known to those skilled in the art, is used for immunological or functional based assays to characterize the PD-1×CTLA-4 bispecific molecules of the invention.

For example, PBMCs may be prepared as described above. Where desired immune cell subsets (e.g., T regulatory, T helper, APCs, etc.) may be isolated from the purified PBMC. The isolated cells are then examined for PD-1 and CTLA-4 expression on various cell subsets (e.g., T regulatory, T helper, APCs, etc.) by co-staining and FACS analysis as described below.

1. Cell Surface Binding (Saturation Assay)

The ability of PD-1×CTLA-4 bispecific molecules to bind to PD-1 and/or CTLA-4 expressed on the cell surface may be measured in saturation/dilution based assays using a cell that expresses PD-1 and/or CTLA-4 (target cells). Such cells may be immune cells stimulated to expressed PD-1 and/or CTLA-4, or a cell line (e.g., NSO cells) engineered to stably over-express PD-1 and/or CTLA-4 molecules. Briefly, cultured targets cells (e.g., NSO cell engineered to express PD1$^+$) are harvested and resuspended (e.g., about 5×10$^6$ cells/ml) in blocking buffer (e.g., FACS buffer+10% human AB Serum). Starting at equal molar concentrations (e.g., 20 nM in total of 200 µl) a PD-1×CTLA-4 bispecific molecule, an anti-PD-1 antibody, an anti-CTLA-4 or a combination of anti-PD-1 and anti-CTLA-4 antibodies are prepared for dilution in a separate microtiter plate and then serially diluted (e.g., 1:4, 1:5, 1:10, etc.) 5-12 times to generate a 5-12 point curve. The highest starting concentration in all experiments is determined empirically. The same volume (e.g., 50 µl) of each dilution is added to a new microtiter plate and target cells are added to each well (e.g., 0.25×10$^6$ cells/well) and incubated (e.g., at 4-25° C. for 30-120 minutes). The cells are washed 1-3 times (e.g., the microtiter plate is spun at 600×g (1620 rpm) for 5 minutes and then washed with blocking buffer and spun again) and resuspended in blocking buffer. For secondary staining, the appropriate secondary regent is selected, for example a goat anti-Human Fc-APC may be used to detect human primary antibodies, while a goat Anti-Mouse IgG Fc Alexa Fluor 647 is used to detect mouse primary antibodies. The selected secondary reagent is diluted in blocking buffer and based on the concentration of the individual secondary, a stock solution is made and the same volume/well of the secondary mixture is aliquoted to individual wells and incubated (e.g., at 4-25° C. 30-120 minutes). The cells are washed as described above and resuspended in blocking buffer. The stained cells are analyzed by flow cytometry. The flow cytometric data may be acquired on a FACSCalibur/Fortessa (Becton Dickinson/Fortessa), analyzed as mean fluorescent intensity using FlowJo software (TreeStar), and plotted and fitted using the log(agonist) vs. response-variable slope (four parameter) function in Prism6 software (Graphpad).

2. Receptor/Ligand Binding and Signaling Assays

Assays that can be used to analyze the ability of the PD-1×CTLA-4 bispecific molecules of the invention to modulate (e.g., block, inhibit, stimulate, etc.) ligand binding and signaling are provided in more detail below.

a. PD-1 Receptor/Ligand Binding

The ability of PD-1×CTLA-4 bispecific molecules to inhibit PD-1 from binding PD-L1 and/or PD-L2 may be evaluated using cells that express PD-1 (target cells). Such cells may be immune cells stimulated to express PD-1, or a cell line engineered to express PD-1 molecule, for example NSO-cells retrovirally transduced with the human PD-1 gene. Briefly, PD-1 expressing cells (e.g., NSO/PDCD1 (NSO-PD1$^+$) are harvested and resuspended (e.g., about 1.5×10$^6$ cells/ml) in blocking buffer (e.g., FACS buffer+10% Human Ab Serum) and plated in a microtiter plate (e.g., 0.25×10$^6$ cells/well). Starting at equal molar concentrations (e.g., 20 nM in total of 200 µl) of a PD-1×CTLA-4 bispecific molecule, an anti-PD-1 antibody, an anti-CTLA-4, or a combination of anti-PD-1 and anti-CTLA-4 antibodies are prepared for dilution in a separate microtiter plate and serially diluted (e.g., 1:4, 1:5, 1:10, etc.) 5-12 times to generate a 5-12 point curve. The highest starting concentration in all experiments is determined empirically. The same volume (e.g., 50 µl) of each dilution is added to each well of the microtiter plate containing the target cells. To evaluate the inhibition of PD-L1 binding a soluble PD-L1 fusion protein (e.g., hPD-L1 (B7H1) TEV-hIgG1-Fc-biotin (Ancell)) is added to each well with the exception of unstained negative control wells and incubated (e.g., at 4-25° C. for 30-120 minutes). To evaluate the inhibition of PD-L2 binding a soluble PD-L2 fusion protein (e.g., CD273 (PD-L2) muIgG/biotin (Ancell)) is added to each well with the exception of unstained negative control wells and incubated (e.g., at 4-25° C. for 30-120 minutes). The cells are washed 1-3 times (e.g., the microtiter plate is spun at 600×g (1620 rpm) for 5 minutes and then washed with blocking buffer and spun again). The cells are resuspended in blocking buffer. With the exception of unstained negative control wells, the appropriate secondary reagent for detection of the PD-L1 or PD-L2 fusion protein (e.g., streptavidin-PE labeled secondary (eBiosciences)) is added and incubated (e.g., at 4-25° C. for 15-120 minutes). The cells are washed as described above and resuspended in blocking buffer. The stained cells may be analyzed by flow cytometry. The flow cytometric data may be acquired on a FACSCalibur/Fortessa (Becton Dickinson/Fortessa), and analyzed for the loss mean fluorescent intensity of labeled sPD-L1 or sPD-L2 in the presence of a PD-1×CTLA-4 bispecific molecule, an anti-PD-1 antibody, an anti-CTLA-4, or a combination of anti-PD-1 and anti-CTLA-4 antibodies using FlowJo software (TreeStar), and plotted and fitted using the log(agonist) vs. response-variable slope (four parameter) function in Prism6 software (Graphpad).

b. CTLA-4 Receptor/Ligand Binding

The ability of PD-1×CTLA-4 bispecific molecules to inhibit CTLA-4 from binding CD80 and/or CD86 may be evaluated using cells that express CTLA-4 (target cells). Such cells may be immune cells stimulated to express CTLA-4, or a cell line engineered to express CTLA-4, for example NSO-cells retrovirally transduced with the human CTLA-4 gene. Briefly, CTLA-4 expressing cells are harvested and resuspended in blocking buffer (e.g., FACS buffer+10% Human Ab Serum) and plated in a microtiter plate (e.g., $0.25 \times 10^6$-$1.0 \times 10^6$ cells/well). Starting at equal molar concentrations (e.g., 20 nM in total of 200 µl) of a PD-1×CTLA-4 bispecific molecule, an anti-PD-1 antibody, an anti-CTLA-4, or a combination of anti-PD-1 and anti-CTLA-4 antibodies are prepared for dilution in a separate microtiter plate and serially diluted (e.g., 1:4, 1:5, 1:10, etc.) 5-12 times to generate a 5-12 point curve. The highest starting concentration in all experiments is determined empirically. The same volume (e.g., 50 µl) of each dilution is added to each well of the microtiter plate containing the target cells. To evaluate the inhibition of CD80 binding a soluble CD80 fusion protein (e.g., hCD80-muIg-biotin (ADIPOGEN®)) is added to each well with the exception of unstained negative control wells and incubated (e.g., at 4-25° C. for 30-120 minutes). To evaluate the inhibition of CD86 binding a soluble CD86 fusion protein (e.g., hCD86-muIg-biotin (ADIPOGEN®)) is added to each well with the exception of unstained negative control wells and incubated (e.g., at 4-25° C. for 30-120 minutes). The cells are washed 1-3 times (e.g., the microtiter plate is spun at 600×g (1620 rpm) for 5 minutes and then washed with blocking buffer and spun again). The cells are resuspended in blocking buffer. With the exception of unstained negative control wells, the appropriate secondary reagent for detection of the CD80 or CD86 fusion protein (e.g., streptavidin-PE labeled secondary (eBiosciences)) is added and incubated (e.g., at 4-25° C. for 15-120 minutes). The cells are washed as described above and resuspended in blocking buffer. The stained cells may be analyzed by flow cytometry. The flow cytometric data may be acquired on a FACSCalibur/Fortessa (Becton Dickinson/Fortessa), and analyzed for the loss mean fluorescent intensity of labeled CD86 or CD80 in the presence of a PD-1×CTLA-4 bispecific molecule, an anti-PD-1 antibody, an anti-CTLA-4, or a combination of anti-PD-1 and anti-CTLA-4 antibodies using FlowJo software (TreeStar), and plotted and fitted using the log(agonist) vs. response-variable slope (four parameter) function in Prism6 software (Graphpad).

C. Reporter Assays

The functional activity of PD-1×CTLA-4 bispecific molecules in blocking the interaction of PD-1 with PD-L1 may be assessed using a commercial reporter system developed by Promega according to the manufacturer's direction. Briefly, two cell lines engineered to function as either a stimulator line or reporter cell line are used. The stimulator line was engineered from a CHO-parental line to express the PD-L1 molecule and a T cell activator, which is a membrane bound anti-CD3 agonist mAb [CHO/PDL1 cells]. The reporter cell line was engineered from a CD3-positive Jurkat parental line to express a luciferase reporter construct under the transcription control of nuclear factor of activated T-cells (NFAT) [NFAT-luc2/PD-1 Jurkat cells]. When cultured together, the anti-CD3 agonist expressed on the CHO-PDL1 cell line drives luciferase expression by the NFAT signal transduction pathway mediated by the engagement of the TCR/CD3 signaling complex present on the Jurkat-NFAT-luc/PD-1 cell line. In the absence of anti-PD-1 or anti-PD-L1 antibodies, luciferase is expressed at a level relative to TCR/CD3 signaling but down-modulated or inhibited by the presence of the PD-1/PD-L1 inhibitory axis, which functions as a brake. In the presence of molecules which inhibit PD-1/PD-L1 signaling (e.g., anti-PD-1 or anti-PD-L1 antibodies), this inhibitory axis or "brake" is released, permitting enhanced luciferase expression that can be measured. Accordingly, the PD-1 inhibitory activity of PD-1×CTLA-4 bispecific molecules may be evaluated by culturing CHO/PDL1 with NFAT-luc2/PD1 Jurkat (3H-D5). Briefly, CHO-PDL1 are plated into a microtiter plate (e.g., at $4.0 \times 10^4$ cells/well) and cultured overnight (e.g., in RPMI media containing 10% FBS+100 ug/mL Hygromycin B+500 ug/mL G418). The next day, assay buffer (e.g., RPMI+2% FBS is prepared along with a 5-12 point serial dilution of a PD-1×CTLA-4 bispecific molecule, or an anti-PD-1 antibody in assay buffer with highest dilution point at equal molar equivalence (e.g., 100-200 nM) and 5-12 serial dilutions (e.g., 1:4, 1:5, 1:10, etc.) are prepared. In the following order, a portion of cell the culture media is removed from the microtiter plate containing adherent CHO/PDL1 cells and aliquots of each dilution are added to the CHO/PDL1 cells. Cultured NFAT-luc2/PD-1 Jurkat cells are harvested and resuspended in assay buffer and added (e.g., $5.0 \times 10^4$ cells/well in 40µl/well) to the CHO/PDL1 cells. The co-culture is incubated (e.g., for 6 hours at 37° C.). At the end of the incubation, Bio-Glo substrate (Promega) is reconstituted and added to the ambient temperature equilibrated microtiter plate. Following incubation (e.g., 5-10 minutes) the optical density of each well is read on a VICTOR™ $X_4$ Multilabel Plate Reader (Perkin Elmer #2030-0040) at 450 nm with luminescence relative light unit (RLU) as the readout. The data may then be plotted and fitted using the log(agonist) vs. response-variable slope (four parameter) function in Prism6 software (Graphpad).

Similar reporter assays are available for CTLA-4 signaling (e.g., CTLA-4 Blockade Bioassay Kit (Promega)) and/or may be readily generated to analyze the functional activity of PD-1×CTLA-4 bispecific molecules in blocking the interaction CTLA-4 with its respective ligand(s).

D. Immunomodulatory Assays

Assays that can be used to analyze the immunomodulatory activity of the PD-1×CTLA-4 bispecific molecules of the invention include mitogen stimulation assays such as the "SEB" assay detailed above, and Mixed Lymphocyte Reaction (MLR) assays such as those provided in more detail below. The ability of the PD-1×CTLA-4 bispecific molecules of the invention to modulate both the PD-1 and the CTLA-4 inhibition pathways is expected to provide enhanced stimulation in assays as compared to anti-PD1 and anti-CTLA-4 antibodies alone or the combination of such antibodies.

PBMCs or T cells are isolated from the blood of the same (autologous) or unrelated (allogeneic) patient(s) healthy donor(s) blood by centrifugation over a Ficoll-Paque™ gradient as described above and resuspended in complete culture medium. For allo-MLR assays that employ mDCs, monocytes are purified and matured as describe above. For one-way (unidirectional) allo-MLR assays responder cells (e.g., PBMCs) are co-cultured with stimulating cells in a microtiter plate. Depending on the context, stimulating cells are DCs, autologous PBMCs (for auto-MLR, i.e., negative control), or allogeneic PBMCs (for allo-MLR, i.e., positive control). The ratio of responder:stimulating cells is typically 1:1 or 2:1, but may be varied. The co-cultures are performed in the presence of equal molar amounts of serial (e.g., 1:4 1:5, 1:10, etc.) dilutions of a PD-1×CTLA-4 bispecific molecule, an anti-PD-1 antibody, an anti-CTLA-4, a combination of anti-PD-1 and anti-CTLA-4 antibodies, or the corresponding isotype mAbs. Serial antibody dilutions may be prepared as described above. In addition, single cell populations controls stimulated with or without anti-CD3+/−anti-CD28 mAbs may be used as controls in such experiments. Stimulating cells (stimulators) are pre-irradiated (e.g., at 45 grays[Gy] (4500 rads) using a Gammacell® 3000 Elan Blood/Cell Irradiator (Theratronics)) to prevent proliferation of the stimulator cells and allow measurement of only the proliferation of the responding cell (responders). After 5-7 days (the time will be adjusted to ensure expression of PD-1 and CTLA-4 during the assay), [$^3$H]-thymidine (e.g., 1 µCi/well (Perkin Elmer)) is added for further 18-48 hours. The radioactivity incorporated into DNA is measured in (e.g., in a TOPCount NXT (3-scintillation counter (Perkin Elmer)). Results are expressed as either mean counts per minute (cpm) or expressed as stimulation index (SI) allowing the comparison of results from different donors. SI is calculated as follows: mean counts per minute (cpm) from stimulated cells divided by mean cpm from non-stimulated cells. MLR responses are considered positive when SI was ≥3 for PBMC-induced stimulation and SI≥6 for DC-induced stimulation. Alternatively, proliferation may be measured, using a CEF SE-based proliferation assay (Boks, M. A., et al. (2010) "*An optimized CFSE based T-cell suppression assay to evaluate the suppressive capacity of regulatory T-cells induced by human tolerogenic dendritic cells,*" Scand J Immunol 72:158-168).

Additional MLR assays which may be used to evaluate the immune stimulatory activity of the PD-1×CTLA-4 bispecific molecules of the invention are known in the art. See, for example, Davies, J. K. et al. (2011) "*Induction of alloantigen-specific anergy in human peripheral blood mononuclear cells by alloantigen stimulation with co-stimulatory signal blockade,*" Journal of Visualized Experiments: JoVE, (49), 2673; Kruisbeek, A. M., et al. (2004) "*Proliferative Assays for T cell Function,*" CURRENT PROTOCOLS IN IMMUNOLOGY, 60:111:3.12.1-3.12.20; Wallgren, A. C. et al. (2006) "*The Direct Pathway Of Human T-Cell Allorecognition Is Not Tolerized By Stimulation With Allogeneic Peripheral Blood Mononuclear Cells Irradiates With High-Dose Ultraviolet,*" Ba. Scand J of Immunol 63:90-96; Levitsky, J. et al. (2009) "*The Human 'Treg MLR' Immune Monitoring for Foxp3+ T regulatory cell generation,* Transplantation 88:1303-11.

E. In Vivo Anti-Tumor Assays

The anti-tumor activity of the PD-1×CTLA-4 bispecific molecules of the invention may be evaluated in various animal models known in the art. Treatment with the PD-1×CTLA-4 bispecific molecules of the invention is expected to inhibit tumor establishment and/or tumor growth to a greater extent than treatment with anti-PD1 and anti-CTLA-4 antibodies alone or the combination of such antibodies.

Murine xenograph tumor models are particularly useful. Briefly, mice are implanted with a cancer cell line, or tumor cells of interest and are treated with (i) a PD-1×CTLA-4 bispecific molecule (ii) an anti-PD-1 antibody (iii) an anti-CTLA-4 antibody (iv) a combination of anti-PD-1 and anti-CTLA-4 antibody, and (vi) no-treatment control which may be vehicle alone and/or an irrelevant antibody. Treatment may begin prior to implantation (e.g., 1 day before (i.e., day −1)); on the same day as implantation (i.e., day 0), or after establishment of a tumor (e.g., day 7). The animals may receive a single treatment or may receive multiple treatments (e.g., weekly post implantation). The animals are monitored over time to determine the in vivo effect of these molecules on tumor establishment and/or growth. Growth of tumors may be monitored my measuring the tumors and determining the tumor volume (height×width×length). Treated animals which show complete tumor regression can be used to examine tumor-specific immunity by rechallenge using the same or tumor cells and irrelevant tumor cells as a control. In addition, these models may be modified to include combination treatment with standard of care treatments such as chemotherapy, radiation, etc.

Numerous transplantable cancer cell lines which may be utilized in such xenograph models are known in the art and include, but are not limited to: MDST8, SW480 and SW620 colorectal cancer cells; AGS gastric cancer cells; UACC-62, A2058, and LOX IMVI melanoma cells; 22ry prostate cancer cells; AsPC-1 and BxPc-3 pancreatic cancer cells; Caki-1, A498 and 786-0 renal cancer cells; HT-1197 Bladder cancer cells; 4T1, MDA-MB-231, mammary cancer cells; A549, WX322 Lung cancer cells; HT1080 Fibrosarcoma cells; HBL-2 human mantle cell lymphoma cells; Raji Burkitt's lymphoma cells. Particularly preferred are Patient-Derived Xenograft (PDX) models. Such cancer cell lines, or patient-derived tumors are engrafted into immunocompromised mice strains (e.g., Nude mice, Scid mice, NOD mice, Rag 1 null mice, etc. (see, e.g., Belizario, J. E., (2009) "*Immunodeficient Mouse Models: An Overview,*" Bentham Open 1874-2262/09) or humanized mice such as transgenic human HLA-A2 mice (see, e.g., Shultz, L. D., et al. (2012) "*Humanized mice for immune system investigation: progress, promise and challenges,*" Nature Rev Immunol 12:786-798) as described above. In addition, for evaluation of molecules which modulate immune checkpoint immune-deficient mice may be engrafted with human immune system components (e.g., reconstituted with human PBMCs, stem cells, immune progenitor cells, etc.) prior to or concurrently with implantation of the desired tumor cells and treatment as detailed above.

Example 5

PD-1×CTLA-4 Bispecific Molecules Binding Studies

Several PD-1×CTLA-4 bispecific molecules were generated, including Fc Region-containing diabodies and Fc-Region-containing trivalent molecules comprising four polypeptides chains. Three diabodies having four polypeptide chains and comprising E/K-coil Heterodimer-Promoting Domains were generated and accorded the designations "DART B," "DART C," and "DART D." One diabody having four chains and comprising CH1/CL Domains was generated and accorded the designation "DART E." Two trivalent binding molecules having four chains and comprising E/K-coil Heterodimer-Promoting Domains and CH1/CL Domains were generated and accorded the designations "TRIDENT A," and "TRIDENT B."

In addition, several antibodies having specificity for PD-1 or CTLA-4 were generated. One antibody specific for PD-1 was generated and accorded the designation "PD-1 mAb 6 G4P." Three antibodies specific for CTLA-4 were generated and accorded the designations "CTLA-4 mAb 1," "CTLA-4 mAb 3 G1AA," and "CTLA-4 mAb 3 G4P."

The structure and amino acid sequences of these PD-1×CTLA-4 bispecific molecules, anti-PD-1 antibodies, anti-CTLA-4 antibodies are provided above and are summarized in Table 9 below.

A. ELISA Binding Studies

Figure 8A:
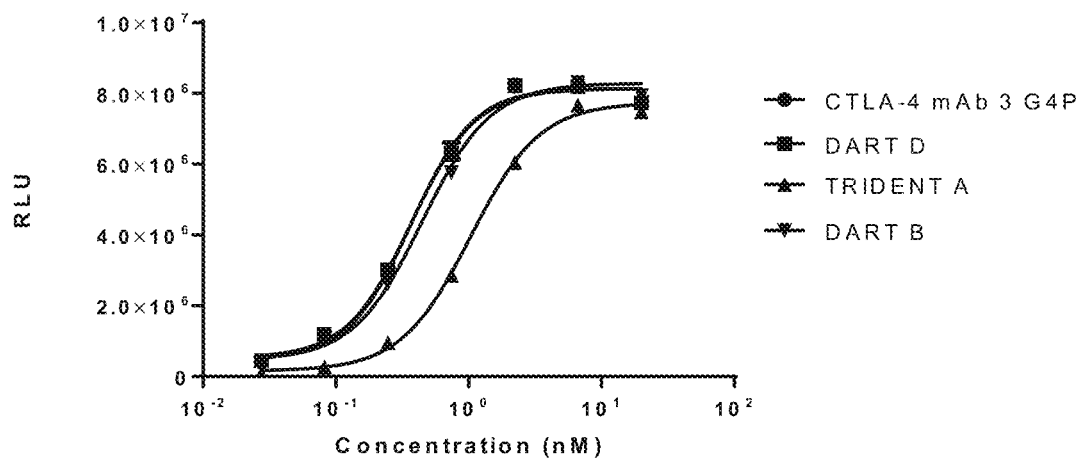
FIGS. 8A-8D show the results of ELISA studies measuring the binding of serially diluted binding molecules to human CTLA-4 and human PD-1.
Figure 8B:
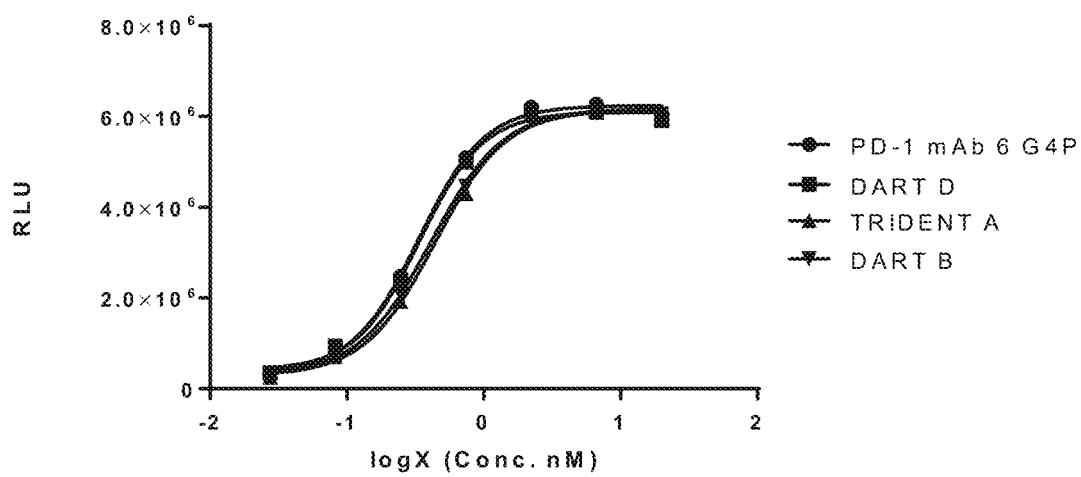

ELISA studies were conducted to measure the binding of serially diluted binding molecules (antibody CTLA-4 mAb 3 G4P, DART D, TRIDENT A or DARTB) to soluble hCTLA-4-Avi-His (1 µg/mL) or hPD-1-His (1 µg/mL) that had been coated onto support plates. Goat anti-human-Fc-HRP (1:10,000) was employed as the secondary detection molecule to detect binding. The results of such studies are shown in Table 10 and in FIGS. 8A-8B. The data shows that PD-1×CTLA-4 bispecific molecules having two binding sites for PD-1 and CTLA-4 (e.g., DART D and DART B) exhibited binding to PD-1 and CTLA-4 that was similar to that of their respective parental anti-PD-1 and anti-CTLA-4

TABLE 9

| Name | Variable Regions | Fc‡ | Chains | SEQ ID NOs: | Other Components |
|---|---|---|---|---|---|
| DART B | CTLA-4 mAb 1 | IgG4 | 1 | 95 | E/K-Coils; see |
|  | PD-1 mAb 6-ISQ | (YTE) | 2 | 96 | FIG. 3B |
|  |  |  | 3 | 95 |  |
|  |  |  | 4 | 96 |  |
| DART C | CTLA-4 mAb 3 | IgG4 | 1 | 97 | E/K-Coils; see |
|  | PD-1 mAb 6-ISQ |  | 2 | 98 | FIG. 3B |
|  |  |  | 3 | 97 |  |
|  |  |  | 4 | 98 |  |
| DART D | PD-1 mAb 6-ISQ | IgG4 | 1 | 99 | E/K-Coils; see |
|  | CTLA-4 mAb 3 | (YTE) | 2 | 100 | FIG. 3B |
|  |  |  | 3 | 99 |  |
|  |  |  | 4 | 100 |  |
| DART E | CTLA-4 mAb 3 | IgG4 | 1 | 102 | CL/CH1; see |
|  | PD-1 mAb 6-ISQ | (YTE) | 2 | 103 | FIG. 3C |
|  |  |  | 3 | 102 |  |
|  |  |  | 4 | 103 |  |
| DART F | PD-1 mAb 6-ISQ | IgG1 | 1 | 101 | E/K-Coils; see |
|  | CTLA-4 mAb 3 | (AA/YTE) | 2 | 100 | FIG. 3B |
|  |  |  | 3 | 101 |  |
|  |  |  | 4 | 100 |  |
| TRIDENT A | PD-1 mAb 6-ISQ | IgG4 | 1 | 104 | E/K-Coils and |
|  | CTLA-4 mAb 3 | (YTE) | 2 | 105 | CL/CH1; see |
|  |  |  | 3 | 106 | FIG. 6A |
|  |  |  | 4 | 107 |  |
| TRIDENT B | PD-1 mAb 6-ISQ | IgG1 | 1 | 108 | E/K-Coils and |
|  | CTLA-4 mAb 3 | (AA/YTE) | 2 | 105 | CL/CH1; see |
|  |  |  | 3 | 109 | FIG. 6A |
|  |  |  | 4 | 107 |  |
| PD-1 mAb 6 G4P | PD-1 mAb 6-ISQ | IgG4 | 1 | 88 | natural antibody structure |
|  |  |  | 2 | 89 |  |
|  |  |  | 3 | 88 |  |
|  |  |  | 4 | 89 |  |
| CTLA-4 mAb 1 | CTLA-4 mAb 1 (ipilimumab replica) | IgG1 | 4 | ** | natural antibody structure |
| CTLA-4 mAb 3 G1AA | CTLA-4 mAb 3 | IgG1 (AA) | 1 | 92 | natural antibody structure |
|  |  |  | 2 | 94 |  |
|  |  |  | 3 | 92 |  |
|  |  |  | 4 | 94 |  |
| CTLA-4 mAb 3 G4P | CTLA-4 mAb 3 | IgG4 | 1 | 93 | natural antibody structure |
|  |  |  | 2 | 94 |  |
|  |  |  | 3 | 93 |  |
|  |  |  | 4 | 94 |  |

‡Molecules incorporating IgG4 Fc regions also incorporate a stabilized IgG4 hinge region.
** the same amino acid sequence as ipilimumab (see, e.g., IMGT 3D and 2D Structural Database Accession Nos. 8568_H and 8568_L)

Additional PD-1×CTLA-4 bispecific molecules comprising alternative PD-1 and/or CTLA-4 epitope-binding sites may be readily generated by incorporating different VH and VL Domains. Similarly, molecules comprising alternative linkers, Fc Regions, and/or having alternative structures may be generated as provided herein (see, e.g., Table 8).

antibodies. PD-1×CTLA-4 bispecific molecules having two binding sites for PD-1 and one binding site for CTLA-4 (e.g., TRIDENT A) exhibited binding to PD-1 that was similar to that of the parental anti-PD-1 antibody and exhibited reduced binding to CTLA-4 (relative to that of the parental antibody) due to the reduced avidity of the trivalent molecule, which comprises only a single binding site for CTLA-4. Similar binding results were observed for DART F and TRIDENT B having IgG1 CH1 and/or IgG1 (AA/YTE) Fc regions.

TABLE 10

| Construct | $EC_{50}$ of CTLA-4 Binding (nM) | $EC_{50}$ of PD-1 Binding (nM) |
|---|---|---|
| CTLA-4 mAb 3 G4P | 0.4 | N/A |
| PD-1 mAb 6 G4P | N/A | 0.3 |
| DART D | 0.4 | 0.3 |
| TRIDENT A | 1.0 | 0.4 |
| DART B | 0.4 | 0.4 |

Figure 8C:
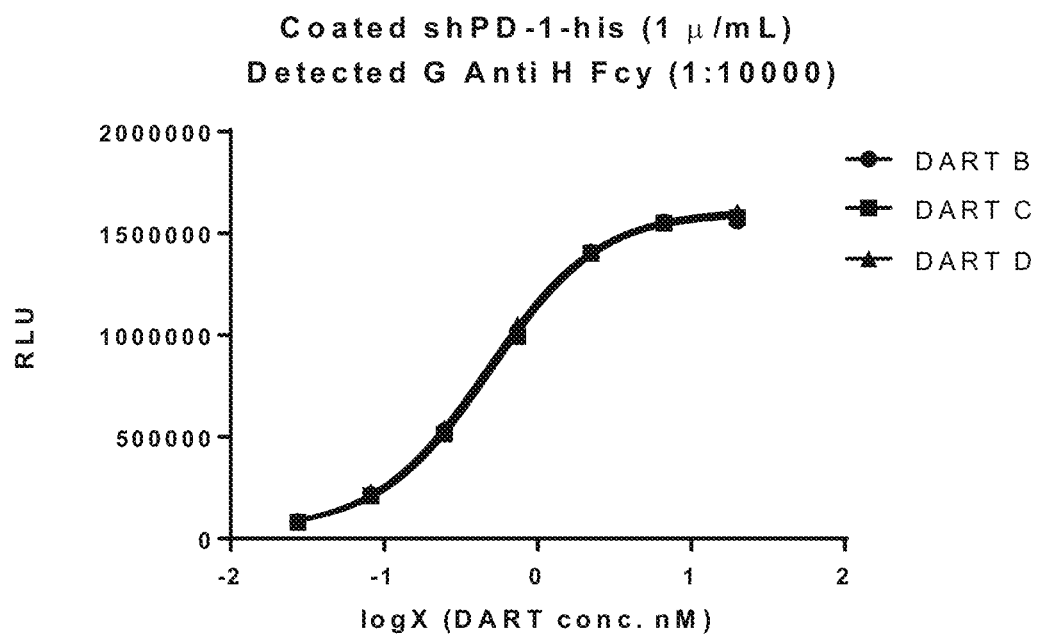
Figure 8D:
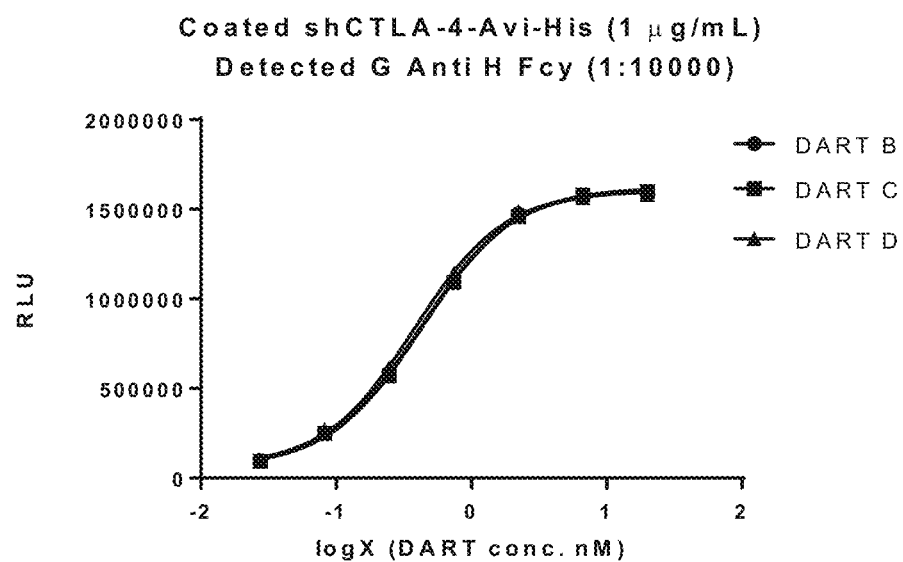

The effect of altering orientations and binding domains on binding was investigated by incubating PD-1×CTLA-4 bispecific molecules comprising the CTLA-4 binding domains of CTLA-4 mAb 1 (e.g., DART B) and CTLA-4 mAb 3 (e.g., DART C and DART D) in the presence of soluble human PD-1 (FIG. 8C), or soluble human CTLA-4-Avi-His (FIG. 8D), that had been coated onto support plates. Goat anti-human-Fcγ-HRP was employed as the secondary detection molecule to detect binding using PICO chemiluminescent substrate. The results indicate that PD-1×CTLA-4 bispecific molecules comprising the CTLA-4 binding domains of CTLA-4 mAb 1 (e.g., DART B) and CTLA-4 mAb 3 (e.g., DART C and DART D) exhibit similar binding to CTLA-4. The orientation of the binding domains (i.e., location on first or second chain) was not found to significantly alter binding to PD-1 or CTLA-4 (compare binding of DART C and DART D).

B. ELISA Blocking Studies

A series of ELISA assays were conducted to evaluate the ability of bispecific molecules of the invention to block ligand binding to PD-1 and CTLA-1, alone and in combination. Blockade of PD-L1 binding to PD-1 was evaluated in the presence of equal amounts of an irrelevant antigen and in the presence of equal amounts of CTLA-4. Plates were coated with a 1:1 mix of His-tagged soluble human PD-1 (shPD-1) and a His-tagged irrelevant antigen (irrAg) (2 µg/ml each), or a 1:1 mix of shPD-1 and a His-tagged soluble human CTLA-4 (shCTLA-4) (2 µg/ml each). PD-1 mAb 6 G4P, DART D, TRIDENT A or a CONTROL TRIDENT (having two binding sites for RSV and one binding site for CTLA-4) at the indicated concentrations were premixed for 5 mins with 6 µg/ml biotin-labeled PD-L1 and added to the plates. PD-L1 binding was detected using streptavidin HRP (1:3,000). The results of this evaluation are presented in FIGS. 9A-9B. All of the PD-1 binding molecules tested were found to be able to inhibit PD-L1 binding to PD-1.

Blockade of B7-1 binding to CTLA-4 was evaluated in the presence of equal amounts of an irrelevant antigen and in the presence of equal amounts of, or four-fold more PD-1. Plates were coated with a 1:1 mix of shCTLA-4 and irrAg (2 µg/ml each), a 1:1 mix of shCTLA-4 shPD-1 (2 µg/ml each), or a 1:4 mix of shCTLA-4 (0.8 µg/ml) and shPD-1 (3.2 µg/ml). PD-1 mAb 6 G4P, DART D, TRIDENT A, CTLA-4 mAb 3 G4P, or CONTROL TRIDENT at indicated concentrations were premixed for 5 mins with 0.2 µg/ml biotin-labeled B7-1 and added to the plates. B7-1 binding was detected using streptavidin HRP (1:3,000). The results of this evaluation are presented in FIG. 9C-9E. All of the CTLA-4 binding molecules tested were found to be able to inhibit B7-1 binding to CTLA-4. TRIDENT A blocking of B7-1 binding was found to be enhanced by the interaction of its PD-1 binding arm interacting with immobilized PD-1 (compare to CONTROL TRIDENT which does not bind PD-1) (FIG. 9D). Moreover, under the 1:4 CTLA-4:PD-1 condition, which better mimics the relative expression levels seen on stimulated cells (see, FIG. 19A), TRIDENT A blocking of B7-1 binding was found to be further enhanced (i.e., the TRIDENT A curve was further shifted compared to the curve of the CONTROL TRIDENT, which does not bind PD-1) (FIG. 9E).

Figure 9A:
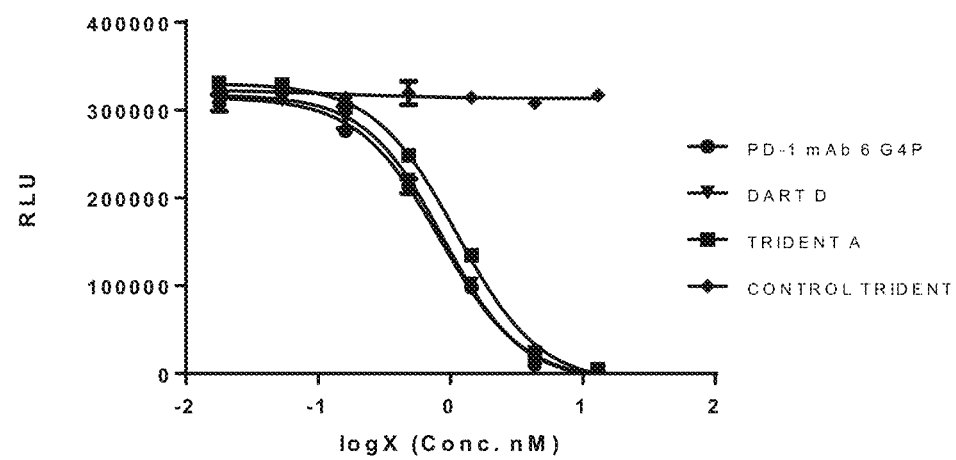
FIGS. 9A-9E show the results of an evaluation of the ability of DART D, TRIDENT A, PD-1 mAb 6 G4P, and CTLA-4 mAb 3 G4P and a control trident (having two binding sites for RSV and one binding site for CTLA-4) to block binding ligand binding to PD-1 and CTLA-1, alone and in combination. Blockade of PD-L1 binding to PD-1 was evaluated in the presence of equal amounts of an irrelevant antigen (FIG. 9A) and in the presence of equal amounts of CTLA-4 (FIG. 9B), and blockade of B7-1 binding to CTLA-4 was evaluated in the presence of equal amounts of an irrelevant antigen (FIG. 9C) and in the presence of equal amounts of PD-1 (FIG. 9D) and in the presence of four fold more PD-1 (FIG. 9E) using an ELISA assay.
Figure 9B:
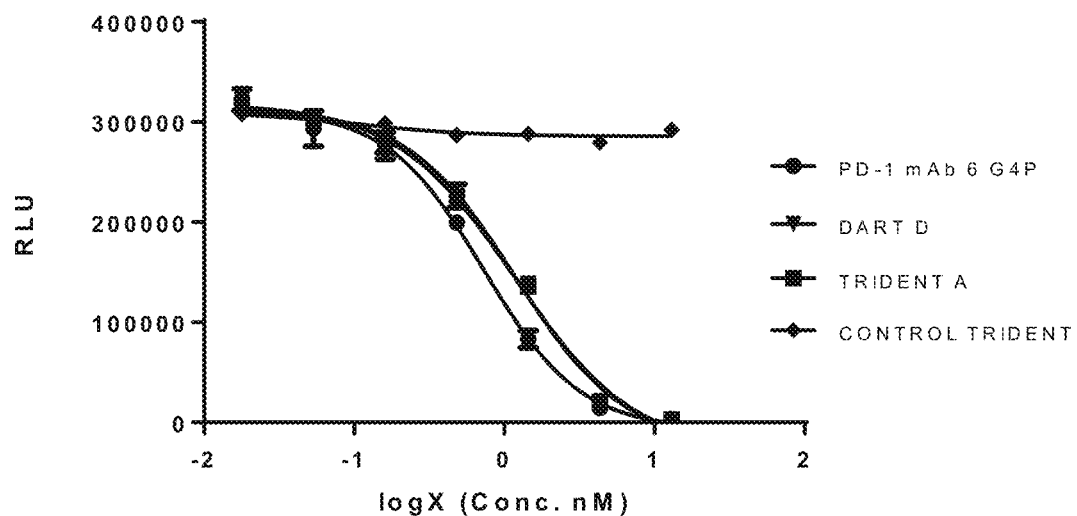
Figure 9C:
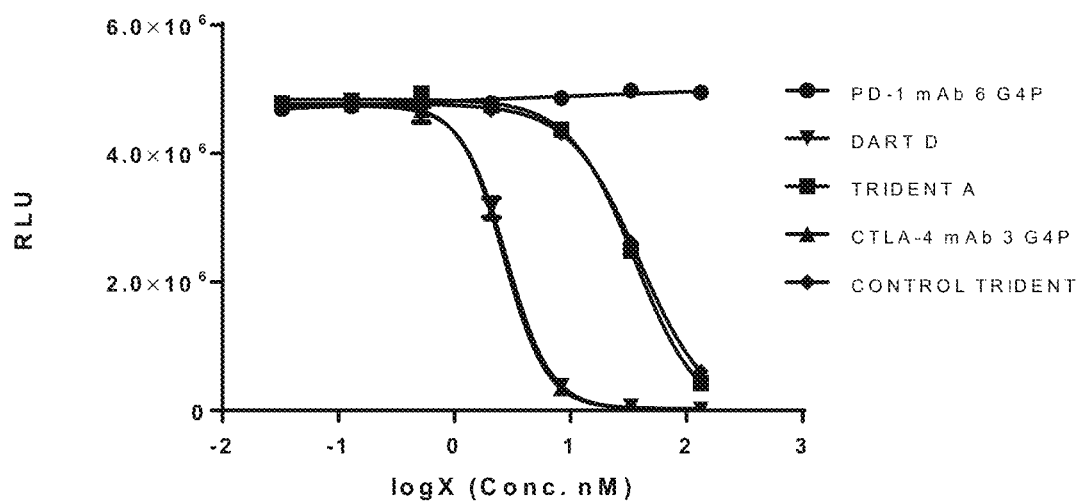
Figure 9D:
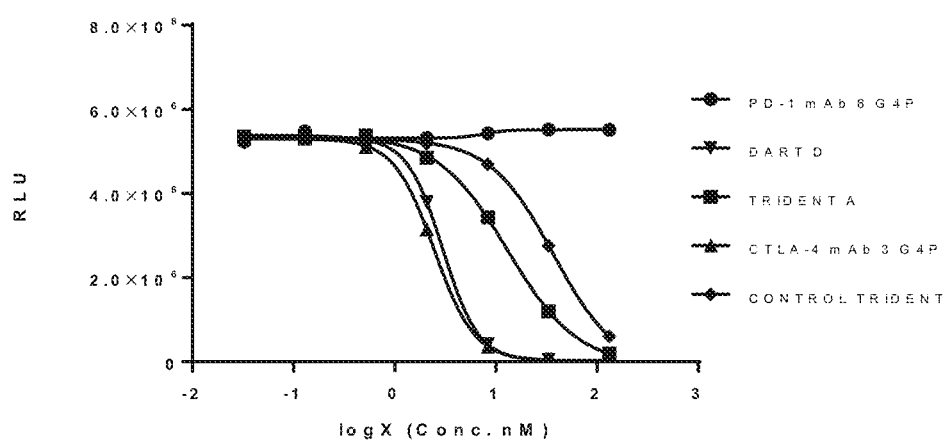
Figure 9E:
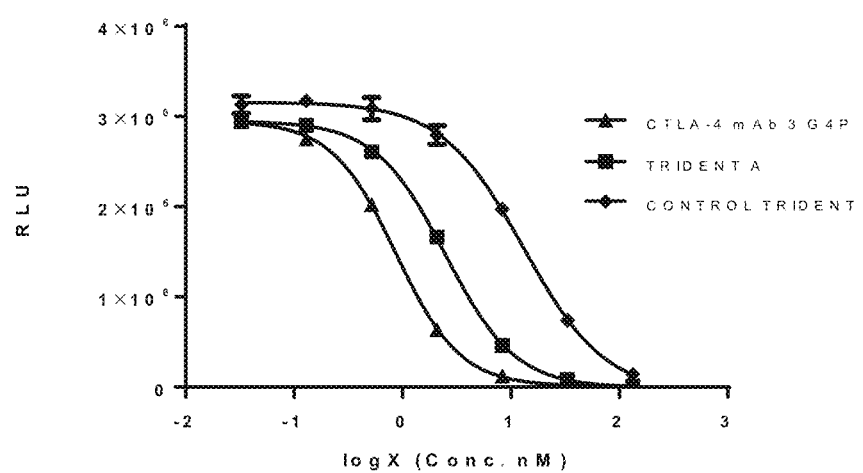

The results of these ELISA studies demonstrate that all of the PD-1 binding molecules tested were able to inhibit PD-L1 from binding to the PD-1 (FIGS. 9A-9B). All such molecules are bivalent for PD-1 and exhibited similar inhibition profiles. All of the CTLA-4 binding molecules tested were able to inhibit B7-1 from binding to immobilized CTLA-4 (FIG. 9C-9E) with molecules comprising two PD-1 binding sites and one CTLA-4 binding site exhibiting stronger inhibition in the presence of PD-1 (FIG. 9D-9E). Thus, the trivalent molecules comprising a single CTLA-4 binding site exhibit a PD-1 biased blockade of CTLA-4 ligands, demonstrating that the CTLA-4 interaction can be tailored by adjusting the valency.

C. BIACORE® Studies

The binding affinity of DART A, TRIDENT A, and CTLA-4 mAb 1 to human CTLA-4 and cynomolgus monkey CTLA-4 was investigated using BIACORE® analysis. Briefly, His-tagged soluble CTLA-4 (an extracellular portion of human or cynomolgus monkey CTLA-4 fused to a histidine-containing peptide) was captured on immobilized anti-PentaHis and then different concentrations (12.5-200 nM) of the CTLA-4 binding molecules were passed over the immobilized CTLA-4 proteins. The kinetics of binding were determined via BIACORE® analysis (affinity by 1:1 Langmuir binding model (simultaneous ka/kd); or avidity by separate ka/kd 1:1 fit). The calculated $k_a$, $k_d$ and $K_D$ from these studies are presented in Table 11.

TABLE 11

| | Human CTLA-4 | | | Cyno CTLA-4 | | |
|---|---|---|---|---|---|---|
| Molecule | $k_a$ (×10⁵) | $k_d$ (×10⁻⁴) | KD (nM) | $k_a$ (×10⁵) | $k_d$ (×10⁻³) | KD (nM) |
| CTLA-4 mAb 1* | 6.6 | 8.9 | 1.4 | 10 | 1.3 | 1.3 |
| DART D* | 2.3 | 7.1 | 3.1 | 3.5 | 1.7 | 4.9 |
| TRIDENT A‡ | 1.2 | 32 | 26.7 | 2.5 | 65 | 260 |

*avidity by separate ka/kd 1:1 fit
‡affinity by 1:1 Langmuir binding model

DART D is bivalent for CTLA-4 and exhibits binding affinities to human and cynomolgus monkey CTLA-4 that are within about 2 to 4-fold that of the CTLA-4 mAb 1. TRIDENT A is monovalent for CTLA-4 exhibits lower affinity for both human and cynomolgus monkey CTLA-4 as expected in view of its reduced avidity.

The binding affinity of DART A, TRIDENT A, PD-1 mAb 6 G4P, and CTLA-4 mAb 3 G1AA to human PD-1 was investigated using BIACORE® analysis. The binding molecules were captured on immobilized F(ab)₂ goat anti-human Fc and then different concentrations (6.25-100 nM) of His-tagged soluble human PD-1 were passed over the immobilized binding molecules, and the kinetics of binding was determined via BIACORE® analysis (Langmuir 1:1 binding fit). The calculated ka, kd and KD from these studies are presented in Table 12 (n.d., not detectable).

TABLE 12

| | Human PD-1 | | |
| Molecule | $k_a$ (×10$^5$) | $k_d$ (×10$^{-4}$) | KD (nM) |
| --- | --- | --- | --- |
| CTLA-4 mAb 3 G1AA | n.d. | n.d. | n.d. |
| PD-1 mAb 6 G4P | 6.2 | 6.7 | 1.1 |
| DART D | 4.8 | 8.1 | 1.7 |
| TRIDENT A | 5.2 | 6.8 | 1.3 |

DART A, TRIDENT A, PD-1 mAb 6 G4P are each bivalent for PD-1 and exhibit comparable binding affinities. As expected, CTLA-4 mAb 3 G1AA did not exhibit any detectable binding for human PD-1.

D. CTLA-4 Cell Based Assays

Figure 10A:
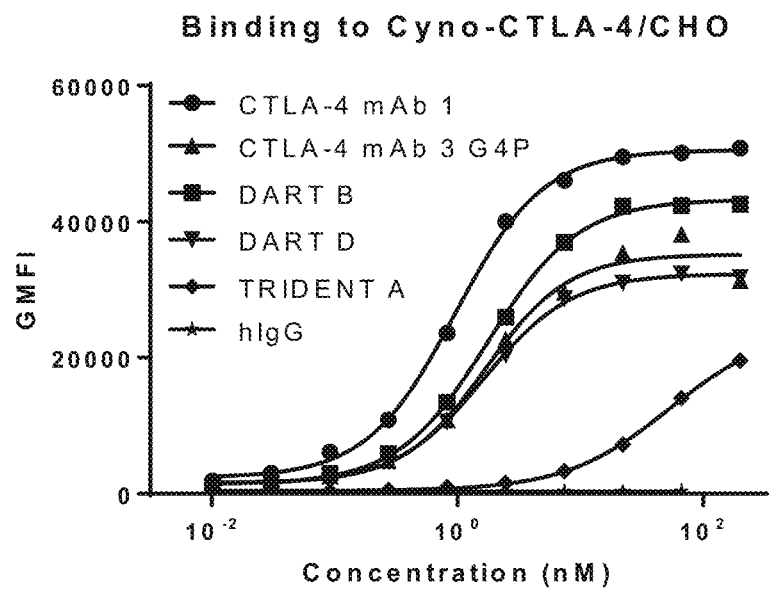
FIGS. 10A-10B show the results of an evaluation of the ability of DART B, DART D, TRIDENT A, the anti-CTLA-4 antibodies CTLA-4 mAb 1, CTLA-4 mAb 3 G4P, and an hIgG control antibody to bind to CHO cells expressing cynomolgus monkey CTLA-4 (FIG. 10A) or human CTLA-4 (FIG. 10B). Binding was detected using an anti-human Fc secondary antibody.
Figure 10B:
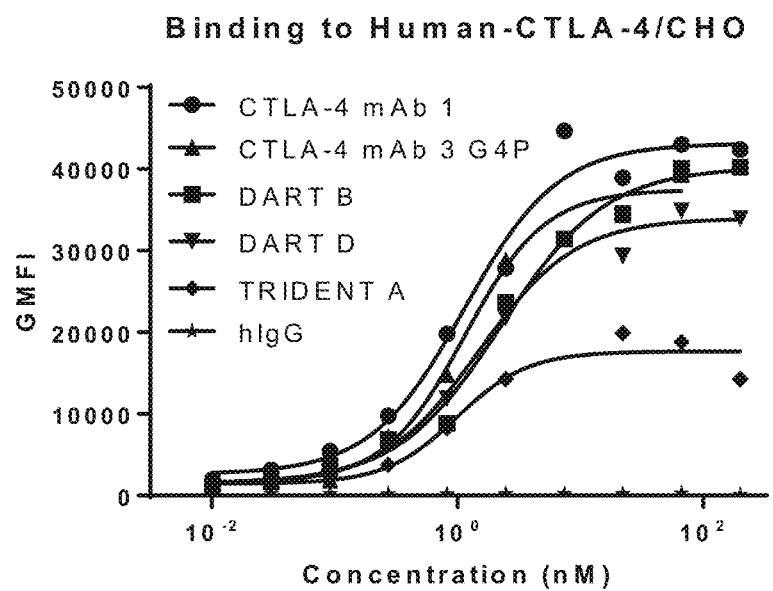

DART B, DART D, TRIDENT A, the anti-CTLA-4 antibodies CTLA-4 mAb 1, CTLA-4 mAb 3 G4P, and an hIgG control antibody were evaluated for binding to CHO cells expressing cynomolgus monkey CTLA-4 (cynoCTLA-4) or human CTLA-4 (huCTLA-4). The results of this evaluation are shown in FIGS. 10A-10B. The binding molecules were incubated in the presence of CHO cells that were expressing either cynomolgus monkey CTLA-4 (FIG. 10A) or human CTLA-4 (FIG. 10B). Binding to such cells was detected using an anti-human Fc secondary antibody. The results show that all the molecules tested were able to bind human and cynomolgus monkey CTLA-4 expressed on the surface of the CHO cells. The anti-CTLA-4 antibodies exhibited similar binding profiles to huCTLA-4; the bivalent, bispecific molecules DART B and DART D exhibited slightly reduced binding, and the trivalent binding molecule. TRIDENT A, which is monovalent for CTLA-4 exhibited lower binding than the molecules having higher valency for CTLA-4. The control antibody did not bind. Similar results were seen for binding to cynoCTLA-4.

Figure 11A:
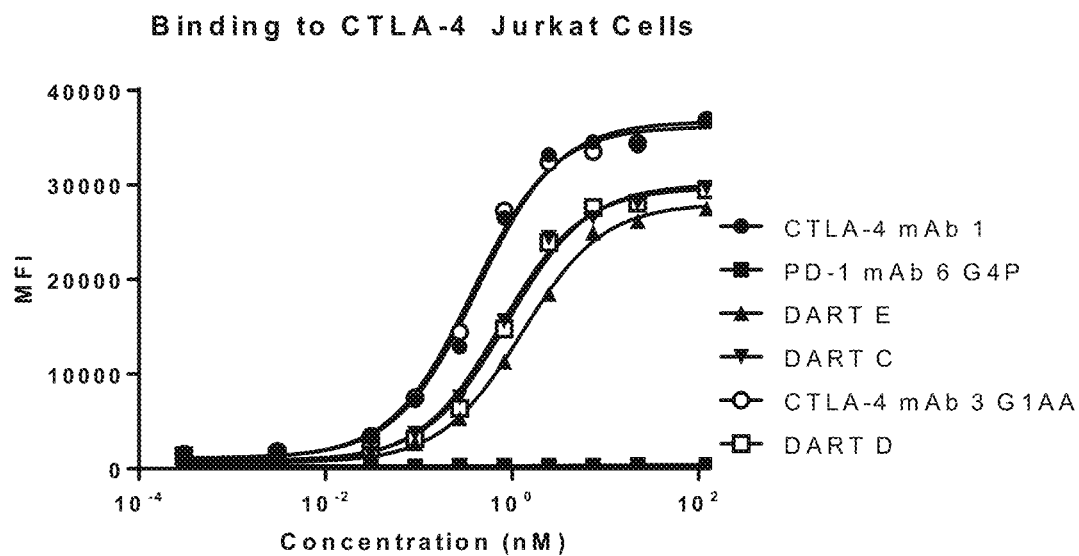
FIGS. 11A-11B show the results of an evaluation of the ability of DART C, DART D, DART E, TRIDENT A, the anti-CTLA-4 antibodies CTLA-4 mAb 1, CTLA-4 mAb 3 G1AA, and the anti-PD-1 antibody PD-1 mAb 6 G4P to bind to Jurkat cells (which express huCTLA-4 but not PD-1 on their surface). Binding of the DART and TRIDENT molecules to human CTLA-4 was detected using anti-human FC secondary Ab (FACS).
Figure 11B:
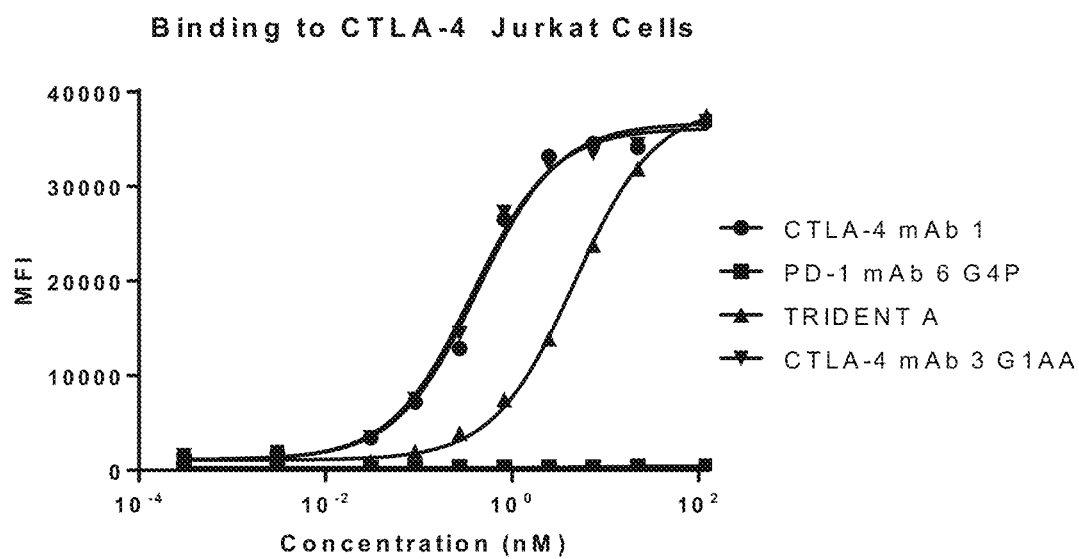

DART C, DART D, DART E, TRIDENT A, the anti-CTLA-4 antibodies CTLA-4 mAb 1, CTLA-4 mAb 3 G1AA, and the anti-PD-1 antibody PD-1 mAb 6 G4P were evaluated for binding to Jurkat cells which express huCTLA-4 but not PD-1 on their surface. Binding of the DART and TRIDENT molecules to human CTLA-4 was detected using anti-human FC secondary Ab (FACS). The results of the evaluation are shown in Table 13 and FIG. 11A (DART C, DART D, DART E, CTLA-4 mAb 1, CTLA-4 mAb 3 G1AA, and PD-1 mAb 6 G4P) and FIG. 11B (CTLA-4 mAb 1, CTLA-4 mAb 3 G1AA, PD-1 mAb 6 G4P and TRIDENT A). As shown in FIGS. 11A-11B, the PD-1 antibody did not bind CTLA-4, but all the CTLA-4 binding molecules tested were able to bind huCTLA-4 expressed on the surface of Jurkat cells. The anti-CTLA-4 antibodies exhibited similar binding profiles; the bivalent, bispecific molecules DART C, DART D, and DART E exhibited slightly reduced binding to Jurkat cells and the trivalent binding molecule. TRIDENT A, which is monovalent for CTLA-4 exhibited lower binding than the molecules having higher valency for CTLA-4.

TABLE 13

| Molecule | EC50 (nM) |
| --- | --- |
| CTLA-4 mAb 1 | 0.4215 |
| PD-1 mAb 6 G4P | 6.557 |
| CTLA-4 mAb 3 G1AA | 0.3728 |
| DART E | 1.269 |
| DART C | 0.7575 |
| DART D | 0.8829 |
| TRIDENT A | 4.638 |

Figure 12A:
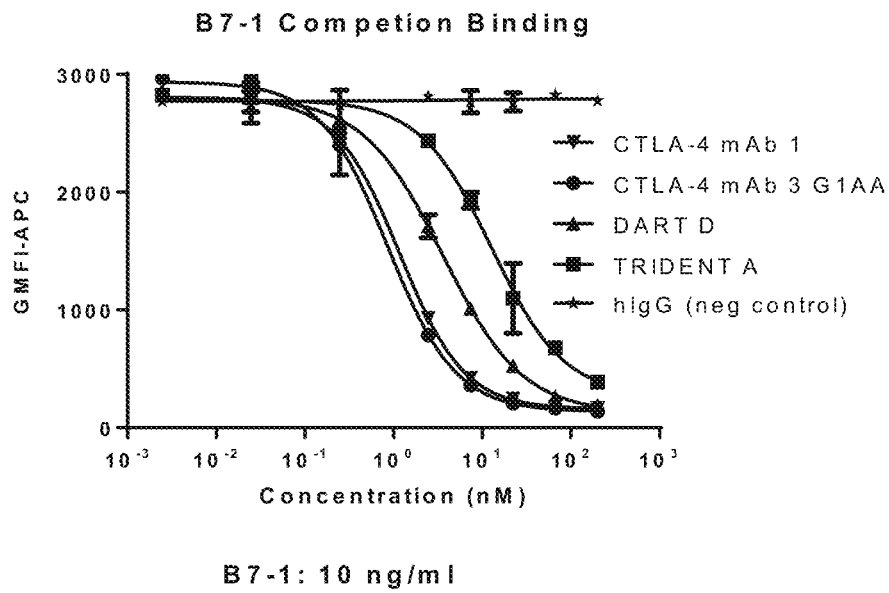
FIGS. 12A-12B show the results of an evaluation of the ability of DART D, TRIDENT A and the anti-CTLA-4 antibodies CTLA-4 mAb 1, CTLA-4 mAb 3 G1AA to block the CTLA-4 ligands B7-1 and B7-2 in a cell-based assay. His-tagged derivatives of B7-1 and B7-2 were incubated in the presence of the Jurkat cells and artificial antigen presenting cells (Promega). Binding of His-B7-1 and His-B7-2 was detected using an anti-His antibody. The results of this evaluation are shown in FIG. 12A (His-B7-1) and FIG. 12B (His-B7-2).
Figure 12B:
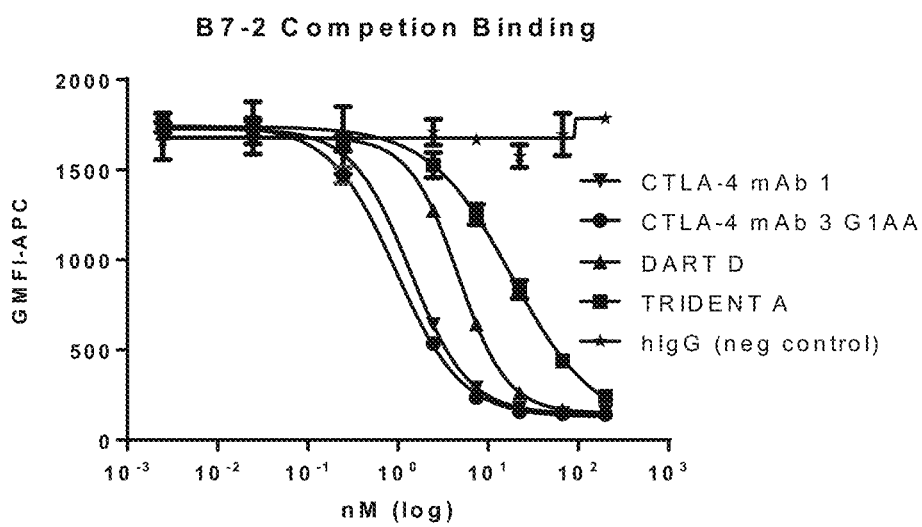

DART D, TRIDENT A and the anti-CTLA-4 antibodies CTLA-4 mAb 1, CTLA-4 mAb 3 G1AA were evaluated for their ability to block the CTLA-4 ligands B7-1 and B7-2. His-tagged derivatives of B7-1 and B7-2 were incubated in the presence of CTLA-4 Jurkat cells. Binding of His-B7-1 and His-B7-2 was detected using an anti-His antibody. The results of this evaluation are shown in FIG. 12A (His-B7-1) and FIG. 12B (His-B7-2). All the molecules tested were found to be able to inhibit B7-1 and B7-2 from binding CTLA-4 expressed on the surface of the Jurkat cells. The anti-CTLA-4 antibodies exhibited similar inhibition profiles; the bivalent, bispecific molecule DART D was slight less potent an inhibitor and the trivalent binding molecule. TRIDENT A, which is monovalent for CTLA-4 was less potent than any of the molecules having higher valency for CTLA-4. The control antibody did not inhibit at all. The ELISA studies described above suggest that TRIDENT A, and similar molecules having two PD-1 binding sites and one CTLA-4 binding site would be more potent inhibitors in the presence of PD-1.

Figure 13:
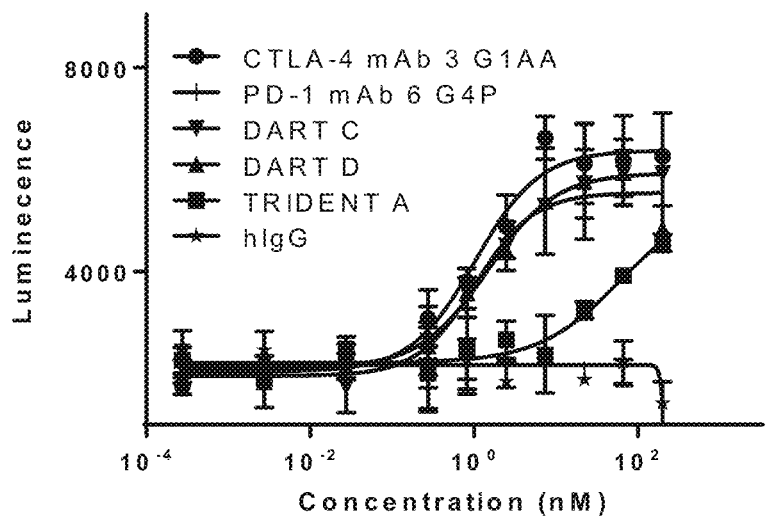
FIG. 13 shows the results of an evaluation of the ability of DART C, DART D, TRIDENT A, CTLA-4 mAb 3 G1AA and PD-1 mAb 6 G4P to reverse CTLA-4 immune checkpoint inhibitory signal as demonstrated in a IL-2/Luc-Jurkat-CTLA-4 reporter assay by increased luciferase expression. IL-2/Luc-Jurkat-CTLA-4 cells were incubated in the presence of the listed binding molecules (R:S=1:0.3) for 30 min at 37° C., after which time artificial antigen presenting Raji cells were added and the incubation continued for 6 hours. Reversal of CTLA-4 immune checkpoint inhibitory signal was determined by the luciferase assay.

An IL-2/Luc Jurkat cell CTLA-4 reporter assay was used to evaluate the ability of DART C, DART D, TRIDENT A, CTLA-4 mAb 3 G1AA and PD-1 mAb 6 G4P to reverse CTLA-4 immune checkpoint inhibitory signal as demonstrated by increased luciferase expression. IL-2/Luc-Jurkat-CTLA-4 cells were therefore incubated in the presence of such molecules (R:S=1:0.3) for 30 min at 37° C., after which time artificial antigen presenting Raji cells were added and the incubation continued for 6 hours. The artificial antigen presenting cells activate the TCR/CD3 complex on the Jurkat reporter cells. The results of the evaluation are shown in FIG. 13. All of the CTLA-4 binding molecules tested were able reverse the CTLA-4 immune checkpoint inhibitory signal as determined by the luciferase assay. TRIDENT A, which is monovalent for CTLA-4 was less potent in this assay than any of the molecules having higher valency for CTLA-4. The control antibody did not inhibit at all. The ELISA studies described above suggest that TRIDENT A, and similar molecules having two PD-1 binding sites and one CTLA-4 binding site would be more potent in the presence of PD-1.

E. PD-1 Cell Based Assays

Figure 14:
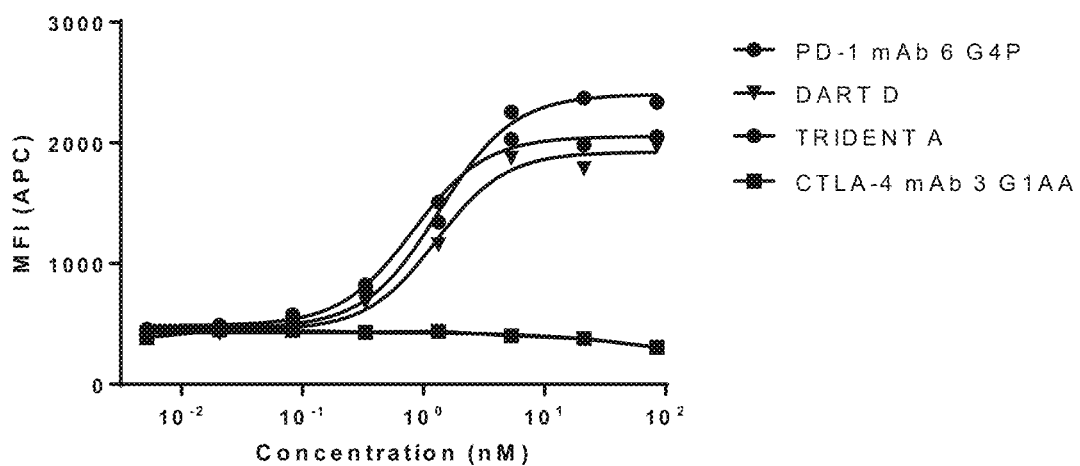
FIG. 14 shows the results of an evaluation of the ability of DART D, TRIDENT A, PD-1 mAb 6 G4P, and CTLA-4 mAb 3 G1AA to bind NSO cells that express PD-1 but not CTLA-4. Binding molecules were incubated in the presence of the cells and the mean fluorescence index of the cells was measured.

DART D, TRIDENT A, PD-1 mAb 6 G4P, and CTLA-4 mAb 3 G1AA were evaluated for their ability to bind NSO cells expressing PD-1 but not CTLA-4. Binding molecules were incubated in the presence of the cells and the mean fluorescence index of the cells was measured. The results of this evaluation are presented in FIG. 14. As expected, the CTLA-4 antibody did not bind, all the bispecific binding molecules were found to be able to bind PD-1 expressed on the surface of NSO cells. All the bispecific molecules are bivalent for PD-1 and exhibited similar binding to NSO cells.

Figure 15A:
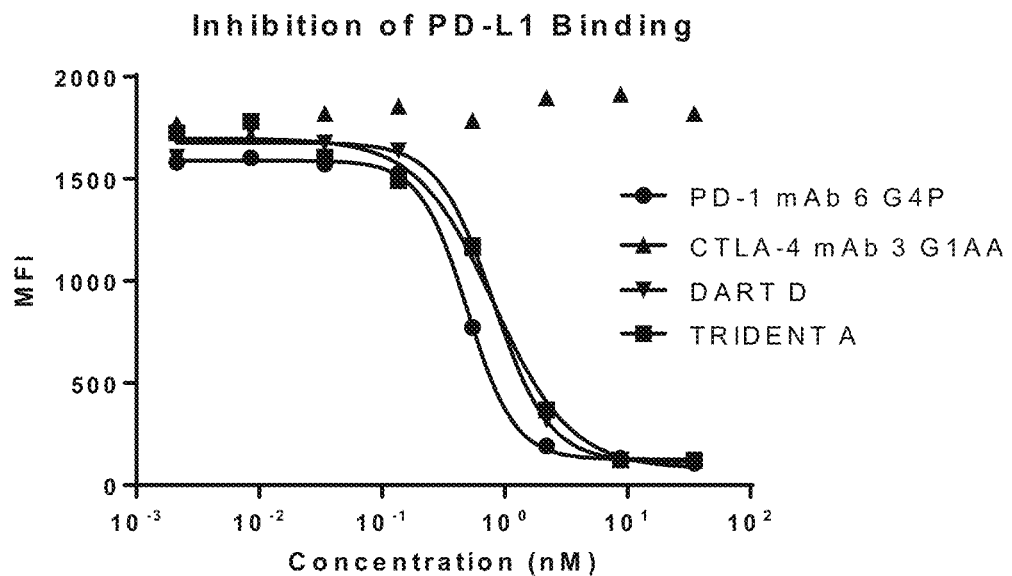
FIGS. 15A-15B show the results of an evaluation of the ability of DART D, TRIDENT A, PD-1 mAb 6 G4P, and CTLA-4 mAb 3 G1AA to block binding between PD-1 and its ligands PD-L1 and PD-L2 in a cell based assay. PD-L1-PE or PD-L2-PE was incubated in the presence of such binding molecules and their ability to bind to NSO-PD-1 cells was evaluated using FACS.
Figure 15B:
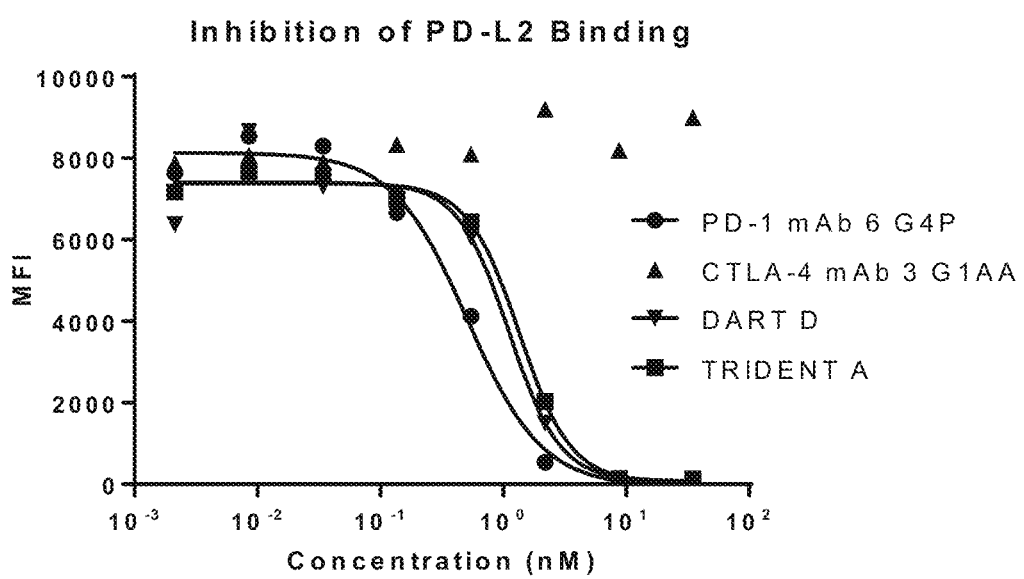

DART D, TRIDENT A, PD-1 mAb 6 G4P, and CTLA-4 mAb 3 G1AA were evaluated for their ability to block binding between PD-1 expressed on the cell surface and its ligands PD-L1 and PD-L2. PD-L1-PE or PD-L2-PE was incubated in the presence of such binding molecules and their ability to bind to NSO-PD-1 cells was evaluated using FACS. The results of this evaluation are presented in FIG. 15A (PD-L1) and FIG. 15B (PD-L2). As expected, the CTLA-4 antibody did not inhibit, all of the PD-1 binding molecules tested were able to inhibit both PD-L1 (FIG. 15A) and PD-L2 (FIG. 15B) from binding to the PD-1 expressed on the surface of the NSO cells. All the PD-1 binding molecules are bivalent for PD-1 and exhibited similar inhibition profiles.

Figure 16:
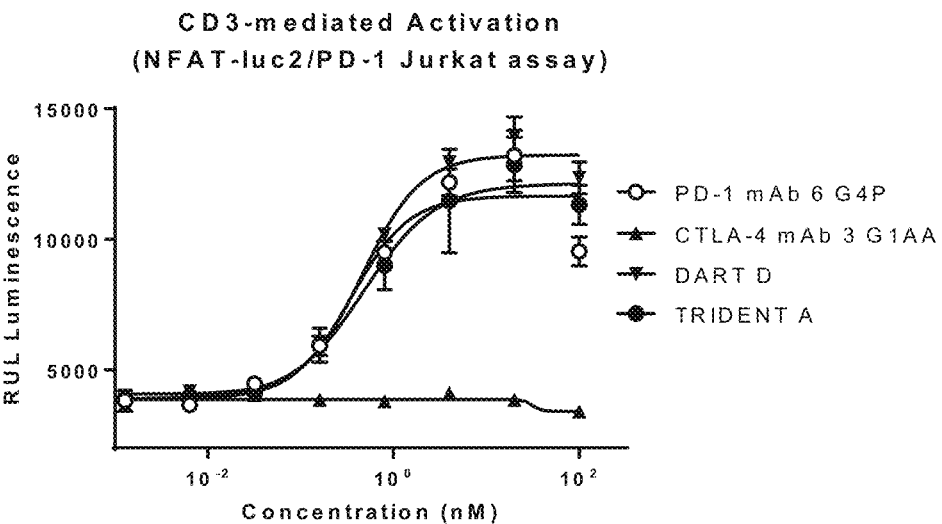
FIG. 16 shows the results of an evaluation of the ability of DART D, TRIDENT A, CTLA-4 mAb 3 G1AA, and PD-1 mAb 6 G4P to block immune inhibition resulting from a PD-1/PD-L1 interaction. Binding molecules were incubated in the presence of PD-L1+ CHO and Jurkat effector cells, and the ability of the binding molecules to block immune inhibition (by blocking the PD-1/PD-L1 interaction) was assessed by following the extent of CD3-mediated activation (as demonstrated by increased luciferase expression in the NFAT-luc/PD-1 Jurkat assay; Promega).

DART D, TRIDENT A, CTLA-4 mAb 3 G1AA, and PD-1 mAb 6 G4P were also evaluated in a PD-1 blockade reporter assay. Such binding molecules were incubated in the presence of PD-L1+ CHO and Jurkat effector cells, and the ability of the binding molecules to block immune inhibition (by blocking the PD-1/PD-L1 interaction) was assessed by following the extent of CD3-mediated activation (as demonstrated by increased luciferase expression in the NFAT-luc/PD-1 Jurkat assay; Promega). The results of this evaluation are presented in FIG. 16. All of the PD-1 binding molecules tested were able to reverse the PD-1 immune checkpoint inhibitory signal as demonstrated by increased luciferase expression. All the PD-1 binding molecules are bivalent for PD-1 and exhibited similar ability to inhibit PD-1 blockade of T cell signaling. The CTLA-4 antibody did not inhibit at all in this system.

F. CTLA-4/PD-1 Cell Based Assays

Figure 17:
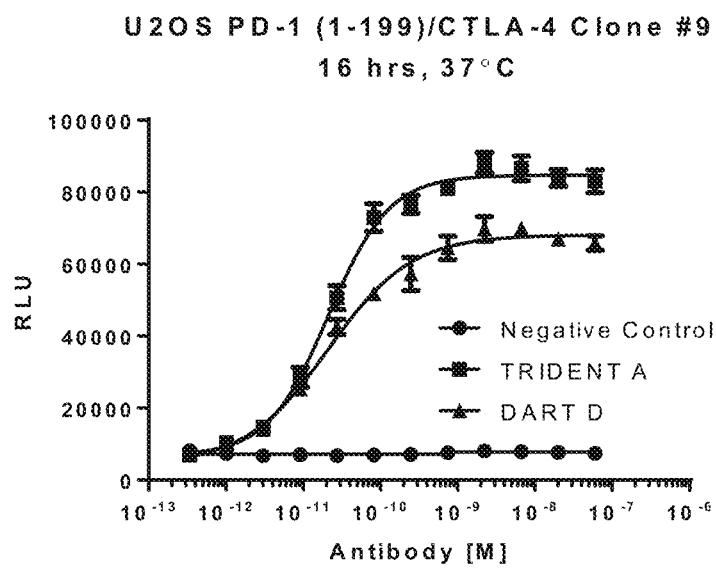
FIG. 17 shows the results of an evaluation of the ability of DART D, TRIDENT A, and a negative control antibody to co-ligate PD-1 and CTLA-4 in an enzyme-fragment complementation assay by DiscoverX. Aliquots of the U2OS CTLA-4(1-195)-PK PD-1(1-199)-EA cell line #9 were plated in quadruplicate at 5,000 cells/well in DiscoverX CP5 plating media on 384-well plates. Cells were allowed to attach for 4 hours at 37° C./5% $CO_2$. 11 point, 1:3 dilution series of each of the binding molecules were then added to the PD-1-CTLA-4 cells and the DART D and TRIDENT A samples were added to the PD-1-LAG-3 cells. The plates were incubated overnight (16 hrs) at 37° C./5% $CO_2$. PathHunter detection reagent was added to the wells, which were then incubated for 1 hour at room temperature in the dark, and the plate was then read on an Envision luminometer.

DART D, TRIDENT A, and a negative control antibody were examined for their ability to co-ligate PD-1 and CTLA-4 in an enzyme-fragment complementation assay by DiscoverX. In brief, aliquots of the U2OS CTLA-4(1-195)-PK PD-1(1-199)-EA cell line #9 were plated in quadruplicate at 5,000 cells/well in DiscoverX CP5 plating media on 384-well plates. Cells were allowed to attach for 4 hours at 37° C./5% $CO_2$. 11 point, 1:3 dilution series of each of the binding molecules were then added to the PD-1-CTLA-4 cells. The plates were incubated overnight (16 hrs) at 37° C./5% $CO_2$. PathHunter detection reagent was added to the wells, which were then incubated for 1 hour at room temperature in the dark, and the plate was then read on an Envision luminometer. The results of this evaluation are presented in Table 14 and FIG. 17 (U2OS CTLA-4(1-195)-PK PD-1(1-199)-EA cell line #9). Both the bispecific DART D and TRIDENT A molecules show comparable co-engagement of PD-1 and CTLA-4 in cells that co-express both receptors, as shown by enzyme-fragment complementation, indicating that the bispecific molecules of the invention are capable of simultaneous binding of PD-1 and CTLA-4, and further indicating that anchoring through PD-1 compensates for the decreased CTLA-4 avidity of the TRIDENT molecule when both target receptors are expressed. This finding is consistant with the ELISA inhibition studies described above. The negative control elicited no significant increase in signal in the PD1-CTLA4 cell line. Incubation with higher concentrations of TRIDENT A elicited a robust signal increase in the U2OS PD1-CTLA4 Dimerization cell line (S:B=12.7). The response with DART D in dose-response testing in the PD-1-CTLA-4 cell line was smaller in magnitude (S:B=9.2) but the EC50 values were similar for both these molecules (EC50=20 pM).

TABLE 14

| | Negative Control | TRIDENT A | DART D |
|---|---|---|---|
| HillSlope | ~15.99 | 1.103 | 0.8095 |
| EC50 (nM) | ~6.883 × 10$^{-10}$ | 2.123 × 10$^{-11}$ | 2.090 × 10$^{-11}$ |

Figure 18:
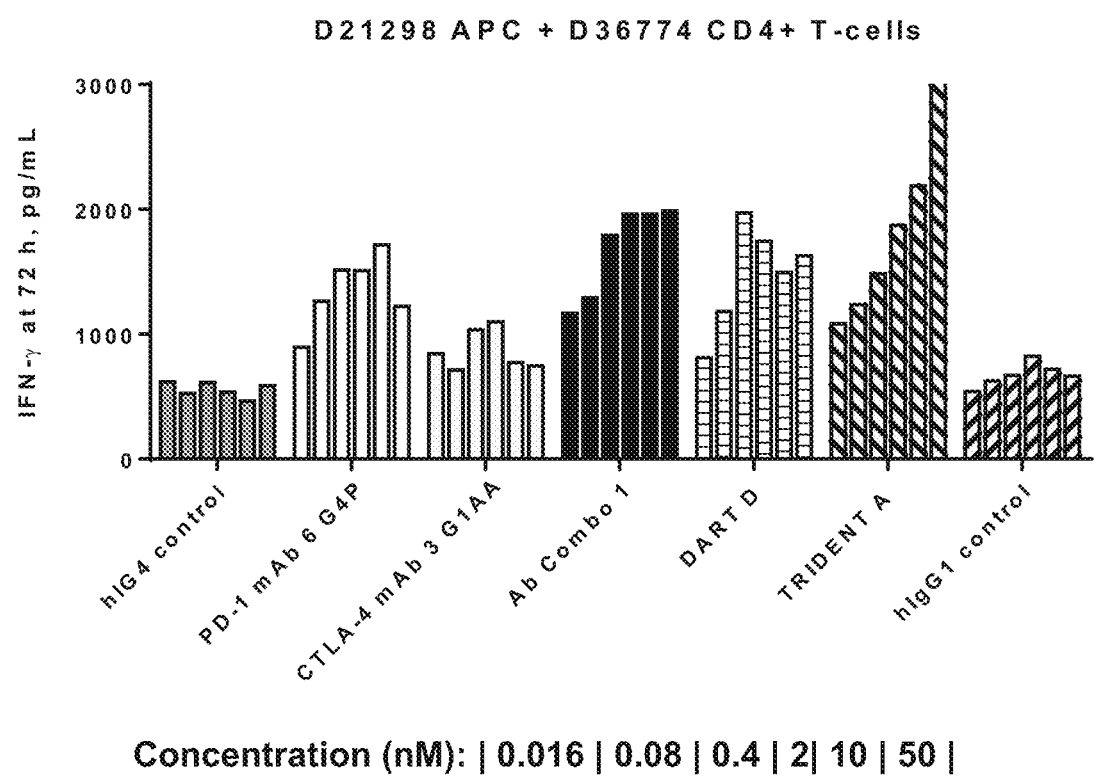
FIG. 18 shows the results of an evaluation of the ability of DART D, TRIDENT A, CTLA-4 mAb 3 G1AA, PD-1 mAb 6 G4P and the combinations of CTLA-4 mAb 3 G1AA/PD-1 mAb 6 G4P (Ab Combo 1) to enhance the response of a Mixed Lymphocyte Reaction. Monocyte-derived dendritic cells were generated by treating CD14+ monocytes with GM-C SF (provided at day 1 of the incubation period) and IL-4 (provided at day 7 of the incubation period). At day 8 of the incubation period, a MLR was set up by incubating the CD4+ T cells with the monocyte-derived dendritic cells (provided at day 8 of the incubation period) and the anti-CTLA-4 and anti-PD-1 binding molecules (provided at day 8 of the incubation period). The release of IFN-γ is plotted in FIG. 18. Both the bispecific DART D and TRIDENT A molecules were found to enhance the MLR response to the same extent or slightly better than the combination of individual parental antibodies. The presented data comprises seven series (each relating to a different binding molecule: hIgG4 control; PD-1 mAb 6 G4P; CTLA-4 mAb 3 G1AA; a combination of CTLA-4 mAb 3 G1AA/PD-1 mAb 6 G4P (Ab Combo 1); DART D; TRIDENT A; and an hIgG1 control, respectively from left to right); each series is composed of six columns (each relating to a different concentration of the provided molecule: 0.016, 0.08, 0.4, 2, 10 or 50 nM, respectively from left to right).

The ability of DART D, TRIDENT A, CTLA-4 mAb 3 G1AA, PD-1 mAb 6 G4P and the combinations of CTLA-4 mAb 3 G1AA/PD-1 mAb 6 G4P (Ab Combo 1) to enhance the response of a Mixed Lymphocyte Reaction (MLR) was evaluated. Monocyte-derived dendritic cells were generated by treating CD14+ monocytes (isolated from PBMCs using Miltenyi positive selection kit) with GM-CSF (100 ng/ml) and IL-4 (10 ng/ml) and then culturing the cells for 7 days. On day 7, cells were harvested and plated into 96-well plates and cultured for 24 h. On day 8, CD4+ T-cells (isolated by negative selection using Myltenyi kit) at 200,000 cells/well and test articles were added and cultured for 3 days. IFN-g levels in culture supernatants were then measured using human DuoSet ELISA Kits for IFN-γ (R&D Systems) according to the manufacturer's instructions. When antibodies were used in combination, each antibody was added at the indicated concentration so that the total concentration of antibody added is doubled. The release of IFN-γ is plotted in FIG. 18. Both the bispecific DART D and TRIDENT A molecules were found to enhance the MLR response to the same extent or slightly better than the combination of individual parental antibodies.

The ability of DART D, TRIDENT A, CTLA-4 mAb 3 G1AA, PD-1 mAb 6 G4P and the combination of CTLA-4 mAb 1/PD-1 mAb 1 (Ab Combo 1) to enhance cytokine release through checkpoint inhibition was also evaluated in a *Staphylococcus aureus* enterotoxin type B (SEB) re-stimulation assay. In general, PBMCs were purified from whole blood (e.g., using the Ficoll-Paque Plus density gradient centrifugation method (GE Healthcare) according to manufacturer's instructions) from healthy donors. Purified PBMCs were cultured in RPMI-media+10% heat inactivated FBS+1% Penicillin/Streptomycin in T-25 bulk flasks for 2-3 days alone or with SEB (e.g., Sigma-Aldrich) at 0.5 ng/mL (primary stimulation). At the end of the first round of SEB-stimulation, PBMCs are washed twice with PBS and immediately plated in 96-well tissue culture plates at a concentration of 1-5×10$^5$ cells/well in media alone, media with a control or a test article, media with SEB at 0.5 ng/mL (secondary stimulation) and no antibody, or media with SEB and a control IgG or a test article, and were cultured for an additional 2-3 days. At the end of the second stimulation, supernatants were harvested to measure cytokine secretion (e.g., using human DuoSet ELISA Kits for IFNγ, IL-2, TNFα, IL-10, and IL-4 (R&D Systems) according to the manufacturer's instructions).

Figure 19A:
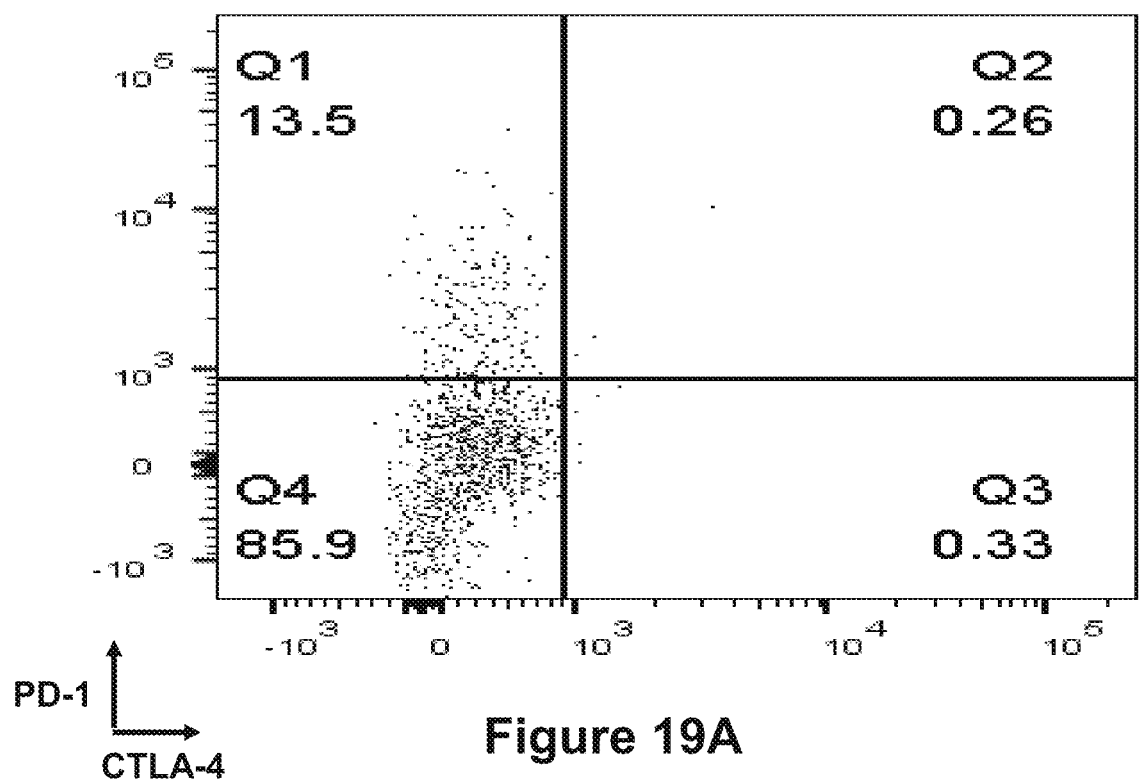
FIGS. 19A-19D show the effect of administration of DART D, TRIDENT A, CTLA-4 mAb 3 G1AA, PD-1 mAb 6 G4P and the combination of CTLA-4 mAb 1/PD-1 mAb 1 (Ab Combo 1) on T-cell responses using a *Staphylococcus aureus* enterotoxin type B (SEB) re-stimulation assay.
Figure 19B:
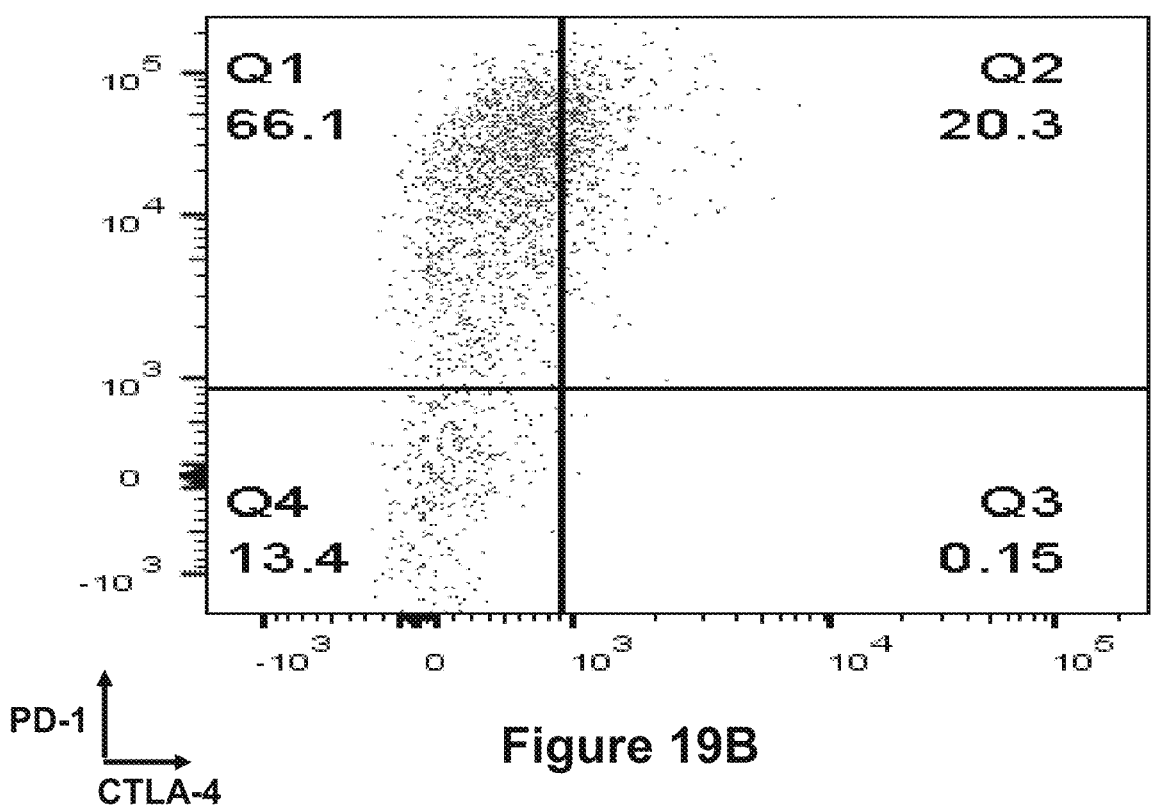
Figure 19C:
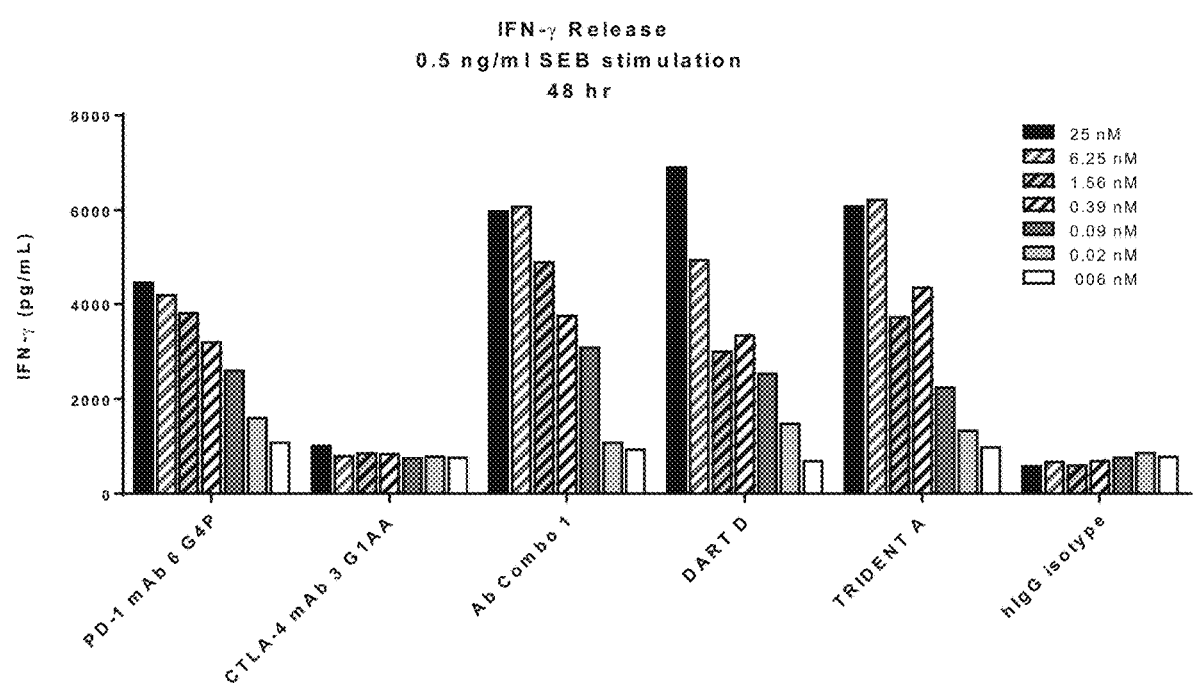
Figure 19D:
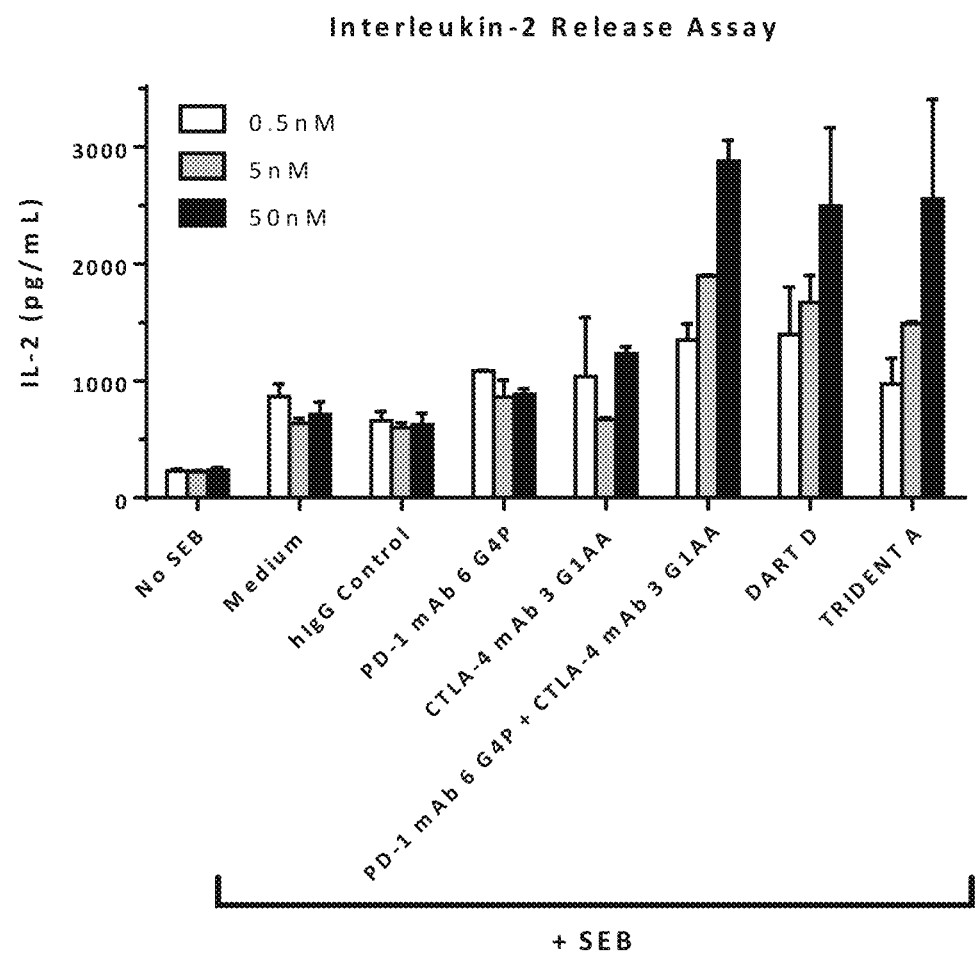

FIGS. 19A-19B show fluorescence-activated cell sorting (FACS) dot plots of the expression of PD-1 vs. CTLA-1 by such PBMCs in the absence (FIG. 19A) or presence (FIG. 19B) of SEB stimulation. FIG. 19C shows the effect of the SEB stimulation on IFN-γ secretion. PBMCs were stimulated with *Staphylococcus aureus* enterotoxin type B (SEB) at 0.5 ng/ml for 48 hours. Cells were then harvested, washed and re-plated in 96 well plates with antibodies at various concentrations with fresh SEB for an additional 48 hours. The supernatant was then harvested and analyzed by flow cytometry ELISA for IFN-γ production. Both the bispecific DART and the TRIDENT protein showed an increase in IFN-γ response that recapitulated the response observed with the combination of the individual parental mAbs. Similar results were seen in a SEB Stimulation assay in which the PBMCs were cultured with a high concentration (500 ng/mL) of SEB for 72 hours. To further investigate the affect of PD1×CTLA-4 bispecific molecules on the T-cell response, PBMCs were stimulated with 0.5 ng/ml SEB for 48 hours, harvested, washed and re-plated in 96-well plates with fresh SEB and either DART D, TRIDENT A, CTLA-4 mAb 3 G1AA, PD-1 mAb 6 G4P or the combination of CTLA-4 mAb 3 G1AA/PD-1 mAb 6 G4P (Ab Combo 1) for an additional 48 hours, and the released IL-2 was measured (FIG. 19D). FIGS. 19A-19D show that the administration of PD1×CTLA-4 bispecific molecules significantly enhanced T-cell responses. When antibodies were used in combination, each antibody was added at the indicated concentration so that the total concentration of antibody added is doubled.

Example 6

In Vivo Studies

A. Activity of a PD-1×CTLA-4 Bispecific Molecule in GVHD Murine Model

The activity of a representative PD1×CTLA-4 bispecific bivalent molecule, DART D was assessed in a PBMC implanted NOG murine model of Graft Versus Host Disease (GVHD). The study design is presented in Table 15.

TABLE 15

| Group | N/sex | Treatment | Dose (µg/kg) | Route/ Schedule | Cell Implant(s) |
|---|---|---|---|---|---|
| 1. | 7/F | DART D | 500 | IV/Q7D × 7 | PBMC (IP, 1E7) |
| 2. | 7/F | DART D | 50 | IV/Q7D × 7 | PBMC (IP, 1E7) |
| 3. | 7/F | DART D | 5 | IV/Q7D × 7 | PBMC (IP, 1E7) |
| 4. | 7/F | Vehicle | 0 | IV/Q7D × 7 | PBMC (IP, 1E7) |

Figure 20A:
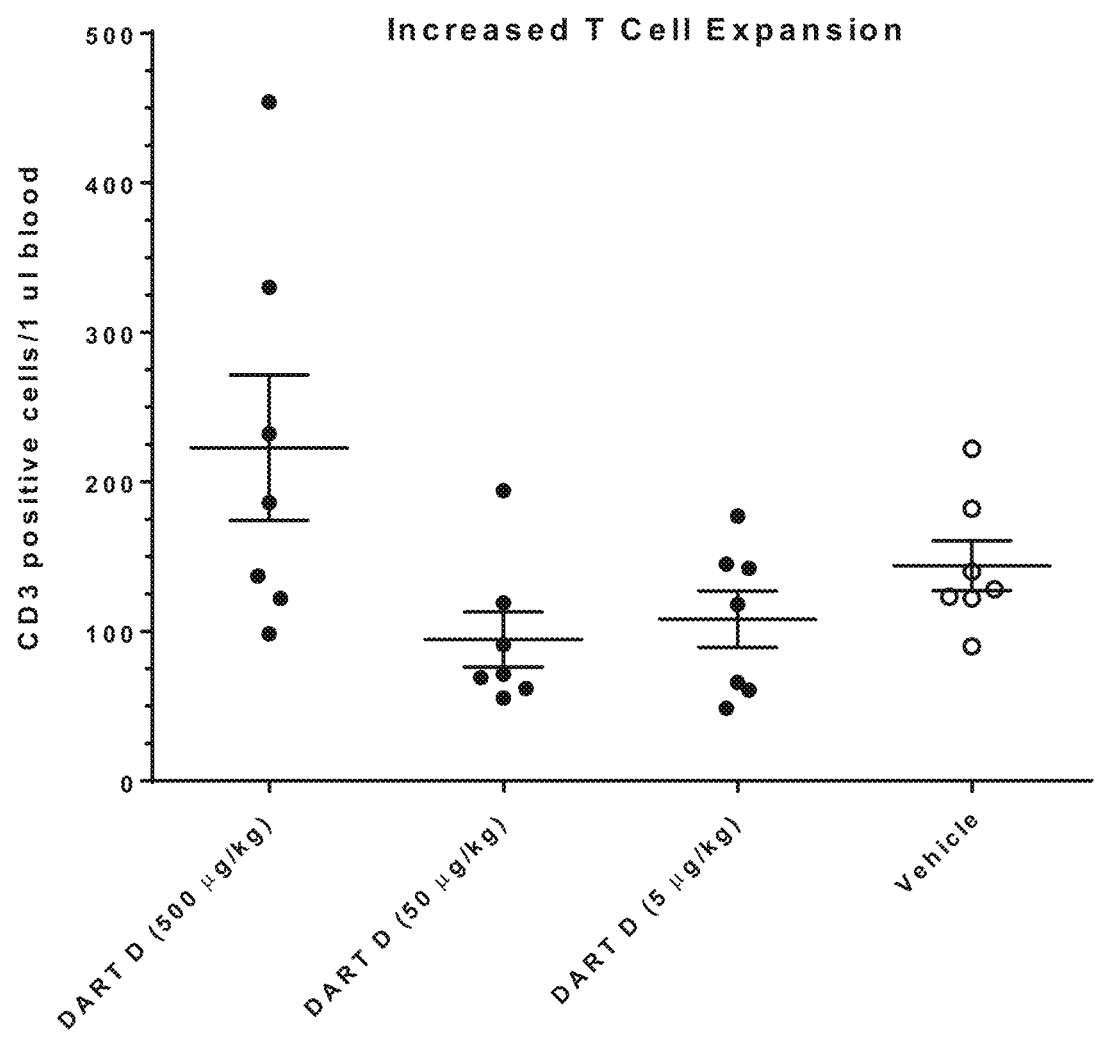
FIGS. 20A-20B show the activity of a PD-1×CTLA-4 bispecific molecule in a PBMC implanted NOG murine model of Graft Versus Host Disease (GVHD). CD3+ T cell counts were performed via FACS on study day (FIG. 20A) on mice that had received DART D at a dose of 50 mg/kg or 500 mg/kg (FIG. 20A). Survival was monitored over the course of the study and is plotted as percent survival in FIG. 20B.
Figure 20B:
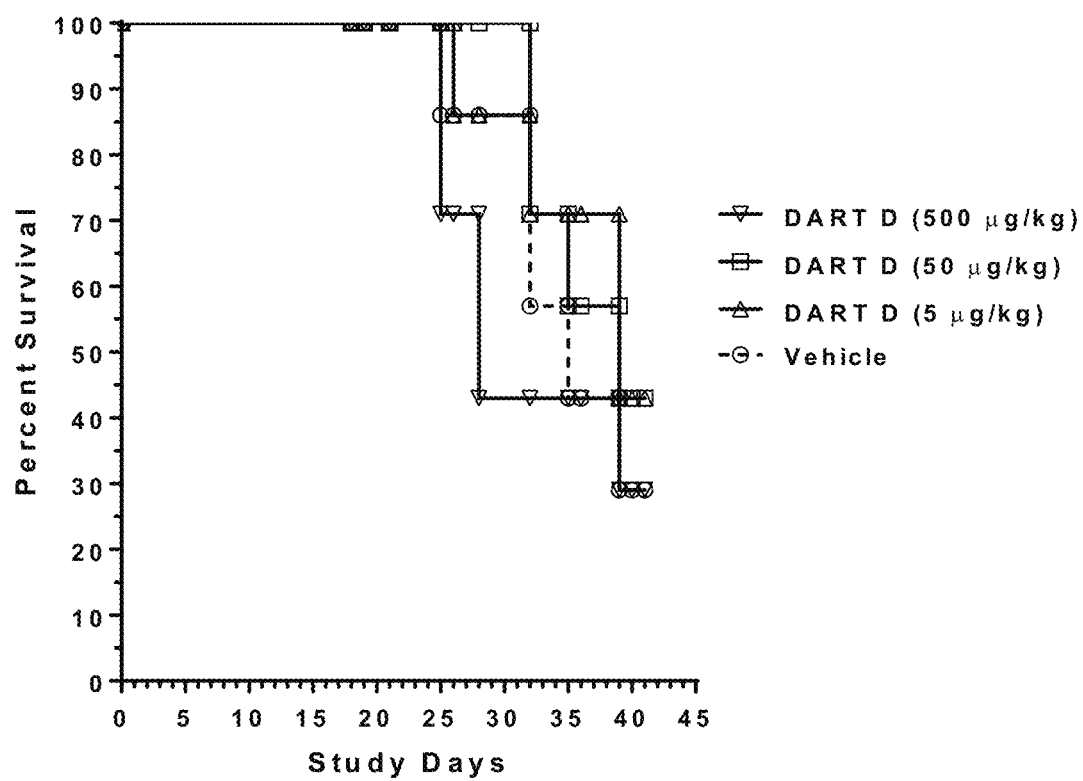

CD3+ T cell counts were performed via FACS on study day 14 and are plotted in FIG. 20A. Survival was monitored over the course of the study and is plotted as percent survival in FIG. 20B. Increased T cell expansion and accelerated GVHD was seen in animal treated with 500 µg/kg DART D, consistence with enhancement of T cell immune responses.

B. Toxicology and Pharmacokinetic Study of PD-1× CTLA-4 Bispecific Molecules

The safety profile of a representative PD1×CTLA-4 bispecific bivalent molecule, DART D, and a representative PD1×CTLA-4 bispecific trivalent molecule, TRIDENT A, was assessed in a non-GLP (Good Laboratory Practice) dosing study in cynomolgus monkeys. In addition, several markers pharmacodynamics activity were examined.

In this study the potential toxicity of the PD-1×CTLA-4 bispecific molecules, when administered by multiple intravenous infusions was evaluated. The study design is presented in Table 16.

TABLE 16

| Group | Test Article | Dose (mg/kg) | Dose Days | Number of Animals |
|---|---|---|---|---|
| 1 | Control | 0 | 1, 8, 15 | 1M 1F |
| 2 | DART D | 50 | 1, 8, 15 | 3M 3F |
| 3 | DART D | 75 | 15, 22, 29 | 3M 3F |
| 4 | TRIDENT A | 5 | 1 | 2M 1F |

A 2-week interval was thus provided between the 50 mg/kg dose and escalation to 75 mg/kg. The following parameters and endpoints were evaluated in this study: clinical signs, body weights, food consumption, body temperature, clinical pathology parameters (coagulation, clinical chemistry and hematology pre-dose and 23 hours post-dose for Groups 1-3; out to day 22 for Group 4), bioanalysis and toxicokinetic parameters, flow cytometry (pre-dose and 23 hours post dose), cytokines (2, 6, 22 hours post-dose). Anti-Drug-Antibodies were evaluated for Group 4 only on days 8, 15 and 22. Necropsy was performed 48 hours after the 3$^{rd}$ dose for Groups 1-3 only. The in vivo binding and activity of the PD-1×CTLA-4 bispecific molecules was also examined as described below.

Figure 21A:
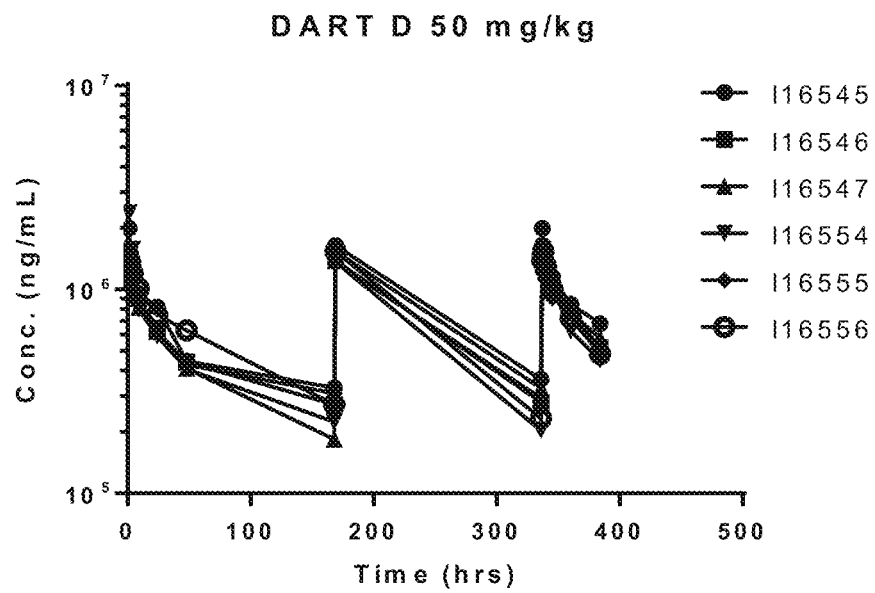
FIGS. 21A-21C show serum concentration-time profiles for cynomolgus monkeys (coded using a 6-character alphanumeric code) that had received DART D at 50 mg/kg on days 1, 8 and 15 of the study (FIG. 21A), DART D at 75 mg/kg on days 1, 8 and 15 of the study (FIG. 21B) or Trident A at 5 mg/kg on day 1 (FIG. 21C).
Figure 21B:
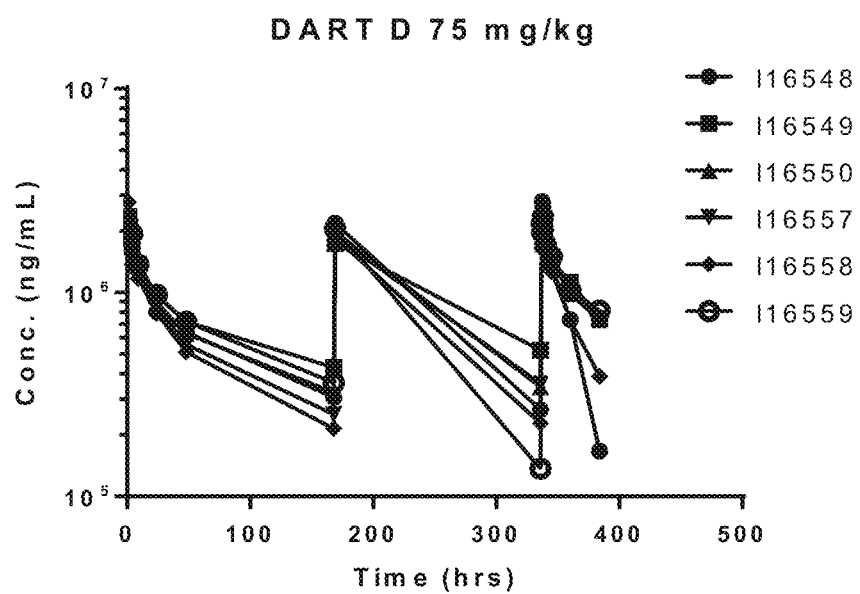
Figure 21C:
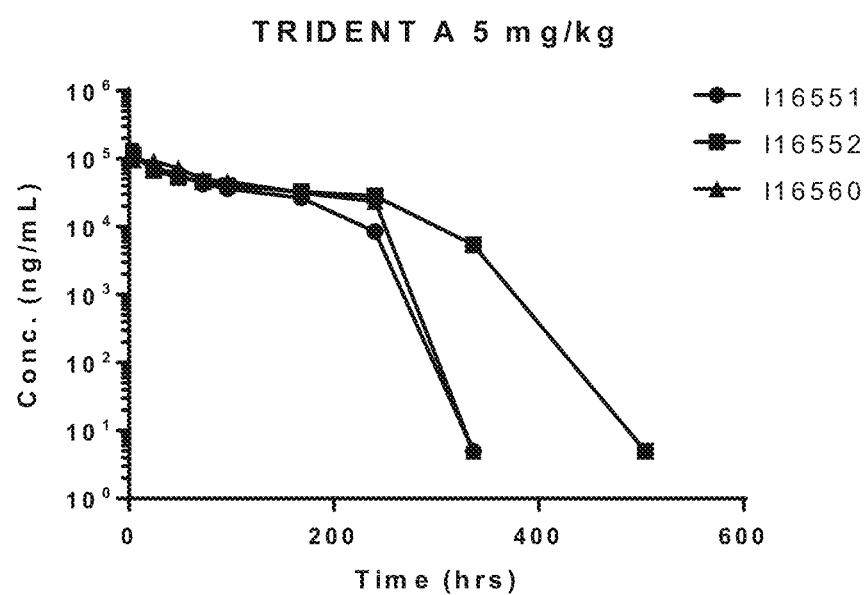

All animals survived until scheduled euthanasia. No adverse clinical observations in animals receiving 3 doses up to 75 mg/kg/week. In particular, no diarrhea was observed. The histopathology was also unremarkable. Increases in globulin levels were observed in the treatment groups and the organ weight of the spleen and thymus were observed to increase in Groups 2-3 (see Table 17, Group 4 was not necropsied), as would be expected upon stimulation of the immune system. The serum concentration-time profiles for each of the treatment groups are shown in FIGS. 21A-21C and are consistent with molecules comprising human Fc regions in cynomolgus monkeys.

TABLE 17

| Group | Test Article | Dose (mg/kg) | Spleen: Body Weight | Thymus: Body Weight |
|---|---|---|---|---|
| 1 | Control | 0 | 0.080 (mean, n = 2) | 0.035 (mean, n = 2) |
| 2 | DART D | 50 | 0.239 (mean, n = 6) | 0.088 (mean, n = 6) |
| 3 | DART D | 75 | 0.225 (mean, n = 6) | 0.084 (mean, n = 6) |

It has been reported that increases in absolute lymphocyte count (ALC) after treatment with the anti-CTLA-4 antibody ipilimumab appear to correlate with clinical benefit and overall survival (see, e.g., Ku, G. Y., et al. (2010) "*Single-Institution Experience With Ipilimumab In Advanced Melanoma Patients In The Compassionate Use Setting: Lymphocyte Count After 2 Doses Correlates With Survival*" Cancer 116(7):1767-1775) indicating that ALC may be a useful pharmacodynamic (PD) endpoint. The ALC counts were examined in each of the above-described groups pre-treatment and post-treatment on days 2, 8, 9, 15 and 16. Occupancy of DART D or TRIDENT A binding sites on PD-1+ T cells was determined by measuring the mean fluorescent intensity (MFI) of anti-human IgG4 Alexa 488+ events in the CD4+/PD-1+ and CD8+/PD-1+ T cell populations under two conditions for each monkey blood sample. Under one condition, the MFI values obtained in the presence of excess DART D or TRIDENT A were used to determine the maximal DART D or TRIDENT A binding intensity on PD-1+ cells within each cell population. Under the second condition, the MFI values obtained in the presence of excess negative control were used to determine the binding intensity of PD-1+ cells within each cell population exhibited in the DART D or TRIDENT A-treated animal at the time of sample collection. The difference between the two conditions was used to calculate % occupancy of DART D or TRIDENT A binding sites on PD-1+ T cell subsets in DART D or TRIDENT A-treated animals as follows:

% Occupancy of DART D or TRIDENT A Binding Sites On PD-1+ T Cell Subsets =

$$\left[ \frac{\left( \begin{array}{c} MFI \text{ of Anti-}HuIgG4 + \text{Events in} \\ \text{the Presence of Excess } AEX1367 \end{array} \right)}{\left( \begin{array}{c} MFI \text{ of Anti-}HuIgG4 + \text{Events in the} \\ \text{Presence of Excess } DART\ D \text{ or } TRIDENT\ A \end{array} \right)} \right] \times 100$$

Figure 22A:
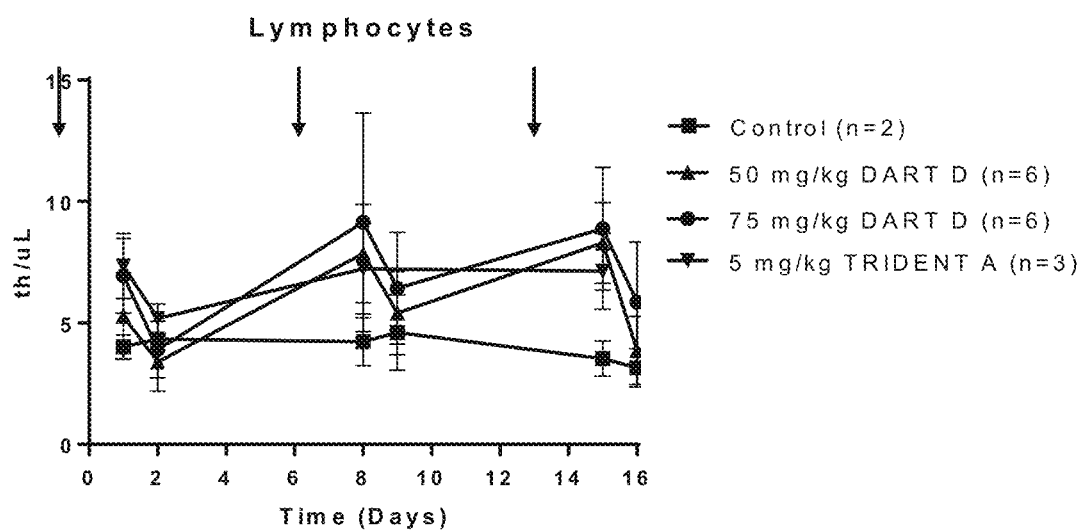
FIGS. 22A-22B show the effect of administration of DART D on absolute lymphocyte count (ALC) in treated cynomolgus monkeys.
Figure 22B:
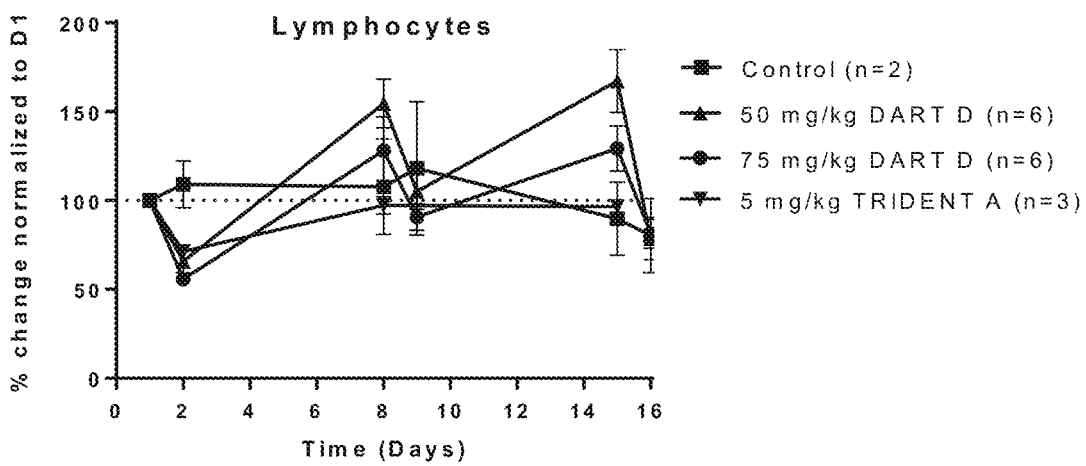

The absolute counts, and the percent change normalized to Day 1 are plotted in FIG. 22A (in thousands of cells/µl (th/µl)) and in FIG. 22B (percent change in the ALC normalized to Day 1 (D1)). Each of the DART D treatment groups exhibited an initial drop in ALC counts immediately after treatment followed by an increase in ALC to levels well above baseline. A similar trend was observed for the TRIDENT A treatment group, which only received only one lower dose.

In addition, CD4+ T cell proliferation and PD-1 occupancy on T cells were examined for the above-described Groups 1-3. Briefly, CD3+/PD-1+ T cells were analyzed by FACS to evaluate the percent cells bound by DART D. Forty microliters of the negative control molecule (respiratory syncytial virus (RSV)×fluorescein IgG4, κ Fc DART) or test article (DART D or TRIDENT A) at 35 µg/mL were added to a 96 deep-well plate. One hundred microliters of well-mixed anticoagulated whole blood were then added into each well, thoroughly mixed using a pipette, and incubated in the dark for 45 to 75 minutes at ambient temperature. One thousand microliters of 1×BD FACS Lysing solution were then added to each well and mixed using a pipette; the plate was then incubated in the dark for an additional 10 to 20 minutes at ambient temperature. The plate was then centrifuged at 400×g for 5 minutes and the supernatant was discarded. One thousand microliters of FACS buffer were added in each well and mixed as a washing step. The plate was then centrifuged at 400×g for 5 minutes and the supernatant was discarded. The cell pellet was resuspended with twenty microliters of Panel 1 antibody mix and incubated for 30 to 60 minutes at ambient temperature. The plate was washed as in previous wash steps. At the end of incubation, the plate was washed again and the cell pellet was finally resuspended in three-hundred microliters of FACS buffer and the samples were analyzed with a BD FACSCanto II cell analyzer. The results of the analysis are shown in FIGS. 23A-23B.

Figure 23A:
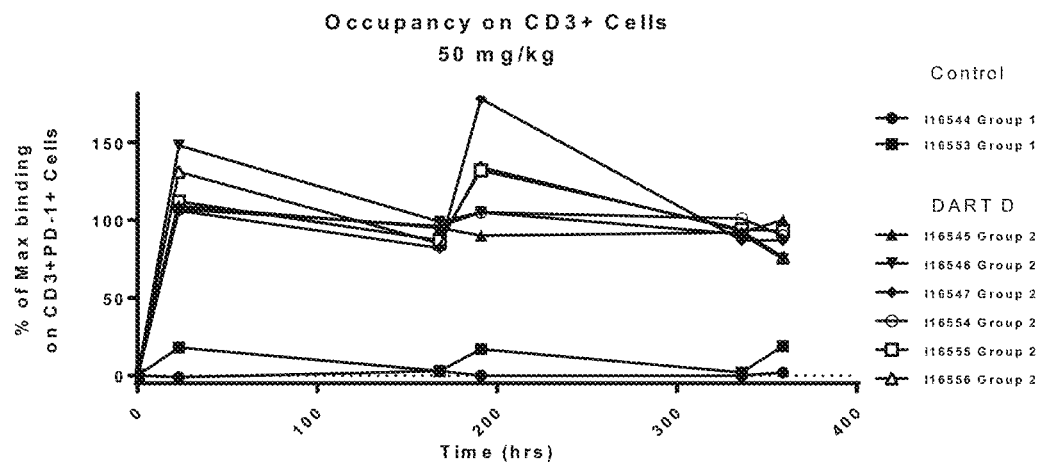
FIGS. 23A-23B show CD4+ T cell proliferation and PD-1 occupancy on T cells in cynomolgus monkeys that had received DART D administered at 50 mg/kg (FIG. 23A) or DART D administered at 75 mg/kg (FIG. 23B).
Figure 23B:
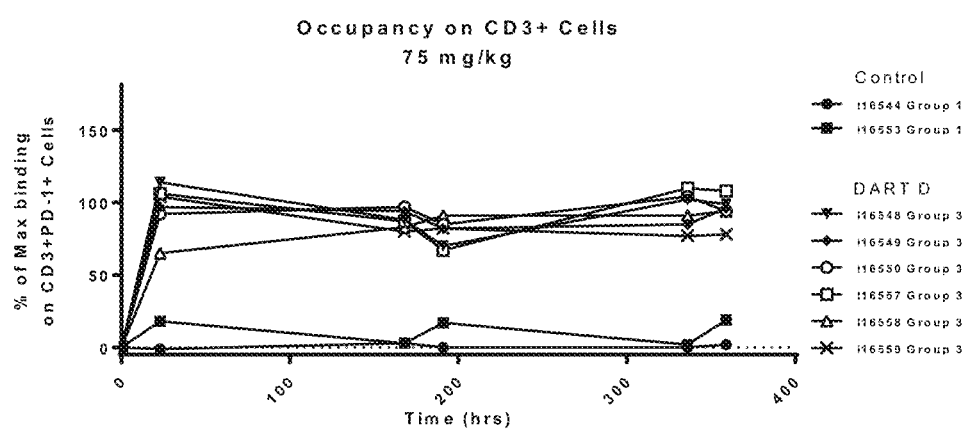

As shown in FIG. 23A (for DART D administered at 50 mg/kg) and FIG. 23B (for DART D administered at 75 mg/kg), PD-1 occupancy (i.e., binding by DART D) was maximal throughout the duration of treatment for Groups 2 and 3. Proliferation CD4+ T cells were evaluated by FACS for co-expression of Ki-67 (a cellular marker for proliferation).

Twenty microliters of an antibody mixture A (containing antibodies that bind cell surface markers: CD45, CD3, CD4, and CD8) were added into a 96 deep-well plate. Fifty microliters of well-mixed anticoagulated whole blood were then added into each well, mixed thoroughly using a pipette, and incubated in the dark for 15 to 45 minutes at ambient temperature. Five hundred microliters of 1×BD FACS Lysing solution were then added to each well and mixed using a pipette; the plate was then incubated in the dark for an additional 10 to 20 minutes at ambient temperature. The plate was centrifuged at 1200 rpm for 5 minutes and the supernatant was discarded. Five hundred microliters of FACS buffer were then added in each well and mixed as a washing step. The plate was then centrifuged at 1200 rpm for 5 minutes and the supernatant was discarded. The cell pellet was resuspend in antibody mixture B (containing antibodies that bind the intracellular marker, Ki 67) or were resuspended in an iso antibody preparation (containing isotype controls for the intracellular marker) and incubated in the dark for 15 to 45 minutes. After washing, the cell pellet was resuspended in three hundred microliters of FACS buffer and the samples were analyzed with a BD FACSCanto II cell analyzer. From a T Cell Intracellular Staining Panel, the percentage of CD4+ and CD8+ cells was determined as the fraction of total CD45+ leukocyte gated cells. The cellular events of Ki 67+ in gated CD4+ cells were counted and the percentage of CD4+/Ki 67+ T cells (proliferative CD4 T cells) was determined as the fraction of total CD4+ cells. In a similar manner, the percentage of CD8+/Ki 67+ T cells (proliferative CD8 T cells) was determined as the fraction of total CD8+ cells. The results of the analysis are shown in FIGS. 24A-24B.

Figure 24A:
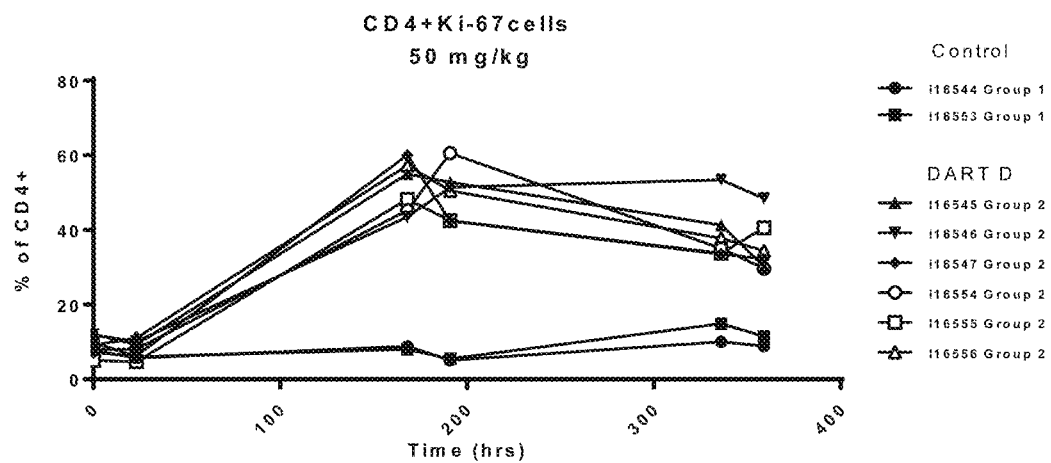
FIGS. 24A-24B show the effect of DART D administration on CD4+ T cell proliferation in cynomolgus monkeys that had received DART D administered at 50 mg/kg (FIG. 24A) or DART D administered at 75 mg/kg (FIG. 24B).
Figure 24B:
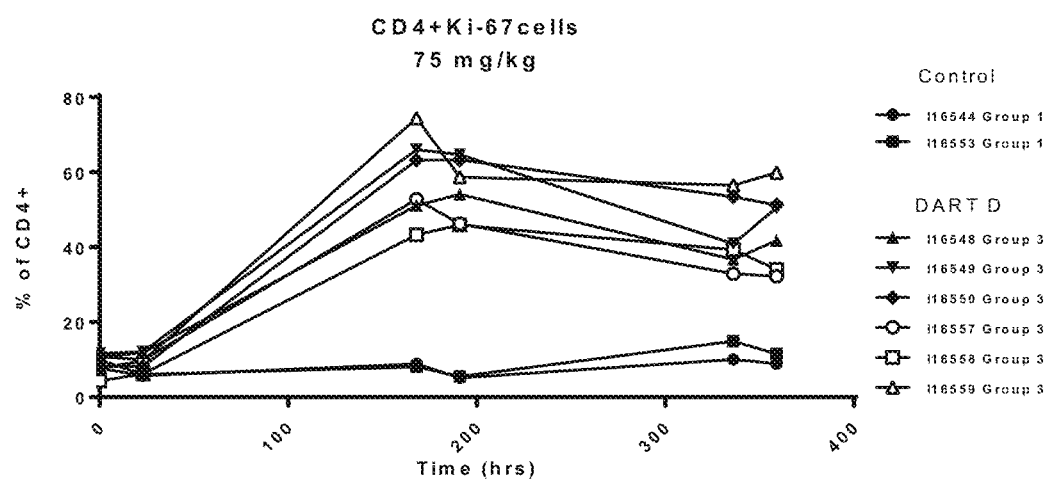

As shown in FIGS. 24A-24B, proliferation of CD4+ T cells was markedly enhanced in treatment Groups 2 and 3 throughout the duration of treatment. The results of this study indicate that administration of PD1×CTLA-4 bispecific molecules is well tolerated in cynomolgus monkeys at concentrations of up to 75 mg/kg. Well above the 5 mg/kg dosage where adverse events have been reported for cynomolgus monkeys treated with Ipilimumab. The molecules exhibited a favorable pharmacokinetic profile and a number of markers pharmacodynamics activity were observed including increased lymphocyte count, increased globulin levels, increased spleen and thymus organ weights, increased T cell proliferation (both T cell counts and expression of Ki-67) and maximal PD-1 occupancy on T cells.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A bispecific molecule comprising two polypeptide chains each comprising the polypeptide of SEQ ID NO:99 and two polypeptide chains each comprising the polypeptide of SEQ ID NO:100.

2. A pharmaceutical composition comprising the bispecific molecule of claim 1 and a pharmaceutically acceptable carrier.

3. A bispecific molecule comprising one polypeptide chain comprising SEQ ID NO:104, one polypeptide chain comprising SEQ ID NO:105, one polypeptide chain comprising SEQ ID NO:106, and one polypeptide chain comprising SEQ ID NO:107.

4. A bispecific molecule comprising two polypeptide chains each comprising SEQ ID NO:101 and two polypeptide chains each comprising SEQ ID NO:100.

5. A bispecific molecule comprising one polypeptide chain comprising SEQ ID NO:108, one polypeptide chain comprising SEQ ID NO:105, one polypeptide chain comprising SEQ ID NO:109, and one polypeptide chain comprising SEQ ID NO:107.

6. A pharmaceutical composition comprising the bispecific molecule of claim 3 and a pharmaceutically acceptable carrier.

7. A pharmaceutical composition comprising the bispecific molecule of claim 4 and a pharmaceutically acceptable carrier.

8. A pharmaceutical composition comprising the bispecific molecule of claim 5 and a pharmaceutically acceptable carrier.

* * * * *

UNITED STATES PATENT AND TRADEMARK OFFICE
CERTIFICATE OF CORRECTION

PATENT NO. : 10,954,301 B2
APPLICATION NO. : 16/060227
DATED : March 23, 2021
INVENTOR(S) : Johnson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
Thirty-first Day of January, 2023

Katherine Kelly Vidal
*Director of the United States Patent and Trademark Office*

SEQUENCE LISTING

```
<160> NUMBER OF SEQ ID NOS: 110

<210> SEQ ID NO 1
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Exemplary Human IgG1
<220> FEATURE:
<221> NAME/KEY: MISC_FEATURE
<222> LOCATION: (217)..(217)
```

<223> OTHER INFORMATION: Xaa is lysine (K) or is absent

<400> SEQUENCE: 1

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 2
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: CH2-CH3 Domain of Exemplary Human IgG2
<220> FEATURE:
<221> NAME/KEY: MISC_FEATURE
<222> LOCATION: (216)..(216)
<223> OTHER INFORMATION: Xaa is lysine (K) or is absent

<400> SEQUENCE: 2

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95
```

-continued

```
Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Xaa
    210                 215

<210> SEQ ID NO 3
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Exemplary Human IgG3
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205
```

```
Lys Ser Leu Ser Leu Ser Pro Gly Xaa
    210             215

<210> SEQ ID NO 4
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Exemplary Human IgG4
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 4

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210             215

<210> SEQ ID NO 5
<211> LENGTH: 8
<212> TYPE: PRT
<213> ORGANISM: Artificial Sequence
<220> FEATURE:
<223> OTHER INFORMATION: Intervening Spacer Peptide (Linker 1)

<400> SEQUENCE: 5

Gly Gly Gly Ser Gly Gly Gly Gly
1               5

<210> SEQ ID NO 6
<211> LENGTH: 5
<212> TYPE: PRT
```

```
<213> ORGANISM: Artificial Sequence
<220> FEATURE:
<223> OTHER INFORMATION: Cysteine-Containing Spacer Peptide (Linker 2)

<400> SEQUENCE: 6

Gly Gly Cys Gly Gly
1               5

<210> SEQ ID NO 7
<211> LENGTH: 4
<212> TYPE: PRT
<213> ORGANISM: Artificial Sequence
<220> FEATURE:
<223> OTHER INFORMATION: Alternativel Spacer Peptide Linker 2

<400> SEQUENCE: 7

Gly Gly Gly Ser
1

<210> SEQ ID NO 8
<211> LENGTH: 6
<212> TYPE: PRT
<213> ORGANISM: Artificial Sequence
<220> FEATURE:
<223> OTHER INFORMATION: Alternativel Spacer Peptide Linker 2

<400> SEQUENCE: 8

Leu Gly Gly Gly Ser Gly
1               5

<210> SEQ ID NO 9
<211> LENGTH: 11
<212> TYPE: PRT
<213> ORGANISM: Artificial Sequence
<220> FEATURE:
<223> OTHER INFORMATION: Alternative Spacer Peptide Linker 2

<400> SEQUENCE: 9

Gly Gly Gly Ser Gly Gly Gly Ser Gly Gly Gly
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Alternative Spacer Peptide Linker 2

<400> SEQUENCE: 10

Ala Ser Thr Lys Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Alternatice Spacer Pepptide Linker 2

<400> SEQUENCE: 11

Leu Glu Pro Lys Ser Ser
1               5

<210> SEQ ID NO 12
<211> LENGTH: 5
<212> TYPE: PRT
<213> ORGANISM: Artificial Sequence
```

```
<220> FEATURE:
<223> OTHER INFORMATION: Alternative Spacer Peptide Linker 2

<400> SEQUENCE: 12

Ala Pro Ser Ser Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 13

Gly Val Glu Pro Lys Ser Cys
1               5

<210> SEQ ID NO 14
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Hinge Region of Human IgG Heterodimer-Promoting
      Domain

<400> SEQUENCE: 14

Val Glu Pro Lys Ser Cys
1               5

<210> SEQ ID NO 15
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Hinge Region of Human IgG Heterodimer-Promoting
      Domain

<400> SEQUENCE: 15

Ala Glu Pro Lys Ser Cys
1               5

<210> SEQ ID NO 16
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Human Kappa Light Chain Heterodimer-Promoting
      Domain

<400> SEQUENCE: 16

Gly Phe Asn Gly Glu Cys
1               5

<210> SEQ ID NO 17
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Human Kappa Light Chain Heterodimer-Promoting
      Domain
```

<400> SEQUENCE: 17

Phe Asn Arg Gly Glu Cys
1               5

<210> SEQ ID NO 18
<211> LENGTH: 28
<212> TYPE: PRT
<213> ORGANISM: Artificial Sequence
<220> FEATURE:
<223> OTHER INFORMATION: E-coil Heterodimer-Promoting Domain

<400> SEQUENCE: 18

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 19
<211> LENGTH: 28
<212> TYPE: PRT
<213> ORGANISM: Artificial Sequence
<220> FEATURE:
<223> OTHER INFORMATION: K-coil Heterodimer-Promoting Domain

<400> SEQUENCE: 19

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 20
<211> LENGTH: 28
<212> TYPE: PRT
<213> ORGANISM: Artificial Sequence
<220> FEATURE:
<223> OTHER INFORMATION: Cysteine-Containing E-coil
      Heterodimer-Promoting Domain

<400> SEQUENCE: 20

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 21
<211> LENGTH: 28
<212> TYPE: PRT
<213> ORGANISM: Artificial Sequence
<220> FEATURE:
<223> OTHER INFORMATION: Cysteine-Containing K-coil
      Heterodimer-Promoting Domain

<400> SEQUENCE: 21

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 22
<211> LENGTH: 46
<212> TYPE: PRT
<213> ORGANISM: Streptococcus dysgalactiae
<220> FEATURE:
<221> NAME/KEY: MISC_FEATURE -continued

```
<222> LOCATION: (1)..(46)
<223> OTHER INFORMATION: Albumin-Binding Domain 3 (ABD3) of protein G of
      Streptococcus strain G148

<400> SEQUENCE: 22

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 23
<211> LENGTH: 46
<212> TYPE: PRT
<213> ORGANISM: Artificial Sequence
<220> FEATURE:
<223> OTHER INFORMATION: Deimmunized Variant of Albumin-Binding Domain 3
      (ABD3) of protein G of Streptococcus strain G148

<400> SEQUENCE: 23

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 24
<211> LENGTH: 46
<212> TYPE: PRT
<213> ORGANISM: Artificial Sequence
<220> FEATURE:
<223> OTHER INFORMATION: Deimmunized Variant of Albumin-Binding Domain 3
      (ABD3) of protein G of Streptococcus strain G148

<400> SEQUENCE: 24

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 25
<211> LENGTH: 46
<212> TYPE: PRT
<213> ORGANISM: Artificial Sequence
<220> FEATURE:
<223> OTHER INFORMATION: Deimmunized Variant of Albumin-Binding Domain 3
      (ABD3) of protein G of Streptococcus strain G148

<400> SEQUENCE: 25

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 26
<211> LENGTH: 10
<212> TYPE: PRT
```

```
<213> ORGANISM: Artificial Sequence
<220> FEATURE:
<223> OTHER INFORMATION: Intervening Spacer Linker

<400> SEQUENCE: 26

Asp Lys Thr His Thr Cys Pro Pro Cys Pro
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Intervening Spacer Linker

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 5
<212> TYPE: PRT
<213> ORGANISM: Artificial Sequence
<220> FEATURE:
<223> OTHER INFORMATION: Intervening Spacer Linker

<400> SEQUENCE: 28

Ala Pro Ser Ser Ser
1               5

<210> SEQ ID NO 29
<211> LENGTH: 8
<212> TYPE: PRT
<213> ORGANISM: Artificial Sequence
<220> FEATURE:
<223> OTHER INFORMATION: Intervening Spacer Linker

<400> SEQUENCE: 29

Ala Pro Ser Ser Ser Pro Met Glu
1               5

<210> SEQ ID NO 30
<211> LENGTH: 15
<212> TYPE: PRT
<213> ORGANISM: Artificial Sequence
<220> FEATURE:
<223> OTHER INFORMATION: Intervening Spacer Linker

<400> SEQUENCE: 30

Leu Glu Pro Lys Ser Ala Asp Lys Thr His Thr Cys Pro Pro Cys
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: Intervening Spacer Linker

<400> SEQUENCE: 31

Gly Gly Gly Asp Lys Thr His Thr Cys Pro Pro Cys Pro
1               5                   10

<210> SEQ ID NO 32
<211> LENGTH: 16
<212> TYPE: PRT
<213> ORGANISM: Artificial Sequence
```

```
<220> FEATURE:
<223> OTHER INFORMATION: Intervening Spacer Linker

<400> SEQUENCE: 32

Leu Glu Pro Lys Ser Ser Asp Lys Thr His Thr Cys Pro Pro Cys Pro
1               5                   10                  15

<210> SEQ ID NO 33
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Exemplary IgG1 Hinge Region

<400> SEQUENCE: 33

Glu Pro Lys Ser Cys Asp Lys Thr His Thr Cys Pro Pro Cys Pro
1               5                   10                  15

<210> SEQ ID NO 34
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Exemplary IgG2 Hinge Region

<400> SEQUENCE: 34

Glu Arg Lys Cys Cys Val Glu Cys Pro Pro Cys Pro
1               5                   10

<210> SEQ ID NO 35
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Exemplary IgG4 Hinge Region

<400> SEQUENCE: 35

Glu Ser Lys Tyr Gly Pro Pro Cys Pro Ser Cys Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: IgG4 Hinge Variant comprising Stabilizing S228P
      Substitution

<400> SEQUENCE: 36

Glu Ser Lys Tyr Gly Pro Pro Cys Pro Pro Cys Pro
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Intervening Spacer Peptide

<400> SEQUENCE: 37

Gly Gly Gly Gly Ser Gly Gly Gly Gly Ser Gly Gly Gly Gly Ser
1               5                   10                  15
```

<210> SEQ ID NO 38
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Exemplary Human IgG CL Kappa Domain

<400> SEQUENCE: 38

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 39
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Exemplary Human IgG CL Lambda Domain

<400> SEQUENCE: 39

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 40
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 41
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG2 CH1 Domain

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 42
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG4 CH1 Domain

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

-continued

Tyr Thr Cys Asn Val Asp His Lys Pro Ser Asn Thr Lys Val Asp Lys
                 85                  90                  95

Arg Val

<210> SEQ ID NO 43
<211> LENGTH: 217
<212> TYPE: PRT
<213> ORGANISM: Artificial Sequence
<220> FEATURE:
<223> OTHER INFORMATION: CH2-CH3 Domains of IgG1 Comprising
      Substitutions L234A and L235A (Kabat)
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 43

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Xaa
    210                 215

<210> SEQ ID NO 44
<211> LENGTH: 217
<212> TYPE: PRT
<213> ORGANISM: Artificial Sequence
<220> FEATURE:
<223> OTHER INFORMATION: "Knob-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 44

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 45
<211> LENGTH: 217
<212> TYPE: PRT
<213> ORGANISM: Artificial Sequence
<220> FEATURE:
<223> OTHER INFORMATION: "Hole-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 45

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
            195                 200                 205

Lys Ser Leu Ser Leu Ser Pro Gly Xaa
            210                 215

<210> SEQ ID NO 46
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Human PD-1, Including Signal Sequence  (NCBI
      Sequence NP_005009.2)
<220> FEATURE:
<221> NAME/KEY: SIGNAL
<222> LOCATION: (1)..(20)
<223> OTHER INFORMATION: Signal Sequence

<400> SEQUENCE: 46

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
```

```
                    245                 250                 255
Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285
```

<210> SEQ ID NO 47
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: VL Domain of Anti-Human PD-1 Antibody PD-1 mAb
      1 (Nivolumab)

<400> SEQUENCE: 47

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser
```

<210> SEQ ID NO 48
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: VL Domain of Anti-Human PD-1 Antibody PD-1 mAb
      1 (Nivolumab)

<400> SEQUENCE: 48

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

<210> SEQ ID NO 49
<211> LENGTH: 120
<212> TYPE: PRT
<213> ORGANISM: Artificial Sequence
<220> FEATURE:
<223> OTHER INFORMATION: VL Domain of Humanized Anti Human PD-1 Antibody
      PD-1 mAb 2 (Pembrolizumab)

<400> SEQUENCE: 49

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 50
<211> LENGTH: 111
<212> TYPE: PRT
<213> ORGANISM: Artificial Sequence
<220> FEATURE:
<223> OTHER INFORMATION: VL Domain of Humanized Anti Human PD-1 Antibody
      PD-1 mAb 2 (Pembrolizumab)

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 51
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: VH Domain of Murine Anti-Human PD-1 Antibody
      PD-1 mAb 3 (EH12.2H7)

<400> SEQUENCE: 51

```
Gln Val Gln Leu Gln Gln Ser Gly Ala Glu Leu Ala Lys Pro Gly Ala
1               5                   10                  15

Ser Val Gln Met Ser Cys Lys Ala Ser Gly Tyr Ser Phe Thr Ser Ser
                20                  25                  30

Trp Ile His Trp Val Lys Gln Arg Pro Gly Gln Gly Leu Glu Trp Ile
            35                  40                  45

Gly Tyr Ile Tyr Pro Ser Thr Gly Phe Thr Glu Tyr Asn Gln Lys Phe
        50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
            115                 120
```

<210> SEQ ID NO 52
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of Murine Anti-Human PD-1 Antibody
      PD-1 mAb 3 (EH12.2H7)

<400> SEQUENCE: 52

```
Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Lys Phe Gly Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

<210> SEQ ID NO 53
<211> LENGTH: 117
<212> TYPE: PRT
<213> ORGANISM: Artificial Sequence
<220> FEATURE:
<223> OTHER INFORMATION: VH Domain of Humanized Anti-Human Antibody PD-1
      mAb 4 (Pidilizumab)

<400> SEQUENCE: 53

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
```

```
                50                  55                  60
Lys Gly Arg Phe Val Phe Ser Leu Asp Thr Ser Val Asn Thr Ala Tyr
 65                  70                  75                  80

Leu Gln Ile Thr Ser Leu Thr Ala Glu Asp Thr Gly Met Tyr Phe Cys
                    85                  90                  95

Val Arg Val Gly Tyr Asp Ala Leu Asp Tyr Trp Gly Gln Gly Thr Leu
                100                 105                 110

Val Thr Val Ser Ser
            115

<210> SEQ ID NO 54
<211> LENGTH: 106
<212> TYPE: PRT
<213> ORGANISM: Artificial Sequence
<220> FEATURE:
<223> OTHER INFORMATION: VL Domain of Humanized Anti-Human Antibody PD-1
      mAb 4 (Pidilizumab)

<400> SEQUENCE: 54

Glu Ile Val Leu Thr Gln Ser Pro Ser Ser Leu Ser Ala Ser Val Gly
  1               5                  10                  15

Asp Arg Val Thr Ile Thr Cys Ser Ala Arg Ser Ser Val Ser Tyr Met
                20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
 50                  55                  60

Gly Ser Gly Thr Ser Tyr Cys Leu Thr Ile Asn Ser Leu Gln Pro Glu
 65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
                100                 105

<210> SEQ ID NO 55
<211> LENGTH: 116
<212> TYPE: PRT
<213> ORGANISM: Artificial Sequence
<220> FEATURE:
<223> OTHER INFORMATION: VH Domain of Humanized Anti-Human PD-1 Antibody
      (PD-1 mAb 5)

<400> SEQUENCE: 55

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Val Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Gly Ser Met Ser Ile Ser Tyr Ala Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Thr Glu Asp Thr Ala Leu Tyr Tyr Cys
                85                  90                  95

Ala Ser Leu Ser Asp Tyr Phe Asp Tyr Trp Gly Gln Gly Thr Thr Val
                100                 105                 110

Thr Val Ser Ser
```

-continued

```
                 115

<210> SEQ ID NO 56
<211> LENGTH: 112
<212> TYPE: PRT
<213> ORGANISM: Artificial Sequence
<220> FEATURE:
<223> OTHER INFORMATION: VL Domain of Humanized Anti-Human PD-1 Antibody
      (PD-1 mAb 5)

<400> SEQUENCE: 56

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Val Pro Trp Thr Phe Gly Gln Gly Thr Lys Leu Glu Ile Lys
            100                 105                 110

<210> SEQ ID NO 57
<211> LENGTH: 119
<212> TYPE: PRT
<213> ORGANISM: Artificial Sequence
<220> FEATURE:
<223> OTHER INFORMATION: VH Domain of Humnaized Anti-Human PD-1 Antibody
      (PD-1 mAb 6)
<220> FEATURE:
<221> NAME/KEY: MISC_FEATURE
<222> LOCATION: (48)..(48)
<223> OTHER INFORMATION: Xaa is isoleucine (I) or alanine (A)

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Xaa
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser
        115

<210> SEQ ID NO 58
<211> LENGTH: 111
<212> TYPE: PRT
<213> ORGANISM: Artificial Sequence
<220> FEATURE:
```

<223> OTHER INFORMATION: VL Domain of Humanized Anti-Human PD-1 Antibody
      (PD-1 mAb 6)
<220> FEATURE:
<221> NAME/KEY: MISC_FEATURE
<222> LOCATION: (26)..(26)
<223> OTHER INFORMATION: Xaa is asparagine (N) or serine (S)
<220> FEATURE:
<221> NAME/KEY: MISC_FEATURE
<222> LOCATION: (58)..(58)
<223> OTHER INFORMATION: Xaa is glutamine (Q) or arginine (R)

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Xaa Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Xaa Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
            100                 105                 110

<210> SEQ ID NO 59
<211> LENGTH: 119
<212> TYPE: PRT
<213> ORGANISM: Artificial Sequence
<220> FEATURE:
<223> OTHER INFORMATION: VH Domain of Humanized Anti-Human PD-1 Antibody
      (PD-1 mAb 7)
<220> FEATURE:
<221> NAME/KEY: MISC_FEATURE
<222> LOCATION: (12)..(12)
<223> OTHER INFORMATION: Xaa is valine (V) or alanine (A)
<220> FEATURE:
<221> NAME/KEY: MISC_FEATURE
<222> LOCATION: (35)..(35)
<223> OTHER INFORMATION: Xaa is serine (S) or glycine (G)
<220> FEATURE:
<221> NAME/KEY: MISC_FEATURE
<222> LOCATION: (48)..(48)
<223> OTHER INFORMATION: Xaa is valine (V) or threonine (T)
<220> FEATURE:
<221> NAME/KEY: MISC_FEATURE
<222> LOCATION: (86)..(86)
<223> OTHER INFORMATION: Xaa is leucine (L) or alanine (A)

<400> SEQUENCE: 59

Glu Val Gln Leu Val Glu Ser Gly Gly Gly Leu Xaa Arg Pro Gly Gly
1               5                   10                  15

Ser Leu Lys Leu Ser Cys Ala Ala Ser Gly Phe Thr Phe Ser Ser Tyr
            20                  25                  30

Leu Val Xaa Trp Val Arg Gln Ala Pro Gly Lys Gly Leu Glu Trp Xaa
        35                  40                  45

Ala Thr Ile Ser Gly Gly Gly Asn Thr Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Xaa Arg Ala Glu Asp Thr Ala Thr Tyr Tyr Cys
                85                  90                  95

Ala Arg Tyr Gly Phe Asp Gly Ala Trp Phe Ala Tyr Trp Gly Gln Gly
            100                 105                 110

Thr Leu Val Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: VL Domain of Humanized Anti-Human PD-1 Antibody
      (PD-1 mAb 7)
<220> FEATURE:
<221> NAME/KEY: MISC_FEATURE
<222> LOCATION: (31)..(31)
<223> OTHER INFORMATION: Xaa is serine (S) or asparagine (N)
<220> FEATURE:
<221> NAME/KEY: MISC_FEATURE
<222> LOCATION: (50)..(50)
<223> OTHER INFORMATION: Xaa is asparagine (N) or asparatate (D)

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Xaa Tyr
            20                  25                  30

Leu Ala Trp Tyr Gln Gln Lys Pro Gly Lys Ala Pro Lys Leu Leu Ile
        35                  40                  45

Tyr Xaa Ala Lys Thr Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105

<210> SEQ ID NO 61
<211> LENGTH: 117
<212> TYPE: PRT
<213> ORGANISM: Artificial Sequence
<220> FEATURE:
<223> OTHER INFORMATION: VH Domain of Humanized Anti-Human PD-1 Antibody
      (PD-1 mAb 8)

<400> SEQUENCE: 61

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Leu Ile Ser Trp Val Arg Gln Ala Pro Gly Lys Gly Leu Glu Trp Val
        35                  40                  45

Ala Ala Ile Ser Gly Gly Gly Ala Asp Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg Arg Gly Thr Tyr Ala Met Asp Tyr Trp Gly Gln Gly Thr Leu
            100                 105                 110

Val Thr Val Ser Ser

<210> SEQ ID NO 62
<211> LENGTH: 107
<212> TYPE: PRT
<213> ORGANISM: Artificial Sequence
<220> FEATURE:
<223> OTHER INFORMATION: VL Domain of Humanized Anti-Human PD-1 Antibody
      (PD-1 mAb 8)

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Asn Tyr
            20                  25                  30

Leu Ala Trp Tyr Gln Gln Lys Pro Gly Lys Ala Pro Lys Leu Leu Ile
        35                  40                  45

Tyr Asp Ala Lys Thr Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105

<210> SEQ ID NO 63
<211> LENGTH: 496
<212> TYPE: PRT
<213> ORGANISM: Artificial Sequence
<220> FEATURE:
<223> OTHER INFORMATION: First and Third Polypeptide Chains of PD-1 x
      LAG-3 DART A

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
    130                 135                 140

Thr Ser Tyr Trp Met Asn Trp Val Arg Gln Ala Pro Gly Gln Gly Leu
145                 150                 155                 160

Glu Trp Ile Gly Val Ile His Pro Ser Asp Ser Glu Thr Trp Leu Asp
                165                 170                 175

Gln Lys Phe Lys Asp Arg Val Thr Ile Thr Val Asp Lys Ser Thr Ser

-continued

```
                180                 185                 190
Thr Ala Tyr Met Glu Leu Ser Ser Leu Arg Ser Glu Asp Thr Ala Val
                    195                 200                 205
Tyr Tyr Cys Ala Arg Glu His Tyr Gly Thr Ser Pro Phe Ala Tyr Trp
                    210                 215                 220
Gly Gln Gly Thr Leu Val Thr Val Ser Ser Gly Gly Cys Gly Gly Gly
225                 230                 235                 240
Glu Val Ala Ala Cys Glu Lys Glu Val Ala Ala Leu Glu Lys Glu Val
                    245                 250                 255
Ala Ala Leu Glu Lys Glu Val Ala Ala Leu Glu Lys Glu Ser Lys Tyr
                    260                 265                 270
Gly Pro Pro Cys Pro Pro Cys Pro Ala Pro Glu Phe Leu Gly Gly Pro
                    275                 280                 285
Ser Val Phe Leu Phe Pro Pro Lys Pro Lys Asp Thr Leu Tyr Ile Thr
                    290                 295                 300
Arg Glu Pro Glu Val Thr Cys Val Val Val Asp Val Ser Gln Glu Asp
305                 310                 315                 320
Pro Glu Val Gln Phe Asn Trp Tyr Val Asp Gly Val Glu Val His Asn
                    325                 330                 335
Ala Lys Thr Lys Pro Arg Glu Glu Gln Phe Asn Ser Thr Tyr Arg Val
                    340                 345                 350
Val Ser Val Leu Thr Val Leu His Gln Asp Trp Leu Asn Gly Lys Glu
                    355                 360                 365
Tyr Lys Cys Lys Val Ser Asn Lys Gly Leu Pro Ser Ser Ile Glu Lys
                    370                 375                 380
Thr Ile Ser Lys Ala Lys Gly Gln Pro Arg Glu Pro Gln Val Tyr Thr
385                 390                 395                 400
Leu Pro Pro Ser Gln Glu Glu Met Thr Lys Asn Gln Val Ser Leu Thr
                    405                 410                 415
Cys Leu Val Lys Gly Phe Tyr Pro Ser Asp Ile Ala Val Glu Trp Glu
                    420                 425                 430
Ser Asn Gly Gln Pro Glu Asn Asn Tyr Lys Thr Thr Pro Pro Val Leu
                    435                 440                 445
Asp Ser Asp Gly Ser Phe Phe Leu Tyr Ser Arg Leu Thr Val Asp Lys
                    450                 455                 460
Ser Arg Trp Gln Glu Gly Asn Val Phe Ser Cys Ser Val Met His Glu
465                 470                 475                 480
Ala Leu His Asn His Tyr Thr Gln Lys Ser Leu Ser Leu Ser Leu Gly
                    485                 490                 495
```

<210> SEQ ID NO 64
<211> LENGTH: 271
<212> TYPE: PRT
<213> ORGANISM: Artificial Sequence
<220> FEATURE:
<223> OTHER INFORMATION: Second and Fourth Polypeptide Chains of PD-1 x
      LAG-3 DART A

<400> SEQUENCE: 64

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Glu Ser Val Asp Asn Tyr
                    20                  25                  30
Gly Met Ser Phe Met Asn Trp Phe Gln Gln Lys Pro Gly Gln Pro Pro
                    35                  40                  45
```

```
Lys Leu Leu Ile His Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
130                 135                 140

Gly Tyr Thr Phe Thr Asp Tyr Asn Met Asp Trp Val Arg Gln Ala Pro
145                 150                 155                 160

Gly Gln Gly Leu Glu Trp Met Gly Asp Ile Asn Pro Asp Asn Gly Val
                165                 170                 175

Thr Ile Tyr Asn Gln Lys Phe Glu Gly Arg Val Thr Met Thr Thr Asp
            180                 185                 190

Thr Ser Thr Ser Thr Ala Tyr Met Glu Leu Arg Ser Leu Arg Ser Asp
        195                 200                 205

Asp Thr Ala Val Tyr Tyr Cys Ala Arg Glu Ala Asp Tyr Phe Tyr Phe
210                 215                 220

Asp Tyr Trp Gly Gln Gly Thr Thr Leu Thr Val Ser Ser Gly Gly Cys
225                 230                 235                 240

Gly Gly Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 65
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of mAb 4-4-20

<400> SEQUENCE: 65

Glu Val Lys Leu Asp Glu Thr Gly Gly Gly Leu Val Gln Pro Gly Arg
 1               5                  10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Tyr Gly Met Asp Tyr Trp Gly Gln Gly Thr
            100                 105                 110

Ser Val Thr Val Ser Ser
        115
```

```
<210> SEQ ID NO 66
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of mAb 4-4-20

<400> SEQUENCE: 66

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 67
<211> LENGTH: 273
<212> TYPE: PRT
<213> ORGANISM: Artificial Sequence
<220> FEATURE:
<223> OTHER INFORMATION: First Polypeptide Chain of Universal Bispecific
      Adaptor Molecule UBA-1

<400> SEQUENCE: 67

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gln Val Gln Leu Val Gln Ser Gly
        115                 120                 125

Ala Glu Val Lys Lys Pro Gly Ala Ser Val Lys Val Ser Cys Lys Ala
    130                 135                 140

Ser Gly Tyr Ser Phe Thr Ser Tyr Trp Met Asn Trp Val Arg Gln Ala
145                 150                 155                 160

Pro Gly Gln Gly Leu Glu Trp Ile Gly Val Ile His Pro Ser Asp Ser
                165                 170                 175

Glu Thr Trp Leu Asp Gln Lys Phe Lys Asp Arg Val Thr Ile Thr Val
            180                 185                 190
```

Asp Lys Ser Thr Ser Thr Ala Tyr Met Glu Leu Ser Ser Leu Arg Ser
            195                 200                 205

Glu Asp Thr Ala Val Tyr Tyr Cys Ala Arg Glu His Tyr Gly Thr Ser
        210                 215                 220

Pro Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys

<210> SEQ ID NO 68
<211> LENGTH: 272
<212> TYPE: PRT
<213> ORGANISM: Artificial Sequence
<220> FEATURE:
<223> OTHER INFORMATION: Second Polypeptide Chain of Universal
      Bispecific Adaptor Molecule UBA-1

<400> SEQUENCE: 68

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Gly Ser Gly Gly Gly Gly Glu Val Lys Leu Asp Glu Thr Gly
        115                 120                 125

Gly Gly Leu Val Gln Pro Gly Arg Pro Met Lys Leu Ser Cys Val Ala
    130                 135                 140

Ser Gly Phe Thr Phe Ser Asp Tyr Trp Met Asn Trp Val Arg Gln Ser
145                 150                 155                 160

Pro Glu Lys Gly Leu Glu Trp Val Ala Gln Ile Arg Asn Lys Pro Tyr
                165                 170                 175

Asn Tyr Glu Thr Tyr Tyr Ser Asp Ser Val Lys Gly Arg Phe Thr Ile
            180                 185                 190

Ser Arg Asp Asp Ser Lys Ser Ser Val Tyr Leu Gln Met Asn Asn Leu
        195                 200                 205

Arg Val Glu Asp Met Gly Ile Tyr Tyr Cys Thr Gly Ser Tyr Tyr Gly
    210                 215                 220

Met Asp Tyr Trp Gly Gln Gly Thr Ser Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

```
<210> SEQ ID NO 69
<211> LENGTH: 503
<212> TYPE: PRT
<213> ORGANISM: Artificial Sequence
<220> FEATURE:
<223> OTHER INFORMATION: First and Third Polypeptides of Universal
      Bispecific Adaptor Molecule UBA-2

<400> SEQUENCE: 69
```

```
Asp Val Val Met Thr Gln Thr Pro Phe Ser Leu Pro Val Ser Leu Gly
  1               5                  10                  15

Asp Gln Ala Ser Ile Ser Cys Arg Ser Gln Ser Leu Val His Ser
             20                  25                  30

Asn Gly Asn Thr Tyr Leu Arg Trp Tyr Leu Gln Lys Pro Gly Gln Ser
         35                  40                  45

Pro Lys Val Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

Gly Gly Gly Ser Gly Gly Gly Gly Gln Val Gln Leu Val Gln Ser Gly
        115                 120                 125

Ala Glu Val Lys Lys Pro Gly Ala Ser Val Lys Val Ser Cys Lys Ala
    130                 135                 140

Ser Gly Tyr Ser Phe Thr Ser Tyr Trp Met Asn Trp Val Arg Gln Ala
145                 150                 155                 160

Pro Gly Gln Gly Leu Glu Trp Ile Gly Val Ile His Pro Ser Asp Ser
                165                 170                 175

Glu Thr Trp Leu Asp Gln Lys Phe Lys Asp Arg Val Thr Ile Thr Val
            180                 185                 190

Asp Lys Ser Thr Ser Thr Ala Tyr Met Glu Leu Ser Ser Leu Arg Ser
        195                 200                 205

Glu Asp Thr Ala Val Tyr Tyr Cys Ala Arg Glu His Tyr Gly Thr Ser
    210                 215                 220

Pro Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365
```

```
Trp Leu Asn Gly Lys Glu Tyr Lys Cys Lys Val Ser Asn Lys Ala Leu
            370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
            450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
            485                 490                 495

Leu Ser Leu Ser Pro Gly Lys
            500

<210> SEQ ID NO 70
<211> LENGTH: 503
<212> TYPE: PRT
<213> ORGANISM: Artificial Sequence
<220> FEATURE:
<223> OTHER INFORMATION: First Polypeptide Chain of Universal Bispecific
      Adaptor Molecule UBA-3

<400> SEQUENCE: 70

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Gln Val Gln Leu Val Gln Ser Gly
        115                 120                 125

Ala Glu Val Lys Lys Pro Gly Ala Ser Val Lys Val Ser Cys Lys Ala
    130                 135                 140

Ser Gly Tyr Ser Phe Thr Ser Tyr Trp Met Asn Trp Val Arg Gln Ala
145                 150                 155                 160

Pro Gly Gln Gly Leu Glu Trp Ile Gly Val Ile His Pro Ser Asp Ser
                165                 170                 175

Glu Thr Trp Leu Asp Gln Lys Phe Lys Asp Arg Val Thr Ile Thr Val
            180                 185                 190

Asp Lys Ser Thr Ser Thr Ala Tyr Met Glu Leu Ser Ser Leu Arg Ser
        195                 200                 205

Glu Asp Thr Ala Val Tyr Tyr Cys Ala Arg Glu His Tyr Gly Thr Ser
```

```
                   210                 215                 220
Pro Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
                260                 265                 270

Lys Gly Gly Asp Lys Thr His Thr Cys Pro Pro Cys Pro Ala Pro
            275                 280                 285

Glu Ala Ala Gly Gly Pro Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
                420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 71
<211> LENGTH: 227
<212> TYPE: PRT
<213> ORGANISM: Artificial Sequence
<220> FEATURE:
<223> OTHER INFORMATION: Third Polypeptide Chain of Universal Bispecific
      Adaptor Molecule UBA-3

<400> SEQUENCE: 71

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
210                 215                 220

Pro Gly Lys
225

<210> SEQ ID NO 72
<211> LENGTH: 449
<212> TYPE: PRT
<213> ORGANISM: Artificial Sequence
<220> FEATURE:
<223> OTHER INFORMATION: Third Polypeptide Chain of Universal Bispecific
      Adaptor Molecule UBA-4

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Ile
            35                  40                  45

Gly Val Ile His Pro Ser Asp Ser Glu Thr Trp Leu Asp Gln Lys Phe
        50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro Gly
        435                 440                 445

Lys

<210> SEQ ID NO 73
<211> LENGTH: 218
<212> TYPE: PRT
<213> ORGANISM: Artificial Sequence
<220> FEATURE:
<223> OTHER INFORMATION: Fourth Polypeptide Chain of Universal
      Bispecific Adaptor Molecule UBA-4

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95
```

```
Glu Val Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 74
<211> LENGTH: 575
<212> TYPE: PRT
<213> ORGANISM: Artificial Sequence
<220> FEATURE:
<223> OTHER INFORMATION: Third Polypeptide Chain of Universal Bispecific
      Adaptor Molecule UBA-5

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Gly Ser Gly Gly Gly Gly Ser Gly Gly Gly Gly Ser Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Ser Phe Thr Ser Tyr Trp Met
145                 150                 155                 160

Asn Trp Val Arg Gln Ala Pro Gly Gln Gly Leu Glu Trp Ile Gly Val
                165                 170                 175

Ile His Pro Ser Asp Ser Glu Thr Trp Leu Asp Gln Lys Phe Lys Asp
            180                 185                 190

Arg Val Thr Ile Thr Val Asp Lys Ser Thr Ser Thr Ala Tyr Met Glu
        195                 200                 205

Leu Ser Ser Leu Arg Ser Glu Asp Thr Ala Val Tyr Tyr Cys Ala Arg
    210                 215                 220

Glu His Tyr Gly Thr Ser Pro Phe Ala Tyr Trp Gly Gln Gly Thr Leu
```

```
                225                 230                 235                 240
        Val Thr Val Ser Ser Ala Ser Thr Lys Gly Pro Ser Val Phe Pro Leu
                        245                 250                 255

Ala Pro Ser Ser Lys Ser Thr Ser Gly Gly Thr Ala Ala Leu Gly Cys
                        260                 265                 270

Leu Val Lys Asp Tyr Phe Pro Glu Pro Val Thr Val Ser Trp Asn Ser
                        275                 280                 285

Gly Ala Leu Thr Ser Gly Val His Thr Phe Pro Ala Val Leu Gln Ser
                        290                 295                 300

Ser Gly Leu Tyr Ser Leu Ser Ser Val Val Thr Val Pro Ser Ser Ser
        305                 310                 315                 320

Leu Gly Thr Gln Thr Tyr Ile Cys Asn Val Asn His Lys Pro Ser Asn
                        325                 330                 335

Thr Lys Val Asp Lys Arg Val Glu Pro Lys Ser Cys Asp Lys Thr His
                        340                 345                 350

Thr Cys Pro Pro Cys Pro Ala Pro Glu Ala Ala Gly Gly Pro Ser Val
                        355                 360                 365

Phe Leu Phe Pro Pro Lys Pro Lys Asp Thr Leu Met Ile Ser Arg Thr
                        370                 375                 380

Pro Glu Val Thr Cys Val Val Val Asp Val Ser His Glu Asp Pro Glu
        385                 390                 395                 400

Val Lys Phe Asn Trp Tyr Val Asp Gly Val Glu Val His Asn Ala Lys
                        405                 410                 415

Thr Lys Pro Arg Glu Glu Gln Tyr Asn Ser Thr Tyr Arg Val Val Ser
                        420                 425                 430

Val Leu Thr Val Leu His Gln Asp Trp Leu Asn Gly Lys Glu Tyr Lys
                        435                 440                 445

Cys Lys Val Ser Asn Lys Ala Leu Pro Ala Pro Ile Glu Lys Thr Ile
        450                 455                 460

Ser Lys Ala Lys Gly Gln Pro Arg Glu Pro Gln Val Tyr Thr Leu Pro
        465                 470                 475                 480

Pro Ser Arg Glu Glu Met Thr Lys Asn Gln Val Ser Leu Ser Cys Ala
                        485                 490                 495

Val Lys Gly Phe Tyr Pro Ser Asp Ile Ala Val Glu Trp Glu Ser Asn
                        500                 505                 510

Gly Gln Pro Glu Asn Asn Tyr Lys Thr Thr Pro Pro Val Leu Asp Ser
                        515                 520                 525

Asp Gly Ser Phe Phe Leu Val Ser Lys Leu Thr Val Asp Lys Ser Arg
        530                 535                 540

Trp Gln Gln Gly Asn Val Phe Ser Cys Ser Val Met His Glu Ala Leu
        545                 550                 555                 560

His Asn Arg Tyr Thr Gln Lys Ser Leu Ser Leu Ser Pro Gly Lys
                        565                 570                 575

<210> SEQ ID NO 75
<211> LENGTH: 223
<212> TYPE: PRT
<213> ORGANISM: Homo sapiens
<220> FEATURE:
<221> NAME/KEY: MISC_FEATURE
<222> LOCATION: (1)..(223)
<223> OTHER INFORMATION: Human CTLA-4, Including Signal Sequence (NCBI
      Sequence NP_005205.2)
<220> FEATURE:
<221> NAME/KEY: SIGNAL
<222> LOCATION: (1)..(34)
<223> OTHER INFORMATION: Signal Sequence
```

<400> SEQUENCE: 75

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 76
<211> LENGTH: 118
<212> TYPE: PRT
<213> ORGANISM: Homo sapiens
<220> FEATURE:
<221> NAME/KEY: MISC_FEATURE
<222> LOCATION: (1)..(118)
<223> OTHER INFORMATION: VH Domain of Anti-Human CTLA-4 Antibody CTLA-4
      mAb 1 (Ipilimumab)

<400> SEQUENCE: 76

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

```
Leu Val Thr Val Ser Ser
        115

<210> SEQ ID NO 77
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: VL Domain of Anti-Human CTLA-4 Antibody CTLA-4
      mAb 1 (Ipilimumab)

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 78
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: VH Domain of Anti-Human CTLA-4 Antibody CTLA-4
      mAb 2 (Tremelimumab)

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Val Thr Val Ser Ser
        115                 120                 125

<210> SEQ ID NO 79
<211> LENGTH: 107
<212> TYPE: PRT
<213> ORGANISM: Homo sapiens
```

```
<220> FEATURE:
<221> NAME/KEY: MISC_FEATURE
<222> LOCATION: (1)..(107)
<223> OTHER INFORMATION: VL Domain of Anti-Human CTLA-4 Antibody CTLA-4
      mAb 2 (Tremelimumab)

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys
            100                 105

<210> SEQ ID NO 80
<211> LENGTH: 217
<212> TYPE: PRT
<213> ORGANISM: Artificial Sequence
<220> FEATURE:
<223> OTHER INFORMATION: CH2-CH3 Domains of IgG1 Fc Region-Comprising
      Substitutions M252Y, S254T and T256E
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 80

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 81
<211> LENGTH: 217
<212> TYPE: PRT
<213> ORGANISM: Artificial Sequence
<220> FEATURE:
<223> OTHER INFORMATION: CH2-CH3 Domains of IgG4 Fc Region-Comprising
      Substitutions M252Y, S254T and T256E
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 81

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 82
<211> LENGTH: 217
<212> TYPE: PRT
<213> ORGANISM: Artificial Sequence
<220> FEATURE:
<223> OTHER INFORMATION: "Knob-Bearing" Variant of CH2-CH3 Domains of
      IgG1 Fc Region-Comprising Substitutions M252Y, S254T and T256E
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 82

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 83
<211> LENGTH: 217
<212> TYPE: PRT
<213> ORGANISM: Artificial Sequence
<220> FEATURE:
<223> OTHER INFORMATION: "Hole-Bearing" Variant of CH2-CH3 Domains of
      IgG1 Fc Region-Comprising Substitutions M252Y, S254T and T256E
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 83

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
```

```
                    115                 120                 125
Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215

<210> SEQ ID NO 84
<211> LENGTH: 217
<212> TYPE: PRT
<213> ORGANISM: Artificial Sequence
<220> FEATURE:
<223> OTHER INFORMATION: "Knob-Bearing" Variant of CH2-CH3 Domains of
      IgG4 Fc Region-Comprising Substitutions M252Y, S254T and T256E
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 84

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 85
```

<211> LENGTH: 217
<212> TYPE: PRT
<213> ORGANISM: Artificial Sequence
<220> FEATURE:
<223> OTHER INFORMATION: "Hole-Bearing" Variant of CH2-CH3 Domains of
      IgG4 Fc Region-Comprising Substitutions M252Y, S254T and T256E
<220> FEATURE:
<221> NAME/KEY: MISC_FEATURE
<222> LOCATION: (217)..(217)
<223> OTHER INFORMATION: Xaa is lysine (K) or is absent

<400> SEQUENCE: 85

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Arg Leu Thr Val Asp Lys Ser Arg Trp Gln Glu Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Leu Gly Xaa
    210                 215

<210> SEQ ID NO 86
<211> LENGTH: 119
<212> TYPE: PRT
<213> ORGANISM: Artificial Sequence
<220> FEATURE:
<223> OTHER INFORMATION: VH Domain of Humanized Anti-Human PD-1 Antibody
      (PD-1 mAb 6 I VH)

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Glu His Tyr Gly Thr Ser Pro Phe Ala Tyr Trp Gly Gln Gly
                100                 105                 110

Thr Leu Val Thr Val Ser Ser
        115

<210> SEQ ID NO 87
<211> LENGTH: 111
<212> TYPE: PRT
<213> ORGANISM: Artificial Sequence
<220> FEATURE:
<223> OTHER INFORMATION: VL Domain of Humanized Anti-Human PD-1 Antibody
      (PD-1 mAb 6 SQ VL)

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Met Ser Phe Met Asn Trp Phe Gln Gln Lys Pro Gly Gln Pro Pro
            35                  40                  45

Lys Leu Leu Ile His Ala Ala Ser Asn Gln Gly Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
                100                 105                 110

<210> SEQ ID NO 88
<211> LENGTH: 445
<212> TYPE: PRT
<213> ORGANISM: Artificial Sequence
<220> FEATURE:
<223> OTHER INFORMATION: Heavy Chain of Anti-Human PD-1 Antibody PD-1
      mAb 6 G4P

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Ile
            35                  40                  45

Gly Val Ile His Pro Ser Asp Ser Glu Thr Trp Leu Asp Gln Lys Phe
        50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Glu His Tyr Gly Thr Ser Pro Phe Ala Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 89
<211> LENGTH: 218
<212> TYPE: PRT
<213> ORGANISM: Artificial Sequence
<220> FEATURE:
<223> OTHER INFORMATION: Light Chain of Anti-Human PD-1 Antibody PD-1
      mAb 6 G4P

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

```
Lys Leu Leu Ile His Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 90
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of Anti-Human CTLA-4 Antibody CTLA-4
      mAb 3

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Ser Asn Lys His Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 91
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: VL Domain of Anti-Human CTLA-4 Antibody CTLA-4
``` mAb 3

<400> SEQUENCE: 91

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 92
<211> LENGTH: 448
<212> TYPE: PRT
<213> ORGANISM: Mus musculus
<220> FEATURE:
<221> NAME/KEY: MISC_FEATURE
<222> LOCATION: (1)..(448)
<223> OTHER INFORMATION: Heavy Chain of Anti-Human CTLA-4 Antibody mAb 3
      G1AA

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Ser Asn Lys His Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

```
His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 93
<211> LENGTH: 444
<212> TYPE: PRT
<213> ORGANISM: Mus musculus
<220> FEATURE:
<221> NAME/KEY: MISC_FEATURE
<222> LOCATION: (1)..(444)
<223> OTHER INFORMATION: Heavy Chain of Anti-Human CTLA-4 Antibody mAb 3
      G4P

<400> SEQUENCE: 93

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Ser Asn Lys His Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 94
<211> LENGTH: 215
<212> TYPE: PRT
<213> ORGANISM: Mus musculus
<220> FEATURE:
<221> NAME/KEY: MISC_FEATURE
<222> LOCATION: (1)..(215)
<223> OTHER INFORMATION: Light Chain of Anti-Human CTLA-4 Antibodies mAb
      3 G1AA and mAb 3 G4P

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Phe Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
210                 215

<210> SEQ ID NO 95
<211> LENGTH: 497
<212> TYPE: PRT
<213> ORGANISM: Artificial Sequence
<220> FEATURE:
<223> OTHER INFORMATION: First and Third Polypeptide Chains of DART B

<400> SEQUENCE: 95

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                 20                  25                  30

Tyr Leu Ala Trp Tyr Gln Gln Lys Pro Gly Gln Ala Pro Arg Leu Leu
                 35                  40                  45

Ile Tyr Gly Ala Phe Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys Gly Gly Gly Ser
                100                 105                 110

Gly Gly Gly Gly Gln Val Gln Leu Val Gln Ser Gly Ala Glu Val Lys
                115                 120                 125

Lys Pro Gly Ala Ser Val Lys Val Ser Cys Lys Ala Ser Gly Tyr Ser
130                 135                 140

Phe Thr Ser Tyr Trp Met Asn Trp Val Arg Gln Ala Pro Gly Gln Gly
145                 150                 155                 160

Leu Glu Trp Ile Gly Val Ile His Pro Ser Asp Ser Glu Thr Trp Leu
                165                 170                 175

Asp Gln Lys Phe Lys Asp Arg Val Thr Ile Thr Val Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu His Tyr Gly Thr Ser Pro Phe Ala Tyr
    210                 215                 220

Trp Gly Gln Gly Thr Leu Val Thr Val Ser Ser Gly Gly Cys Gly Gly
225                 230                 235                 240

Gly Glu Val Ala Ala Cys Glu Lys Glu Val Ala Ala Leu Glu Lys Glu
                245                 250                 255

Val Ala Ala Leu Glu Lys Glu Val Ala Ala Leu Glu Lys Glu Ser Lys
                260                 265                 270

Tyr Gly Pro Pro Cys Pro Pro Cys Pro Ala Pro Glu Phe Leu Gly Gly
                275                 280                 285

Pro Ser Val Phe Leu Phe Pro Pro Lys Pro Lys Asp Thr Leu Tyr Ile
    290                 295                 300

Thr Arg Glu Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Asn Ser Thr Tyr Arg
                340                 345                 350

Val Val Ser Val Leu Thr Val Leu His Gln Asp Trp Leu Asn Gly Lys
            355                 360                 365

Glu Tyr Lys Cys Lys Val Ser Asn Lys Gly Leu Pro Ser Ser Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
    435                 440                 445

Leu Asp Ser Asp Gly Ser Phe Phe Leu Tyr Ser Arg Leu Thr Val Asp
450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Leu
                485                 490                 495

Gly

<210> SEQ ID NO 96
<211> LENGTH: 271
<212> TYPE: PRT
<213> ORGANISM: Artificial Sequence
<220> FEATURE:
<223> OTHER INFORMATION: Second and Fourth Polypeptide Chains of DART B

<400> SEQUENCE: 96

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

```
Gly Met Ser Phe Met Asn Trp Phe Gln Gln Lys Pro Gly Gln Pro Pro
         35                  40                  45

Lys Leu Leu Ile His Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Glu Ser Gly Gly
        115                 120                 125

Gly Val Val Gln Pro Gly Arg Ser Leu Arg Leu Ser Cys Ala Ala Ser
    130                 135                 140

Gly Phe Thr Phe Ser Ser Tyr Thr Met His Trp Val Arg Gln Ala Pro
145                 150                 155                 160

Gly Lys Gly Leu Glu Trp Val Thr Phe Ile Ser Tyr Asp Gly Asn Asn
                165                 170                 175

Lys Tyr Tyr Ala Asp Ser Val Lys Gly Arg Phe Thr Ile Ser Arg Asp
            180                 185                 190

Asn Ser Lys Asn Thr Leu Tyr Leu Gln Met Asn Ser Leu Arg Ala Glu
        195                 200                 205

Asp Thr Ala Ile Tyr Tyr Cys Ala Arg Thr Gly Trp Leu Gly Pro Phe
    210                 215                 220

Asp Tyr Trp Gly Gln Gly Thr Leu Val Thr Val Ser Ser Gly Gly Cys
225                 230                 235                 240

Gly Gly Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 97
<211> LENGTH: 497
<212> TYPE: PRT
<213> ORGANISM: Artificial Sequence
<220> FEATURE:
<223> OTHER INFORMATION: First and Third Polypeptide Chains of DART C

<400> SEQUENCE: 97

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Phe Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys Gly Gly Gly Ser
            100                 105                 110

Gly Gly Gly Gly Gln Val Gln Leu Val Gln Ser Gly Ala Glu Val Lys
        115                 120                 125
```

Lys Pro Gly Ala Ser Val Lys Val Ser Cys Lys Ala Ser Gly Tyr Ser
    130                 135                 140

Phe Thr Ser Tyr Trp Met Asn Trp Val Arg Gln Ala Pro Gly Gln Gly
145                 150                 155                 160

Leu Glu Trp Ile Gly Val Ile His Pro Ser Asp Ser Glu Thr Trp Leu
                165                 170                 175

Asp Gln Lys Phe Lys Asp Arg Val Thr Ile Thr Val Asp Lys Ser Thr
                180                 185                 190

Ser Thr Ala Tyr Met Glu Leu Ser Ser Leu Arg Ser Glu Asp Thr Ala
            195                 200                 205

Val Tyr Tyr Cys Ala Arg Glu His Tyr Gly Thr Ser Pro Phe Ala Tyr
    210                 215                 220

Trp Gly Gln Gly Thr Leu Val Thr Val Ser Ser Gly Gly Cys Gly Gly
225                 230                 235                 240

Gly Glu Val Ala Ala Cys Glu Lys Glu Val Ala Ala Leu Glu Lys Glu
                245                 250                 255

Val Ala Ala Leu Glu Lys Glu Val Ala Ala Leu Glu Lys Glu Ser Lys
            260                 265                 270

Tyr Gly Pro Pro Cys Pro Pro Cys Pro Ala Pro Glu Phe Leu Gly Gly
            275                 280                 285

Pro Ser Val Phe Leu Phe Pro Pro Lys Pro Lys Asp Thr Leu Tyr Ile
    290                 295                 300

Thr Arg Glu Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Asn Ser Thr Tyr Arg
            340                 345                 350

Val Val Ser Val Leu Thr Val Leu His Gln Asp Trp Leu Asn Gly Lys
    355                 360                 365

Glu Tyr Lys Cys Lys Val Ser Asn Lys Gly Leu Pro Ser Ser Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Arg Leu Thr Val Asp
450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Leu
                485                 490                 495

Gly

<210> SEQ ID NO 98
<211> LENGTH: 271
<212> TYPE: PRT
<213> ORGANISM: Artificial Sequence
<220> FEATURE:
<223> OTHER INFORMATION: Second and Fourth Polypeptide Chains of DART C

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Glu Ser Gly Gly
        115                 120                 125

Gly Val Val Gln Pro Gly Arg Ser Leu Arg Leu Ser Cys Ala Ala Ser
    130                 135                 140

Gly Phe Thr Phe Ser Ser Tyr Thr Met His Trp Val Arg Gln Ala Pro
145                 150                 155                 160

Gly Lys Gly Leu Glu Trp Val Thr Phe Ile Ser Tyr Asp Gly Ser Asn
                165                 170                 175

Lys His Tyr Ala Asp Ser Val Lys Gly Arg Phe Thr Val Ser Arg Asp
            180                 185                 190

Asn Ser Lys Asn Thr Leu Tyr Leu Gln Met Asn Ser Leu Arg Ala Glu
        195                 200                 205

Asp Thr Ala Ile Tyr Tyr Cys Ala Arg Thr Gly Trp Leu Gly Pro Phe
    210                 215                 220

Asp Tyr Trp Gly Gln Gly Thr Leu Val Thr Val Ser Ser Gly Gly Cys
225                 230                 235                 240

Gly Gly Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 99
<211> LENGTH: 499
<212> TYPE: PRT
<213> ORGANISM: Artificial Sequence
<220> FEATURE:
<223> OTHER INFORMATION: First and Third Polypeptide Chains of DART D

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys

```
                        85                  90                  95
Glu Val Pro Tyr Thr Phe Gly Gly Thr Lys Val Glu Ile Lys Gly
                    100                 105                 110
Gly Gly Ser Gly Gly Gly Gln Val Gln Leu Val Glu Ser Gly Gly
                    115                 120                 125
Gly Val Val Gln Pro Gly Arg Ser Leu Arg Leu Ser Cys Ala Ala Ser
130                 135                 140
Gly Phe Thr Phe Ser Ser Tyr Thr Met His Trp Val Arg Gln Ala Pro
145                 150                 155                 160
Gly Lys Gly Leu Glu Trp Val Thr Phe Ile Ser Tyr Asp Gly Ser Asn
                    165                 170                 175
Lys His Tyr Ala Asp Ser Val Lys Gly Arg Phe Thr Val Ser Arg Asp
                    180                 185                 190
Asn Ser Lys Asn Thr Leu Tyr Leu Gln Met Asn Ser Leu Arg Ala Glu
                    195                 200                 205
Asp Thr Ala Ile Tyr Tyr Cys Ala Arg Thr Gly Trp Leu Gly Pro Phe
210                 215                 220
Asp Tyr Trp Gly Gln Gly Thr Leu Val Thr Val Ser Ser Gly Gly Cys
225                 230                 235                 240
Gly Gly Gly Glu Val Ala Ala Cys Glu Lys Glu Val Ala Ala Leu Glu
                    245                 250                 255
Lys Glu Val Ala Ala Leu Glu Lys Glu Val Ala Ala Leu Glu Lys Glu
                    260                 265                 270
Ser Lys Tyr Gly Pro Pro Cys Pro Pro Cys Pro Ala Pro Glu Phe Leu
                    275                 280                 285
Gly Gly Pro Ser Val Phe Leu Phe Pro Pro Lys Pro Lys Asp Thr Leu
                    290                 295                 300
Tyr Ile Thr Arg Glu Pro Glu Val Thr Cys Val Val Val Asp Val Ser
305                 310                 315                 320
Gln Glu Asp Pro Glu Val Gln Phe Asn Trp Tyr Val Asp Gly Val Glu
                    325                 330                 335
Val His Asn Ala Lys Thr Lys Pro Arg Glu Glu Gln Phe Asn Ser Thr
                    340                 345                 350
Tyr Arg Val Val Ser Val Leu Thr Val Leu His Gln Asp Trp Leu Asn
                    355                 360                 365
Gly Lys Glu Tyr Lys Cys Lys Val Ser Asn Lys Gly Leu Pro Ser Ser
                    370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Gln Glu Glu Met Thr Lys Asn Gln Val
                    405                 410                 415
Ser Leu Thr Cys Leu Val Lys Gly Phe Tyr Pro Ser Asp Ile Ala Val
                    420                 425                 430
Glu Trp Glu Ser Asn Gly Gln Pro Glu Asn Asn Tyr Lys Thr Thr Pro
                    435                 440                 445
Pro Val Leu Asp Ser Asp Gly Ser Phe Phe Leu Tyr Ser Arg Leu Thr
450                 455                 460
Val Asp Lys Ser Arg Trp Gln Glu Gly Asn Val Phe Ser Cys Ser Val
465                 470                 475                 480
Met His Glu Ala Leu His Asn His Tyr Thr Gln Lys Ser Leu Ser Leu
                    485                 490                 495

Ser Leu Gly
```

-continued

```
<210> SEQ ID NO 100
<211> LENGTH: 269
<212> TYPE: PRT
<213> ORGANISM: Artificial Sequence
<220> FEATURE:
<223> OTHER INFORMATION: Second and Fourth Polypeptide Chains of DART D

<400> SEQUENCE: 100

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ala Ser Val Lys Val Ser Cys Lys Ala Ser Gly Tyr Ser
130                 135                 140

Phe Thr Ser Tyr Trp Met Asn Trp Val Arg Gln Ala Pro Gly Gln Gly
145                 150                 155                 160

Leu Glu Trp Ile Gly Val Ile His Pro Ser Asp Ser Glu Thr Trp Leu
                165                 170                 175

Asp Gln Lys Phe Lys Asp Arg Val Thr Ile Thr Val Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu His Tyr Gly Thr Ser Pro Phe Ala Tyr
    210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 101
<211> LENGTH: 503
<212> TYPE: PRT
<213> ORGANISM: Artificial Sequence
<220> FEATURE:
<223> OTHER INFORMATION: First and Third Polypeptide Chains of DART F

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45
```

-continued

```
Lys Leu Leu Ile His Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Thr Lys Val Glu Ile Lys Gly
            100                 105                 110

Gly Gly Ser Gly Gly Gly Gly Gln Val Gln Leu Val Glu Ser Gly Gly
            115                 120                 125

Gly Val Val Gln Pro Gly Arg Ser Leu Arg Leu Ser Cys Ala Ala Ser
    130                 135                 140

Gly Phe Thr Phe Ser Ser Tyr Thr Met His Trp Val Arg Gln Ala Pro
145                 150                 155                 160

Gly Lys Gly Leu Glu Trp Val Thr Phe Ile Ser Tyr Asp Gly Ser Asn
                165                 170                 175

Lys His Tyr Ala Asp Ser Val Lys Gly Arg Phe Thr Val Ser Arg Asp
            180                 185                 190

Asn Ser Lys Asn Thr Leu Tyr Leu Gln Met Asn Ser Leu Arg Ala Glu
        195                 200                 205

Asp Thr Ala Ile Tyr Tyr Cys Ala Arg Thr Gly Trp Leu Gly Pro Phe
    210                 215                 220

Asp Tyr Trp Gly Gln Gly Thr Leu Val Thr Val Ser Ser Gly Gly Cys
225                 230                 235                 240

Gly Gly Gly Glu Val Ala Ala Cys Glu Lys Glu Val Ala Ala Leu Glu
                245                 250                 255

Lys Glu Val Ala Ala Leu Glu Lys Glu Val Ala Ala Leu Glu Lys Leu
            260                 265                 270

Glu Pro Lys Ser Ala Asp Lys Thr His Thr Cys Pro Pro Cys Pro Ala
        275                 280                 285

Pro Glu Ala Ala Gly Gly Pro Ser Val Phe Leu Phe Pro Pro Lys Pro
    290                 295                 300

Lys Asp Thr Leu Tyr Ile Thr Arg Glu Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460
```

```
Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly
                500

<210> SEQ ID NO 102
<211> LENGTH: 567
<212> TYPE: PRT
<213> ORGANISM: Artificial Sequence
<220> FEATURE:
<223> OTHER INFORMATION: First and Third Polypeptide Chains of DART E

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ala Ser Val Lys Val Ser Cys Lys Ala Ser Gly Tyr Ser
130                 135                 140

Phe Thr Ser Tyr Trp Met Asn Trp Val Arg Gln Ala Pro Gly Gln Gly
145                 150                 155                 160

Leu Glu Trp Ile Gly Val Ile His Pro Ser Asp Ser Glu Thr Trp Leu
                165                 170                 175

Asp Gln Lys Phe Lys Asp Arg Val Thr Ile Thr Val Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu His Tyr Gly Thr Ser Pro Phe Ala Tyr
210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
290                 295                 300

Ser Leu Ser Ser Val Val Thr Val Pro Ser Ser Ser Leu Gly Thr Lys
305                 310                 315                 320
```

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
        355                 360                 365

Lys Asp Thr Leu Tyr Ile Thr Arg Glu Pro Glu Val Thr Cys Val Val
    370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Gly
        435                 440                 445

Leu Pro Ser Ser Ile Glu Lys Thr Ile Ser Lys Ala Lys Gly Gln Pro
    450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
    530                 535                 540

Ser Cys Ser Val Met His Glu Ala Leu His Asn His Tyr Thr Gln Lys
545                 550                 555                 560

Ser Leu Ser Leu Ser Leu Gly
                565

<210> SEQ ID NO 103
<211> LENGTH: 350
<212> TYPE: PRT
<213> ORGANISM: Artificial Sequence
<220> FEATURE:
<223> OTHER INFORMATION: Second and Fourth Polypeptide Chains of DART E

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gln Val Gln Leu Val Glu Ser Gly Gly
            115                 120                 125

Gly Val Val Gln Pro Gly Arg Ser Leu Arg Leu Ser Cys Ala Ala Ser
130                 135                 140

Gly Phe Thr Phe Ser Ser Tyr Thr Met His Trp Val Arg Gln Ala Pro
145                 150                 155                 160

Gly Lys Gly Leu Glu Trp Val Thr Phe Ile Ser Tyr Asp Gly Ser Asn
            165                 170                 175

Lys His Tyr Ala Asp Ser Val Lys Gly Arg Phe Thr Val Ser Arg Asp
            180                 185                 190

Asn Ser Lys Asn Thr Leu Tyr Leu Gln Met Asn Ser Leu Arg Ala Glu
            195                 200                 205

Asp Thr Ala Ile Tyr Tyr Cys Ala Arg Thr Gly Trp Leu Gly Pro Phe
            210                 215                 220

Asp Tyr Trp Gly Gln Gly Thr Leu Val Thr Val Ser Ser Leu Gly Gly
225                 230                 235                 240

Gly Ser Gly Arg Thr Val Ala Ala Pro Ser Val Phe Ile Phe Pro Pro
            245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
            275                 280                 285

Ala Leu Gln Ser Gly Asn Ser Gln Glu Ser Val Thr Glu Gln Asp Ser
            290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
            325                 330                 335

Leu Ser Ser Pro Val Thr Lys Ser Phe Asn Arg Gly Glu Cys
            340                 345                 350

<210> SEQ ID NO 104
<211> LENGTH: 500
<212> TYPE: PRT
<213> ORGANISM: Artificial Sequence
<220> FEATURE:
<223> OTHER INFORMATION: First Polypeptide Chain of TRIDENT A

<400> SEQUENCE: 104

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
            35                  40                  45

Lys Leu Leu Ile His Ala Ala Ser Asn Gln Gly Ser Gly Val Pro Ser
            50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
            85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Gln Ser Gly Ala
            115                 120                 125

```
Glu Val Lys Lys Pro Gly Ala Ser Val Lys Val Ser Cys Lys Ala Ser
    130                 135                 140

Gly Tyr Ser Phe Thr Ser Tyr Trp Met Asn Trp Val Arg Gln Ala Pro
145                 150                 155                 160

Gly Gln Gly Leu Glu Trp Ile Gly Val Ile His Pro Ser Asp Ser Glu
                165                 170                 175

Thr Trp Leu Asp Gln Lys Phe Lys Asp Arg Val Thr Ile Thr Val Asp
            180                 185                 190

Lys Ser Thr Ser Thr Ala Tyr Met Glu Leu Ser Ser Leu Arg Ser Glu
        195                 200                 205

Asp Thr Ala Val Tyr Tyr Cys Ala Arg Glu His Tyr Gly Thr Ser Pro
    210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

Glu Ser Lys Tyr Gly Pro Pro Cys Pro Pro Cys Pro Ala Pro Glu Phe
        275                 280                 285

Leu Gly Gly Pro Ser Val Phe Leu Phe Pro Pro Lys Pro Lys Asp Thr
    290                 295                 300

Leu Tyr Ile Thr Arg Glu Pro Glu Val Thr Cys Val Val Val Asp Val
305                 310                 315                 320

Ser Gln Glu Asp Pro Glu Val Gln Phe Asn Trp Tyr Val Asp Gly Val
                325                 330                 335

Glu Val His Asn Ala Lys Thr Lys Pro Arg Glu Glu Gln Phe Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Gly Leu Pro Ser
    370                 375                 380

Ser Ile Glu Lys Thr Ile Ser Lys Ala Lys Gly Gln Pro Arg Glu Pro
385                 390                 395                 400

Gln Val Tyr Thr Leu Pro Pro Ser Gln Glu Glu Met Thr Lys Asn Gln
                405                 410                 415

Val Ser Leu Trp Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Arg Leu
    450                 455                 460

Thr Val Asp Lys Ser Arg Trp Gln Glu Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Leu Gly
            500

<210> SEQ ID NO 105
<211> LENGTH: 272
<212> TYPE: PRT
<213> ORGANISM: Artificial Sequence
<220> FEATURE:
<223> OTHER INFORMATION: Second Polypeptide Chain of TRIDENT A
```

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Ser Phe Thr Ser Tyr Trp Met Asn Trp Val Arg Gln Ala Pro
145                 150                 155                 160

Gly Gln Gly Leu Glu Trp Ile Gly Val Ile His Pro Ser Asp Ser Glu
                165                 170                 175

Thr Trp Leu Asp Gln Lys Phe Lys Asp Arg Val Thr Ile Thr Val Asp
            180                 185                 190

Lys Ser Thr Ser Thr Ala Tyr Met Glu Leu Ser Ser Leu Arg Ser Glu
        195                 200                 205

Asp Thr Ala Val Tyr Tyr Cys Ala Arg Glu His Tyr Gly Thr Ser Pro
    210                 215                 220

Phe Ala Tyr Trp Gly Gln Gly Thr Leu Val Thr Val Ser Ser Gly Gly
225                 230                 235                 240

Cys Gly Gly Lys Val Ala Ala Cys Lys Glu Lys Val Ala Ala Leu
                245                 250                 255

Lys Glu Lys Val Ala Ala Leu Lys Glu Lys Val Ala Ala Leu Lys Glu
    260                 265                 270

<210> SEQ ID NO 106
<211> LENGTH: 444
<212> TYPE: PRT
<213> ORGANISM: Artificial Sequence
<220> FEATURE:
<223> OTHER INFORMATION: Third Polypeptide Chain of TRIDENT A

<400> SEQUENCE: 106

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Ser Asn Lys His Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                    85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Tyr Ile Thr Arg Glu Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

Arg Tyr Thr Gln Lys Ser Leu Ser Leu Ser Leu Gly
        435                 440

<210> SEQ ID NO 107
<211> LENGTH: 215
<212> TYPE: PRT
<213> ORGANISM: Artificial Sequence
<220> FEATURE:
<223> OTHER INFORMATION: Fourth Polypeptide Chain of TRIDENT A

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 108
<211> LENGTH: 502
<212> TYPE: PRT
<213> ORGANISM: Artificial Sequence
<220> FEATURE:
<223> OTHER INFORMATION: First Polypeptide Chain of TRIDENT B

<400> SEQUENCE: 108

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

```
Gly Tyr Ser Phe Thr Ser Tyr Trp Met Asn Trp Val Arg Gln Ala Pro
145                 150                 155                 160

Gly Gln Gly Leu Glu Trp Ile Gly Val Ile His Pro Ser Asp Ser Glu
            165                 170                 175

Thr Trp Leu Asp Gln Lys Phe Lys Asp Arg Val Thr Ile Thr Val Asp
            180                 185                 190

Lys Ser Thr Ser Thr Ala Tyr Met Glu Leu Ser Ser Leu Arg Ser Glu
            195                 200                 205

Asp Thr Ala Val Tyr Tyr Cys Ala Arg Glu His Tyr Gly Thr Ser Pro
            210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Cys Glu Lys Glu Val Ala Ala Leu
            245                 250                 255

Glu Lys Glu Val Ala Ala Leu Glu Lys Glu Val Ala Ala Leu Glu Lys
            260                 265                 270

Gly Gly Gly Asp Lys Thr His Thr Cys Pro Pro Cys Pro Ala Pro Glu
            275                 280                 285

Ala Ala Gly Gly Pro Ser Val Phe Leu Phe Pro Pro Lys Pro Lys Asp
290                 295                 300

Thr Leu Tyr Ile Thr Arg Glu Pro Glu Val Thr Cys Val Val Val Asp
305                 310                 315                 320

Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
            355                 360                 365

Leu Asn Gly Lys Glu Tyr Lys Cys Lys Val Ser Asn Lys Ala Leu Pro
            370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
            405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Lys
450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
            485                 490                 495

Ser Leu Ser Pro Gly Lys
            500

<210> SEQ ID NO 109
<211> LENGTH: 448
<212> TYPE: PRT
<213> ORGANISM: Artificial Sequence
<220> FEATURE:
<223> OTHER INFORMATION: Third Polypeptide Chain of TRIDENT B

<400> SEQUENCE: 109
```

```
Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Ser Asn Lys His Tyr Ala Asp Ser Val
    50                  55                  60

Lys Gly Arg Phe Thr Val Ser Arg Asp Asn Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
```

Leu His Asn Arg Tyr Thr Gln Lys Ser Leu Ser Leu Ser Pro Gly Lys
            420                 425                 430
            435                 440                 445

<210> SEQ ID NO 110
<211> LENGTH: 469
<212> TYPE: PRT
<213> ORGANISM: Artificial Sequence
<220> FEATURE:
<223> OTHER INFORMATION: Third Polypeptide Chain of TRIDENT C

<400> SEQUENCE: 110

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Gln Val Gln Leu Val
            115                 120                 125

Glu Ser Gly Gly Gly Val Val Gln Pro Gly Arg Ser Leu Arg Leu Ser
130                 135                 140

Cys Ala Ala Ser Gly Phe Thr Phe Ser Ser Tyr Thr Met His Trp Val
145                 150                 155                 160

Arg Gln Ala Pro Gly Lys Gly Leu Glu Trp Val Thr Phe Ile Ser Tyr
                165                 170                 175

Asp Gly Ser Asn Lys His Tyr Ala Asp Ser Val Lys Gly Arg Phe Thr
            180                 185                 190

Val Ser Arg Asp Asn Ser Lys Asn Thr Leu Tyr Leu Gln Met Asn Ser
        195                 200                 205

Leu Arg Ala Glu Asp Thr Ala Ile Tyr Tyr Cys Ala Arg Thr Gly Trp
    210                 215                 220

Leu Gly Pro Phe Asp Tyr Trp Gly Gln Gly Thr Leu Val Thr Val Ser
225                 230                 235                 240

Ser Glu Ser Lys Tyr Gly Pro Pro Cys Pro Pro Cys Pro Ala Pro Glu
                245                 250                 255

Phe Leu Gly Gly Pro Ser Val Phe Leu Phe Pro Pro Lys Pro Lys Asp
            260                 265                 270

Thr Leu Tyr Ile Thr Arg Glu Pro Glu Val Thr Cys Val Val Val Asp
        275                 280                 285

Val Ser Gln Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Gly Leu Pro

```
                    340                 345                 350
Ser Ser Ile Glu Lys Thr Ile Ser Lys Ala Lys Gly Gln Pro Arg Glu
        355                 360                 365

Pro Gln Val Tyr Thr Leu Pro Pro Ser Gln Glu Glu Met Thr Lys Asn
    370                 375                 380

Gln Val Ser Leu Ser Cys Ala Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Val Ser Arg
                420                 425                 430

Leu Thr Val Asp Lys Ser Arg Trp Gln Glu Gly Asn Val Phe Ser Cys
        435                 440                 445

Ser Val Met His Glu Ala Leu His Asn Arg Tyr Thr Gln Lys Ser Leu
    450                 455                 460

Ser Leu Ser Leu Gly
465
```